US009192629B2

(12) United States Patent
Presnell et al.

(10) Patent No.: US 9,192,629 B2
(45) Date of Patent: *Nov. 24, 2015

(54) ISOLATED RENAL CELLS AND USES THEREOF

(71) Applicant: RegenMedTX, LLC, Winston-Salem, NC (US)

(72) Inventors: Sharon C. Presnell, Lewisville, NC (US); Andrew Bruce, Lexington, NC (US); Shay M. Wallace, Winston-Salem, NC (US); Sumana Choudhury, Kernersville, NC (US); Russell W. Kelley, Winston-Salem, NC (US); Manuel J. Jayo, Winston-Salem, NC (US); Jessica J. Reinsch, Charlotte, NC (US); Patricia D. Tatsumi, Greensboro, NC (US); Timothy A. Bertram, Winston-Salem, NC (US); Eric S. Werdin, Lewisville, NC (US); Oluwatoyin A. Knight, Winston-Salem, NC (US); H. Scott Rapoport, Winston-Salem, NC (US); Roger M. Ilagan, Burlington, NC (US)

(73) Assignee: REGENMEDTX, LLC, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/661,668

(22) Filed: Oct. 26, 2012

(65) Prior Publication Data
US 2013/0149347 A1 Jun. 13, 2013

Related U.S. Application Data

(62) Division of application No. 12/617,721, filed on Nov. 12, 2009, now Pat. No. 8,318,484.

(60) Provisional application No. 61/114,025, filed on Nov. 12, 2008, provisional application No. 61/114,030, filed on Nov. 12, 2008, provisional application No. 61/201,056, filed on Dec. 5, 2008, provisional application No. 61/201,305, filed on Dec. 8, 2008, provisional application No. 61/121,311, filed on Dec. 10, 2008.

(51) Int. Cl.
*A01N 63/00* (2006.01)
*A61K 35/22* (2015.01)
*C12N 5/071* (2010.01)
*A61K 35/12* (2015.01)

(52) U.S. Cl.
CPC .............. *A61K 35/22* (2013.01); *C12N 5/0686* (2013.01); *A61K 35/12* (2013.01); *C12N 2500/02* (2013.01)

(58) Field of Classification Search
None
See application file for complete search history.

(56) References Cited

U.S. PATENT DOCUMENTS

| | | | |
|---|---|---|---|
| 4,377,513 A | 3/1983 | Sugimoto et al. | |
| 4,769,037 A | 9/1988 | Midcalf | |
| 4,996,154 A | 2/1991 | Gabriels | |
| 5,085,629 A | 2/1992 | Goldberg et al. | |
| 5,092,886 A | 3/1992 | Dobos-Hardy | |
| 5,429,938 A | 7/1995 | Humes | |
| 5,516,680 A | 5/1996 | Naughton et al. | |
| 5,545,131 A | 8/1996 | Davankov | |
| 5,549,674 A | 8/1996 | Humes et al. | |
| 5,854,006 A | 12/1998 | Hanigan et al. | |
| 5,952,226 A | 9/1999 | Aebischer et al. | |
| 5,994,127 A | 11/1999 | Selden et al. | |
| 6,060,270 A | 5/2000 | Humes | |
| 6,140,039 A | 10/2000 | Naughton et al. | |
| 6,376,244 B1 | 4/2002 | Atala | |
| 6,410,320 B1 | 6/2002 | Humes | |
| 6,548,081 B2 | 4/2003 | Sadozai et al. | |
| 6,673,339 B1* | 1/2004 | Atala et al. | 424/93.2 |
| 6,747,002 B2 | 6/2004 | Cheung et al. | |
| 6,777,205 B1 | 8/2004 | Carcagno et al. | |
| 6,784,154 B2 | 8/2004 | Westenfelder | |
| 6,827,938 B2 | 12/2004 | Hart et al. | |
| 7,326,570 B2 | 2/2008 | Nigam et al. | |
| 2003/0124099 A1 | 7/2003 | Atala | |
| 2004/0167634 A1 | 8/2004 | Atala et al. | |
| 2004/0185503 A1 | 9/2004 | Yamanouchi et al. | |
| 2006/0153894 A1 | 7/2006 | Gharbrial et al. | |
| 2007/0059293 A1 | 3/2007 | Atala | |
| 2007/0078084 A1 | 4/2007 | Kishore et al. | |
| 2007/0116679 A1 | 5/2007 | Atala | |
| 2007/0128174 A1 | 6/2007 | Kleinsck et al. | |
| 2007/0184033 A1* | 8/2007 | Sevrain et al. | 424/93.7 |

(Continued)

FOREIGN PATENT DOCUMENTS

| | | |
|---|---|---|
| CN | 1044496 | 8/1990 |
| KR | 2001-0026239 | 4/2001 |

(Continued)

OTHER PUBLICATIONS

Aboushwareb et al. "Erythropoietin producing cells for potential cell therapy" World J. Urol. 26:295-300 (2008).
Amann et al. "Cardiac remodeling in experimental renal failure—an immunohistochemical study" Nephrology Dial Transplant, 13: 1958-1966 (1998).
Anglani et al., "The renal stem cell system in kidney repair and regeneration", Frontiers in Bioscience, 13: pp. 6395-6405 (2008).
PCT/US00/33891 International Search Report, Mar. 26, 2001, PCT.
PCT/US09/64418 Int'l. Search Report and Written Opinion, Jan. 19, 2010, PCT.
PCT/US09/64421 Int'l. Search Report and Written Opinion, Feb. 19, 2010, PCT.

(Continued)

*Primary Examiner* — Lora E Barnhart Driscoll
(74) *Attorney, Agent, or Firm* — Christopher DeVry; Arnold & Porter LLP

(57) ABSTRACT

The invention is directed to isolated renal cells, including tubular and erythropoietin (EPO)-producing kidney cell populations, and methods of isolating and culturing the same, as well as methods of treating a subject in need with the cell populations.

16 Claims, 107 Drawing Sheets

(56) References Cited

U.S. PATENT DOCUMENTS

| | | | |
|---|---|---|---|
| 2008/0305146 | A1 | 12/2008 | Atala et al. |
| 2009/0186004 | A1 | 7/2009 | Fukui et al. |
| 2010/0104544 | A1 | 4/2010 | Atala et al. |
| 2010/0112062 | A1 | 5/2010 | Atala et al. |

FOREIGN PATENT DOCUMENTS

| | | |
|---|---|---|
| WO | WO 90/02796 | 3/1990 |
| WO | WO 90/12604 | 11/1990 |
| WO | WO 93/07913 | 4/1993 |
| WO | WO 95/11048 | 4/1995 |
| WO | WO 96/40175 | 12/1996 |
| WO | WO 02/061053 | 8/2002 |
| WO | WO 03/043674 | 5/2003 |
| WO | WO 2007/035843 | 3/2007 |
| WO | WO 2008/045498 | 4/2008 |
| WO | WO 2008/153970 | 12/2008 |
| WO | WO 2010/057013 | 5/2010 |
| WO | WO 2010/057015 | 5/2010 |

OTHER PUBLICATIONS

Ben-Ze'ev et al. "Cell-cell and cell-matrix interactions differently regulate the expression of hepatic and cytoskeletal genes in primary cultures of rat hepatocytes", PNAS vol. 85, 2161-2165 Apr. 1998.
Brenner "Nephron adaptation to renal injury or ablation", Am. J. Physiol. 249: F324-F337 (1985).
Brown et al "Characterization of human tubular cell monolayers as a model of proximal tubular xenobiotic handling" Toxicology and applied pharmacology, 233: 428-438 (2008).
Castrop et al "Mediators of tubuloglomerular feedback regulation of glomerular filtration: ATP and adenosine" Act Phsiol. 189:3-14 (2007).
Chade et al. "Endothelial progenitor cells restore renal function in chronic experimental renovascular disease" Circulation, 119 pp. 547-557 (2009).
Daley et al. "Realistic prospects for stem cell therapeuies", Ficmatol:398-418 (2003).
Donnelly S. "New insights into renal anemia.", Canadian J of Diabetes, 2003; 27(2): 176-181.
Ding et al. "The bioartificial kidney and bioengineered membranes in acute kidney injury" Nephron Experimental Nephrology 109: e118-e122 (2008).
Eliopoulos et al "Erythropoietin delivery by genetically engineered bone marrow stromal cells for correction of anemia in mice with chronic renal failure" J. Am. Soc. Nephrol. 17:1576-1584 (2006).
Fisher et al., "Erythropoietin: physiology and pharmacology update", Experimental Biology and Medicine, 2003; 228: 1-14.
Fontaine et al. "Transplantation of genetically altered hepatocytes using cell-polymer constructs" Transplatation Proceedings, vol. 25, No. 1, 1002-4 Feb. 1993.
Genestie, I. et al., "Polarity and Transport Properties of Rabbit Kidney Proximal Tubule Cells on Collagen IV-coated Porous Membranes," (Abst) Am. J. Physiol.,269(1):pt, 2, f22-30 (Jul. 1995).
Guo et al. "Cellular maintenance and repair of the kidney" Annu. Rev. Physiol. 72: 357-376 (2010).
Hammerman et al "Growing kidneys" Current opinion nephrology and hypertension, 10:13-17 (2001).
Held et al. "In vivo genetic selection of renal proximal tubules" Molecular Therapy vol. 13, No. 1 pp. 49-58 (2006).
Hopkins et al. "Stem cell options for kidney disease", J. of Pathology, 217: 265-281 (2009).
Humes et al. "Initial clinical results of the bioartificial kidney containing human cells in ICU patients with acute renal failure", Kidney International, vol. 66, pp. 1578-1588 (2004).
Humes et al. "Replacement of renal function in uremic animals with a tissue-engineered kidney", Nature, vol. 17, pp. 451-455 (1999).
Humphreys et al "Mesenchymal stem cells in acute kidney injury" vol. 59: 311-325 (2008).
Jarad et al. "Update on the glomerular filtration barrier", Curr. Opin. Nephrol Hypertens, 15:226-232 (2009).
Joraku et al "In vitro generation of three-dimensional renal structures" Methods vol. 47: 129-133 (2009).
Kaufman et al "Compensatory adaptation of structure and function following progressive renal ablation" Kidney International vol. 6 pp. 10-17 (1974).
Kim et al "Kidney tissue reconstruction by fetal kidney cell transplantation: Effect of gestation stage of fetal kidney cells" Stem cells 25: 1393-1401 (2007).
Kucic et al. "Mesenchymal stromal cells genetically engineered to overexpress IGF-I enhance cell-based gene therapy of renal failure-induced anemia" Am. J. Physiol. Renal Physiol. 295: F488-F496 (2008).
Krantz SB. Erythropoietin. Blood, Feb. 1, 1991; 77(3): 419-434.
Kreisberg et al. "Separation of proximal tubule cells from suspensions of Rat Kidney cells in density gradients of ficoll in tissue culture medium" Am J. Pathol. 86: 591-602 (1977).
Kurtz A et al. "Renal mesangial cell cultures as a model for study of erythropoietin production", Proc. Natl. Acad. Sci. USA, Jul. 1983; 80: 4008-4011.
Lin et al. "Intrarenal cells, not bone marrow-derived cells, are the major source for regeneration in postischemic kidney", The Journal of Clinical Investigation, vol. 115, No. 7, pp. 1756-1764, (2005).
Marshall et al. "Increasing renal mass improves survival in anephric rats following metanephros tranplantation" Experimental Physiology 92.1: 263-271 (2007).
Nangaku M. "Chronic hypoxia and tubulointerstitial injury: a final common pathway to end-stage renal failure" J Am Soc Nephrol, 2006; 17: 17-25.
Newsome "Yet another role for mesenchmyal stem cells" Transplantation, vol. 85 No. 11, pp. 1548-1549 (2008).
Ormrod et al. "Experimental uremia: description of a model producing varying degrees of stable uremia" Nephron 26: 249-254 (1980).
Patschan et al. "Therapeutic use of stern and endothelial progenitor cells in acute renal injury: ca ira" Current Opinion in Pharmacology, 6: 176-183 (2006).
Platt et al. "Experimental renal failure" Department of Medicine, University of Manchester, pp. 217-231 (1952).
Plotkin et al. "Mesenchymal cells from adult kidney support angiogenesis and differentiate into multiple interstitial cell types including crythropoictinproducing fibroblasts." Am J Physiol Renal Physiol, Apr. 18, 2006; 291: F902-F912.
Powe et al. "Public health surveillance of CKD: Principles, Steps and challenges" Am J. Kidney Diseases, vol. 53, No. 3, Supp. 3, S37-S45 (2009).
Prodromidi et al. "Bone marrow-derived cells contribute to podocyte regeneration and melioration of renal disease in a mouse model of Alport syndrome", Stem Cells, 24:2448-2455 (2006).
Rinsch et al. "Delivery of erythropoietin by encapsulated myoblasts in a genetic model of severe anemia", Kidney Intl, 2002; 62: 1395-1401.
Rossert et al. "Anemia management and the delay of chronic renal failure progression", J Am Soc Nephrol, 2003; 14: S173-S177.
Satchell et al. "Conditionally immortalized human glomerular endothelial cells expressing fenestrations in response to VEGF", Kidney International, 69: 1633-1640, (2006).
Sugimoto et al. "Bone-marrowed-derived stem cells repair basement membrane collagen defects and reverse genetic kidney disease", PNAS, vol. 103, No. 19, pp. 7321-7326 (2006).
Yokoo et al. "Generation of a transplantable erythropoietin-producer derived from human mesenchymal stem cells" Transplantation, 85: 1654-1658 (2008).
Yokoo et al. "Xenobiotic kidney organogenesis from human mesenchymal stem cells using a growing rodent embryo", J. Am. Soc. Nephrol. 17: 1026-1034 (2006).
Kelley, R. et al. "Tubular cell-enriched subpopulation of primary renal cells improves survival and augments kidney function in rodent model chronic kidney disease", Am J. Physiol Renal Physiol. 299(5):F1026-F1039, Nov. 2010.
Presnell, S. et al. "Isolation, characterization, and expansion methods for defined primary renal cell populations from rodent, canine, and human normal and diseased kidneys", Tissue Engineering, Part C vol. 17(3):261-273, Mar. 2011.

* cited by examiner

*8700 OPLA 50_50 perfused 101X.jpg*

*8701 OPLA 50_50 perfused 424X.jpg*

*8702 OPLA 50_50 Static 101X.jpg*

*8703 OPLA 50_50 Static 424X.jpg*

*8705 Col I 50_50 perfused 101X.jpg*

*HK01p0 Collagen I 50_50 perfused 424X.jpg*

*HK01p0 Collagen I 50_50 Static 101X.jpg*

*HK01p0 Collagen I 50_50 Static 424X.jpg*

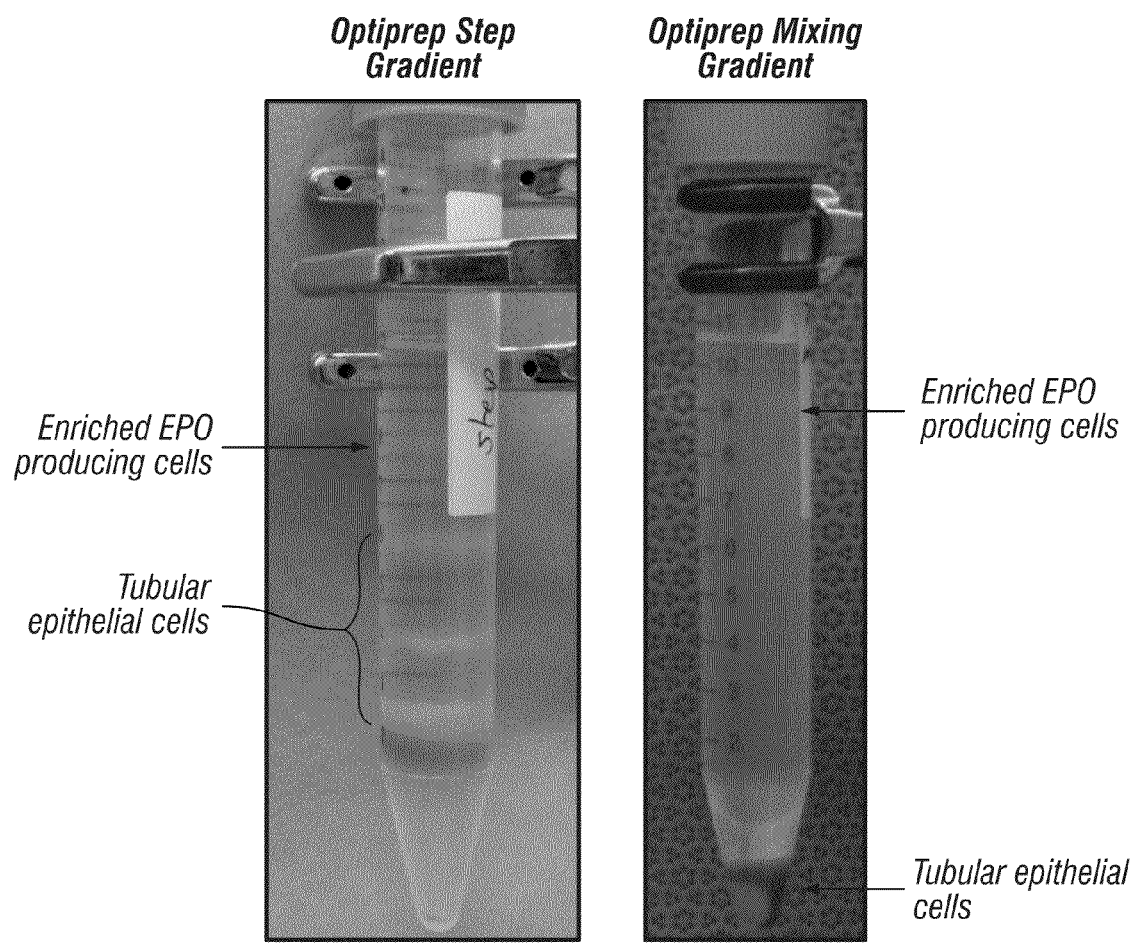
*FIG. 48A*  *FIG. 48B*

| Gene | B2 | B4 | Fold Enrichment |
|---|---|---|---|
| CYP2R1 | 0.73 | 0.17 | 4.27 (B2) |
| Cubilin | 16.51 | 5.49 | 3.01 (B2) |
| E-cadherin | 21.21 | 12.82 | 1.65 (B2) |
| Kdr | 0.41 | 6.47 | 15.89 (B4) |
| Nephrin | 0.88 | 207.34 | 236.69 (B4) |
| Podocin | 3.83 | 659.17 | 172.15 (B4) |
| Hif2a | 0.28 | 1.64 | 5.78 (B4) |
| Epo | 1.09 | 3.81 | 3.51 (B4) |
*FIG. 74I*
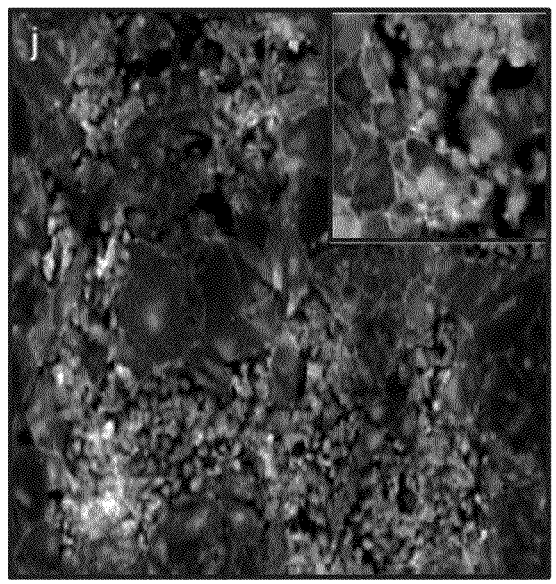
*FIG. 74J*
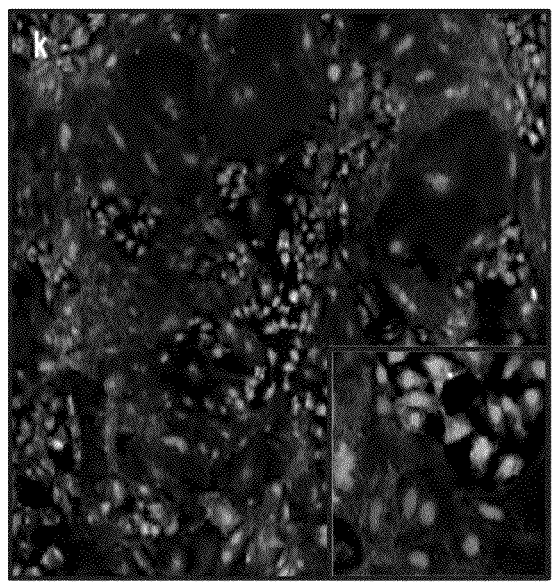
*FIG. 74K*

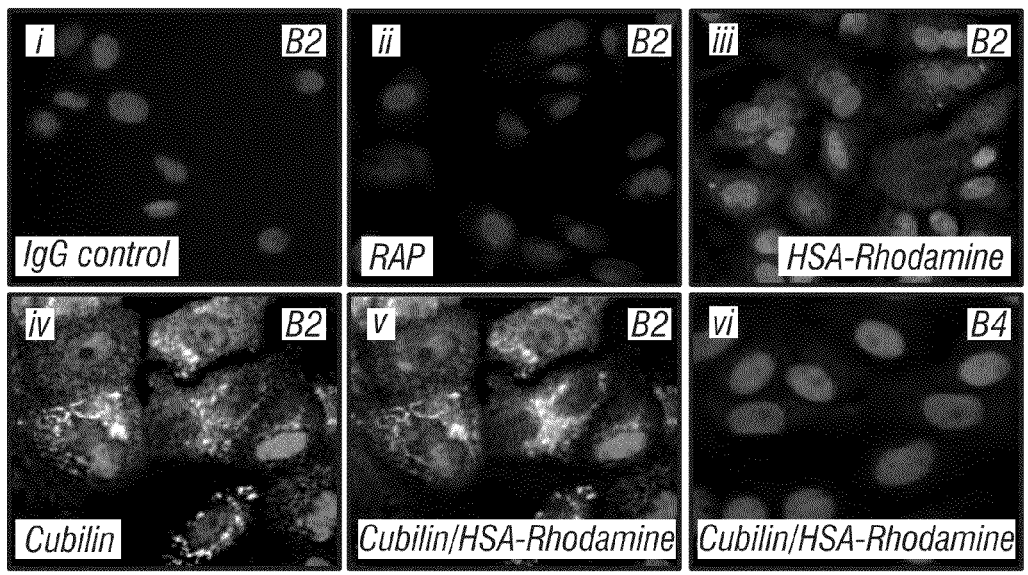
FIG. 75A
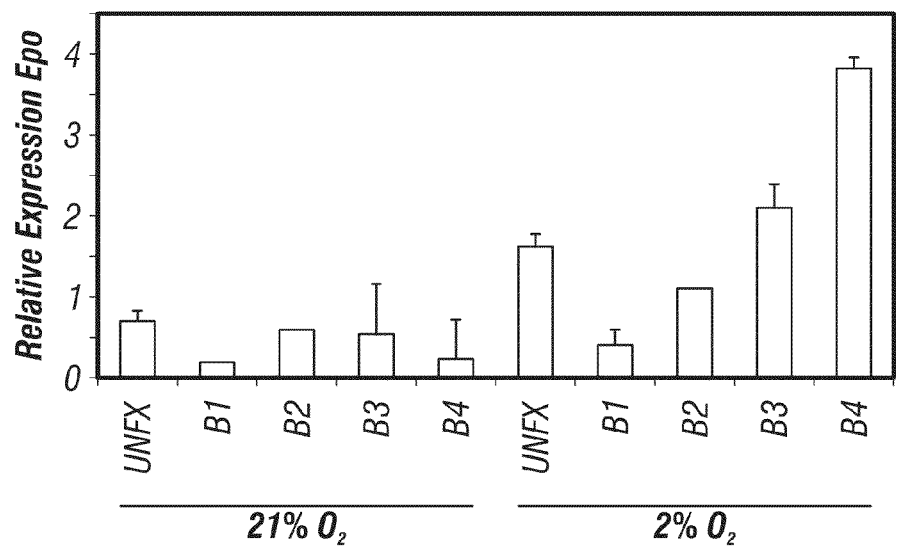
FIG. 75B
| Sample | Epo Expression | | |
|---|---|---|---|
| | 21% O$_2$ | 2% O$_2$ | Fold at 2% O$_2$ |
| UNFX | 0.685 | 1.612 | 2.35 |
| B1 | 0.196 | 0.403 | 2.1 |
| B2 | 0.601 | 1.086 | 1.8 |
| B3 | 0.526 | 2.102 | 4.0 |
| B4 | 0.242 | 3.812 | 15.8 |
FIG. 75C

| Clinical Value as % Healthy control (12-14 Wks Post-Tx) | Sham | Nx | Vehicle | UNFX | B4 | B2 | 100IU/KG rEpo |
|---|---|---|---|---|---|---|---|
| SERUM ALBUMIN | 1.00+/-0.01 | 0.69+/-0.01 | 0.73+/-0.05 | 0.63+/-0.02 | 0.71+/-0.021 | 0.80+/-0.02 | 0.73+/-0.03 |
| A:G RATIO | 0.99+/-0.02 | 0.66+/-0.01 | 0.77+/-0.05 | 0.62+/-0.05 | 0.74+/-0.04 | 0.87+/-0.05 | 0.77+/-0.06 |
| SERUM PHOSPHOROUS | 1.07+/-0.03 | 1.09+/-0.05 | 1.19+/-0.12 | 1.36+/-0.28 | 1.12+/-0.08 | 1.02+/-0.02 | 1.14+/-0.09 |
| SERUM CALCIUM | 1.00+/-0.03 | 1.01+/-0.08 | 0.72+/-0.13 | 0.97+/-0.15 | 1.07+/-0.03 | 1.02+/-0.00 | 1.04+/-0.03 |
| PHOS:CALCIUM RATIO | 0.52+/-0.03 | 0.59+/-0.08 | 0.81+/-0.09 | 0.72+/-0.13 | 0.50+/-0.025 | 0.48+/-0.02 | 0.50+/-0.07 |
| SERUM POTASSIUM | 0.98+/-0.07 | 1.04+/-0.03 | 1.15+/-0.03 | 1.03+/-0.03 | 1.10+/-0.05 | 0.97+/-0.04 | 1.08+/-0.04 |
| SERUM CREATININE | 0.96+/-0.07 | 3.78+/-0.24 | 2.84+/-1.02 | 2.80+/-0.23 | 2.99+/-0.48 | 1.78+/-0.20 | 3.13+/-0.70 |
| BUN | 0.94+/-0.04 | 3.08+/-0.18 | 2.49+/-0.38 | 2.07+/-0.30 | 2.51+/-0.26 | 1.92+/-0.31 | 2.56+/-0.36 |
| CHOLESTEROL | 1.11+/-0.03 | 2.47+/-0.09 | 1.67+/-0.10 | 2.07+/-0.3 | 1.96+/-0.28 | 1.57+/-0.08 | 1.85+/-0.79 |
| TRIGLYCERIDES | 1.20+/-0.09 | 1.97+/-0.19 | 1.02+/-0.21 | 1.69+/-0.63 | 1.44+/-0.09 | 0.95+/-0.18 | 1.76+/-0.42 |
| HEMOGLOBIN | 1.00+/-0.03 | 0.90+/-0.01 | 0.89+/-0.02 | 0.87+/-0.04 | 0.93+/-0.03 | 0.94+/-0.04 | 0.79+/-0.23 |
| HEMATOCRIT | 1.01+/-0.01 | 0.88+/-0.01 | 0.91+/-0.02 | 0.90+/-0.03 | 0.96+/-0.01 | 0.96+/-0.02 | 0.94+/-0.19 |
| RBC # | 1.01+/-0.02 | 0.90+/-0.01 | 0.93+/-0.06 | 0.92+/-0.03 | 0.96+/-0.02 | 0.96+/-0.01 | 0.90+/-0.19 |

*FIG. 78A*

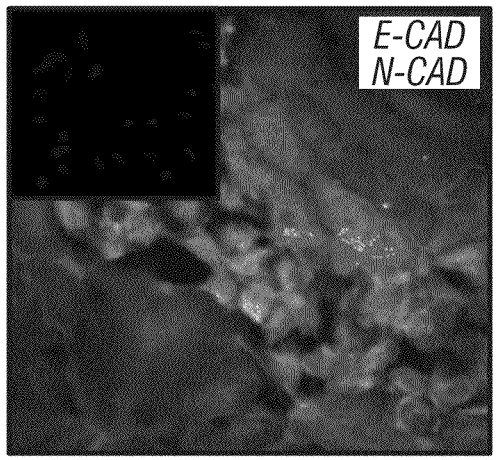
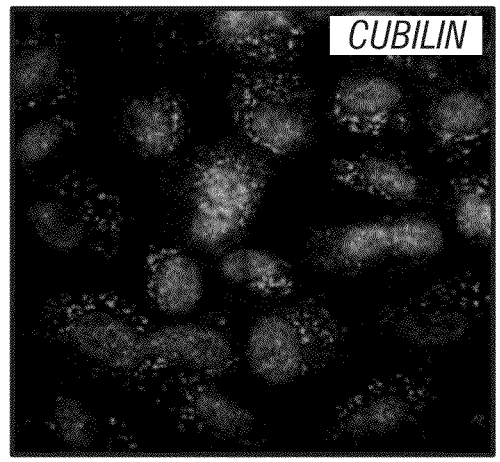
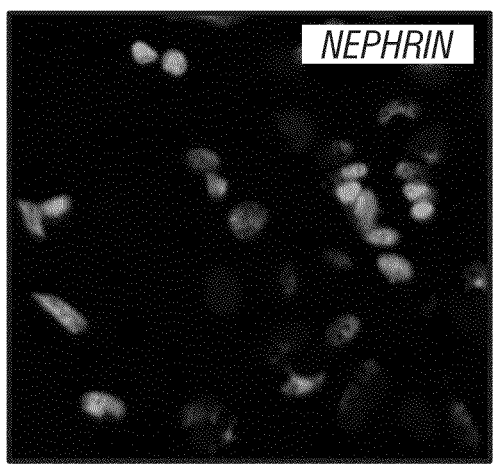
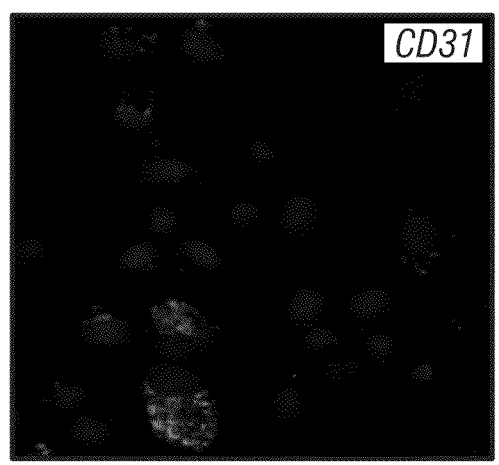
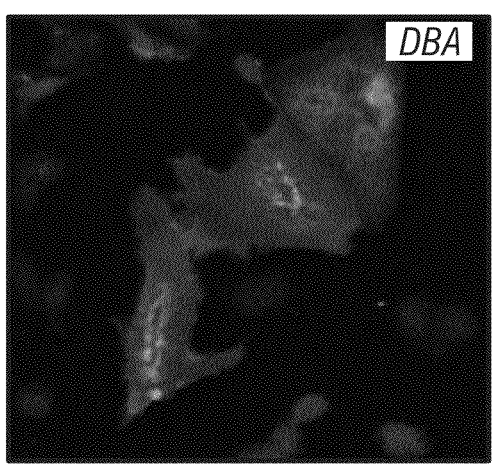
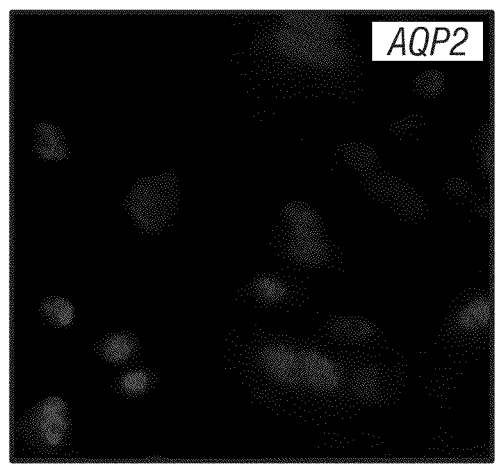
*FIG. 119*

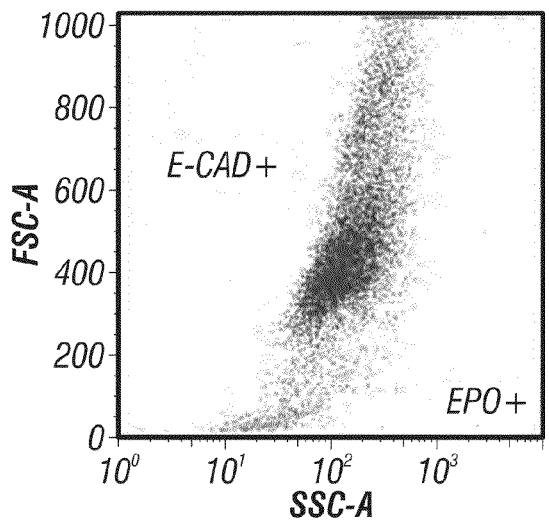
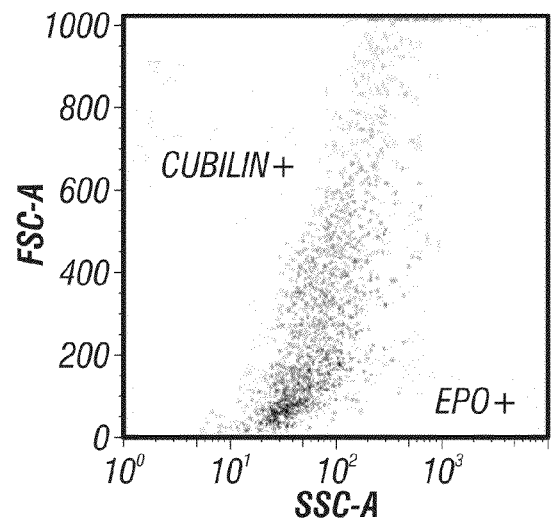
FIG. 120A   FIG. 120B
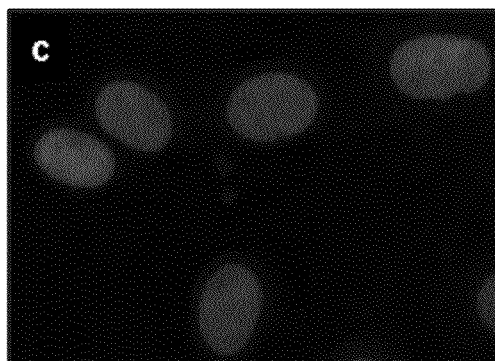
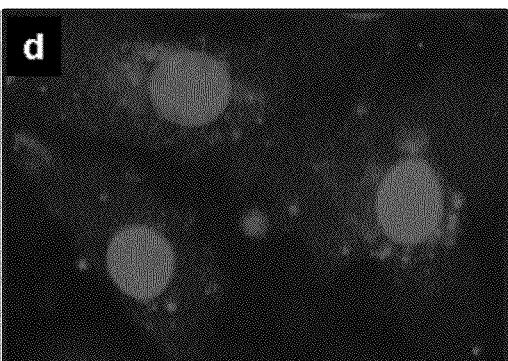
FIG. 120C   FIG. 120D
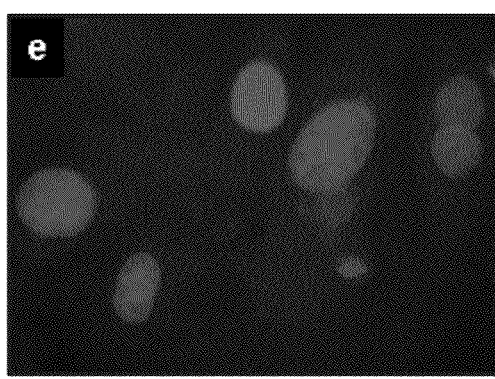
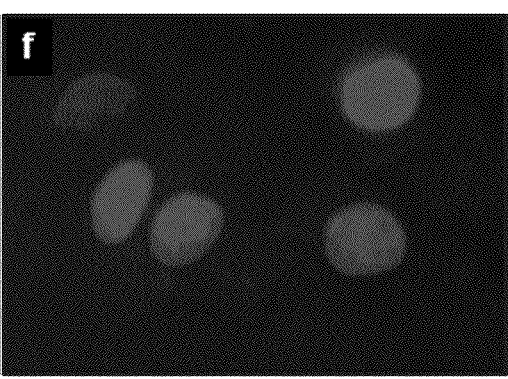
FIG. 120E   FIG. 120F

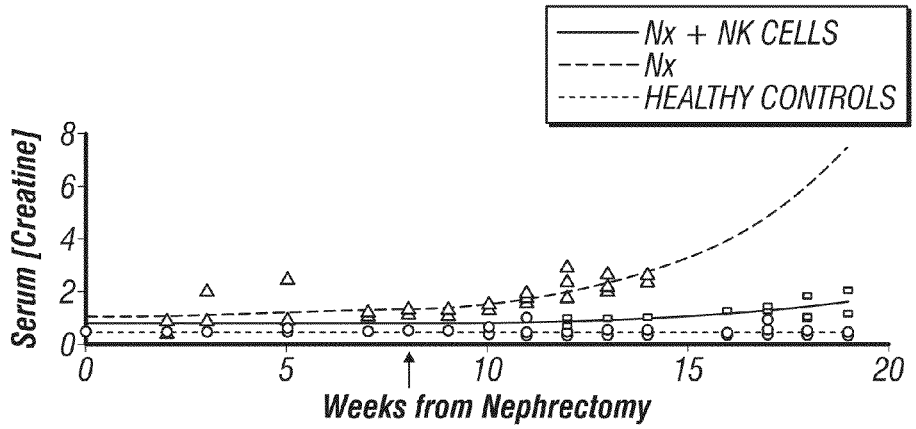
FIG. 121A
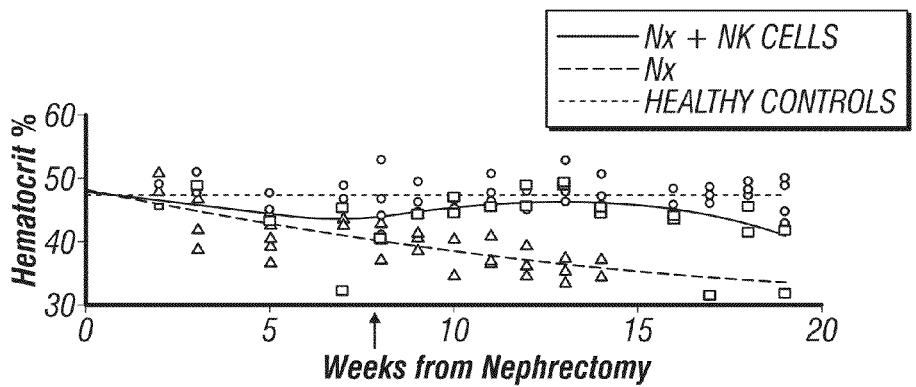
FIG. 121B
| Assessment | Pre-Treatment | | Post-Treatment | | |
|---|---|---|---|---|---|
| | Sham Nx | Nx | Sham Nx | Nx | Nx + NK CELLS |
| HCT | 45.4±2.3 | 40.0±2.5 | 45.6±1.3 | 36.9±2.3 | 47.0±2.3* |
| RBC# | 8.3±0.3 | 7.6±0.5 | 8.1±0.2 | 6.7±0.4 | 8.4±0.1* |
| BUN | 23.5±2.1 | 47.0±4.0 | 20.5±1.0 | 86.0±12.2 | 43.5±3.5* |
| sCREAT | 0.5±0.1 | 0.8±0.0 | 0.4±0.0 | 2.3±0.3 | 0.9±0.0* |
| HB | nd | nd | 13.8±0.3 | 5.9±6.4 | 11.2±2.2 |
| sALB (g/dL) | nd | nd | 3.8±0.2 | 2.4±0.1 | 2.8±0.3* |
| sTPRO (g/dL) | nd | nd | 6.8±0.4 | 5.0±0.6 | 5.9±0.1* |
| sPHOS | nd | nd | 6.8±0.7 | 10.0±1.8 | 6.4±0.5* |
| Survival (3-month) | | | 100% | 0% | 100% |
FIG. 121C

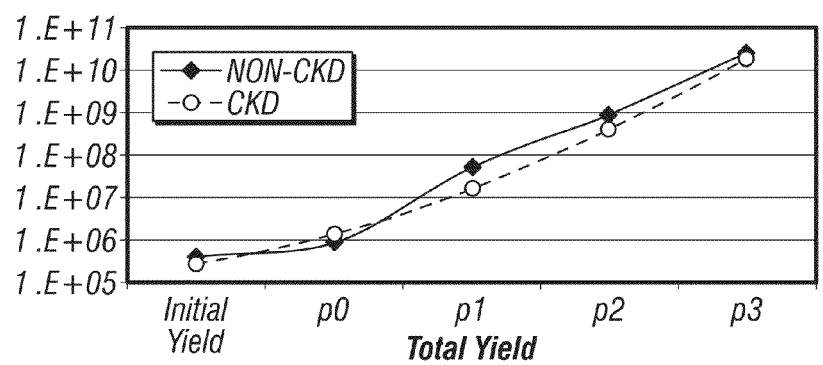
FIG. 124A
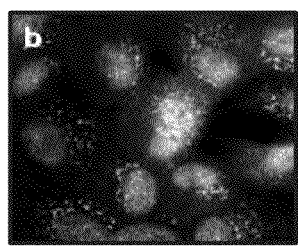 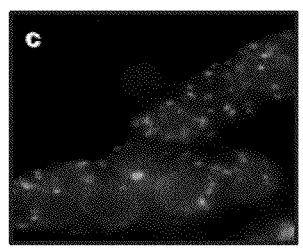 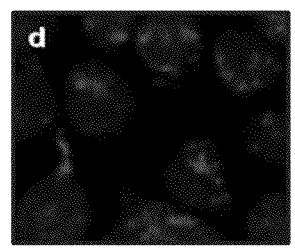
FIG. 124B　　　　FIG. 124C　　　　FIG. 124D

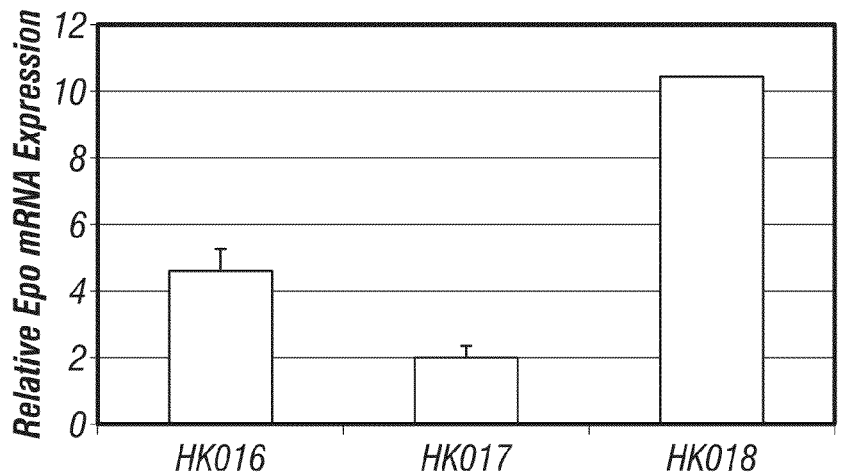
FIG. 125A
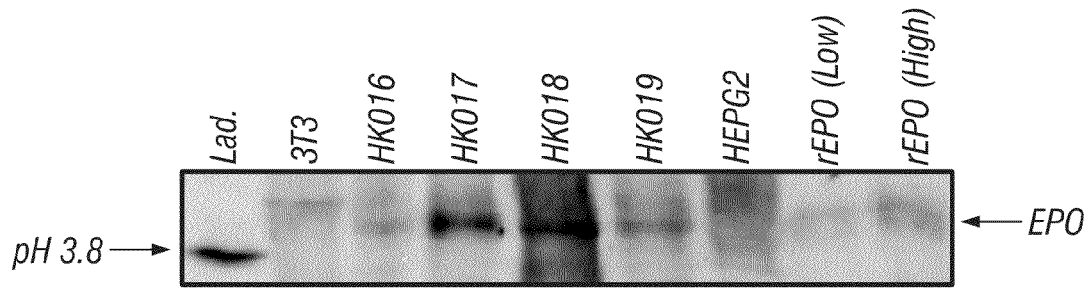
FIG. 125B
| SAMPLE | EPO EXPRESSION | | |
|---|---|---|---|
| | 21% O2 | 2% O2 | Fold Increase |
| PK001 | 0.363 | 2.427 | 6.7 |
| PK002 | 0.21 | 2.32 | 11.0 |
| HK016 | 0.162 | 0.702 | 4.3 |
| HK017 | 0.249 | 0.769 | 3.1 |
| HK018 | 0.271 | 0.464 | 1.7 |
| HK019 | nd | 1.467 | >1.5 |
| HK020 | 0.065 | 0.208 | 3.2 |
| RK | 0.685 | 1.612 | 2.4 |
FIG. 125C

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 1
aagcgcccca tgaatgc                                                  17

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 2
agccaacttg cgcctctct                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 3
tttatggtgt ggtcccgtg                                                19
```

ISOLATED RENAL CELLS AND USES THEREOF

RELATED APPLICATIONS

This application is a divisional of, and claims the benefit under 35 U.S.C. §120 of U.S. application Ser. No. 12/617,721, filed Nov. 12, 2009, which claims priority under 35 U.S.C. §119(e) to U.S. provisional application Nos. 61/114,025, filed Nov. 12, 2008, 61/114,030, filed Nov. 12, 2008, 61/201,056, filed Dec. 5, 2008, 61/201,305, filed Dec. 8, 2008, and 61/121,311, filed Dec. 10, 2008, the entire contents of which are incorporated herein by reference. The subject matter of the present application is related to U.S. Provisional Application No. 61/260,833 filed on Nov. 12, 2009, the disclosure of which is incorporated herein by reference.

FIELD OF THE INVENTION

The invention is directed to isolated renal cells, including tubular and erythropoietin (EPO)-producing kidney cell populations, and methods of isolating and culturing the same, as well as methods of treating a subject in need with the cell populations.

BACKGROUND OF THE INVENTION

Chronic Kidney Disease (CKD) affects over 19M people in the United States and is frequently a consequence of metabolic disorders involving obesity, diabetes, and hypertension. Examination of the data reveals that the rate of increase is due to the development of renal failure secondary to hypertension and non-insulin dependent diabetes mellitus (NIDDM) (United States Renal Data System: Costs of CKD and ESRD. ed. Bethesda, Md., National Institutes of Health, National Institute of Diabetes and Digestive and Kidney Diseases, 2007 pp 223-238)—two diseases that are also on the rise worldwide. Obesity, hypertension, and poor glycemic control have all been shown to be independent risk factors for kidney damage, causing glomerular and tubular lesions and leading to proteinuria and other systemically-detectable alterations in renal filtration function (Aboushwareb, et al., World J Urol, 26: 295-300, 2008; Amann, K. et al., Nephrol Dial Transplant, 13: 1958-66, 1998). CKD patients in stages 1-3 of progression are managed by lifestyle changes and pharmacological interventions aimed at controlling the underlying disease state(s), while patients in stages 4-5 are managed by dialysis and a drug regimen that typically includes anti-hypertensive agents, erythropoiesis stimulating agents (ESAs), iron and vitamin D supplementation. According to the United States Renal Data Service (USRDS), the average end-stage renal disease (ESRD) patient expends>$600 per month on injectable erythropoiesis-stimulating agents (ESAs), Vitamin D supplements, and iron supplements (United States Renal Data System: Costs of CKD and ESRD. ed. Bethesda, Md., National Institutes of Health, National Institute of Diabetes and Digestive and Kidney Diseases, 2007 pp 223-238). When paired with the annual average cost of dialysis ($65,405), the healthcare cost for maintenance of a single patient rises to >$72,000/yr (United States Renal Data System: Costs of CKD and ESRD. ed. Bethesda, Md., National Institutes of Health, National Institute of Diabetes and Digestive and Kidney Diseases, 2007 pp 223-238)—a number that reflects only standard procedural costs and does not include treatment of other complications, emergency procedures, or ancillary procedures such as the placement of vascular grafts for dialysis access. Combined medicare costs for CKD and ESRD in 2005 totaled $62B—representing 19% of all medicare spending for that year (United States Renal Data System: Costs of CKD and ESRD. ed. Bethesda, Md., National Institutes of Health, National Institute of Diabetes and Digestive and Kidney Diseases, 2007 pp 223-238). Kidney transplantation is an effective option for stage 4-5 patients as a pre-emptive measure to avoid dialysis or when dialysis is no longer sufficient to manage the disease state, but the number of stage 5 CKD patients in the US (>400,000) who could benefit from whole kidney transplant far exceeds the number of suitable donor kidneys available in any given year (~16,000) (Powe, N R et al., Am J Kidney Dis, 53: S37-45, 2009). Thus, new treatment paradigms are needed to delay or reduce dependency on dialysis and to fill the void left by the shortage of donor kidneys.

Progressive renal disease results from a combination of the initial disease injury (e.g, hypertension), followed by a maladaptive renal response to that injury. Such a response includes the production of pro-inflammatory and pro-fibrotic cytokines and growth factors. Therefore, one strategy to slow CKD progression is to ameliorate the inflammatory and fibrotic response as well as mitigate or reverse renal degeneration through the repair and/or regeneration of renal tissue.

Chronic renal failure is prevalent in humans as well as some domesticated animals. Patients with renal failure experience not only the loss of kidney function (uremia), but also develop anemia due to the inability of the bone marrow to produce a sufficient number of red blood cells (RBCs) via erythropoiesis. Erythroid homeostasis is dependent on both the production of erythropoietin (EPO) by specialized interstitial fibroblasts that reside in the kidney and the ability of targeted erythroid progenitors in the bone marrow to respond to EPO and manufacture more RBCs. The anemia of renal failure is due to both reduced production of EPO in the kidney and the negative effects of uremic factors on the actions of EPO in the bone marrow.

To date, clinical approaches to the treatment of chronic renal failure involve dialysis and kidney transplantation for restoration of renal filtration and urine production, and the systemic delivery of recombinant EPO or EPO analogs to restore erythroid mass. Dialysis offers survival benefit to patients in mid-to-late stage renal failure, but causes significant quality-of-life issues. Kidney transplant is a highly desired (and often the only) option for patients in the later stages of renal failure, but the supply of high-quality donor kidneys does not meet the demand for the renal failure population. Bolus dosing with recombinant EPO to treat anemia has now been associated with serious downstream health risks, leading to black box warnings from the FDA for the drug, and necessitating further investigation into alternative treatments to restore erythroid homeostasis in this population. Preclinical investigations have examined in vivo efficacy and safety of EPO-producing cells that have been generated via gene therapy approaches. These studies have shown that it is possible to transiently stimulate erythropoiesis and RBC number by in vivo delivery of epo-producing cells. However, to date, none of these approaches have offered regulated erythroid homeostasis or long-term in vivo functionality. Consequently, HCT and RBC number are often increased beyond normal values, leading to polycythemia vera and other complications. Delivery of EPO-producing cells that are therapeutically-relevant and provide advantages over delivery of recombinant EPO must not only increase HCT, but should restore erythroid homeostasis, with both positive and negative regulatory mechanisms intact. It is important to note that EPO-deficient anemias, while prevalent in patients with kidney disease, can also develop as a result of other disease states, including heart failure, multi-organ system failure, and other chronic diseases.

The kidney is a unique organ comprised of many different specialized cell types (>10), all of which originate developmentally from the intermediate mesoderm but at maturity form morphologically and functionally distinct compartments, and anatomical units that act in concert to provide filtration of the blood, production of urine, regulation of acid-base and electrolyte balance, and regulated endocrine functions such as the production of erythropoietin (Epo), Vitamin D, renin, and angiotensin. The cellular compartments of the kidney are heavily interdependent for homeostatic function, as highlighted by the following examples. Cells of the afferent arterioles act in concert with specialized tubular cells in the thick ascending limb of the loop of Henle (Macula Densa) to regulate blood flow through the glomerulus (Castrop, H. Acta Physiol (Oxf), 189: 3-14, 2007). Protein handling by the kidney is orchestrated by the fenestrated endothelial cells, podocytes, and basement membrane of the glomerulus paired with the receptor-mediated endocytosis and resorption of protein from the glomerular filtrate by specialized proximal tubular cells (Jarad, G & Miner, J H. Curr Opin Nephrol Hypertens, 18: 226-32, 2009). Production of active vitamin D by tubular cells regulates homeostasis of interstitial cells through direct and indirect mechanisms that control extracellular matrix deposition, conversion of interstitial cells to myofibroblasts, and epithelial-mesenchymal transformation (Tan, X, et al. J Steroid Biochem Mol Biol, 103: 491-6, 2007). Regardless of the specific example, all cell-cell interactions in the kidney are at least partially dependent on spatial and architectural relationships. At the cellular level, progression of CKD may involve loss of a particular cell type or loss of function of one or more cell types due to cellular insufficiencies or loss of homeostatic cell-cell interactions. Thus, successful regenerative approaches to the treatment of CKD must re-establish homeostasis in part through restoration of cellular organization and intercellular communication.

Augmentation of specific kidney functions, such as tubular transport or production of Epo, has been contemplated with the intention of reducing the morbidity and mortality associated with progression of CKD. The majority of cell-based treatment approaches for kidney disease have focused on therapeutic intervention of acute renal failure (ARF) with stem or progenitor cell types (Hopkins, C, et al. J Pathol, 217: 265-81, 2009). There have been many preclinical studies involving the delivery of various cell types immediately before or after induction of ARF, including intrarenal or systemic delivery of MSCs (Humphreys B D & Bonventre J V, Annu Rev Med 2008, 59:311-325), endothelial progenitors (EPCs) (Chade A R, et al., Circulation 2009, 119:547-557, Patschan D, et al., Curr Opin Pharmacol 2006, 6:176-183), and fetal cells or tissue rudiments (Hammerman M R, Curr Opin Nephrol Hypertens 2001, 10:13-17; Kim S S, et al, Stem Cells 2007, 25:1393-1401; Marshall D, et al., Exp Physiol 2007, 92:263-271; Yokoo T, et al., J Am Soc Nephrol 2006, 17:1026-1034). An extracorporeal hollow-fiber filtration device containing renal tubular cells was tested as an adjunct to traditional dialysis for the treatment of ARF in humans (Ding, F & Humes, H D. Nephron Exp Nephrol, 109: e118-22, 2008, Humes, H D, et al. Kidney Int, 66: 1578-88, 2004, Humes, H D, et al. Nat Biotechnol, 17: 451-5, 1999). Transplantation of mesenchymal stem cells via the renal artery is also being tested clinically in a population of patients at high risk for an ARF episode secondary to cardiovascular surgical procedures (Westenfelder, C. Experimental Biology. New Orleans, La., 2009). Limited preclinical studies have been conducted that address cell-based therapeutic intervention of CKD (Chade, A R, et al. Circulation, 119: 547-57, 2009, Eliopoulos, N, et al. J Am Soc Nephrol, 17: 1576-84, 2006, Kucic, T, et al. Am J Physiol Renal Physiol, 295: F488-96, 2008). The combination of fetal kidney rudiments+/−mesenchymal stem cells has been investigated in rodents (Yokoo, T, et al. Transplantation, 85: 1654-8, 2008, Yokoo, T, et al. J Am Soc Nephrol, 17: 1026-34, 2006), where it is clear that whole fetal kidney tissue transplanted to an appropriate environment, such as the omentum, can develop into kidney structures with limited function. However, the therapeutic role of the MSCs as a component of the fetal tissue rudiment is unclear, and sourcing of human fetal kidney tissue for therapeutic purposes poses many operational and ethical challenges. In other studies, cells derived from healthy donor bone marrow were transplanted into irradiated COL4A3 (−/−) mice, a model of Alport Syndrome with glomerulonephritis, protein loss, and fibrosis, where they partially slowed progression in the model via replacement of leaky glomerular podocytes with healthy cells lacking the collagen gene mutations (Prodromidi, E I, et al. Stem Cells, 24: 2448-55, 2006, Sugimoto, H, et al. Proc Natl Acad Sci USA, 103: 7321-6, 2006). Cell transplantation was credited with stabilization of sCREAT, BUN, and sodium levels, but untreated/kidney-damaged controls were not presented for comparison in the studies24. Chade et al employed a swine model of unilateral renal artery stenosis to examine the effects of autologous EPCs, delivered intrarenally 6 weeks post-injury (Chade A R, et al., Circulation 2009, 119:547-557). The EPCs improved tubulo-interstitial fibrosis somewhat, significantly improved glomerulosclerosis, and improved renal blood flow, although no change in blood pressure was observed with treatment (Chade A R, et al., Circulation 2009, 119:547-557). To date, studies that examined the in vivo efficacy of cell-based therapies for CKD have yielded transient and/or partial effects, and few studies have collected both systemic and histologic evidence of function. The limited number of studies that provide evidence of clinically-relevant benefits after intervention in progressive models of CKD raises questions about the potential of cell-based therapies to restore renal function completely. However, regenerative therapies that stabilize renal function and delay progression can address an unmet medical need within this patient population.

Reproducible in vivo model(s) of progressive CKD are essential for assessment of the therapeutic potential of candidate treatments. While models of ARF are numerous and include a variety of chemical- or ischemia/reperfusion-induced tubular injuries, there are fewer models of CKD that are progressive and terminal without significant intervention. The two-step 5/6 nephrectomy procedure in rats reproducibly generates a terminal and progressive state of renal failure, resulting in systemically- and histologically-detectable disease complete with several key features of CKD, including hypertension, reduced glomerular filtration rate (GFR), elevated serum creatinine (sCREAT) and BUN, glomerular and tubulo-interstitial fibrosis, hyperlipidemia, hyperphosphatemia, and anemia (Kaufman, J M, et al. Kidney Int, 6: 10-7, 197422, Platt, R, et al. Clin Sci (Lond), 11: 217-31, 1952, Ormrod, D & Miller, T. Nephron, 26: 249-54, 1980, Brenner, B M. Am J Physiol, 249: F324-37, 1985). The presence of these clinically-relevant features, combined with technical reproducibility and commercial availability provided the basis for selection of this model for the studies described herein.

Thus, new treatment paradigms are needed that provide substantial and durable augmentation of kidney functions, to slow progression and improve quality of life in this patient population and reduce the annual cost burden on the healthcare system. Regenerative medicine technologies may provide next-generation therapeutic options for CKD.

SUMMARY OF THE INVENTION

In one aspect, the present invention provides an admixture of human renal cells comprising a first cell population, B2, and a second cell population, wherein B2 comprises an isolated, enriched population of tubular cells and wherein the second cell population comprises erythropoietin (EPO)-producing cells, glomerular cells and vascular cells. In some embodiments, the admixture further includes a third cell population. In one embodiment, the B2 cell population further includes collecting duct epithelial cells. In one embodiment, the B2 cell population is hypoxia-resistant. In one embodiment, the B2 cell population is capable of producing and/or stimulating production of a high-molecular weight species of hyaluronic acid (HA) both in vitro and in vivo, via expression of HAS-2 (hyaluronic synthase-2). In another embodiment, the B2 cell population is iodixanol-resistant. In certain embodiments, the B2 cell population has a density between about 1.045 g/mL and about 1.052 g/mL. In further embodiments, the second cell population is a B4 cell population. In one embodiment, the B4 cell population has a density between about 1.063 g/mL and about 1.091 g/mL. In certain other embodiments, the second cell population is a B3 cell population. In one embodiment, the B3 cell population has a density of between about 1.052 g/ml and about 1.063 g/ml. In still further embodiments, the admixture includes both B2 and B3 cell populations.

In further embodiments, the admixture is depleted of inactive or undesired components. In one embodiment, the admixture does not include or is depleted of a B1 cell population. In one embodiment, the B1 cell population includes large granular cells of the collecting duct and tubular system having a density of <~1.045 g/ml. In certain other embodiments, the admixture does not include or is depleted of a B5 cell population. In one embodiment, the admixture does not include a B5 cell population comprising debris and small cells of low granularity and viability with a density>~1.091 g/ml.

In certain embodiments, the admixture(s) of cells provide stabilization and/or improvement and/or regeneration of kidney function. In one embodiment, the admixture is capable of receptor-mediated albumin uptake. In other embodiments, the admixture of cells is capable of oxygen-tunable erythropoietin (EPO) expression. In yet other embodiments, the admixture contains HAS-2-expressing cells capable of producing and/or stimulating the production of high-molecular weight species of hyaluronic acid (HA) both in vitro and in vivo. In one embodiment, the admixture is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery.

In all embodiments, the first and second cell populations may be derived from kidney tissue or cultured kidney cells. In one embodiment, B2 is characterized by expression of a tubular cell marker selected from the group consisting of megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In another embodiment, B2 is further characterized by expression of collecting duct marker Aquaporin-4 (Aqp4) marker.

In all embodiments, B4 may be characterized by the expression of a vascular marker selected from the group consisting of PECAM, VEGF, KDR, HIF1α. In certain other embodiments, B4 may be characterized by the expression of a glomerular marker Podocin (Podn) or Nephrin (Neph). In another embodiment, B4 may be characterized as an oxygen-tunable EPO enriched population compared to unfractionated (UNFX), B2 and B3 cell populations. In another embodiment, B4 is characterized by the expression of a marker selected from the group consisting of chemokine (C—X—C motif) receptor 4 (Cxcr4), endothelin receptor type B (Ednrb), collagen, type V, alpha 2 (Col5a2), Cadherin 5 (Cdh5), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo).

In all embodiments, B3 may be characterized by the expression of a marker selected from the group consisting of aquaporin 7 (Aqp7), FXYD domain-containing ion transport regulator 2 (Fxyd2), solute carrier family 17 (sodium phosphate), member 3 (Slc17a3), solute carrier family 3, member 1 (Slc3a1), claudin 2 (Cldn2), napsin A aspartic peptidase (Napsa), solute carrier family 2 (facilitated glucose transporter), member 2 (Slc2a2), alanyl (membrane) aminopeptidase (Anpep), transmembrane protein 27 (Tmem27), acyl-CoA synthetase medium-chain family member 2 (Acsm2), glutathione peroxidase 3 (Gpx3), fructose-1,6-biphosphatase 1 (Fbp1), and alanine-glyoxylate aminotransferase 2 (Agxt2). In certain other embodiments, B3 is characterized by the vascular expression marker Platelet endothelial cell adhesion molecule (Pecam) and the glomerular expression marker podocin (Podn).

In one aspect, the present invention provides an admixture of human renal cells comprising a first cell population, B2, and a second cell population, wherein B2 comprises an isolated, enriched population of tubular cells and wherein the second cell population comprises one or more cell populations which express the vascular expression marker Platelet endothelial cell adhesion molecule (Pecam) and the glomerular expression marker podocin (Podn).

In another aspect, the invention provides an isolated, enriched population of human renal cells comprising a B2 cell population, wherein B2 comprises an isolated, enriched population of tubular cells. In one embodiment, the B2 cell population is capable of producing and/or stimulating production of a high-molecular weight species of hyaluronic acid (HA) both in vitro and in vivo, via expression of HAS-2 (hyaluronic synthase-2). In certain embodiments, the B2 cell population does not include a B1 cell population comprising large granular cells of the collecting duct and tubular system having a density of <~1.045 g/ml. In another embodiment, the B2 cell population does not include the B3 cell population comprising erythropoietin (EPO)-producing cells, glomerular cells and vascular cells having a density of between about 1.052 g/ml and about 1.063 g/ml. In yet another embodiment, the B2 cell population does not include the B4 cell population having a density between about 1.063 g/mL and about 1.091 g/mL. In still another embodiment, the B2 cell population does not include a B5 cell population comprising debris and small cells of low granularity and viability with a density>~1.091 g/ml.

In another aspect, the instant invention provides a method of preparing a human B2 cell population, comprising a) exposing a cell suspension comprising a non-enriched, heterogeneous kidney cell population to hypoxic culture conditions; and b) extracting a first cell fraction comprising the B2 cell population. In one embodiment, the B2 cell population obtained by the methods of the invention comprises a greater proportion of tubular cells, and lesser proportions of EPO producing cells, glomerular cells and vascular cells when compared to the non-enriched cell population. In another embodiment, the method further includes a step between step a) and step b), comprising contacting the cell suspension with a density gradient to separate one or more cell fractions, wherein the first cell fraction is present in the gradient after centrifugation at a specific density between about 1.045 g/mL and about 1.052 g/mL.

In still another aspect, the instant invention provides a method of preparing a human B4 cell population, comprising a) exposing a cell suspension comprising a non-enriched, heterogeneous kidney cell population to hypoxic culture conditions; and b) extracting a first cell fraction comprising the B4 cell population. In one embodiment, the B4 cell population obtained by the methods of the invention comprises a greater proportion of EPO-producing cells, vascular cells and glomerular cells and a lesser proportion of non-EPO producing cells, non-vascular cells, and non-glomerular cells when compared to the non-enriched cell population. In another embodiment, the method further comprises a step between step a) and step b), comprising contacting the cell suspension with a density gradient to separate one or more cell fractions, wherein the first cell fraction is present in the gradient after centrifugation at a specific density between about 1.063 g/mL and about 1.091 g/mL.

In still another aspect, the instant invention provides a method of preparing a human B3 cell population, comprising a) exposing a cell suspension comprising a non-enriched, heterogeneous kidney cell population to hypoxic culture conditions; and b) extracting a first cell fraction comprising the B3 cell population. In another embodiment, the method further comprises a step between step a) and step b), comprising contacting the cell suspension with a density gradient to separate one or more cell fractions, wherein the first cell fraction is present in the gradient after centrifugation at a specific density between 1.052 g/ml and about 1.063 g/ml.

The instant invention also provides, in another aspect, a method of generating a B2 cell preparation, comprising a) exposing a cell suspension comprising a non-enriched, heterogeneous kidney cell population to hypoxic culture conditions; b) applying the cell suspension to a flow cytometric instrument capable of simultaneous measurement of forward scatter and side scatter in one or more individual cells within the cell population; c) selecting a cell subpopulation from the cell population; d) sorting a cell subpopulation from the cell population; and e) isolating the B2 cell subpopulation from the cell population, wherein the B2 cell subpopulation is characterized by high forward scatter and high side scatter relative to the majority of the population.

In another aspect, the invention provides a method of generating a B4 cell preparation, comprising a) exposing a cell suspension comprising a non-enriched, heterogeneous kidney cell population to hypoxic culture conditions; b) applying the cell suspension to a flow cytometric instrument capable of simultaneous measurement of forward scatter and side scatter in one or more individual cells within the cell population; c) selecting a cell subpopulation from the cell population; d) sorting a cell subpopulation from the cell population; and e) isolating the B4 cell subpopulation from the cell population, wherein the B4 cell subpopulation is characterized by low forward scatter and low side scatter relative to the majority of the population. In all embodiments, the forward scatter corresponds to cell size. In all embodiments, the side scatter corresponds to cell granularity.

In yet another aspect, the invention provides an implantable construct for providing stabilized and/or improved kidney function to a subject in need comprising: a) a biomaterial comprising one or more biocompatible synthetic polymers or naturally-occurring proteins or peptides; and b) an admixture of mammalian renal cells comprising a first cell population, B2, and a second cell population, coated with, deposited on or in, entrapped in, suspended in, embedded in and/or otherwise combined with the biomaterial. In one embodiment, the second cell population coated with, deposited on or in, entrapped in, suspended in, embedded in and/or otherwise combined with the biomaterial is B4. In another embodiment, the second cell population coated with, deposited on or in, entrapped in, suspended in, embedded in and/or otherwise combined with the biomaterial is B3. In yet another embodiment, the admixture coated with, deposited on or in, entrapped in, suspended in, embedded in and/or otherwise combined with the biomaterial further comprises a third cell population. In certain embodiments, the admixture coated with, deposited on or in, entrapped in, suspended in, embedded in and/or otherwise combined with the biomaterial includes both B3 and B4. In all embodiments, the admixture may be derived from mammalian kidney tissue or cultured kidney cells. In one embodiment, the construct includes a biomaterial configured as a three-dimensional (3-D) porous biomaterial suitable for entrapment and/or attachment of the admixture. In another embodiment, the construct includes a biomaterial configured as a liquid or semi-liquid gel suitable for embedding, attaching, suspending, or coating mammalian cells. In yet another embodiment, the construct includes a biomaterial configured comprised of a predominantly high-molecular weight species of hyaluronic acid (HA) in hydrogel form. In another embodiment, the construct includes a biomaterial comprised of a predominantly high-molecular weight species of hyaluronic acid in porous foam form. In still another embodiment, the construct includes a biomaterial comprised of HA molecules ranging in size from 5.1 kDA to >2×10$^6$ kDa. In yet another embodiment, the construct includes a biomaterial comprised of a poly-lactic acid-based foam having pores of between about 50 microns to about 300 microns. In still another embodiment, the construct includes one or more cell populations derived from an autologous kidney sample. In one embodiment, the kidney sample is a kidney biopsy. In a further embodiment, the construct includes one or more cell populations derived from a non-autologous kidney sample. In one embodiment, the construct provides erythroid homeostasis.

In yet another aspect, the invention provides a method of treating a kidney disease in a subject in need, comprising: a) administering to the subject a composition comprising an admixture of mammalian renal cells comprising a first cell population, B2, and a second cell population; and b) determining in a test sample from the subject that the level of a kidney function indicator is different relative to the indicator level in a control, wherein the difference in indicator level is indicative of a reduction in decline, a stabilization, or an improvement of one or more kidney functions in the subject. In certain embodiments, the methods include an admixture of cells comprising a third cell population. In one embodiment, the second cell population is B4 or B3. In another embodiment, the third cell population is B4 or B3. In certain embodiments, the kidney disease to be treated by the methods of the invention is accompanied by an erythropoietin (EPO) deficiency. In certain embodiments, the EPO deficiency is anemia. In some embodiments, the EPO deficiency or anemia occurs secondary to renal failure in the subject. In some other embodiments, the EPO deficiency or anemia occurs secondary to a disorder selected from the group consisting of chronic renal failure, primary EPO deficiency, chemotherapy or antiviral therapy, non-myeloid cancer, HIV infection, liver disease, cardiac failure, rheumatoid arthritis, or multi-organ system failure. In certain embodiments, the composition used in the method further comprises a biomaterial comprising one or more biocompatible synthetic polymers and/or naturally-occurring proteins or peptides, wherein the admixture is coated with, deposited on or in, entrapped in, suspended in, embedded in and/or otherwise combined with the biomaterial.

In yet another aspect, the invention provides a use of the cell preparations and admixtures thereof or an implantable construct of the instant invention for the preparation of a medicament useful in the treatment of a kidney disease, anemia or EPO deficiency in a subject in need thereof.

In one aspect, the instant invention provides a selected population of renal cells, isolatable by centrifugation through a density gradient, after having been exposed to about 1% to about 5% oxygen levels for about 12 to about 24 hours, with the gradient including a portion with density from about 1.045 g/mL to about 1.052 g/mL, wherein the cell population (i) is retained in the gradient after centrifugation at a density between 1.045 g/mL to about 1.052 g/mL, (ii) comprises a renal tubular cell population characterized by expression of at least one tubular cell marker, (iii) comprises a subpopulation of renal tubular cells capable of receptor-mediated albumin transport, (iv) is capable of modulating one or more renal functions when delivered to a subject at risk of or having a renal disease.

In yet another aspect, the instant invention provides a selected population of renal cells, isolatable by centriguation through a density gradient, after having been exposed to about 1% to about 5% oxygen levels for about 12 hours to about 24 hours, with the gradient including a portion with density from about 1.063 g/mL to about 1.091 g/mL, wherein the cell population (i) is retained in the gradient after centrifugation, at a density between 1.063 g/mL to about 1.091 g/mL, (ii) comprises oxygen-tunable erythropoietin (EPO)-expressing cells, glomerular cells, and vascular cells, (iii) is capable of modulating one or more renal functions when delivered to a subject at risk of or having a renal disease, and (iv) is capable of enhancing the modulation of one or more renal functions by another population of renal cells upon co-administration.

In still another aspect, the instant invention provides a population of renal cells that, wherein the cells have been: i) placed into adherent culture on standard tissue-culture-treated plastic dishes at an initial density of 25,000 cells/cm$^2$, in a media consisting of a 1:1 mixture of High-Glucose DMEM and fully-supplemented KSFM, with 5% fetal bovine serum, at 37° C. and 21% oxygen for a period of 24-72 hours; ii) subjected to a 50-100% media change with the same media and cultured for 18-24 hours at 37° C. and 2% oxygen; iii) harvested via trypsinization, resuspended, and washed with serum-free KSFM media or PBS; iv) loaded onto a prepared density gradient, said gradient containing a layer with a defined density between 1.045 g/mL to about 1.052 g/mL and containing at least one layer of greater density and at least one layer of lesser density, whereby the gradient has been prepared in a 15 mL conical tube in a total liquid volume of not less than 5 and not more than 14 mL, and the number of cells loaded onto the gradient is at least 50 million but does not exceed 100 million; v) forced through the gradient by centrifugation at 800× G for 20-30 minutes with no brake; and segmented at a density between 1.045 g/mL and 1.052 g/mL; and/or is characterized by a marker selected from the group consisting of megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (S1c9a4), aldehyde dehydrogenase 3 family, member B1 (Aldh3b1), aldehyde dehydrogenase 1 family, member A3 (Aldh1a3), Calpain-8 (Capn8), and Aquaporin-4 (Aqp4) marker; and/or is capable of stabilizing, reducing the decline, or improving one or more renal functions in an immunocompatible subject that has renal disease.

In still another aspect, the instant invention provides a population of renal cells that, wherein the cells have been: i) placed into adherent culture on standard tissue-culture-treated plastic dishes at an initial density of 25,000 cells/cm$^2$, in a media consisting of a 1:1 mixture of High-Glucose DMEM and fully-supplemented KSFM, with 5% fetal bovine serum, at 37° C. and 21% oxygen for a period of 24-72 hours; ii) subjected to a 50-100% media change with the same media and cultured for 18-24 hours at 37° C. and 2% oxygen; iii) harvested via trypsinization, resuspended, and washed with serum-free KSFM media or PBS; iv) loaded onto a prepared density gradient, said gradient containing a layer with a defined density between 1.063 g/mL to about 1.091 g/mL and containing at least one layer of greater density and at least one layer of lesser density, whereby the gradient has been prepared in a 15 mL conical tube in a total liquid volume of not less than 5 and not more than 14 mL, and the number of cells loaded onto the gradient is at least 50 million but does not exceed 100 million; v) forced through the gradient by centrifugation at 800× G for 20-30 minutes with no brake; and segmented at a density between 1.063 g/mL and about 1.091 g/mL; and/or is characterized by a marker selected from the group consisting of VEGF, KDR, HIF1α, Podocin (Podn) or Nephrin (Neph), chemokine (C—X—C motif) receptor 4 (Cxcr4), endothelin receptor type B (Ednrb), collagen, type V, alpha 2 (Col5a2), Cadherin 5 (Cdh5), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo); and/or is capable of stabilizing, reducing the decline, or improving one or more renal functions in an immunocompatible subject that has renal disease.

In one aspect, the present invention provides isolated populations of erythropoietin (EPO)-producing kidney cells. In one embodiment, the population is an isolated, enriched population of EPO-producing mammalian cells. In another embodiment, the population is an isolated, enriched population of erythropoietin (EPO)-producing mammalian cells comprising a greater proportion of EPO-producing cells than a non-enriched population containing erythropoietin (EPO)-producing mammalian cells.

The population may be derived from a kidney tissue or cultured kidney cells. The population may be derived from a kidney sample obtained from a subject. The sample may be kidney tissue or cultured kidney cells derived from a kidney sample obtained from a subject. In another embodiment, the cell populations contain a greater proportion of EPO-producing cells than a non-enriched population containing EPO-producing mammalian cells. In one other embodiment, the cell populations contain a lesser proportion of renal tubular cells than a non-enriched population containing erythropoietin (EPO)-producing mammalian cells.

In all embodiments, the cell populations may be enriched for EPO-producing cells. In all embodiments, the cell populations may be enriched for non-EPO-producing cells. In all embodiments, the cell populations may be enriched for renal tubular cells.

In another aspect, the present invention provides cell populations of erythropoietin (EPO)-producing cells that are bio-responsive under certain culturing conditions. In one other embodiment, the bio-responsiveness is the induction of EPO expression when the cell population is cultured under hypoxic conditions when compared to a cell population cultured under non-hypoxic conditions. In yet another embodiment, the bio-responsiveness is an increase in EPO expression when the cell population is cultured under hypoxic conditions when compared to a cell population cultured under non-hypoxic conditions. In some embodiments, the hypoxic culture conditions include, without limitation, subjecting a cell population to a reduction in available oxygen levels in the culture system relative to a cell population cultured under conditions where the oxygen level is not reduced. In one other embodiment, the reduction in available oxygen levels is about less than 5% and the conditions where oxygen levels are not reduced is atmospheric oxygen levels (about 21%). In another embodiment, an increase in expression of EPO may be observed at oxygen levels less than atmospheric (21%) when compared to cultures tested at levels≥21%. In another embodiment, the induction of EPO expression and/or the increased EPO expression may be observed upon culturing cells in about less than 5% oxygen, i.e., hypoxic culture conditions, and comparing the level of induction and/or increased expression to cells cultured at atmospheric oxygen levels (about 21%), i.e., non-hypoxic culture conditions. In one embodiment, the EPO expression that is bio-responsive to hypoxic conditions is regulated by hypoxia inducible factor HIF. In another embodiment, the EPO expression that is bio-responsive to hypoxic conditions is regulated by HIF1α. In yet another embodiment, the EPO expression that is bio-responsive to hypoxic conditions is regulated by hypoxia inducible factor HIF2α.

In one embodiment, the bio-responsiveness is the induction of EPO expression when the cell population is cultured via perfusion when compared to a cell population not cultured via perfusion. In another embodiment, the bio-responsiveness is an increase in the expression of EPO when compared to a cell population not cultured via perfusion. In some embodiments, the perfusion conditions include, without limitation, transient, intermittent or continuous circulation or agitation of fluid such that dynamic forces are transferred to the cells via the flow of fluid. In another embodiment, the perfusion culture conditions are carried such that the cell populations are cultured in or on a material that provides a framework and/or space that allows for the formation of three-dimensional structures.

In one other aspect, the present invention provides admixtures or combinations of kidney cells that contain the cell populations described herein. In one embodiment, the cell admixture includes a first cell population enriched for EPO-producing cells and a second cell population not enriched for EPO producing cells. In one other embodiment, the second cell population may contain one or more types of kidney-derived cells, which may include, without limitation, one or more of the following: tubular-derived cells, glomerulus-derived cells, interstitium-derived cells, collecting duct-derived cells, connective tissue-derived cells, blood-derived cells, or blood vessel-derived cells. In another embodiment, the second cell population is enriched for renal tubular cells.

In all embodiments, the renal tubular cells described herein may be characterized by expression of a tubular cell marker, which may include, without limitation, one or more of the following: Hyaluronic acid synthase 2 (HAS2), CYP2D25 (Vitamin D3 25-Hydroxylase), megalin, cubilin, N-cadherin, E-cadherin, Aquaporin-1, Aquaporin-2, RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (S1c9a4), aldehyde dehydrogenase 3 family, member B1 (Aldh3b1), aldehyde dehydrogenase 1 family, member A3 (Aldh1a3), and Calpain-8 (Capn8)

In one aspect, the present invention provides isolated, enriched mammalian renal tubular cell populations. In one embodiment, the isolated cell population is enriched for renal tubular cells and contains at least some EPO-producing mammalian cells. In another embodiment, the cell population has a greater proportion of tubular cells than a non-enriched population containing tubular cells. In one other embodiment, the isolated, enriched population of mammalian renal tubular cells contains a greater proportion of tubular cells than a non-enriched population containing tubular cells and at least some EPO-producing mammalian cells. In another embodiment, the enriched mammalian renal tubular cell population is relatively depleted of EPO-producing cells, compared to unfractionated, heterogeneous mixtures or compared to enriched populations of EPO-producing cells.

In all embodiments, the types of sources from which kidney cell populations or admixtures of kidney cell populations described herein are derived may be autologous or allogeneic, syngeneic (autogeneic or isogeneic), and any combination thereof. For example, in some embodiments the admixture of cells may contain (i) a first cell population derived from an autologous source and a second cell population derived from an autologous source; or (ii) a first cell population derived from an autologous source and a second cell population derived from an allogeneic source.

In another aspect, the present invention provides methods of generating a cell population enriched for EPO-producing cells. In one embodiment, the method includes the steps of a) preparing a cell suspension having a non-enriched, heterogeneous rodent kidney cell population from mechanically-dissociated or enzymatically digested mammalian kidney tissue; b) contacting the cell suspension with a density gradient to separate one or more cell fractions based on buoyant density; c) centrifuging the cell suspension of step b) to define the one or more cell fractions; and d) extracting a first cell fraction that contains the enriched cell population, wherein the enriched cell population has a greater proportion of EPO-producing cells and a lesser proportion of non-EPO producing cells when compared to the non-enriched cell population. In one other embodiment, the density gradient includes a layer with specific density between about 1.025 g/mL and about 1.035 g/mL, or less than about 1.045 g/mL. In another embodiment, the first cell fraction of step d) is present in the gradient after centrifugation at a specific density between about 1.025 g/mL and about 1.035 g/mL, or less than about 1.045 g/mL. In one other embodiment, the centrifuging step (c) further generates at least one additional cell fraction that is not enriched for said enriched EPO-producing cell population. In another embodiment, the method further includes step e) extracting the at least one additional cell fraction. In one other embodiment, the density gradient includes a layer with specific density between about 1.062 g/mL and about 1.088 g/mL. In another embodiment, the additional cell fraction is present in the gradient after centrifugation at a specific density between about 1.062 g/mL and about 1.088 g/mL.

In another embodiment, the method includes the steps of a) preparing a cell suspension from a population of cultured non-enriched, heterogeneous mammalian cells that comprise at least some cells expressing or capable of expressing EPO; b) contacting the cell suspension with a density gradient to separate one or more cell fractions based on buoyant density; c) centrifuging the cell suspension of step b) to define the one or more cell fractions; and d) extracting a first cell fraction that contains the enriched cell population, wherein the enriched cell population has a greater proportion of EPO-producing cells and a lesser proportion of non-EPO producing cells when compared to the non-enriched cell population. In one embodiment, the cell suspension in step a) is obtained from a population of cultured non, enriched heterogeneous rodent cells. In such embodiment, the density gradient includes a layer with specific density between about 1.073 g/mL and about 1.091 g/mL. In one embodiment, the first cell fraction of step d) is present in the gradient after centrifugation at a specific density between about 1.073 g/mL and about 1.091 g/mL. In one other embodiment, the centrifuging step (c) further generates at least one additional cell fraction that is not enriched for said enriched EPO-producing cell population. In another embodiment, the method further includes step e) extracting the at least one additional cell fraction. In one other embodiment, the density gradient includes a layer with specific density between about 1.041 g/mL and about 1.062 g/mL. In another embodiment, the additional cell fraction is present in the gradient after centrifugation at a specific density between about 1.041 g/mL and about 1.062 g/mL.

In some embodiments, the enriched cell population is enriched for EPO-producing cells and depleted of non-EPO-producing cells. In other embodiments, the enriched cell population is enriched for interstitial fibroblasts and depleted of tubular cells and collecting duct cells. In another embodiment, the enriched cell population is enriched for EPO-producing cells, glomerular cells, and vascular cells. In another embodiment, the centrifuging step (c) further generates at least one additional cell fraction that is not enriched for said enriched cell population. In some embodiments, the additional cell fraction contains a greater proportion of non-EPO-producing cells and a lesser proportion of EPO-producing cells when compared to the non-enriched cell population. In one embodiment, the at least one additional cell fraction has a lesser proportion of EPO-producing cells when compared to the first cell fraction. In another embodiment, the additional cell fraction contains a greater proportion of renal tubular cells when compared to the first cell fraction.

In some embodiments, the density gradient used in the methods of generating cell populations enriched for EPO-producing cells is an iodixanol density gradient.

In another aspect, the present invention provides methods of generating an enriched population of erythropoietin EPO-producing cells using flow cytometry techniques. In one embodiment, the method includes the steps of a) preparing a cell suspension comprising a non-enriched, heterogeneous kidney cell population from mechanically-dissociated or enzymatically digested mammalian kidney tissue; b) applying the cell suspension to a flow cytometric instrument capable of simultaneous measurement of forward scatter and side scatter in one or more individual cells within the cell population; c) selecting a cell subpopulation from the cell population, d) sorting a cell subpopulation from the cell population, and e) isolating a cell subpopulation from the cell population, wherein the cell subpopulation is characterized by low forward scatter and low side scatter relative to the whole population.

In another embodiment, the method includes the steps of a) preparing a cell suspension from a population of cultured mammalian cells that comprise at least some cells expressing or capable of expressing EPO; b) applying the cell suspension to a flow cytometric instrument capable of simultaneous measurement of forward scatter and side scatter in one or more individual cells within the cell population; c) selecting a cell subpopulation from the cell population; d) sorting a cell subpopulation from the cell population; and e) isolating a cell subpopulation from the cell population, wherein the cell subpopulation is characterized by low forward scatter and low side scatter relative to the whole population.

In yet another embodiment, the forward scatter corresponds to cell size. In one embodiment, the side scatter corresponds to cell granularity. Other embodiments of the invention provide enriched cell fractions that are i) enriched for EPO-producing cells and depleted of non-EPO-producing cells, or ii) enriched for specialized interstitial cortical fibroblasts that produce EPO and depleted of epithelial cells. In one other embodiment, the selecting step c) comprises generating at least one additional fraction that is not enriched for said cell population. In another embodiment, the additional fraction or fractions contain a lesser proportion of EPO-producing cells when compared to the EPO-enriched fraction.

In an additional aspect of the present invention, the methods include the further step of in vitro culturing. In one embodiment, the enriched cell population is cultured in vitro following the isolation. In another embodiment, the culturing step includes the use of a two-dimensional monolayer culture on a glass or plastic surface suitable for mammalian cell culture in a media suitable to support growth and/or maintenance of said cell population. In other embodiments, the culturing step includes culturing cells on a three-dimensional (3D) scaffolding suitable for cell maintenance and/or growth. In one other embodiment, the scaffolding is contains one or more biocompatible synthetic polymers or naturally-occurring proteins or peptides. In another embodiment, the scaffolding is configured as a porous scaffold suitable for trapping or attaching mammalian cells. In other embodiments, the scaffolding is configured as a gel suitable for embedding, attaching, or coating mammalian cells.

In another aspect, the present invention provides methods that include the step of culturing under perfusion conditions. In one embodiment, the perfusion conditions include, without limitation, transient, intermittent or continuous circulation or agitation of fluid such that dynamic forces are transferred to the cells via the flow of fluid. In another embodiment, the perfusion culture conditions are carried such that the cell populations are cultured in or on a material that provides a framework and/or space that allows for the formation of three-dimensional structures.

In another aspect, the present invention provides methods that include the step of culturing under hypoxic conditions. In some embodiments, the hypoxic culture conditions include, without limitation, subjecting a cell population to a reduction in available oxygen levels in the culture system relative to a cell population cultured under conditions where the oxygen level is not reduced. In one other embodiment, the reduction in available oxygen levels is about less than 5% and the conditions where oxygen levels are not reduced is atmospheric oxygen levels (about 21%). In another embodiment, reduced oxygen conditions are represented by oxygen levels<21% (atmospheric).

In one additional aspect, the present invention provides methods that include the step of measuring EPO expression in the cell population. In all embodiments, the EPO expression is EPO mRNA expression. In all embodiments, the EPO expression is detectable and/or detected. In another embodiment, the EPO expression is induced in a cell population cultured via perfusion when compared to a cell population not cultured via perfusion. In other embodiments, the EPO expression is induced in a cell population cultured under hypoxic conditions when compared to a cell population cultured under non-hypoxic conditions. In another embodiment, the detectable EPO expression is greater in a cell population cultured via perfusion when compared to a cell population not cultured via perfusion. In additional embodiments, the detectable EPO expression is greater in a cell population cultured under hypoxic conditions when compared to a cell population cultured under non-hypoxic conditions. In one other embodiment, the induction of EPO expression and/or the increased EPO expression may be observed upon culturing cells in about less than 5% oxygen, i.e., hypoxic culture conditions, and comparing the level of induction and/or increased expression to cells cultured at atmospheric oxygen levels (about 21%), i.e., non-hypoxic culture conditions. In another embodiment, increased EPO expression may be observed upon culturing cells in less than 21% oxygen (atmostpheric) conditions.

In yet another aspect, the present invention provides implantable constructs that contain one or more cell populations described herein. In one embodiment, the present invention provides an implantable construct for providing an erythropoietin (EPO)-producing cell population to a subject in need, where the construct includes a) a scaffold containing one or more biocompatible synthetic polymers or naturally-occurring proteins or peptides; and b) a first cell population enriched for EPO-producing mammalian cells deposited on or in a surface of the scaffold.

In another embodiment, the present invention provides an implantable construct for providing an erythropoietin EPO-producing cell population to a subject in need where the construct includes a) a porous scaffold containing one or more biocompatible synthetic polymers or naturally-occurring proteins or peptides; and b) an admixture of cells that contains i) a first cell population enriched for EPO-producing mammalian cells, and ii) a second cell population enriched for non-EPO producing cells, where the admixture of cells is deposited on the surface of and/or within the pores of the scaffold. In some embodiments, the EPO expression is greater in the first cell population relative to the second cell population. In one other embodiment, the second cell population comprises one or more kidney-derived cell types, which may include, without limitation, one or more of the following: tubular-derived cells, glomerulus-derived cells, interstitium-derived cells, connective tissue-derived cells, collecting duct-derived cells, blood-derived cells, or blood vessel-derived cells. In another embodiment, the second cell population is enriched for renal tubular cells. Some embodiments of the present invention provide populations enriched for renal tubular cells that are characterized by expression of a tubular cell marker, which include, without limitation, one or more of the following: megalin, cubilin, N-cadherin, E-cadherin, Aquaporin-1, and Aquaporin-2.

In one embodiment, the admixtures of kidney cells provided by the present invention may include cell populations that are derived from types of kidney tissue sources as described herein. In other embodiments, the first cell population and the second cell population are derived from kidney tissue or cultured kidney cells. In another embodiment, the first cell population contains a greater proportion of EPO-producing cells than a non-enriched population containing erythropoietin (EPO)-producing mammalian cells. In another embodiment, the first cell population contains glomerular cells and vascular cells in addition to the EPO-producing cells. In yet another embodiment, the first cell population contains a greater proportion of EPO-producing cells than the second cell population. Additional embodiments of the present invention include a first cell population containing a lesser proportion of renal tubular cells than a non-enriched population of erythropoietin (EPO)-producing mammalian cells. In other embodiments, the first cell population contains a lesser proportion of renal tubular cells than the second cell population. In some embodiments, the cells are paired with a biomaterial. In one embodiment, the scaffold or biomaterial is configured as a three-dimensional (3-D) porous scaffold. In another embodiment, the 3-D porous scaffold is suitable for entrapment or attachment of the mammalian cells. In yet another embodiment, the scaffold or biomaterial is configured as a liquid or semi-liquid gel suitable for embedding, attaching, or coating mammalian cells. In one embodiment, the cell populations suitable for use in the constructs of the present invention are derived from an autologous or non-autologous kidney sample. In one other embodiment, the sample is a kidney biopsy.

In one other aspect, the present invention provides methods for the treatment of subjects in need of cell populations enriched for EPO-producing cells. In one embodiment, the method is for the treatment of an erythropoietin (EPO) deficiency in a subject in need that includes the step of administering to the subject a composition that contains a first cell population enriched for EPO-producing mammalian cells. In another embodiment, the first cell population is enriched for EPO-producing cells, glomerular cells, and vascular cells. In one embodiment, the EPO deficiency is anemia. In another embodiment, the EPO deficiency or anemia occurs secondary to renal failure in the subject. In one other embodiment, the EPO deficiency or anemia occurs secondary to a disorder selected from the group consisting of chronic renal failure, primary EPO deficiency, chemotherapy or anti-viral therapy, non-myeloid cancer, HIV infection, liver disease, cardiac failure, rheumatoid arthritis, or multi-organ system failure.

In another embodiment, the method is for the treatment of a kidney disease in a subject in need that includes the step of administering to the subject a composition that contains a first cell population enriched for EPO-producing mammalian cells. In another embodiment, the first cell population is enriched for EPO-producing cells, glomerular cells, and vascular cells.

In some embodiments, the compositions that are administered to subjects in need further contain a second kidney cell population that is not enriched for EPO producing cells. In other embodiments, the compositions further include a porous scaffold containing one or more biocompatible synthetic polymers and/or naturally-occurring proteins or peptides, wherein the first cell population is deposited on the surface of and/or within the pores of the scaffold. In an additional embodiment, the composition further comprises a porous scaffold containing one or more biocompatible synthetic polymers and/or naturally-occurring proteins or peptides, wherein the first cell population and the second cell population are deposited on the surface of and/or within the pores of the scaffold. In another embodiment, the first cell population and/or the second cell population is derived from mammalian kidney tissue or cultured mammalian kidney cells. In other embodiments, the first cell population and/or the second cell population is derived from an autologous or non-autologous kidney sample. In one embodiment, the sample is a kidney biopsy.

In one embodiment, the second cell population is enriched for renal tubular cells. In another embodiment, the renal tubular cells are characterized by expression of a tubular cell marker, which may include, without limitation, one or more of the following: megalin, cubilin, N-cadherin, E-cadherin, Aquaporin-1, and Aquaporin-2.

In all embodiments, the second cell populations contains one or more kidney-derived cell types selected from the group consisting of tubular-derived cells, glomerulus-derived cells, interstitium-derived cells, collecting duct-derived cells, connective tissue-derived cells, blood-derived cells, or blood vessel-derived cells. In all embodiments, the second cell population is relatively depleted of glomerular cells, vascular cells, and oxygen-responsive epo-producing cells, compared to the heterogeneous unfractionated population or to the first cell population.

In another aspect, the present invention includes methods of providing erythroid homeostasis in a subject in need. In one embodiment, the method includes the steps of a) administering to the subject a composition containing a first cell population enriched for EPO-producing mammalian cells; and b) determining in a test sample from the subject that the level of an erythropoiesis function indicator is different relative to the indicator level in a control, wherein the difference in indicator level is indicative of erythroid homeostasis in the subject.

In another embodiment, the method includes the steps of a) administering to the subject a composition containing a first cell population enriched for EPO-producing mammalian cells and a second cell population that is not enriched for EPO producing cells; and b) determining in a test sample from the subject that the level of an erythropoiesis function indicator is different relative to the indicator level in a control, wherein the difference in indicator level is indicative of erythroid homeostasis in the subject.

In another aspect, the present invention includes methods of improving kidney function in a subject in need. In one other embodiment, the method includes the steps of a) administering to the subject a composition containing a first cell population enriched for EPO-producing mammalian cells; and b) determining in a test sample from the subject that the level of a kidney function indicator is different relative to the indicator level in a control, wherein the difference in indicator level is indicative of improved kidney function in the subject. In another embodiment, the composition further includes a porous scaffold containing one or more biocompatible synthetic polymers and/or naturally-occurring proteins or peptides, wherein the first cell population is deposited on the surface and/or within the pores of the scaffold.

In another embodiment, the method includes the steps of a) administering to the subject a composition containing a first cell population enriched for EPO-producing mammalian cells and a second cell population that is not enriched for EPO producing cells; and b) determining in a test sample from the subject that the level of a kidney function indicator is different relative to the indicator level in a control, wherein the difference in indicator level is indicative of improved kidney function in the subject. In another embodiment, the composition further includes a porous scaffold containing one or more biocompatible synthetic polymers and/or naturally-occurring proteins or peptides, wherein the first cell population and the second cell population are deposited on the surface of and/or within the pores of the scaffold.

In other embodiments, the first cell population and/or the second cell population are derived from mammalian kidney tissue or cultured mammalian kidney cells. In another embodiment, the first cell population and/or the second cell population are derived from an autologous or a non-autologous kidney sample. In one other embodiment, the sample is a kidney biopsy.

In one embodiment, the first cell population is enriched for hypoxia-responsive epo-producing cells. In another embodiment, the first cell population is enriched for hypoxia-responsive epo-producing cells, glomerular cells, and vascular cells.

In one embodiment, the second cell population is enriched for renal tubular cells. In another embodiment, the renal tubular cells are characterized by expression of a tubular cell marker, which may include, without limitation, one or more of the following: Hyaluronic acid synthase 2 (HAS2), CYP2D25 (Vitamin D3 25-Hydroxylase), megalin, cubilin, N-cadherin, E-cadherin, Aquaporin-1, Aquaporin-2 and Aquaporin-4. In another embodiment, the second cell population is enriched for renal tubular cells and contains epithelial cells of the collecting duct. In another embodiment, the second cell population is relatively enriched for tubular cells, contains collecting duct epithelial cells, and is relatively depleted for hypoxia-responsive epo-producing cells, glomerular cells, and vascular cells.

BRIEF DESCRIPTION OF THE DRAWINGS

FIG. 48A-B shows enrichment of epo-producing cell fraction from freshly-dissociated kidney tissue using a multilayered step gradient technique (left panel) or a single-layer mixing gradient technique (right panel). Both methods result in the partial depletion of non epo-producing cell components (predominantly tubular cells) from the epo band, which appears between 1.025 g/mL and 1.035 g/mL.

FIG. 74A-K depicts the results of the compositional analysis of B2 and B4 subfractions. Quantitative real-time PCR (qRTPCR) was used to assess expression of kidney cell-type specific genes in the B2 and B4 subfractions. (A, B) Subfraction B2 was enriched for proximal tubular cells, based on relative expression of Vitamin D Hydroxylase (CYP2R1) and Cubilin, compared to B4 and all other subfractions. (C) The distal tubular marker, E-cadherin, was also enriched in subfraction B2 in comparison to B4. (E,F) The glomerular markers nephrin and podocin were enriched in subfraction B4, as was the vascular marker, kdr (D). (G, H) The oxygen-regulated interstitial markers, Hif2α and Epo, were also enriched in B4. (I) Results are presented quantitatively for B2 and B4. (J) Robust expression of proximal (N-cadherin/green) and distal (E-cadherin/red) tubular markers by B2 was confirmed via immunocytochemistry on cells cultured after subfractionation (K) In contrast, E-cadherin- or N-cadherin-positive cells were infrequent in B4 cultures.

FIG. 75A-C depicts functional attributes of B2 and B4 subfractions. (A) B2 and B4 cells were subcultured and evaluated for cubilin expression and receptor-mediated albumin uptake. Panels represent: i. B2 cells stained with isotype-matched IgG control antibody for cubilin; ii. B2 cells, pre-treated with the competitive inhibitor, RAP, and pulsed with rhodamine-conjugated human serum albumin (HSA-Rhodamine) for 15 minutes (10 μg/ml); iii. B2 cells, pulsed with HSA-Rhodamine for 15 minutes (10 μg/ml) (red) and labeled with an anti-cubilin antibody (green); iv. Overlayed image of (iii) showing co-localization of cubilin+ cells (green) with uptake of HSA-Rhodamine (red); v. Same as (iii/iv), but with B4 cells, showing very few cubilin+ cells (green) and little to no albumin uptake (red). In all conditions, nuclei were counterstained with Hoechst (blue). (B) Expression of Epo was examined in each fraction (B1-B4), generated after a 24-hr exposure to atmospheric (21%) or low (2%) oxygen tension (both at 37° C.). The relative proportion of Epo-expressing cells capable of Epo upregulation in response to a reduction in oxygen tension was greatest in subfraction B4 (C). Note the consistency in relative expression of Epo in B2 and B4 with results described in FIG. 74I.

FIG. 78A-C shows results of the clinical assessment of study midpoint (Wk 12-14). Blood was collected at the study midpoint (12-14 weeks) for clinical chemistry, and parameters that highlight differences between Healthy Controls and Nx, or Nx vs. B2-, B4-, or UNFX-treated are shown in panel (A). Two significant effects unique to B2 treatment were (B) enhanced retention of protein, as demonstrated by increased serum albumin (sALB) and Albumin/Globulin (A/G) ratio in B2 vs. Nx (p<0.001), and (C) reduction of serum triglycerides and cholesterol in B2 vs. Nx (p<0.001).

FIG. 119 depicts immunocytochemistry results on cells.

FIG. 120A-F shows results of flow cytometry demonstrating that the EPO-expressing cells contained within the rat cultures were distinct from both proximal and distal tubular cells (FIG. 120 A, B). Functionality of cubilin-positive proximal tubular cells in the cultures was assessed via uptake of fluorescence-conjugated albumin, and specificity of the uptake was confirmed by the addition of a competitive inhibitor, RAP (FIG. 120 C-F).

FIG. 121A-C shows monthly monitoring of filtration function (sCREAT shown in (A); HCT shown in (B); comparative clinical chemistry results are shown in (C).

FIG. 122A-D depicts histologic analyses conducted to identify tissue-level effects in both the kidney and bone marrow.

Figure 123:
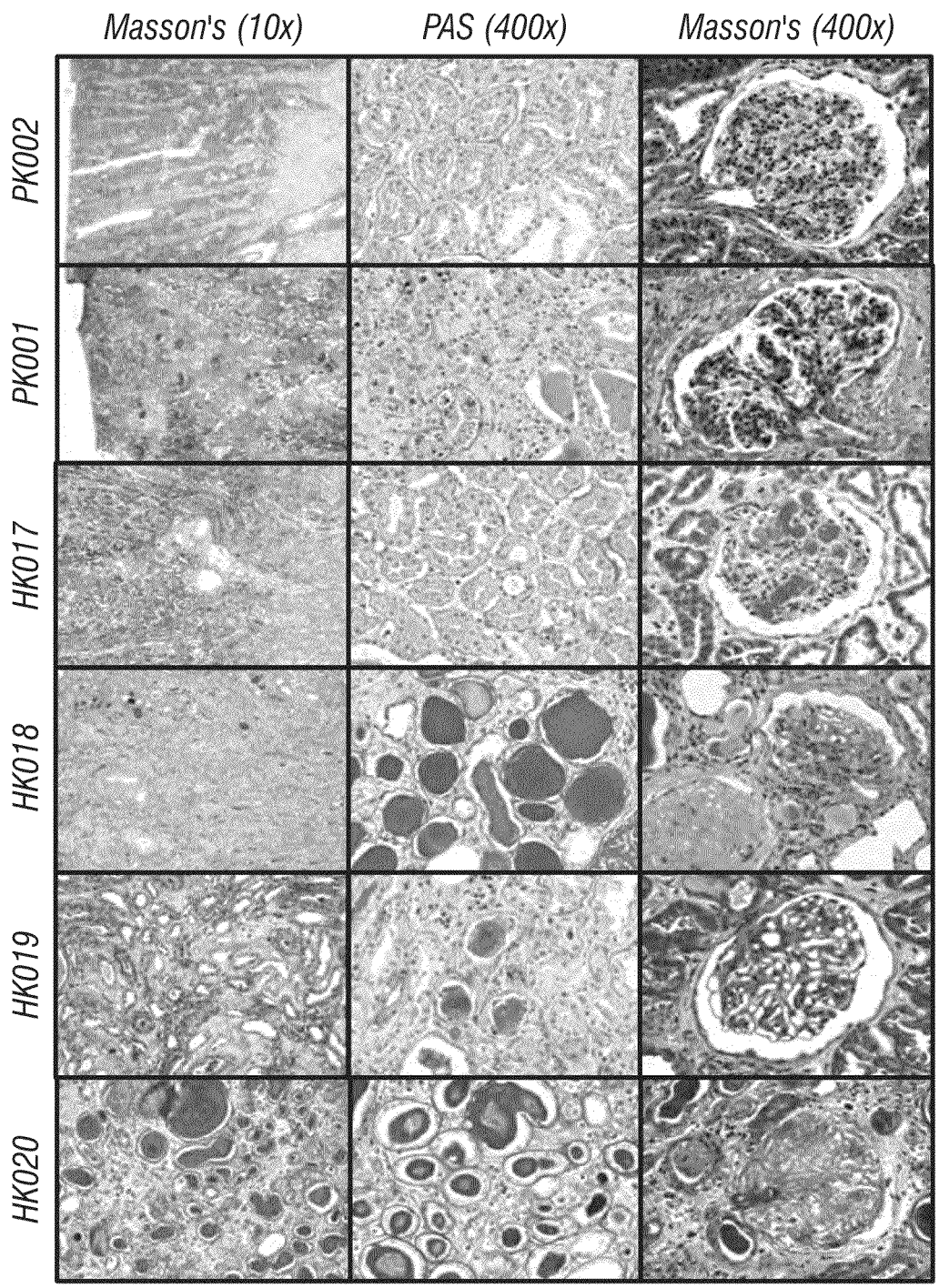

FIG. 123 shows histopathologic features of the CKD specimens contrasted with histologic features of non-CKD kidney specimens from both swine and human.

FIG. 124A-D shows expansion capacity between CKD- and non-CKD-derived cultures (A tubular cell function confirmed in the established cultures by observing receptor-mediated uptake of albumin in a portion of cubilin positive cells (B-D).

FIG. 125A-C shows EPO mRNA expression in CKD vs. non-CKD tissue specimens (A); isoelectric focusing and western blot analysis of these samples confirmed that the gene expression patterns were recapitulated in general at the protein level (B); EPO-expressing cell cultures established from both CKD and non-CKD kidney specimens responded to a hypoxic stimulus with variable upregulation of EPO gene transcription within 24 hours of the stimulus (C).

Figure 126:
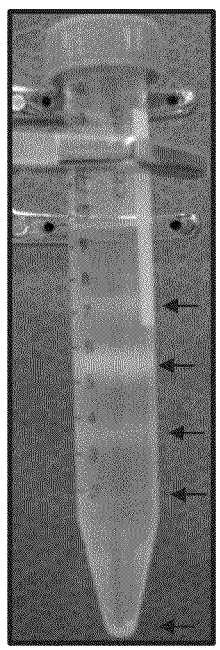

FIG. 126 depicts cell bands of rodent adult step gradient.

Figure 127:
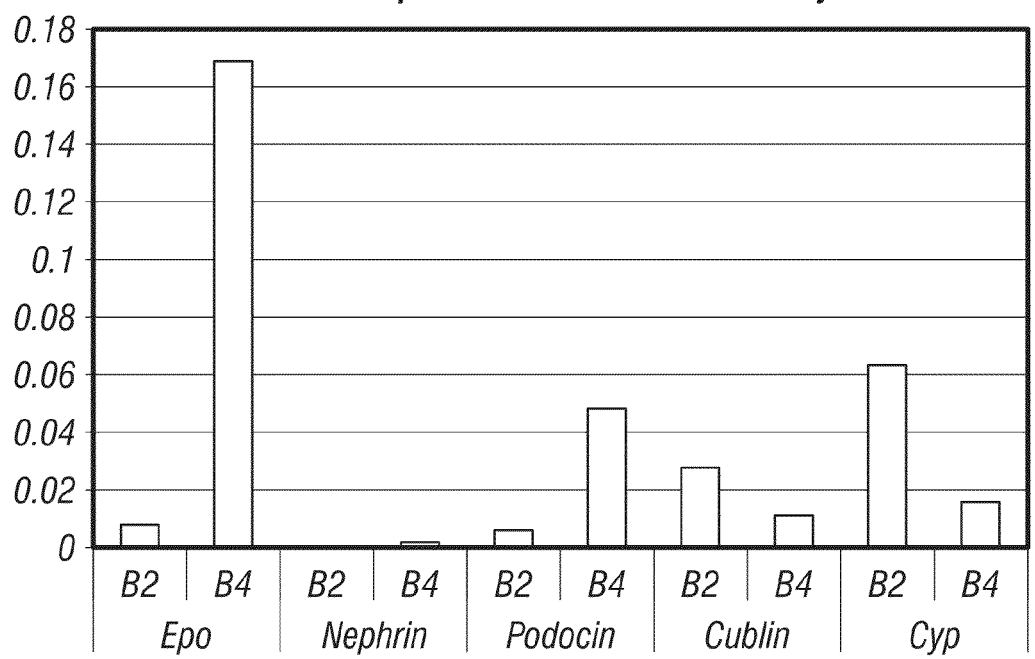

FIG. 127 depicts gene expression patterns of erythropoietin, nephrin, podocin, cubilin, and Cyp in adult rodent cell preparations.

Figure 128:
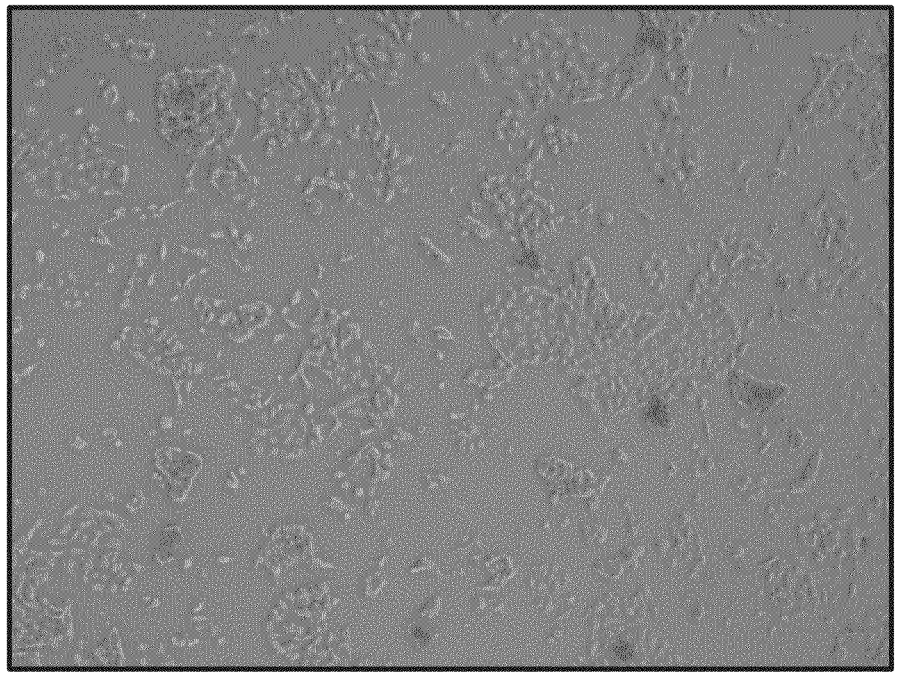

FIG. 128 depicts isolated cell preparations from diseased Adult Rodent Kidney (5×).

Figure 129:
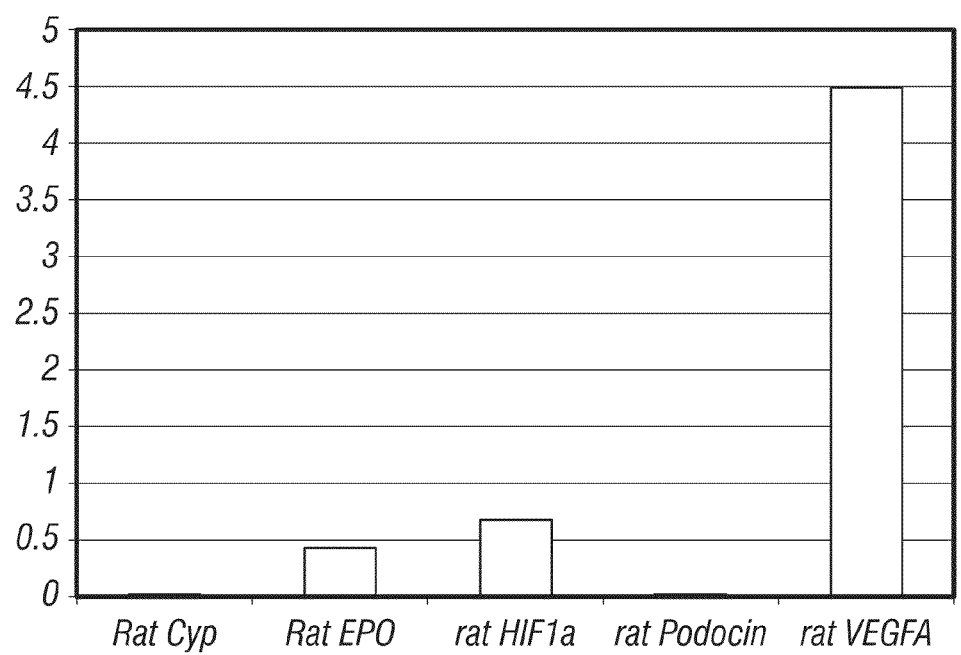

FIG. 129 shows expression of B4-specific genes in cells isolated from adult rat with terminal renal failure.

Figure 130:
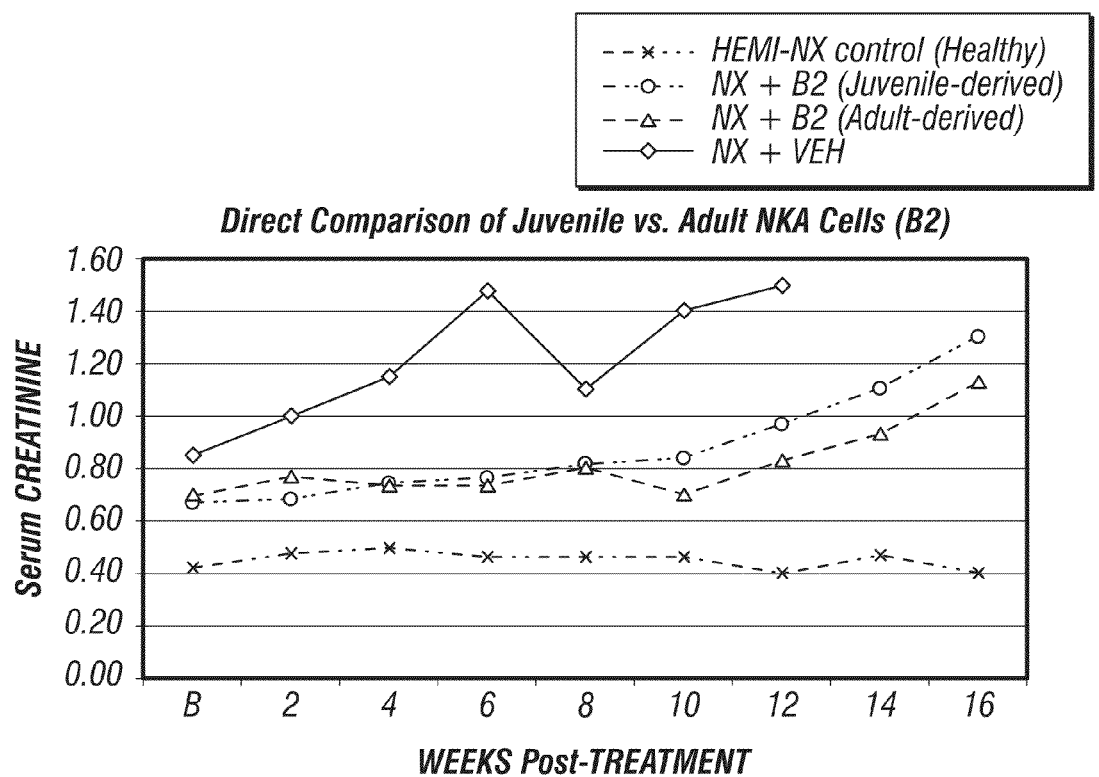

FIG. 130 depicts direct comparison of creatinine values in juvenile and adult B2 cell preparations.

Figure 131:
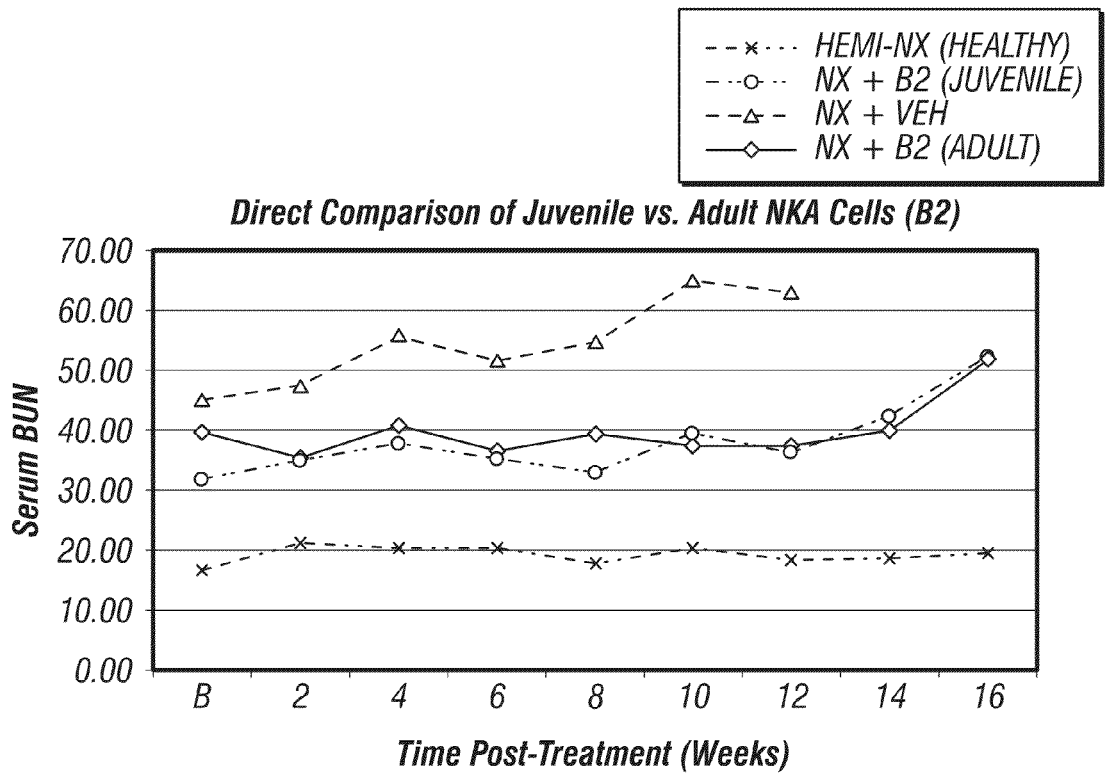

FIG. 131 depicts direct comparison of serum BUN values in juvenile and adult B2 cell preparations.

Figure 132:
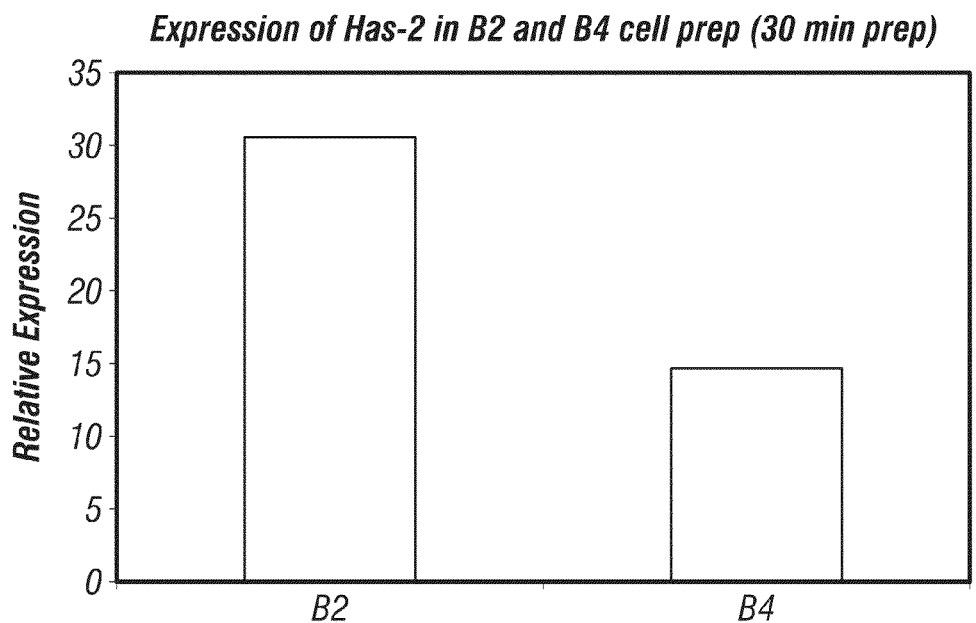

FIG. 132 shows the expression of Has-2 in B2 and B4 cell preparations.

Figure 133:
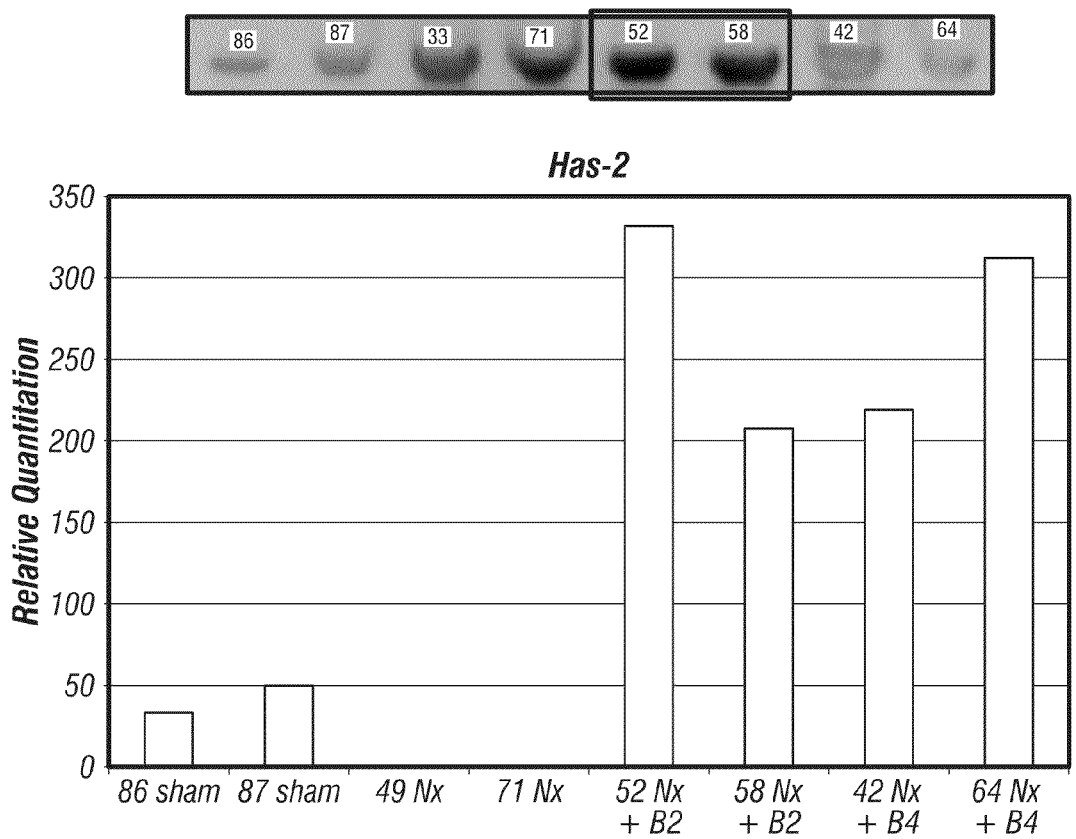

FIG. 133 shows in vivo expression of HAS mRNA (qRT-PCR, bottom graph) and protein (top figure, western blot).

DETAILED DESCRIPTION OF THE INVENTION

The present invention is directed to isolated renal cells including tubular and erythropoietin (EPO)-producing kidney cells and methods of isolating and culturing the same, as well as methods of treating a subject in need with the bioactive renal cells, including the enriched tubular and EPO-producing cell populations.

Definitions

Unless defined otherwise, technical and scientific terms used herein have the same meaning as commonly understood by one of ordinary skill in the art to which this invention belongs. *Principles of Tissue Engineering*, 3$^{rd}$ Ed. (Edited by R Lanza, R Langer, & J Vacanti), 2007 provides one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "cell population" as used herein refers to a number of cell obtained by isolation directly from a suitable tissue source, usually from a mammal. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be an unfractionated, heterogeneous cell population dervived from the kidney. For example, a heterogeneous cell population may be isolated from a kidney biopsy or from whole kidney tissue. Alternatively, the heterogeneous cell population may be derived from in vitro cultures of mammalian cells, established from kidney biopsies or whole kidney tissue. An unfractionated heterogeneous cell population may also be referred to as a non-enriched cell population.

The term "admixture" as used herein refers to a combination of two or more isolated, enriched cell populations derived from an unfractionated, heterogeneous cell population. According to certain embodiments, the cell populations of the present invention are renal cell populations.

An "enriched" cell population or preparation refers to a cell population derived from a starting kidney cell population (e.g., an unfractionated, heterogeneous cell population) that contains a greater percentage of a specific cell type than the percentage of that cell type in the starting population. For example, a starting kidney cell population can be enriched for a first, a second, a third, a fourth, a fifth, and so on, cell population of interest. As used herein, the terms "cell population", "cell preparation" and "cell prototype" are used interchangeably.

In one aspect, the term "enriched" cell population as used herein refers to a cell population derived from a starting kidney cell population (e.g., a cell suspension from a kidney biopsy or cultured mammalian kidney cells) that contains a percentage of cells capable of producing EPO that is greater than the percentage of cells capable of producing EPO in the starting population. For example, the term "B4" is a cell population derived from a starting kidney cell population that contains a greater percentage of EPO-producing cells, glomerular cells, and vascular cells as compared to the starting population. The cell populations of the present invention may be enriched for one or more cell types and depleted of one or more other cell types. For example, an enriched EPO-producing cell population may be enriched for interstitial fibroblasts and depleted of tubular cells and collecting duct epithelial cells relative to the interstitial fibroblasts and tubular cells in a non-enriched cell population, i.e. the starting cell population from which the enriched cell population is derived. In all embodiments citing EPO-enriched or "B4" populations, the enriched cell populations are heterogeneous populations of cells containing cells that can produce EPO in an oxygen-regulated manner, as demonstrated by oxygen-tunable EPO expression from the endogenous native EPO gene.

In another aspect, an enriched cell population may also refer to a cell population derived from a starting kidney cell population as discussed above that contains a percentage of cells expressing one or more tubular cell markers that is greater than the percentage of cells expressing one or more tubular cell markers in the starting population. For example, the term "B2" refers to a cell population derived from a starting kidney cell population that contains a greater percentage of tubular cells as compared to the starting population. In addition, a cell population enriched for cells that express one or more tubular cell markers (or "B2") may contain some epithelial cells from the collecting duct system. Although the cell population enriched for cells that express one or more tubular cell markers (or "B2") is relatively depleted of EPO-producing cells, glomerular cells, and vascular cells, the enriched population may contain a smaller percentage of these cells (EPO-producing, glomerular, and vascular) in comparison to the starting population. In general, a heterogeneous cell population is depleted of one or more cell types such that the depleted cell population contains a lesser proportion of the cell type(s) relative to the proportion of the cell type(s) contained in the heterogeneous cell population prior to depletion. The cell types that may be depleted are any type of kidney cell. For example, in certain embodiments, the cell types that may be depleted include cells with large granularity of the collecting duct and tubular system having a density of <about 1.045 g/ml, referred to as "B1". In certain other embodiments, the cell types that may be depleted include debris and small cells of low granularity and viabilty having a density of >about 1.095 g/ml, referred to as "B5". In some embodiments, the cell population enriched for tubular cells is relatively depleted of all of the following: "B1", "B5", oxygen-tunable EPO-expressing cells, glomerular cells, and vascular cells.

The term "hypoxic" culture conditions as used herein refers to culture conditions in which cells are subjected to a reduction in available oxygen levels in the culture system relative to standard culture conditions in which cells are cultured at atmospheric oxygen levels (about 21%). Non-hypoxic conditions are referred to herein as normal or normoxic culture conditions.

The term "oxygen-tunable" as used herein refers to the ability of cells to modulate gene expression (up or down) based on the amount of oxygen available to the cells. "Hypoxia-inducible" refers to the upregulation of gene expression in response to a reduction in oxygen tension (regardless of the pre-induction or starting oxygen tension).

The term "biomaterial" as used here refers to a natural or synthetic biocompatible material that is suitable for introduction into living tissue. A natural biomaterial is a material that is made by a living system. Synthetic biomaterials are materials which are not made by a living system. The biomaterials disclosed herein may be a combination of natural and synthetic biocompatible materials. As used herein, biomaterials include, for example, polymeric matrices and scaffolds. Those of ordinary skill in the art will appreciate that the biomaterial(s) may be configured in various forms, for example, as liquid hydrorgel suspsensions, porous foam, and may comprise one or more natural or synthetic biocompatible materials.

The term "anemia" as used herein refers to a deficit in red blood cell number and/or hemoglobin levels due to inadequate production of functional EPO protein by the EPO-producing cells of a subject, and/or inadequate release of EPO protein into systemic circulation, and/or the inability of erythroblasts in the bone marrow to respond to EPO protein. A subject with anemia is unable to maintain erythroid homeostasis. In general, anemia can occur with a decline or loss of kidney function (e.g., chronic renal failure), anemia associated with relative EPO deficiency, anemia associated with congestive heart failure, anemia associated with myelo-suppressive therapy such as chemotherapy or anti-viral therapy (e.g., AZT), anemia associated with non-myeloid cancers, anemia associated with viral infections such as HIV, and anemia of chronic diseases such as autoimmune diseases (e.g., rheumatoid arthritis), liver disease, and multi-organ system failure.

The term "EPO-deficiency" refers to any condition or disorder that is treatable with an erythropoietin receptor agonist (e.g., recombinant EPO or EPO analogs), including anemia.

The term "kidney disease" as used herein refers to disorders associated with any stage or degree of acute or chronic renal failure that results in a loss of the kidney's ability to perform the function of blood filtration and elimination of excess fluid, electrolytes, and wastes from the blood. Kidney disease also includes endocrine dysfunctions such as anemia (erythropoietin-deficiency), and mineral imbalance (Vitamin D deficiency). Kidney disease may originate in the kidney or may be secondary to a variety of conditions, including (but not limited to) heart failure, hypertension, diabetes, autoimmune disease, or liver disease.

The term "treatment" refers to both therapeutic treatment and prophylactic or preventative measures for kidney disease, anemia, EPO deficiency, tubular transport deficiency, or glomerular filtration deficiency wherein the object is to reverse, prevent or slow down (lessen) the targeted disorder. Those in need of treatment include those already having a kidney disease, anemia, EPO deficiency, tubular transport deficiency, or glomerular filtration deficiency as well as those prone to having a kidney disease, anemia, EPO deficiency, tubular transport deficiency, or glomerular filtration deficiency or those in whom the kidney disease, anemia, EPO deficiency, tubular transport deficiency, or glomerular filtration deficiency is to be prevented. The term "treatment" as used herein includes the stabilization and/or improvement of kidney function.

The term "construct" refers to one or more cell populations deposited on or in a surface of a scaffold or matrix made up of one or more synthetic or naturally-occurring biocompatible materials. The one or more cell populations may be coated with, deposited on, embedded in, attached to, or entrapped in a biomaterial made up of one or more synthetic or naturally-occurring biocompatible polymers, proteins, or peptides. The one or more cell populations may be combined with a biomaterial or scaffold or matrix in vitro or in vivo. In general, the one or more biocompatible materials used to form the scaffold/biomaterial is selected to direct, facilitate, or permit the formation of multicellular, three-dimensional, organization of at least one of the cell populations deposited thereon. The one or more biomaterials used to generate the construct may also be selected to direct, facilitate, or permit dispersion and/or integration of the construct or cellular components of the construct with the endogenous host tissue, or to direct, facilitate, or permit the survival, engraftment, tolerance, or functional performance of the construct or cellular components of the construct.

The term "subject" shall mean any single human subject, including a patient, eligible for treatment, who is experiencing or has experienced one or more signs, symptoms, or other indicators of a kidney disease, anemia, or EPO deficiency. Such subjects include without limitation subjects who are newly diagnosed or previously diagnosed and are now experiencing a recurrence or relapse, or are at risk for a kidney disease, anemia, or EPO deficiency, no matter the cause. The subject may have been previously treated for a kidney disease, anemia, or EPO deficiency, or not so treated.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "sample" or "patient sample" or "biological sample" shall generally mean any biological sample obtained from a subject or patient, body fluid, body tissue, cell line, tissue culture, or other source. The term includes tissue biopsies such as, for example, kidney biopsies. The term includes cultured cells such as, for example, cultured mammalian kidney cells. Methods for obtaining tissue biopsies and cultured cells from mammals are well known in the art. If the term "sample" is used alone, it shall still mean that the "sample" is a "biological sample" or "patient sample", i.e., the terms are used interchangeably.

The term "test sample" refers to a sample from a subject that has been treated by a method of the present invention. The test sample may originate from various sources in the mammalian subject including, without limitation, blood, semen, serum, urine, bone marrow, mucosa, tissue, etc.

The term "control" or "control sample" refers a negative or positive control in which a negative or positive result is expected to help correlate a result in the test sample. Controls that are suitable for the present invention include, without limitation, a sample known to exhibit indicators characteristic of normal erythroid homeostasis, a sample known to exhibit indicators characteristic of anemia, a sample obtained from a subject known not to be anemic, and a sample obtained from a subject known to be anemic. Additional controls suitable for use in the methods of the present invention include, without limitation, samples derived from subjects that have been treated with pharmacological agents known to modulate erythropoiesis (e.g., recombinant EPO or EPO analogs). In addition, the control may be a sample obtained from a subject prior to being treated by a method of the present invention. An additional suitable control may be a test sample obtained from a subject known to have any type or stage of kidney disease, and a sample from a subject known not to have any type or stage of kidney disease. A control may be a normal healthy matched control. Those of skill in the art will appreciate other controls suitable for use in the present invention.

Cell populations

The present invention provides isolated, heterogeneous populations of kidney cells, and admixtures thereof, enriched for specific bioactive components or cell types and/or depleted of specific inactive or undesired components or cell types for use in the treatment of kidney disease, i.e., providing stabilization and/or improvement and/or regeneration of kidney function.

Bioactive cell populations

In one aspect, the present invention is based on the surprising finding that certain subfractions of a heterogeneous population of renal cells, enriched for bioactive components and depleted of inactive or undesired components, provide superior therapeutic and regenerative outcomes than the starting population. For example, bioactive components of the invention, e.g., B2, B4, and B3, which are depleted of inactive or undesired components, e.g., B1 and B5, alone or admixed, provide unexpected stabilization and/or improvement and/or regeneration of kidney function. In a preferred embodiment, the bioactive cell population is B2. In certain embodiments, the B2 cell population is admixed with B4. In other embodiments, the B2 cell population is admixed with B3.

The B2 cell population is characterized by expression of a tubular cell marker selected from the group consisting of one or more of the following: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8), and collecting duct marker Aquaporin-4 (Aqp4), being larger and more granulated than B3 and/or B4 and thus having a buoyant density between about 1.045 g/ml and about 1.063 g/ml (rodent), between about 1.045 g/ml and 1.052 g/ml (human), and between about 1.045 g/ml and about 1.058 g/ml (canine).

The B3 cell population is characterized by the expression of vascular, glomerular and proximal tubular markers with some EPO-producing cells, being of an intermediate size and granularity in comparison to B2 and B4, and thus having a buoyant density between about 1.063 g/ml and about 1.073 g/ml (rodent), between about 1.052 g/ml and about 1.063 g/ml (human), and between about 1.058 g/ml and about 1.063 g/ml (canine). B3 is characterized by expression of markers selected from the group consisting of one or more of the following: aquaporin 7 (Aqp7), FXYD domain-containing ion transport regulator 2 (Fxyd2), solute carrier family 17 (sodium phosphate), member 3 (Slc17a3), solute carrier family 3, member 1 (Slc3a1), claudin 2 (Cldn2), napsin A aspartic peptidase (Napsa), solute carrier family 2 (facilitated glucose transporter), member 2 (Slc2a2), alanyl (membrane) aminopeptidase (Anpep), transmembrane protein 27 (Tmem27), acyl-CoA synthetase medium-chain family member 2 (Acsm2), glutathione peroxidase 3 (Gpx3), fructose-1,6-biphosphatase 1 (Fbp1), and alanine-glyoxylate aminotransferase 2 (Agxt2). B3 is also characterized by the vascular expression marker Platelet endothelial cell adhesion molecule (Pecam) and the glomerular expression marker podocin (Podn).

The B4 cell population is characterized by the expression of a vascular marker set containing one or more of the following: PECAM, VEGF, KDR, HIF1α; a glomerular marker set containing one or more of the following: Podocin (Podn), and Nephrin (Neph); and an oxygen-tunable EPO enriched population compared to unfractionated (UNFX), B2 and B3. B4 is also characterized by the expression of one or more of the following markers: chemokine (C—X—C motif) receptor 4 (Cxcr4), endothelin receptor type B (Ednrb), collagen, type V, alpha 2 (Col5a2), Cadherin 5 (Cdh5), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo). B4 is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

Hyaluronic acid production by B2 and B4

Hyaluronan (also called hyaluronic acid or hyaluronate) is a glycosaminoglycan (GAG), which consists of a regular repeating sequence of non-sulfated disaccharide units, specifically N-acetylglucosamine and glucuronic acid. Its molecular weight can range from 400 daltons (the disaccharide) to over a million daltons. It is found in variable amounts in all tissues, such as the skin, cartilage, and eye, and in most if not all fluids in adult animals. It is especially abundant in early embryos. Space created by hyaluronan, and indeed GAGs in general, permit it to play a role in cell migration, cell attachment, during wound repair, organogenesis, immune cell adhesion, activation of intracellular signalling, as well as tumour metastasis. These roles are mediated by specific protein and proteoglycan binding to Hyaluronan. Cell motility and immune cell adhesion is mediated by the cell surface receptor RHAMM (Receptor for Hyaluronan-Mediated Motility; Hardwick et al., 1992) and CD44 (Jalkenan et al., 1987; Miyake et al., 1990). Hyaluronan is synthesized directly at the inner membrane of the cell surface with the growing polymer extruded through the membrane to the outside of the cell as it is being synthesized. Synthesis is mediated by a single protein enzyme, hyaluronan synthetase (HAS) whose gene family consists of at least 3 members.

It has recently been shown that hyaluronic acid interacts with CD44, and such interactions may, among other actions, recruit non-resident cells (such as mesenchymal stem cells (MSCs)) to injured renal tissue and enhance renal regeneration (*Kidney International* (2007) 72, 430-441).

Unexpectedly, it has been found that the B2 and B4 cell preparations are capable of expressing higher molecular weight species of hyaluronic acid (HA) both in vitro and in vivo, through the actions of hyaluronic acid synthase-2 (HAS-2)—a marker that is enriched more specifically in the B2 cell population. Treatment with B2 in a 5/6 Nx model was shown to reduce fibrosis, concomitant with strong expression HAS-2 expression in vivo and the expected production of high-molecular-weight HA within the treated tissue. Notably, the 5/6 Nx model left untreated resulted in fibrosis with limited detection of HAS-2 and little production of high-molecular-weight HA. Without wishing to be bound by theory, it is hypothesized that this anti-inflammatory high-molecular weight species of HA produced predominantly by B2 (and to some degree by B4) acts synergystically with the cell preparations in the reduction of renal fibrosis and in the aid of renal regeneration. Accordingly, the instant invention includes delivery of the cellular prototypes of the invention in a biomaterial comprising hyaluronic acid. Also comtemplated by the instant invention is the provision of a biomaterial component of the regenerative stimulus via direct production or stimulation of production by the implanted cells.

In one aspect, the present invention provides isolated, heterogeneous populations of EPO-producing kidney cells for use in the treatment of kidney disease, anemia and/or EPO deficiency in a subject in need. In one embodiment, the cell populations are derived from a kidney biopsy. In another embodiment, the cell populations are derived from whole kidney tissue. In one other embodiment, the cell populations are derived from in vitro cultures of mammalian kidney cells, established from kidney biopsies or whole kidney tissue. In all embodiments, these populations are unfractionated cell populations, also referred to herein as non-enriched cell populations.

In another aspect, the present invention provides isolated populations of erythropoietin (EPO)-producing kidney cells that are further enriched such that the proportion of EPO-producing cells in the enriched subpopulation is greater relative to the proportion of EPO-producing cells in the starting or initial cell population. In one embodiment, the enriched EPO-producing cell fraction contains a greater proportion of interstitial fibroblasts and a lesser proportion of tubular cells relative to the interstitial fibroblasts and tubular cells contained in the unenriched initial population. In certain embodiments, the enriched EPO-producing cell fraction contains a greater proportion of glomerular cells and vascular cells and a lesser proportion of collecting duct cells relative to the glomerular cells, vascular cells and collecting duct cells contained in the unenriched initial population. In such embodiments, these populations are referred to herein as the "B4" cell population, which In another aspect, the present invention provides an EPO-producing kidney cell population that is admixed with one or more additional kidney cell populations. In one embodiment, the EPO-producing cell population is a first cell population enriched for EPO-producing cells, e.g., B4. In another embodiment, the EPO-producing cell population is a first cell population that is not enriched for EPO-producing cells, e.g., B2. In another embodiment, the first cell population is admixed with a second kidney cell population. In some embodiments, the second cell population is enriched for tubular cells, which may be demonstrated by the presence of a tubular cell phenotype. In another embodiment, the tubular cell phenotype may be indicated by the presence of one tubular cell marker. In another embodiment, the tubular cell phenotype may be indicated by the presence of one or more tubular cell markers. The tubular cell markers include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (S1c9a4), aldehyde dehydrogenase 3 family, member B1 (Aldh3b1), aldehyde dehydrogenase 1 family, member A3 (Aldh1a3), and Calpain-8 (Capn8). In another embodiment, the first cell population is admixed with at least one of several types of kidney cells including, without limitation, interstitium-derived cells, tubular cells, collecting duct-derived cells, glomerulus-derived cells, and/or cells derived from the blood or vasculature.

In one aspect, the EPO-producing kidney cell populations of the present invention are characterized by EPO expression and bioresponsiveness to oxygen, such that a reduction in the oxygen tension of the culture system results in an induction in the expression of EPO. In one embodiment, the EPO-producing cell populations are enriched for EPO-producing cells. In one embodiment, the EPO expression is induced when the cell population is cultured under conditions where the cells are subjected to a reduction in available oxygen levels in the culture system as compared to a cell population cultured at normal atmospheric (~21%) levels of available oxygen. In one embodiment, EPO-producing cells cultured in lower oxygen conditions express greater levels of EPO relative to EPO-producing cells cultured at normal oxygen conditions. In general, the culturing of cells at reduced levels of available oxygen (also referred to as hypoxic culture conditions) means that the level of reduced oxygen is reduced relative to the culturing of cells at normal atmospheric levels of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen.

In one other embodiment, the induction or increased expression of EPO is obtained and can be observed by culturing cells at about less than 5% available oxygen and comparing EPO expression levels to cells cultured at atmospheric (about 21%) oxygen. In another embodiment, the induction of EPO is obtained in a culture of cells capable of expressing EPO by a method that includes a first culture phase in which the culture of cells is cultivated at atmospheric oxygen (about 21%) for some period of time and a second culture phase in which the available oxygen levels are reduced and the same cells are cultured at about less than 5% available oxygen. In another embodiment, the EPO expression that is responsive to hypoxic conditions is regulated by HIF1α. Those of ordinary skill in the art will appreciate that other oxygen manipulation culture conditions known in the art may be used for the cells described herein.

In one aspect, the enriched populations of EPO-producing mammalian cells are characterized by bio-responsiveness (e.g., EPO expression) to perfusion conditions. In one embodiment, the perfusion conditions include transient, intermittent, or continuous fluid flow (perfusion). In one embodiment, the EPO expression is mechanically-induced when the media in which the cells are cultured is intermittently or continuously circulated or agitated in such a manner that dynamic forces are transferred to the cells via the flow. In one embodiment, the cells subjected to the transient, intermittent, or continuous fluid flow are cultured in such a manner that they are present as three-dimensional structures in or on a material that provides framework and/or space for such three-dimensional structures to form. In one embodiment, the cells are cultured on porous beads and subjected to intermittent or continuous fluid flow by means of a rocking platform, orbiting platform, or spinner flask. In another embodiment, the cells are cultured on three-dimensional scaffolding and placed into a device whereby the scaffold is stationary and fluid flows directionally through or across the scaffolding. Those of ordinary skill in the art will appreciate that other perfusion culture conditions known in the art may be used for the cells described herein.

Inactive cell populations

As described herein, the present invention is based, in part, on the surprising finding that certain subfractions of a heterogeneous population of renal cells, enriched for bioactive components and depleted of inactive or undesired components, provide superior therapeutic and regenerative outcomes than the starting population. In preferred embodiments, the cellular populations of the instant invention are depleted of B1 and/or B5 cell populations.

The B1 cell population comprises large, granular cells of the collecting duct and tubular system, with the cells of the population having a buoyant density less than about 1.045 g/m. The B5 cell population is comprised of debris and small cells of low granularity and viability and having a buoyant density greater than about 1.091 g/ml.

Methods of Isolating and Culturing Cell Populations

The present invention, in one aspect, provides methods for separating and isolating renal cellular components, e.g., enriched cell populations, for therapeutic use, including the treatment of kidney disease, anemia, EPO deficiency, tubular transport deficiency, and glomerular filtration deficiency. In one embodiment, the cell populations are isolated from freshly digested, i.e., mechanically or enzymatically digested, kidney tissue or from heterogeneous in vitro cultures of mammalian kidney cells.

It has unexpectedly been discovered that culturing heterogeneous mixtures of renal cells in hypoxic culture conditions prior to separation on a density gradient provides for enhanced distribution and composition of cells in both B4 and B2 fractions. The enrichment of oxygen-dependent cells in B4 from B2 was observed for renal cells isolated from both diseased and non-diseased kidneys. Without wishing to be bound by theory, this may be due to one or more of the following phenomena: 1) selective survival, death, or proliferation of specific cellular components during the hypoxic culture period; 2) alterations in cell granularity and/or size in response to the hypoxic culture, thereby effecting alterations in buoyant density and subsequent localization during density gradient separation; and 3) alterations in cell gene/protein expression in response to the hypoxic culture period, thereby resulting in differential characteristics of the cells within any given fraction of the gradient. Thus, in one embodiment, the cell populations enriched for tubular cells, e.g., B2, are hypoxia-resistant.

Exemplary techniques for separating and isolating the cell populations of the invention include separation on a density gradient based on the differential specific gravity of different cell types contained within the population of interest. The specific gravity of any given cell type can be influenced by the degree of granularity within the cells, the intracellular volume of water, and other factors. In one aspect, the present invention provides optimal gradient conditions for isolation of the cell preparations of the instant invention, e.g., B2 and B4, across multiple species including, but not limited to, human, canine, and rodent. In a preferred embodiment, a density gradient is used to obtain a novel enriched population of tubular cells fraction, i.e., B2 cell population, derived from a heterogeneous population of renal cells. In one embodiment, a density gradient is used to obtain a novel enriched population of EPO-producing cells fraction, i.e., B4 cell population, derived from a heterogeneous population of renal cells. In other embodiments, a density gradient is used to obtain enriched subpopulations of tubular cells, glomerular cells, and endothelial cells of the kidney. In one embodiment, both the EPO-producing and the tubular cells are separated from the red blood cells and cellular debris. In one embodiment, the EPO-producing, glomerular, and vascular cells are separated from other cell types and from red blood cells and cellular debris, while a subpopulation of tubular cells and collecting duct cells are concomitantly separated from other cell types and from red blood cells and cellular debris.

The instant invention generated the novel cell populations by using, in part, the OPTIPREP® (Axis-Shield) density gradient medium, comprising 60% nonionic iodinated compound iodixanol in water, based on certain key features described below. One of skill in the art, however, will recognize that any density gradient or other means, e.g., immunological separation using cell surface markers known in the art, comprising necessary features for isolating the cell populations of the instant invention may be used in accordance with the invention. It should also be recognized by one skilled in the art that the same cellular features that contribute to separation of cellular subpopulations via density gradients (size and granularity) can be exploited to separate cellular subpopulations via flow cytometry (forward scatter=a reflection of size via flow cytometry, and side scatter=a reflection of granularity). Importantly, the density gradient medium should have low toxicity towards the specific cells of interest. While the density gradient medium should have low toxicity toward the specific cells of interest, the instant invention contemplates the use of gradient mediums which play a role in the selection process of the cells of interest. Without wishing to be bound by theory, it appears that the cell populations of the instant invention recovered by the gradient comprising iodixanol are iodixanol-resistant, as there is an appreciable loss of cells between the loading and recovery steps, suggesting that exposure to iodixanol under the conditions of the gradient leads to elimination of certain cells. The cells appearing in the specific bands after the iodixanol gradient are resistant to any untoward effects of iodixanol and/or density gradient exposure. Accordingly, the present invention also contemplates the use of additional contrast medias which are mild to moderate nephrotoxins in the isolation and/or selection of the cell populations of the instant invention. In addition, the density gradient medium should also not bind to proteins in human plasma or adversely affect key functions of the cells of interest.

In another aspect, the present invention provides methods of three-dimensional culturing of the renal cell populations. In one aspect, the present invention provides methods of culturing the cell populations via continuous perfusion. In one embodiment, the cell populations cultured via three-dimensional culturing and continuous perfusion demonstrate greater cellularity and interconnectivity when compared to cell populations cultured statically. In another embodiment, the cell populations cultured via three dimensional culturing and continuous perfusion demonstrate greater expression of EPO, as well as enhanced expression of renal tubule-associate genes such as e-cadherin when compared to static cultures of such cell populations.

In yet another embodiment, the cell populations cultured via continuous perfusion demonstrate greater levels of glucose and glutamine consumption when compared to cell populations cultured statically.

Those of ordinary skill in the art will appreciate that other methods of isolation and culturing known in the art may be used for the cells described herein.

Biomaterials (Polymeric Matrices or Scaffolds)

As described in Bertram et al. U.S. Published Application 20070276507 (incorporated herein by reference in its entirety), polymeric matrices or scaffolds may be shaped into any number of desirable configurations to satisfy any number of overall system, geometry or space restrictions. In one embodiment, the matrices or scaffolds of the present invention may be three-dimensional and shaped to conform to the dimensions and shapes of an organ or tissue structure. For example, in the use of the polymeric scaffold for treating kidney disease, anemia, EPO deficiency, tubular transport deficiency, or glomerular filtration deficiency, a three-dimensional (3-D) matrix may be used. A variety of differently shaped 3-D scaffolds may be used. Naturally, the polymeric matrix may be shaped in different sizes and shapes to conform to differently sized patients. The polymeric matrix may also be shaped in other ways to accommodate the special needs of the patient. In another embodiment, the polymeric matrix or scaffold may be a biocompatible, porous polymeric scaffold. The scaffolds may be formed from a variety of synthetic or naturally-occurring materials including, but not limited to, open-cell polylactic acid (OPLA®), cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, collagens, laminins, fibronectin, silk, elastin, alginate, hyaluronic acid, agarose, or copolymers or physical blends thereof. Scaffolding configurations may range from liquid hydrogel suspensions to soft porous scaffolds to rigid, shape-holding porous scaffolds.

Hydrogels may be formed from a variety of polymeric materials and are useful in a variety of biomedical applications. Hydrogels can be described physically as three-dimensional networks of hydrophilic polymers. Depending on the type of hydrogel, they contain varying percentages of water, but altogether do not dissolve in water. Despite their high water content, hydrogels are capable of additionally binding great volumes of liquid due to the presence of hydrophilic residues. Hydrogels swell extensively without changing their gelatinous structure. The basic physical features of hydrogel can be specifically modified, according to the properties of the polymers used and the additional special equipments of the products.

Preferably, the hydrogel is made of a polymer, a biologically derived material, a synthetically derived material or combinations thereof, that is biologically inert and physiologically compatible with mammalian tissues. The hydrogel material preferably does not induce an inflammatory response. Examples of other materials which can be used to form a hydrogel include (a) modified alginates, (b) polysaccharides (e.g. gellan cum and carrageenans) which gel by exposure to monovalent cations, (c) polysaccharides (e.g., hyaluronic acid) that are very viscous liquids or are thixotropic and form a gel over time by the slow evolution of structure, and (d) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention.

Scaffolding or biomaterial characteristics may enable cells to attach and interact with the scaffolding or biomaterial material, and/or may provide porous spaces into which cells can be entrapped. In one embodiment, the porous scaffolds or biomaterials of the present invention allow for the addition or deposition of one or more populations or admixtures of cells on a biomaterial configured as a porous scaffold (e.g., by attachment of the cells) and/or within the pores of the scaffold (e.g., by entrapment of the cells). In another embodiment, the scaffolds or biomaterials allow or promote for cell:cell and/or cell:biomaterial interactions within the scaffold to form constructs as described herein.

In one embodiment, the biomaterial used in accordance with the present invention is comprised of hyaluronic acid (HA) in hydrogel form, containing HA molecules ranging in size from 5.1 kDA to $>2\times10^6$ kDa. In another embodiment, the biomaterial used in accordance with the present invention is comprised of hyaluronic acid in porous foam form, also containing HA molecules ranging in size from 5.1 kDA to $>2\times10^6$ kDa. In yet another embodiment, the biomaterial used in accordance with the present invention is comprised of a poly-lactic acid (PLA)-based foam, having an open-cell structure and pore size of about 50 microns to about 300 microns. In yet another embodiment, the specific cell populations, preferentially B2 but also B4, provide directly and/or stimulate synthesis of high molecular weight Hyaluronic Acid through Hyaluronic Acid Synthase-2 (HAS-2), especially after intra-renal implantation.

Those of ordinary skill in the art will appreciate that other types of synthetic or naturally-occurring materials known in the art may be used to form scaffolds as described herein.

In one aspect, the present invention provides constructs as described herein made from the above-referenced scaffolds or biomaterials.

Constructs

In one aspect, the invention provides implantable constructs having one or more of the cell populations described herein for the treatment of kidney disease, anemia, or EPO deficiency in a subject in need. In one embodiment, the construct is made up of a biocompatible material or biomaterial, scaffold or matrix composed of one or more synthetic or naturally-occurring biocompatible materials and one or more cell populations or admixtures of cells described herein deposited on or embedded in a surface of the scaffold by attachment and/or entrapment. In certain embodiments, the construct is made up of a biomaterial and one or more cell populations or admixtures of cells described herein coated with, deposited on, deposited in, attached to, entrapped in, embedded in, or combined with the biomaterial component(s). In another embodiment, the deposited cell population or cellular component of the construct is a first kidney cell population enriched for oxygen-tunable EPO-producing cells. In another embodiment, the first kidney cell population contains glomerular and vascular cells in addition to the oxygen-tunable EPO-producing cells. In one other embodiment, the deposited cell population or cellular component(s) of the construct includes both the first enriched renal cell population and a second renal cell population. In some embodiments, the second cell population is not enriched for oxygen-tunable EPO producing cells. In another embodiment, the second cell population is enriched for renal tubular cells. In another embodiment, the second cell population is enriched for renal tubular cells and contains collecting duct epithelial cells. In other embodiments, the renal tubular cells are characterized by the expression of one or more tubular cell markers that may include, without limitation, megalin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (S1c9a4), aldehyde dehydrogenase 3 family, member B1 (Aldh3b1), aldehyde dehydrogenase 1 family, member A3 (Aldh1a3), and Calpain-8 (Capn8).

In one embodiment, the cell populations deposited on or combined with biomaterials or scaffolds to form constructs of the present invention are derived from a variety of sources, such as autologous, allogeneic, or syngeneic (autogeneic or isogeneic) sources.

Those of ordinary skill in the art will appreciate there are several suitable methods for depositing or otherwise combining cell populations with biomaterials to form a construct.

In one aspect, the constructs of the present invention are suitable for use in the methods of use described herein. In one embodiment, the constructs are suitable for administration to a subject in need of treatment for a kidney disease of any etiology, anemia, or EPO deficiency of any etiology. In other embodiments, the constructs are suitable for administration to a subject in need of an improvement in or restoration of erythroid homeostasis. In another embodiment, the constructs are suitable for administration to a subject in need of improved kidney function.

Methods of use

In one aspect, the present invention provides methods for the treatment of a kidney disease, anemia, or EPO deficiency in a subject in need with the kidney cell populations and admixtures of kidney cells described herein. In one embodiment, the method comprises administering to the subject a composition that includes a first kidney cell population enriched for EPO-producing cells. In another embodiment, the first cell population is enriched for EPO-producing cells, glomerular cells, and vascular cells. In another embodiment, the composition may further include one or more additional kidney cell populations. In one embodiment, the additional cell population is a second cell population not enriched for EPO-producing cells. In another embodiment, the additional cell population is a second cell population not enriched for EPO-producing cells, glomerular cells, or vascular cells. In another embodiment, the composition also includes a kidney cell population or admixture of kidney cells deposited in, deposited on, embedded in, coated with, or entrapped in a biomaterial to form an implantable construct, as described herein, for the treatment of a disease or disorder described herein. In one embodiment, the cell populations are used alone or in combination with other cells or biomaterials, e.g., hydrogels, porous scaffolds, or native or synthetic peptides or proteins, to stimulate regeneration in acute or chronic disease states.

In another aspect, the effective treatment of a kidney disease, anemia, or EPO deficiency in a subject by the methods of the present invention can be observed through various indicators of erythropoiesis and/or kidney function. In one embodiment, the indicators of erythroid homeostasis include, without limitation, hematocrit (HCT), hemoglobin (HB), mean corpuscular hemoglobin (MCH), red blood cell count (RBC), reticulocyte number, reticulocyte %, mean corpuscular volume (MCV), and red blood cell distribution width (RDW). In one other embodiment, the indicators of kidney function include, without limitation, serum albumin, albumin to globulin ratio (A/G ratio), serum phosphorous, serum sodium, kidney size (measurable by ultrasound), serum calcium, phosphorous:calcium ratio, serum potassium, proteinuria, urine creatinine, serum creatinine, blood nitrogen urea (BUN), cholesterol levels, triglyceride levels and glomerular filtration rate (GFR). Furthermore, several indicators of general health and well-being include, without limitation, weight gain or loss, survival, blood pressure (mean systemic blood pressure, diastolic blood pressure, or systolic blood pressure), and physical endurance performance.

In another embodiment, an effective treatment is evidenced by stabilization of one or more indicators of kidney function. The stabilization of kidney function is demonstrated by the observation of a change in an indicator in a subject treated by a method of the present invention as compared to the same indicator in a subject that has not been treated by a method of the present invention. Alternatively, the stabilization of kidney function may be demonstrated by the observation of a change in an indicator in a subject treated by a method of the present invention as compared to the same indicator in the same subject prior to treatment. The change in the first indicator may be an increase or a decrease in value. In one embodiment, the treatment provided by the present invention may include stabilization of blood urea nitrogen (BUN) levels in a subject where the BUN levels observed in the subject are lower as compared to a subject with a similar disease state who has not been treated by the methods of the present invention. In one other embodiment, the treatment may include stabilization of serum creatinine levels in a subject where the serum creatinine levels observed in the subject are lower as compared to a subject with a similar disease state who has not been treated by the methods of the present invention. In another embodiment, the treatment may include stabilization of hematocrit (HCT) levels in a subject where the HCT levels observed in the subject are higher as compared to a subject with a similar disease state who has not been treated by the methods of the present invention. In another embodiment, the treatment may include stabilization of red blood cell (RBC) levels in a subject where the RBC levels observed in the subject are higher as compared to a subject with a similar disease state who has not been treated by the methods of the present invention. Those of ordinary skill in the art will appreciate that one or more additional indicators described herein or known in the art may be measured to determine the effective treatment of a kidney disease in the subject.

In another aspect, the present invention concerns a method of providing erythroid homeostasis in a subject in need. In one embodiment, the method includes the step of (a) administering to the subject a renal cell population, e.g., B2 or B4, or admixture of renal cells, e.g., B2/B4 and/or B2/B3, as described herein; and (b) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject. In another embodiment, the method includes the step of (a) administering to the subject a composition comprising a renal cell population or admixture of renal cells as described herein; and (b) determining, in a biological sample from the subject, that the level of an erythropoiesis indicator is different relative to the indicator level in a control, wherein the difference in indicator level (i) indicates the subject is responsive to the administering step (s), or (ii) is indicative of erythroid homeostasis in the subject. In another embodiment, the method includes the step of (a) providing a biomaterial or biocompatible polymeric scaffold; (b) depositing a renal cell population or admixture of renal cells of the present invention on or within the biomaterial or scaffold in a manner described herein to form an implantable construct; (c) implanting the construct into the subject; and (d) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject.

In another aspect, the present invention concerns a method of providing both stabilization of kidney function and restoration of erythroid homeostasis to a subject in need, said subject having both a deficit in kidney function and an anemia and/or EPO-deficiency. In one embodiment, the method includes the step of administering a renal cell population or admixture of renal cells as described herein that contain at least one of the following cell types: tubular-derived cells, glomerulus-derived cells, insterstitium-derived cells, collecting duct-derived cells, stromal tissue-derived cells, or cells derived from the vasculature. In another embodiment, the population or admixture contains both EPO-producing cells and tubular epithelial cells, the tubular cells having been identified by at least one of the following markers: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In this embodiment, treatment of the subject would be demonstrated by an improvement in at least one indicator of kidney function concomitant with improvement in at least one indicator of erythropoiesis, compared to either an untreated subject or to the subject's pre-treatment indicators.

In one aspect, the present invention provides methods of (i) treating a kidney disease, anemia, or an EPO-deficiency; (ii) stabilizing kidney function, (iii) restoring erythroid homeostasis, or (iv) any combination of thereof by administering a renal cell population enriched for EPO-producing cells or admixture of renal cells containing a cell population enriched for EPO-producing cells as described herein, wherein the beneficial effects of the administration are greater than the effects of administering a cell population not enriched for EPO-producing cells. In another embodiment, the enriched cell population provides an improved level of serum blood urea nitrogen (BUN). In another embodiment, the enriched cell population provides an improved retention of protein in the serum. In another embodiment, the enriched cell population provides improved levels of serum cholesterol and/or triglycerides. In another embodiment, the enriched cell population provides an improved level of Vitamin D. In one embodiment, the enriched cell population provides an improved phosphorus:calcium ratio as compared to a non-enriched cell population. In another embodiment, the enriched cell population provides an improved level of hemoglobin as compared to a non-enriched cell population. In a further embodiment, the enriched cell population provides an improved level of serum creatinine as compared to a non-enriched cell population. In yet another embodiment, the enriched cell population provides an improved level of hematocrit as compared to a non-enriched cell population. In a further embodiment, the enriched cell population provides an improved level of red blood cell number (RBC#) as compared to a non-enriched cell population. In one embodiment, the improved level of hematocrit is restored to 95% normal healthy level. In a further embodiment, the enriched cell population provides an improved reticulocyte number as compared to a non-enriched cell population. In other embodiments, the enriched cell population provides an improved reticulocyte percentage as compared to a non-enriched cell population. In yet other embodiments, the enriched cell population provides an improved level of red blood cell volume distribution width (RDW) as compared to a non-enriched cell population. In yet another embodiment, the enriched cell population provides an improved level of hemoglobin as compared to a non-enriched cell population. In yet another embodiment, the enriched cell population provides an erythroietic response in the bone marrow, such that the marrow cellularity is near-normal and the myeloid:erythroid ratio is near normal.

In another aspect, the present invention provides methods of (i) treating a kidney disease, anemia, or an EPO-deficiency; (ii) stabilizing kidney function, (iii) restoring erythroid homeostasis, or (iv) any combination of thereof by administering an enriched cell population, wherein the beneficial effects of administering a renal cell population or admixture of renal cell populations described herein are characterized by improved erythroid homeostasis when compared to the beneficial effects provided by the administering of recombinant EPO (rEPO). In one embodiment, the population or admixture, when administered to a subject in need provides improved erythroid homeostasis (as determined by hematocrit, hemoglobin, or RBC#) when compared to the administration of recombinant EPO protein. In one embodiment, the population or admixture, when administered provides an improved level of hematocrit, RBC, or hemoglobin as compared to recombinant EPO, being no greater than about 10% lower or higher than hematocrit in a control. In a further embodiment, a single dose or delivery of the population or admixture, when administered provides improvement in erythroid homeostasis (as determined by increase in hematocrit, hemoglobin, or RBC#) in the treated subject for a period of time that significantly exceeds the period of time that a single dose or delivery of the recombinant EPO protein provides improvement in erythroid homeostasis. In another embodiment, the population or admixture, when administered at a dose described herein does not result in hematocrit, hemoglobin, or RBC# greater than about 110% of normal levels in matched healthy controls. In a further embodiment, the population or admixture, when administered at a dose described herein provides superior erythroid homeostasis (as determined by hematocrit, hemoglobin, or RBC#) compared to recombinant EPO protein delivered at a dose described herein. In another embodiment, the recombinant EPO is delivered at a dose of about 100 IU/kg, about 200 IU/kg, about 300 IU/kg, about 400 IU/kg, or about 500 IU/kg. Those of ordinary skill in the art will appreciate that other dosages of recombinant EPO known in the art may be suitable.

Another embodiment of the present invention is directed to the use of at least one cell populations described herein, or an implantable construct described herein, for the preparation of a medicament useful in the treatment of a kidney disease, anemia, or EPO deficiency in a subject in need, the providing of erythroid homeostasis in a subject in need, or the improvement of kidney function in a subject in need.

Another embodiment of the present invention is directed to the use of specific enriched cell population(s) (described herein) for the treatement of a kidney disease of a specific etiology, based on selection of specific cell subpopulation(s) based on specific verified therapeutic attributes.

Methods and Routes of Administration

The cell preparations of the instant invention can be administered alone or in combination with other bioactive components.

The therapeutically effective amount of the renal cell populations or admixtures of renal cell populations described herein can range from the maximum number of cells that is safely received by the subject to the minimum number of cells necessary for treatment of kidney disease, e.g., stabilization, reduced rate-of-decline, or improvement of one or more kidney functions. In certain embodiments, the methods of the present invention provide the administration of renal cell populations or admixtures of renal cell populations described herein at a dosage of about 10,000 cells/kg, about 20,000 cells/kg, about 30,000 cells/kg, about 40,000 cells/kg, about 50,000 cells/kg, about 100,000 cells/kg, about 200,000 cells/kg, about 300,000 cells/kg, about 400,000 cells/kg, about 500,000 cells/kg, about 600,000 cells/kg, about 700,000 cells/kg, about 800,000 cells/kg, about 900,000 cells/kg, about $1.1 \times 10^6$ cells/kg, about $1.2 \times 10^6$ cells/kg, about $1.3 \times 10^6$ cells/kg, about $1.4 \times 10^6$ cells/kg, about $1.5 \times 10^6$ cells/kg, about $1.6 \times 10^6$ cells/kg, about $1.7 \times 10^6$ cells/kg, about $1.8 \times 10^6$ cells/kg, about $1.9 \times 10^6$ cells/kg, about $2.1 \times 10^6$ cells/kg, about $2.1 \times 10^6$ cells/kg, about $1.2 \times 10^6$ cells/kg, about $2.3 \times 10^6$ cells/kg, about $2.4 \times 10^6$ cells/kg, about $2.5 \times 10^6$ cells/kg, about $2.6 \times 10^6$ cells/kg, about $2.7 \times 10^6$ cells/kg, about $2.8 \times 10^6$ cells/kg, about $2.9 \times 10^6$ cells/kg, about $3 \times 10^6$ cells/kg, about $3.1 \times 10^6$ cells/kg, about $3.2 \times 10^6$ cells/kg, about $3.3 \times 10^6$ cells/kg, about $3.4 \times 10^6$ cells/kg, about $3.5 \times 10^6$ cells/kg, about $3.6 \times 10^6$ cells/kg, about $3.7 \times 10^6$ cells/kg, about $3.8 \times 10^6$ cells/kg, about $3.9 \times 10^6$ cells/kg, about $4 \times 10^6$ cells/kg, about $4.1 \times 10^6$ cells/kg, about $4.2 \times 10^6$ cells/kg, about $4.3 \times 10^6$ cells/kg, about $4.4 \times 10^6$ cells/kg, about $4.5 \times 10^6$ cells/kg, about $4.6 \times 10^6$ cells/kg, about $4.7 \times 10^6$ cells/kg, about $4.8 \times 10^6$ cells/kg, about $4.9 \times 10^6$ cells/kg, or about $5 \times 10^6$ cells/kg. In another embodiment, the dosage of cells to a subject may be a single dosage or a single dosage plus additional dosages. In other embodiments, the dosages may be provided by way of a construct as described herein. In other embodiments, the dosage of cells to a subject may be calculated based on the estimated renal mass or functional renal mass.

The therapeutically effective amount of the renal cell populations or admixtures thereof described herein can be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration. Accordingly, the invention provides a use of renal cell populations or admixtures thereof, for example, the B2 cell population alone or admixed with the B3 and/or B4 cell population, for the manufacture of a medicament to treat kidney disease in a subject. In some embodiments, the medicament further comprises recombinant polypeptides, such as growth factors, chemokines or cytokines. In further embodiments, the medicaments comprise a human kidney-derived cell population. The cells used to manufacture the medicaments can be isolated, derived, or enriched using any of the variations provided for the methods described herein.

The renal cell preparation(s), or admixtures thereof, or compositions are formulated in accordance with routine procedures as a pharmaceutical composition adapted for administration to human beings. Typically, compositions for intravenous administration, intra-arterial administration or administration within the kidney capsule, for example, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (see, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

One aspect of the invention further provides a pharmaceutical formulation, comprising a renal cell preparation of the invention, for example, the B2 cell preparation alone or incombination with the B3 and/or B4 cell preparation, and a pharmaceutically acceptable carrier. In some embodiments, the formulation comprises from $10^4$ to $10^9$ mammalian kidney-derived cells.

In one aspect, the present invention provides methods of providing one or more of the cell populations described herein, including admixtures, to a subject in need. In one embodiment, the source of the cell population(s) may be autologous or allogeneic, syngeneic (autogeneic or isogeneic), and any combination thereof. In instances where the source is not autologous, the methods may include the administration of an immunosuppressant agent. Suitable immunosuppressant drugs include, without limitation, azathioprine, cyclophosphamide, mizoribine, ciclosporin, tacrolimus hydrate, chlorambucil, lobenzarit disodium, auranofin, alprostadil, gusperimus hydrochloride, biosynsorb, muromonab, alefacept, pentostatin, daclizumab, sirolimus, mycophenolate mofetil, leflonomide, basiliximab, dornase α, bindarid, cladribine, pimecrolimus, ilodecakin, cedelizumab, efalizumab, everolimus, anisperimus, gavilimomab, faralimomab, clofarabine, rapamycin, siplizumab, saireito, LDP-03, CD4, SR-43551, SK&F-106615, IDEC-114, IDEC-131, FTY-720, TSK-204, LF-080299, A-86281, A-802715, GVH-313, HMR-1279, ZD-7349, IPL-423323, CBP-1011, MT-1345, CNI-1493, CBP-2011, J-695, LJP-920, L-732531, ABX-RB2, AP-1903, IDPS, BMS-205820, BMS-224818, CTLA4-1g, ER-49890, ER-38925, ISAtx-247, RDP-58, PNU-156804, LJP-1082, TMC-95A, TV-4710, PTR-262-MG, and AGI-1096 (see U.S. Pat. No. 7,563,822). Those of ordinary skill in the art will appreciate other suitable immunosuppressant drugs.

The treatment methods of the subject invention involve the delivery of an isolated renal cell population, or admixture thereof, into individuals. In one embodiment, direct administration of cells to the site of intended benefit is preferred. In one embodiment, the cell preparations, or admixtures thereof, of the instant invention are delivered to an individual in a delivery vehicle.

A variety of means for administering cells to subjects will, in view of this specification, be apparent to those of skill in the art. Such methods include injection of the cells into a target site in a subject. Cells can be inserted into a delivery device or vehicle, which facilitates introduction by injection or implantation into the subjects. In certain embodiments, the delivery vehicle can include natural materials. In certain other embodiments, the delivery vehicle can include synthetic materials. In one embodiment, the delivery vehicle provides a structure to mimic or appropriately fit into the organ's architecture. In other embodiments, the delivery vehicle is fluid-like in nature. Such delivery devices can include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In a some embodiments, mammalian kidney-derived cell populations are formulated for administration into a blood vessel via a catheter (where the term "catheter" is intended to include any of the various tube-like systems for delivery of substances to a blood vessel). Alternatively, the cells can be inserted into or onto a biomaterial or scaffold, including but not limited to textiles, such as weaves, knits, braids, meshes, and non-wovens, perforated films, sponges and foams, and beads, such as solid or porous beads, microparticles, nanoparticles, and the like. The cells can be prepared for delivery in a variety of different forms. For example, the cells can be suspended in a solution or gel. Cells can be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. One of skill in the art will appreciate that the delivery vehicle used in the delivery of the cell populations and admixtures thereof of the instant invention can include combinations of the above-mentioned characteristics.

Modes of administration of the isolated renal cell population(s), for example, the B2 cell population alone or admixed with B4 and/or B3, include, but are not limited to, systemic, intra-renal (e.g., parenchymal), intravenous or intra-arterial injection and injection directly into the tissue at the intended site of activity. Additional modes of administration to be used in accordance with the present invention include single or multiple injection(s) via direct laparotomy, via direct laparoscopy, transabdominal, or percutaneous. Still yet additional modes of administration to be used in accordance with the present invention include, for example, retrograde and ureteropelvic infusion. Surgical means of administration include one-step procedures such as, but not limited to, partial nephrectomy and construct implantation, partial nephrectomy, partial pyelectomy, vascularization with omentum±peritoneum, multifocal biopsy needle tracks, cone or pyramidal, to cylinder, and renal pole-like replacement, as well as two-step procedures including, for example, organoid-internal bioreactor for replanting. In one embodiment, the admixtures of cells are delivered via the same route at the same time. In another embodiment, each of the cell compositions comprising the controlled admixture are delivered separately to specific locations or via specific methodologies, either simultaneously or in a temporally-controlled manner, by one or more of the methods described herein.

The appropriate cell implantation dosage in humans can be determined from existing information relating to either the activity of the cells, for example EPO production, or extrapolated from dosing studies conducted in preclinical studies. From in vitro culture and in vivo animal experiments, the amount of cells can be quantified and used in calculating an appropriate dosage of implanted material. Additionally, the patient can be monitored to determine if additional implantation can be made or implanted material reduced accordingly.

One or more other components can be added to the cell populations and admixtures thereof of the instant invention, including selected extracellular matrix components, such as one or more types of collagen or hyaluronic acid known in the art, and/or growth factors, platelet-rich plasma and drugs.

All patents, patent applications, and literature references cited in the present specification are hereby incorporated by reference in their entirety.

The following examples are offered for illustrative purposes only, and are not intended to limit the scope of the present invention in any way.

EXAMPLES

Example 1

Isolation and Characterization of Bioresponsive Renal Cells from Adult Pig with Renal Failure A case of idiopathic progressive chronic kidney disease (CKD) with anemia in an adult male swine (*Sus scrofa*) provided fresh diseased kidney tissue for the assessment of cellular composition and characterization with direct comparison to age-matched normal swine kidney tissue.

Histological examination of the kidney tissue at the time of harvest confirmed renal disease characterized by severe diffuse chronic interstitial fibrosis and crescentic glomerulonephritis with multifocal fibrosis. Clinical chemistry confirmed azotemia (elevation of blood urea nitrogen and serum creatinine), and mild anemia (mild reduction in hematocrit and depressed hemoglobin levels). Cells were isolated, expanded, and characterized from both diseased and normal kidney tissue.

Figure 1:
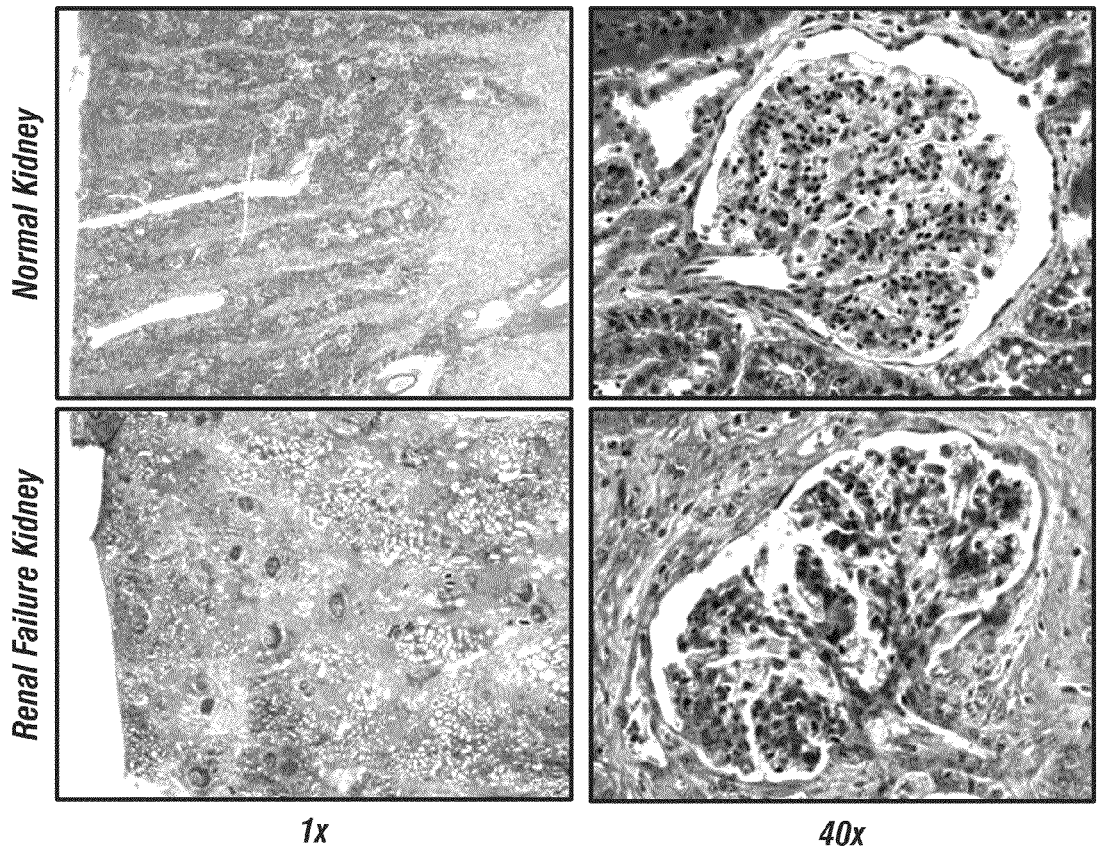
FIG. 1 shows a Gomori's Trichrome stain highlighting the fibrosis in the diseased kidney tissue compared to the normal kidney tissue.

FIG. 1 shows a Gomori's Trichrome stain highlighting the fibrosis (blue staining indicated by arrows) in the diseased kidney tissue compared to the normal kidney tissue. Functional tubular cells, expressing cubulin:megalin and capable of receptor-mediated albumin transport, were propagated from both normal and diseased kidney tissue. Erythropoietin (EPO)-expressing cells were also present in the cultures and were retained through multiple passages and freeze/thaw cycles. Furthermore, molecular analyses confirmed that the EPO-expressing cells from both normal and diseased tissue responded to hypoxic conditions in vitro with HIF1α-driven induction of EPO and other hypoxia-regulated gene targets, including vEGF.

Figure 2:
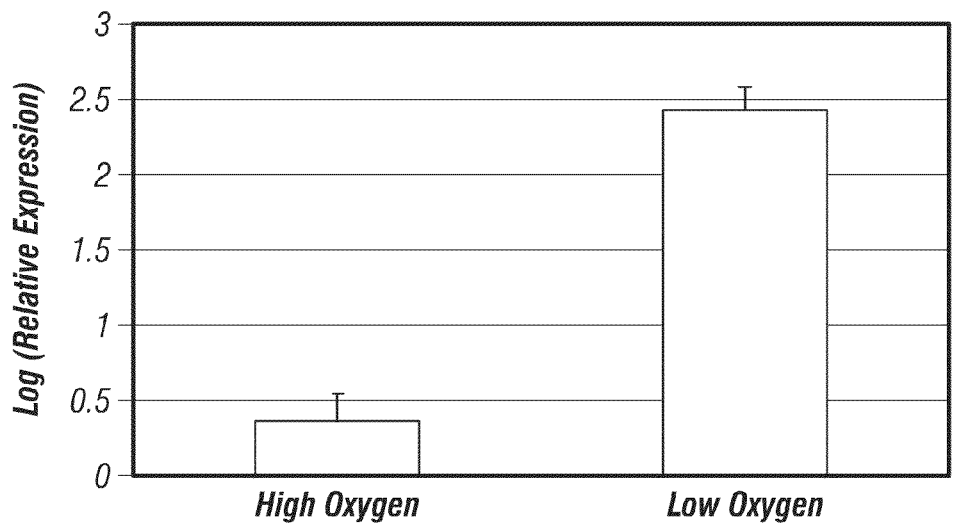
FIG. 2 demonstrates the oxygen-regulated expression of the erythropoietin gene in cells from a pig with chronic kidney disease.

Cells were isolated from the porcine kidney tissue via enzymatic digestion with collagenase+dispase, and were also isolated in separate experiments by performing simple mechanical digestion and explant culture. At passage two, explant-derived cell cultures containing epo-expressing cells were subjected to both atmospheric (21%) and varying hypoxic (<5%) culture conditions to determine whether exposure to hypoxia culminated in upregulation of EPO gene expression. As noted with rodent cultures (see Example 3), the normal pig displayed oxygen-dependent expression and regulation of the EPO gene. Surprisingly, despite the uremic/anemic state of the CKD pig (Hematocrit<34, Creatinine>9.0) EPO expressing cells were easily isolated and propagated from the tissue and expression of the EPO gene remained hypoxia regulated, as shown in FIG. 2.

Figure 3:
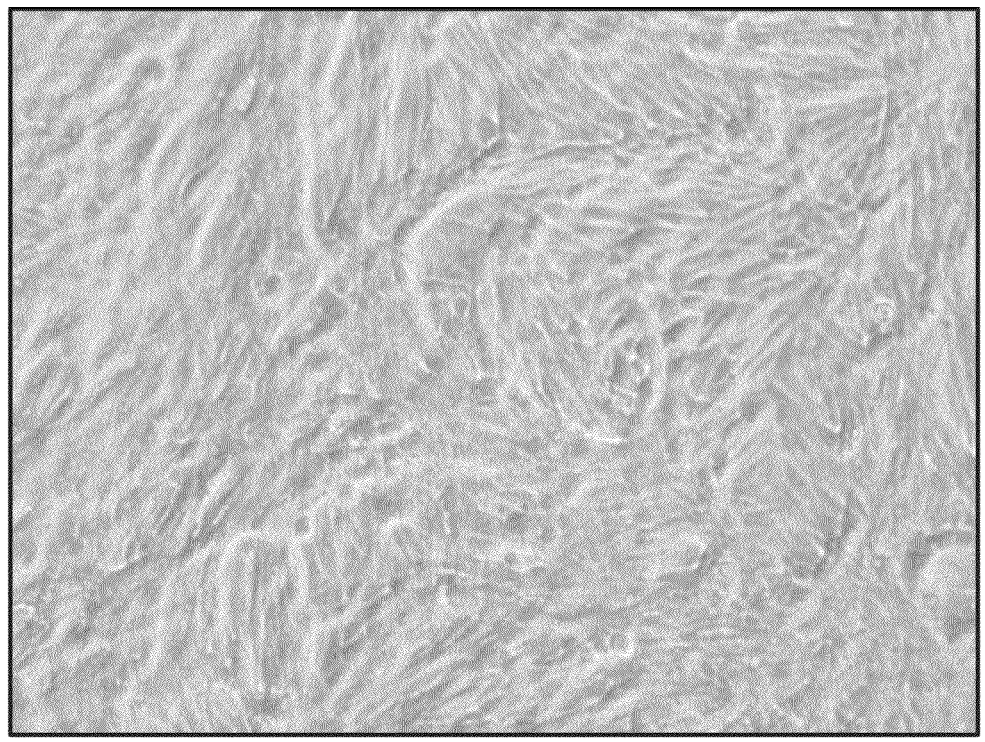
FIG. 3 depicts tubule-like structures in propagated cultures.

As shown in FIG. 3, cells in the propagated cultures demonstrated the ability to self-organize into tubule-like structures.

Figure 4:
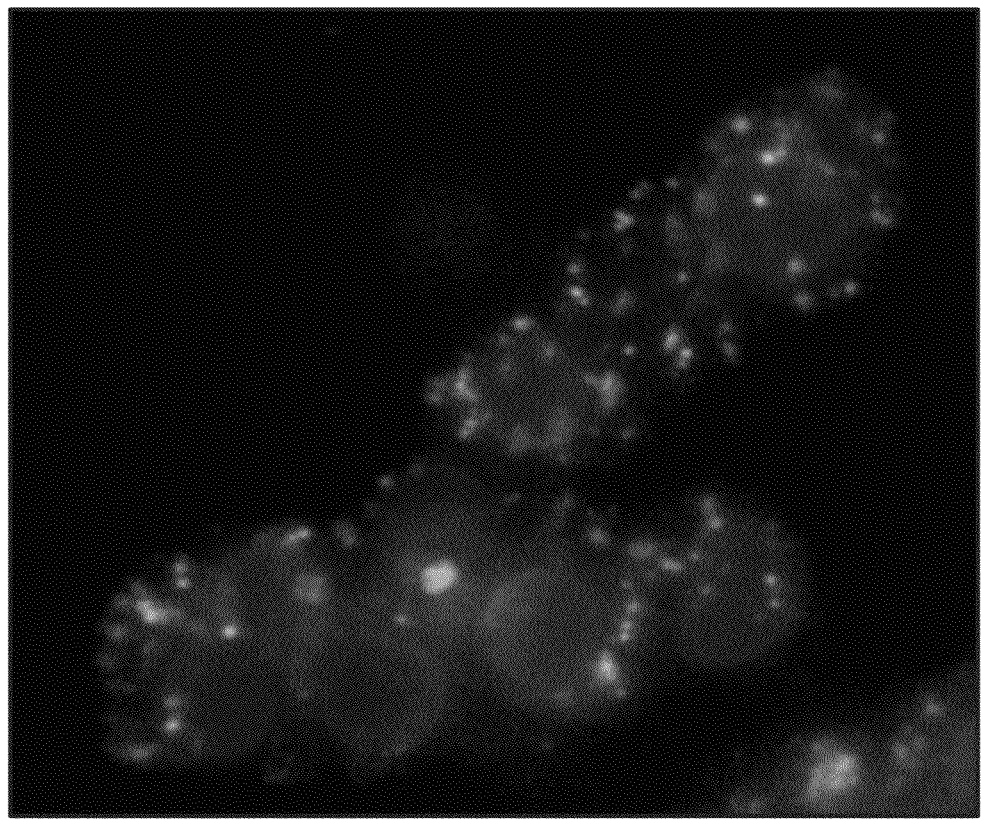
FIG. 4 depicts receptor-mediated uptake of albumin by cultured functional tubular cells.

As shown in FIG. 4, the presence of functional tubular cells in the culture (at passage 3) was confirmed by observing receptor-mediated uptake of FITC-conjugated Albumin by the cultured cells. The green dots (indicated by thin white arrows) represent endocytosed fluorescein-conjugated albumin which is mediated by tubular cell-specific receptors, Megalin and Cubilin, indicating protein reabosroption by functional tubular cells. The blue staining (indicated by thick white arrows) is Hoescht-stained nuclei.

Taken together, these data suggest that functional tubular and endocrine cells can be isolated and propagated from porcine renal tissues, even in renal tissues that have been severely compromised with CKD. Furthermore, these findings support the advancement of autologous cell-based therapeutic products for the treatment of CKD.

Example 2

Isolation of Bioresponsive EPO Cells from Human Kidney

Figure 5:
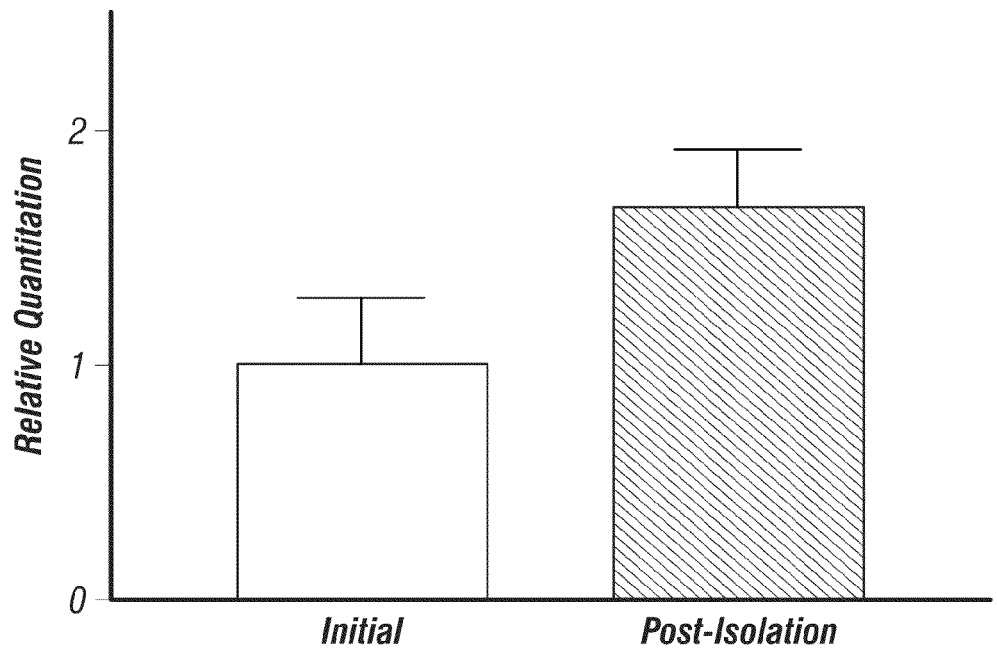
FIG. 5 shows more relative EPO expression after isolation than in the initial human kidney tissue.
Figure 6:
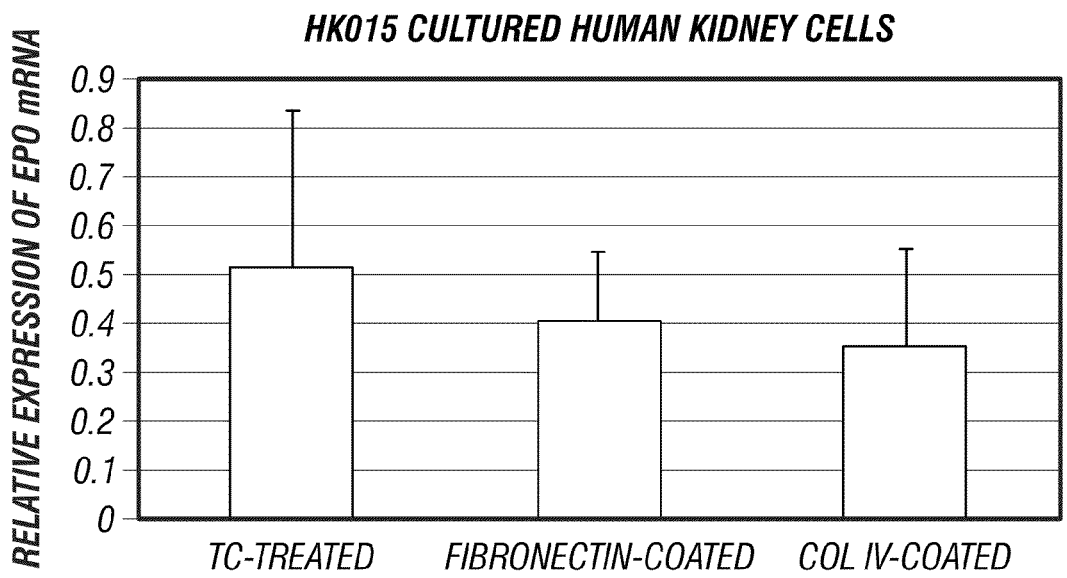
FIG. 6 demonstrates the retention of EPO gene expression in cultured cells from human kidney.

EPO-producing cells were isolated enzymatically from normal adult human kidney (as described above in Example 1). As shown in FIG. 5, the isolation procedure resulted in more relative EPO expression after isolation than in the initial tissue. As shown in FIG. 6, it is possible to maintain the human EPO producing cells in culture with retention of EPO gene expression. Human cells were cultured/propagated on plain tissue-culture treated plastic or plastic that had been coated with some extracellular matrix, such as, for instance, fibronectin or collagen, and all were found to support EPO expression over time.

Example 3

Culture of Bioresponsive EPO-Expressing and Tubular Cells from Rodent Kidney

This study analyzed in vitro EPO expression and tubular marker expression in response to hypoxia and shear forces using primary kidney cells isolated from Lewis rats.

Primary kidney cells were isolated from Lewis rats using standard methods adapted from mouse (Aboushwareb et al., 2008. World J. Urol. August; 26(4):295-300), and propagated in low vs. high oxygen or static vs. dynamic 3D culture.

The oxygen-dependency of Epo-producing cells was determined by culturing cells under atmospheric "normoxic" culture conditions (37° C. incubator equilibrated to 21% O2, 5% CO2) and then lowering the oxygen-tension to hypoxic culture (37° C. incubator equilibrated to 2% O2, 5% CO2) in order to activate low-oxygen-dependent gene transcription of Epo. A final switch back to normoxic conditions would inhibit the gene transcription that occurred under hypoxic conditions. Primary kidney cells were cultured on both 2-dimensional (2D) plates and 3D (see Cultisphere example below) constructs under normoxic conditions in order to allow the cells to attach (generally 48 hours). Attached cells were then moved to a low-oxygen incubator and allowed to culture over a period of 48 hours. After the final 48 hour hypoxic culture timepoint, cells were moved back to normoxic culture. Cells from three plate replicates were harvested for each specified timepoint under the initial normoxic culture, followed by hypoxic culture and for the final switch back to normoxic culture. Harvested samples were snap-frozen in liquid nitrogen, stored at −80° C. prior to analysis. Gene expression analysis was performed by isolating total mRNA from each replicate, cDNA synthesis from total mRNA, and real-time quantitative per (qrtpcr) was used to determine the relative gene expression. In addition to 3 plate replicates, 2 technical replicates were analyzed by qrtpcr to give a total of 6 replicates per timepoint of each culture condition.

Cultisphere-S gelatin microcarrier beads

Primary kidney cells isolated from juvenile rats using standard methods. Approximately 200,000 cells were placed in culture with 200 µl of a 50% (v/v) slurry of sterile Cultisphere-S (Sigma-Aldrich cat # M9043) gelatin macroporous microcarrier beads (130-380 µm) on low attachment 6-well plates. The cells were placed in either a 2% or 21% oxygen chamber under static conditions (the plates containing the cells did not undergo any movement throughout the course of the experiment) or under dynamic (constant movement) conditions. Samples were collected from each condition periodically over the time-course of the study (7 days). Three samples were collected from each condition per day. Gene expression for all samples was normalized to starting material, the unfractionated cell suspension of primary cells from the initial isolation. QRTPCR was performed to examine expression of tubular and endocrine cell markers, E-Cadherin and EPO, respectively.

Figure 7:
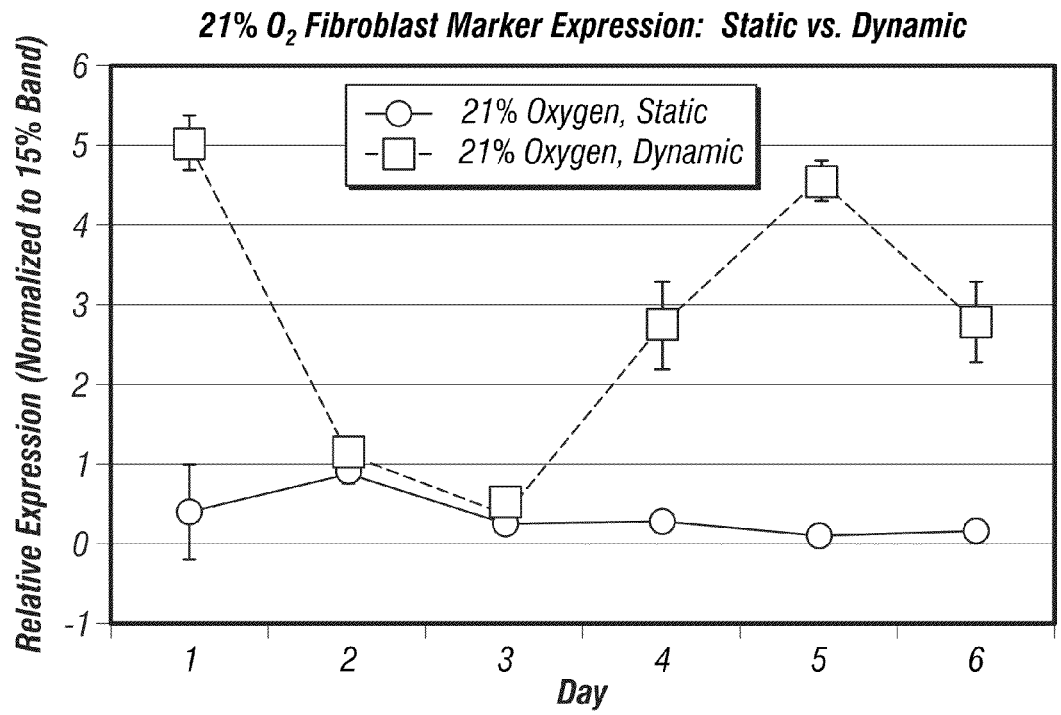
FIG. 7 depicts the results of dynamic cultured (+) EPO Expression in 3D at atmospheric (21%) oxygen levels.
Figure 8:
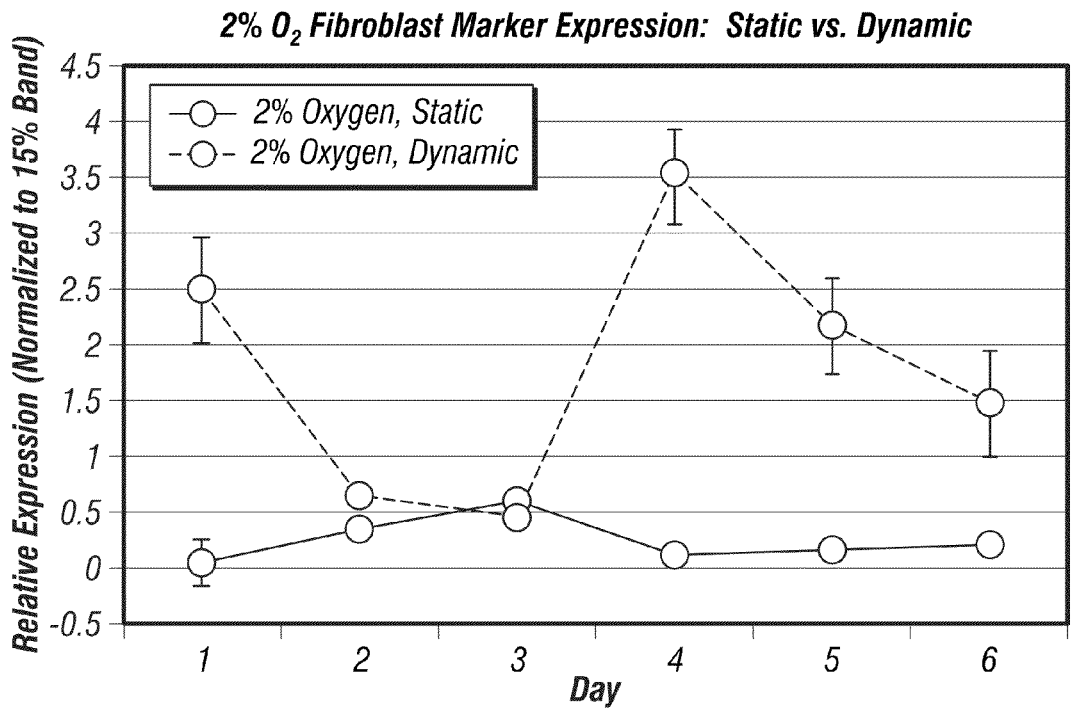
FIG. 8 shows dynamic cultured (+) EPO expression in 3D at low (2%) oxygen levels.
Figure 9:
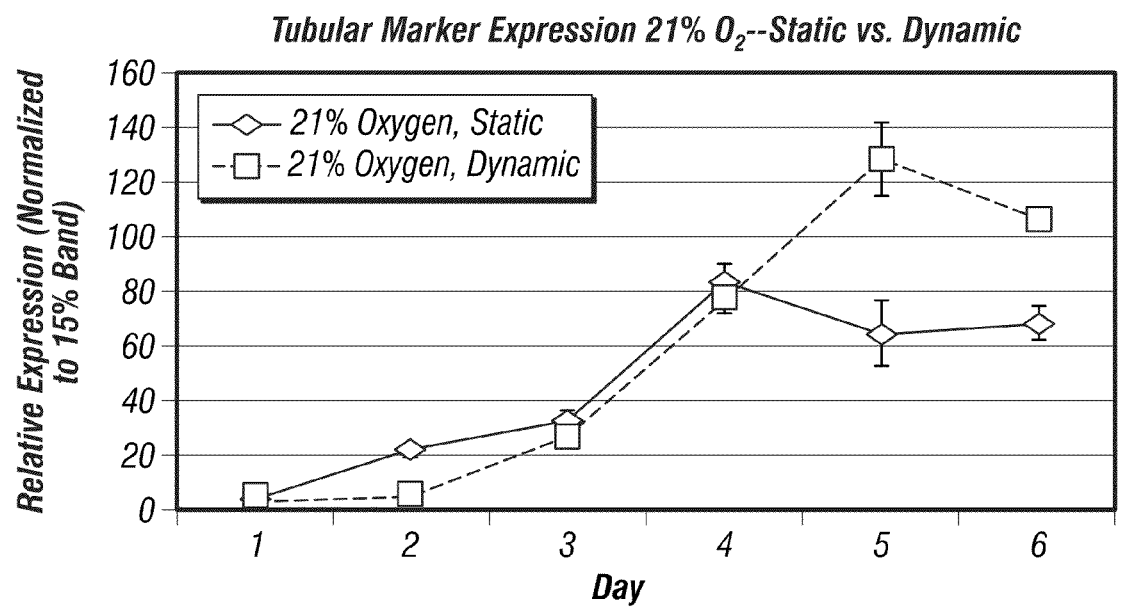
FIG. 9 depicts dynamic cultured (+) tubular gene expression in prolonged culture.
Figure 10:
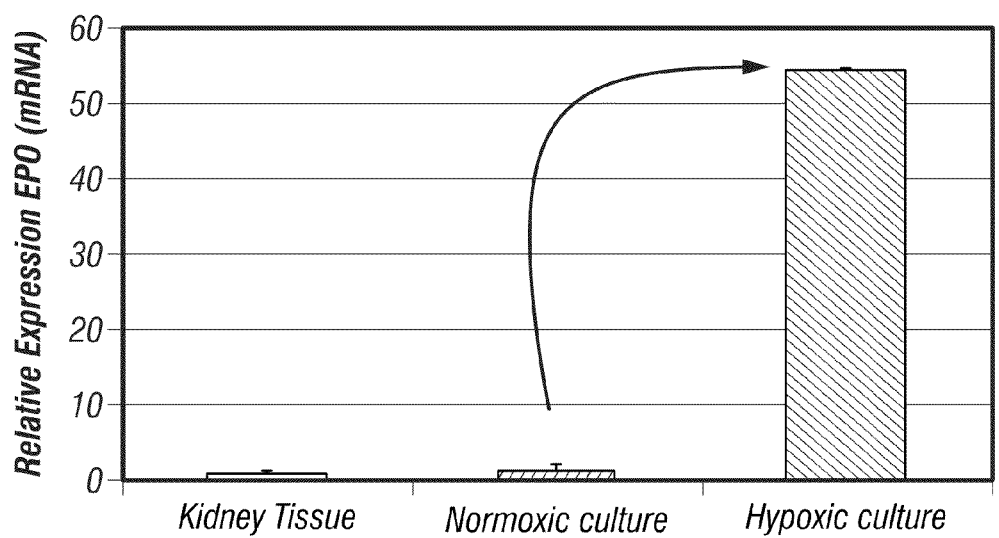
FIG. 10 shows EPO expression in hypoxic culture versus normoxic culture.
Figure 11:
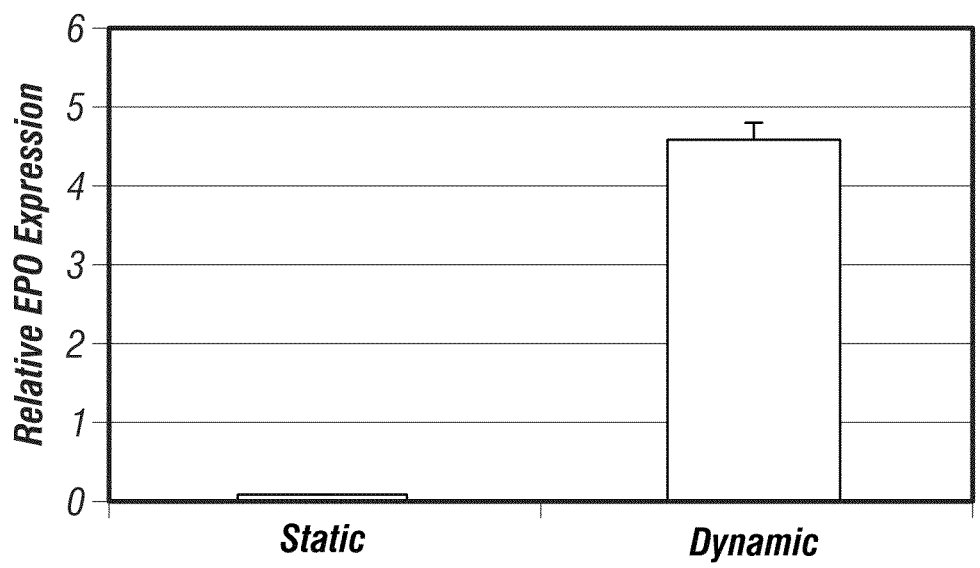
FIG. 11 depicts stimulation of EPO expression by dynamic 3D culture in vitro.

Results: EPO expression in the cultured endocrine cells was upregulated by dynamic culture, as opposed to static culture, and/or hypoxia. The results of dynamic cultured (+) EPO Expression in 3D at atmospheric (21%) oxygen levels are shown in FIG. 7. FIG. 8 depicts dynamic cultured (+) EPO expression in 3D at low (2%) oxygen levels. FIG. 9 shows dynamic culture also (+) tubular gene expression in prolonged culture. Both low oxygen and dynamic 3D culture significantly ($p<0.05$) increased EPO expression relative to high oxygen and static culture, respectively. FIG. 10 shows EPO expression in hypoxic culture versus normoxic culture. FIG. 11 shows stimulation of EPO expression by dynamic 3D culture in vitro. Increased expression of EPO was always accompanied by increased expression of its regulator, HIF1α, and other HIF1α target genes, such as VEGF. Thus, it is clear that EPO expression in cultured neo-kidney cells was regulated by oxygen levels via HIF1α. The above results show that bioresponsive primary rodent kidney cells retaining oxygen and mechanically-transduced regulation of EPO expression can be isolated and propagated in vitro.

Example 4

3D Constructs And Comparative Cultures

To determine the best in vitro indication of in vivo functionality, such as therapeutic potential, of neo-tissue/neo-organ configurations comprising cells, scaffold and media, a number of three-dimensional culture configurations were designed. The neo-tissue/neo-organ configurations were designed as follows: Primary renal cell cultures (containing both epo-producing cells and renal tubular cells) were seeded onto porous cylindrical scaffolds with a diameter of 5 mm and a height of 5 mm. Cells were seeded at a density of 500K to 1 million cells/scaffold and cultured in a prototype multiwell perfusion system (MPS, BD Technologies) that provided continuous unidirectional fluid flow throughout the experiment. Media was comprised of either DMEM+10% FBS (media A) or a 1:1 mixture of DMEM+10% FBS and KSFM medias (media B). Scaffolds evaluated in these experiments included open-cell polylactic acid (OPLA) and collagen 1 scaffolds (both from BD), and poly-glycolic-acid-based scaffolds (PGA) fabricated using standard methodology.

Characteristics included: pore size and structure sufficient to allow fluid to flow through the cell-scaffold composite; scaffold architecture and composition that provides microenvironment permissive for cell-scaffold and cell-cell interactions; presence of cells that express and/or produce and/or transport, or possess the potential to express and produce and/or transport proteins and/or molecules involved in kidney regeneration and/or homeostasis.

For example, a preferred 3D scaffold, composed of open-cell polylactic acid (OPLA), was seeded with mammalian kidney cells and subjected to in vitro culture in a bioreactor apparatus that provides continuous perfusion of culture media throughout the scaffold. In vitro-conditioned scaffold+ cells composite was characterized by the following: presence of viable, metabolically-active cells; cell-cell and cell-material interactions; expression of kidney tubular markers, including, but not limited to, megalin, gamma-glutamyl-transpeptidase (GGT), E-cadherin, and N-cadherin; and expression of kidney endocrine markers, including, but not limited to, erythropoietin.

Figure 12A:
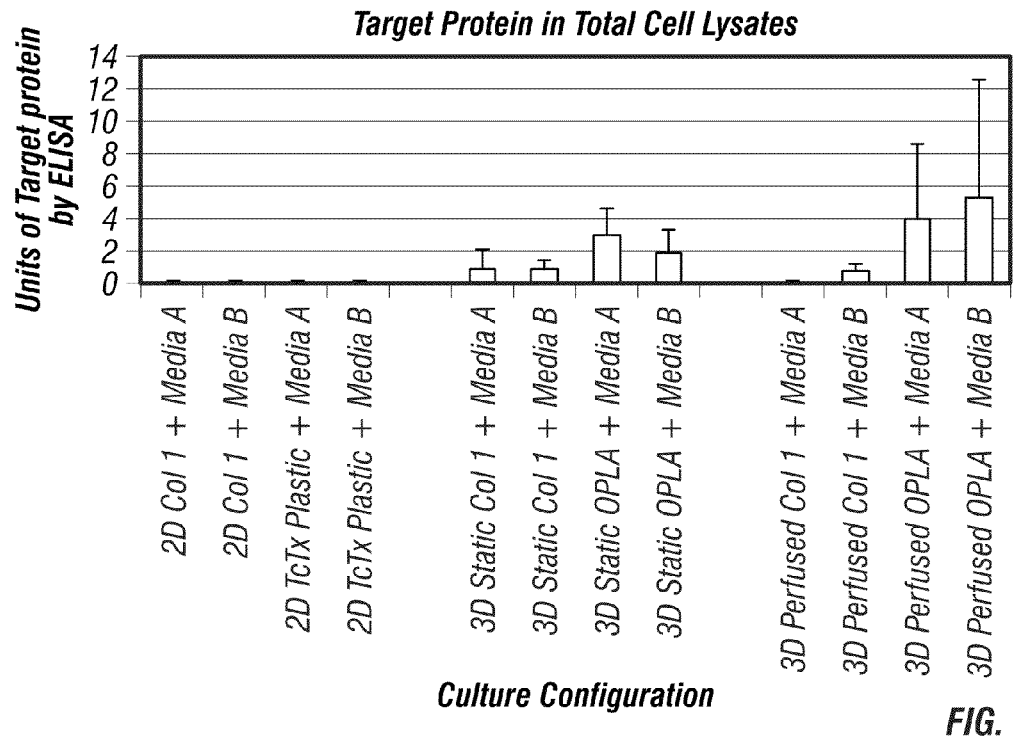
FIG. 12A-B depicts ELISA results of quantitated target protein in both cell lysates (upper panel) and conditioned media (lower panel) collected from 2D and 3D cultures.
Figure 12B:
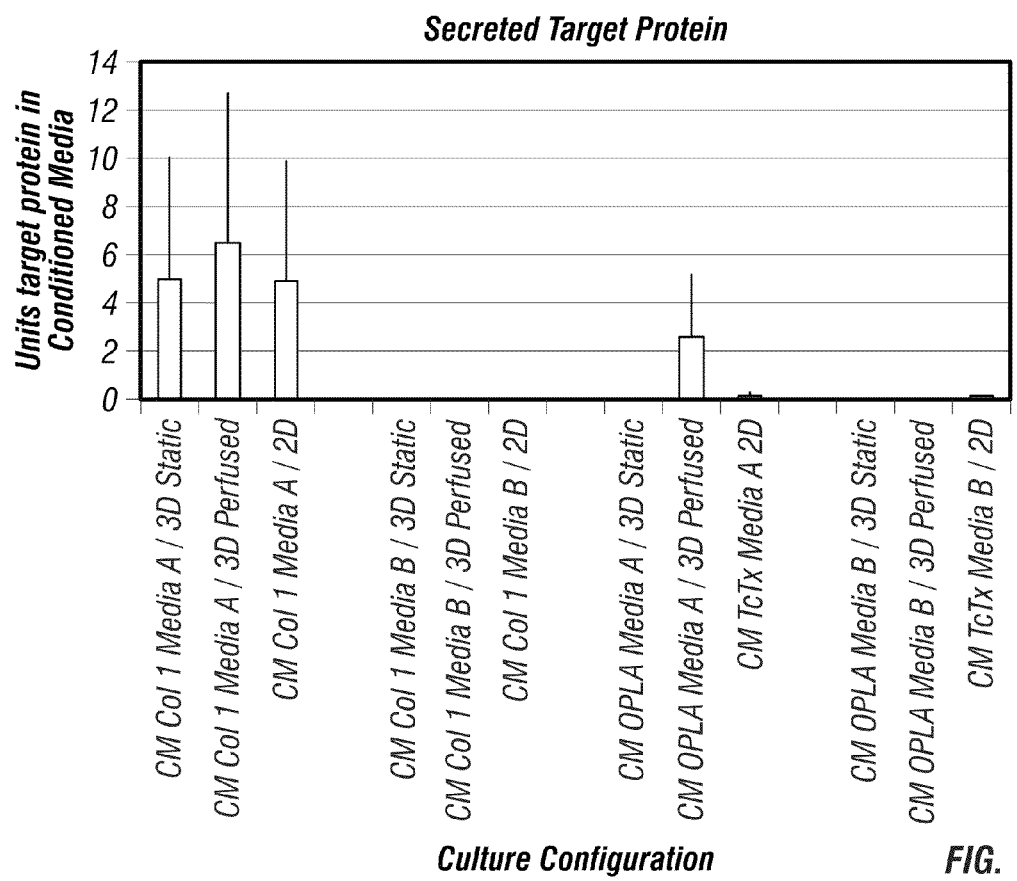

Results: Conditioned media and total protein lysates were collected from 2D and 3D cultures as indicated. ELISA analysis was performed to quantitate target protein in both cell lysates (upper panel of FIG. 12) and conditioned media (lower panel of FIG. 12).

Figure 13:
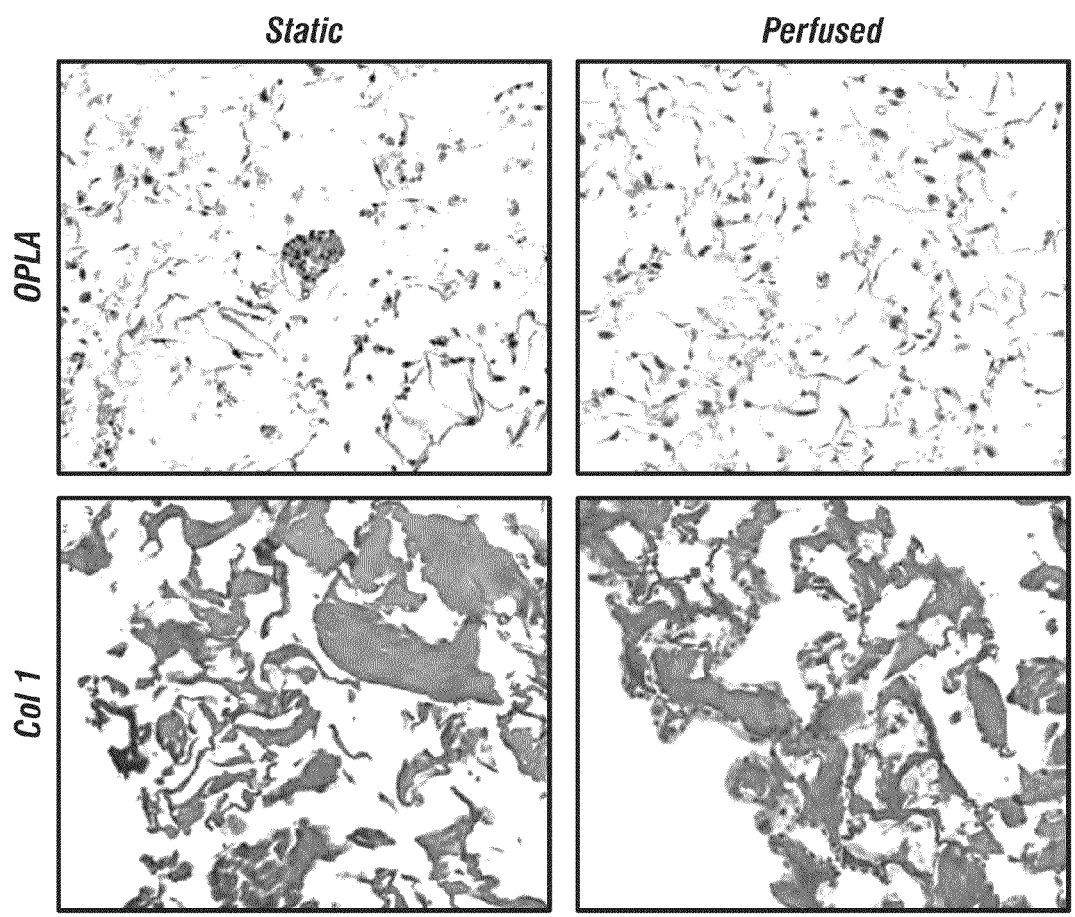
FIG. 13 shows H&E stained seeded OPLA and Col1 scaffolds (stained after (7) days of perfused or static culture), which were fixed in 10% buffered formalin and paraffin-embedded using standard techniques. H&E staining was performed to examine presence of cells and morphology. The cellularity was greater in the perfused vs. static scaffolds, more notably in the Col1 scaffolds compared to the OPLA scaffolds. More striking was the cellular organization present in the perfused Col1 scaffolds compared to the static Col1 scaffolds.
Figure 14A:
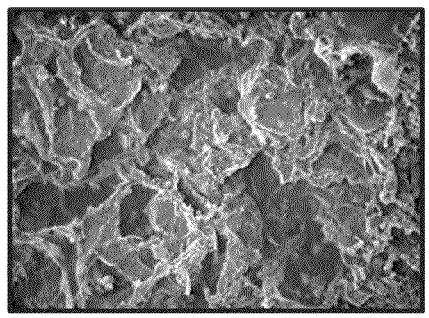
FIG. 14A-H depicts SEM of OPLA and Col1 scaffolds after (7) days of culture (static and perfused). Note the greater cellularity in the perfused vs. static, as well as the superior cellular organization and interconnectivity in the Col1 perfused vs. static conditions.
Figure 14B:
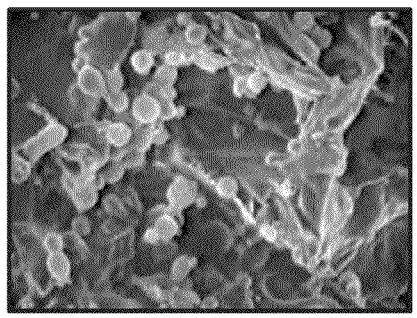
Figure 14C:
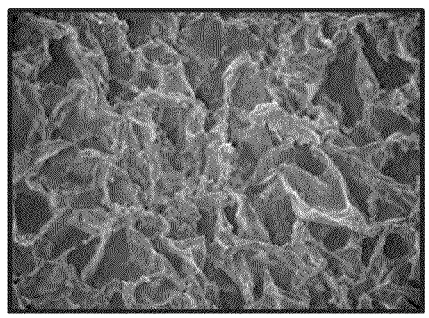
Figure 14D:
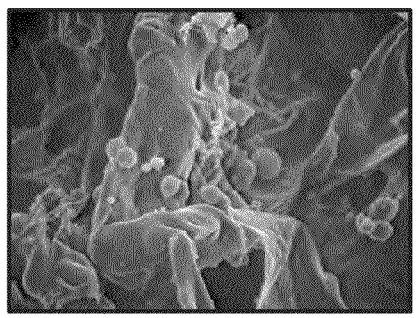
Figure 14E:
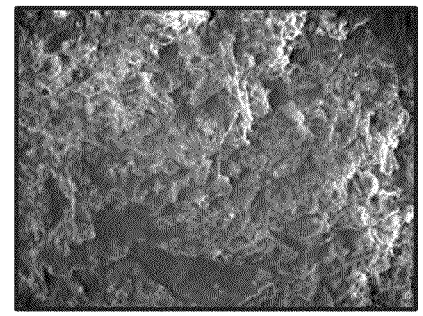
Figure 14F:
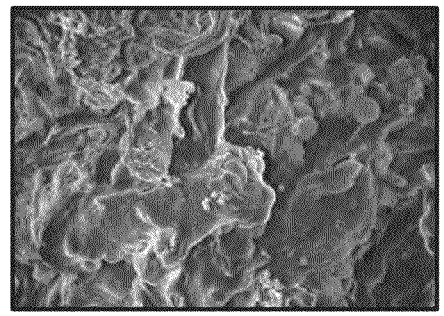
Figure 14G:
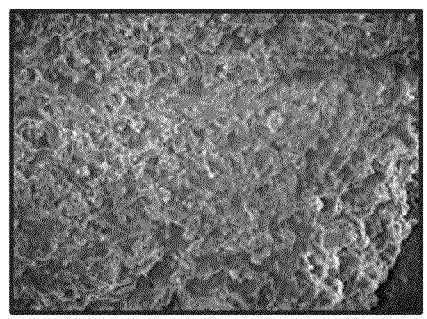
Figure 14H:
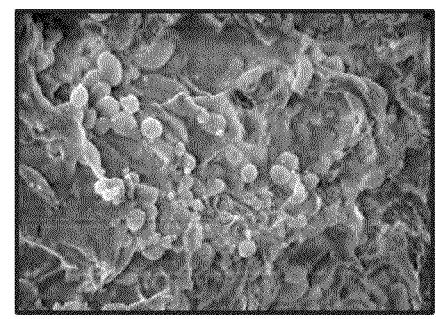

After seven days of perfused or static culture, seeded OPLA and Col1 scaffolds were fixed in 10% buffered formalin and paraffin-embedded using standard techniques. Hematoxylin and eosin (H&E) staining was performed to examine the presence of cells and morphology. The cellularity was greater in the perfused vs. static scaffolds, with the distribution of cells throughout the scaffold more notable in the OPLA scaffolds compared to the Col1 scaffolds (see FIG. 13).

FIG. 14 shows the results of scanning electron microscope (SEM) images of OPLA and Col1 scaffolds after seven days of culture (static and perfused). Perfused cultures showed greater cellularity and cellular organization as compared to static cultures.

mRNA was isolated from scaffolds or 2D cultures by the addition of lysis buffer (Qiagen) and from 3D scaffolds by electric homogenization (polytron) in lysis buffer. Purified mRNA subjected to RT-PCR analysis with intron-spanning primers specific for the target gene of interest showed that 3/7 of the 3D configurations examined exhibited expression of the target gene, i.e., EPO, over 5 days in culture.

Figure 15:
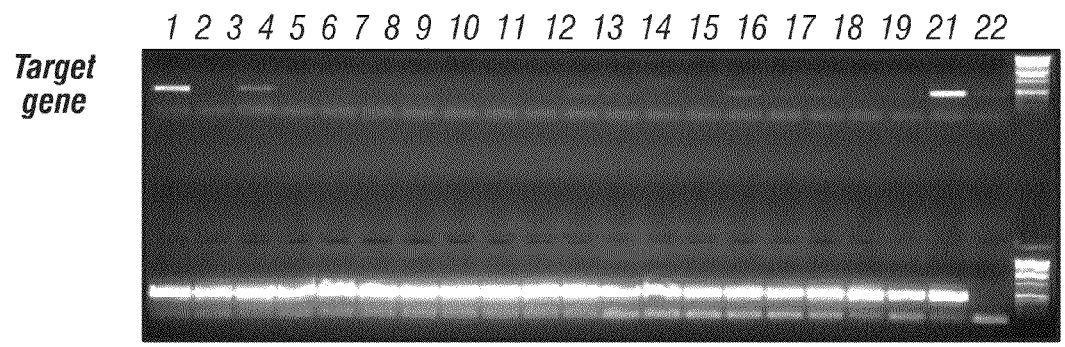
FIG. 15 shows RT-PCR results of mRNA isolated from scaffolds or 2D cultures by the addition of lysis buffer (Qiagen). In the case of 3D scaffolds, electric homogenization (polytron) was utilized to insure complete lysis and liberation of RNA. Purified mRNA was subjected to RT-PCR analysis with intron-spanning primers specific for target gene of interest. (Lanes 1-7: Various 3D configurations (perfused)/5 days culture; Lanes 8-10: Various 2D configurations/ 5 days culture; Lanes 11-17: Various initial cell populations (prior to seeding); Lanes 18-19: 2D cultures/4 days culture; Lane 21: Macrodissected fresh tissue).

In contrast, the 2D configurations (lanes 8-10 of FIG. 15) had no detectable target gene mRNA at 5 days. Lane 1 of FIG. 15 represents a 3D configuration that achieves expression levels in 5 days approaching the levels seen in the macrodissected fresh tissue known to express the target gene (lane 21).

Figure 16:
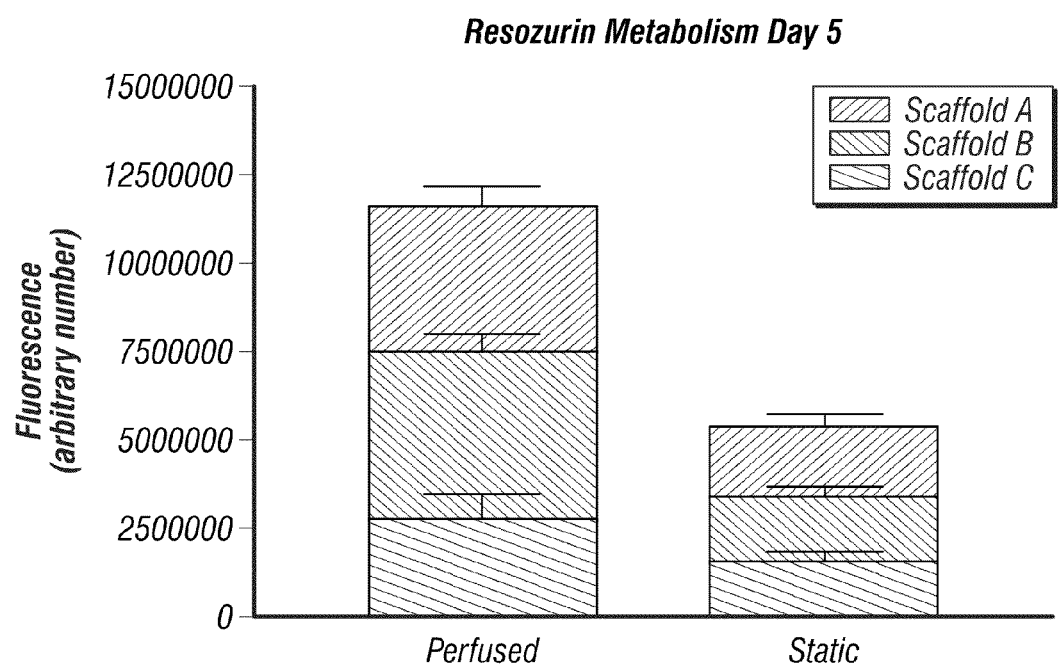
FIG. 16 depicts metabolic activity in three different seeded scaffolds.
Figure 17A:
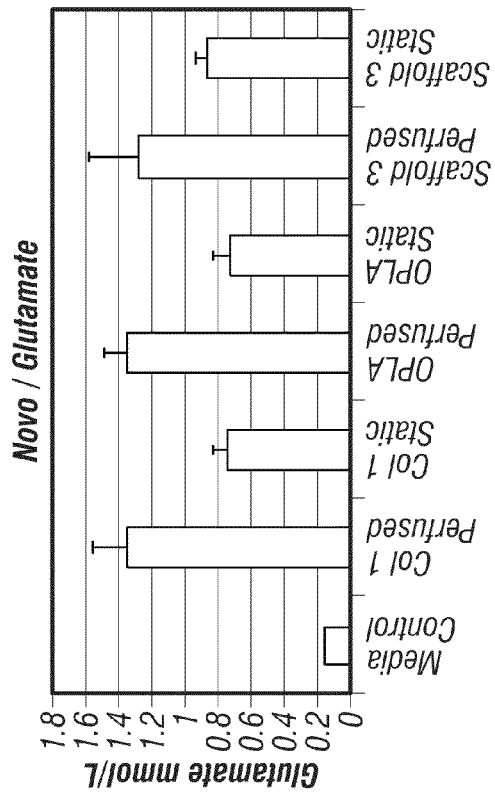
FIG. 17A-D shows consumption of glucose and glutamine by perfused and static 3D cultures of primary kidney cells.
Figure 17B:
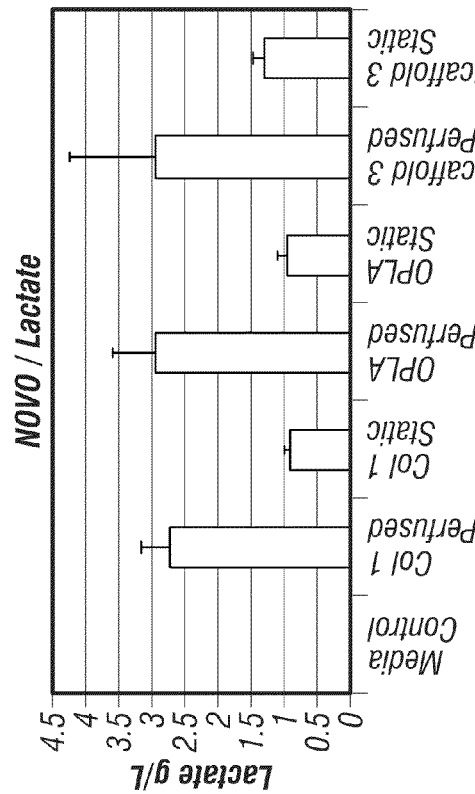
Figure 17C:
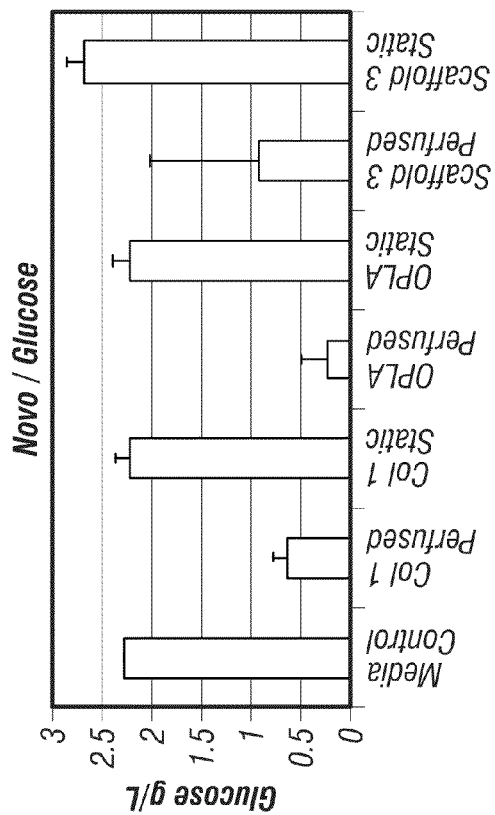
Figure 17D:
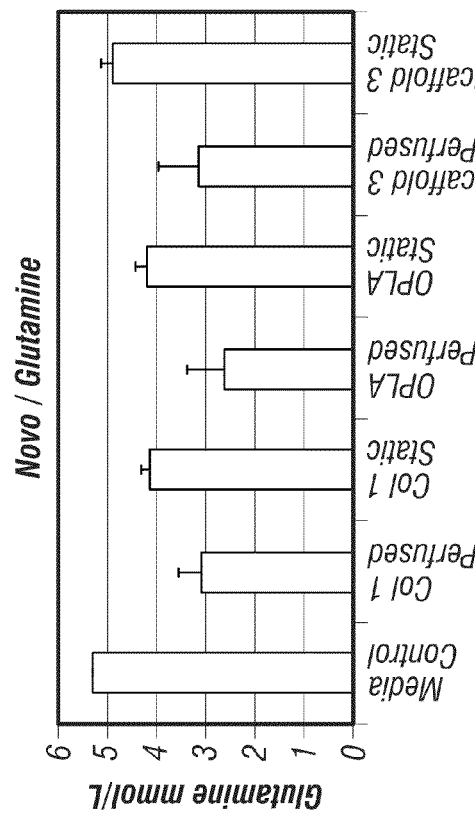

FIG. 16 shows the result of CellTiter Blue™ (Resazurin metabolism), which was used to assess metabolic activity in the scaffolds. Scaffold configuration C gave the best metabolic response in both perfused and static conditions, followed by Scaffold B and Scaffold A, respectively. In all scaffold configurations, perfused cultures outperformed static cultures with respect to Resazurin metabolism.

To examine consumption of glucose and glutamine by perfused and static 3D cultures of primary kidney cells, conditioned media was collected and analyzed on a Nova Bio-Profile® 400. Consumption of glucose was markedly accelerated in the perfused vs. static conditions. Glutamine was consumed to some degree in all 3D conditions, with a slightly greater consumption in perfused vs. static culture. Production of glutamate, which is a byproduct of glutamine metabolism, was greater in perfused vs. static conditions in all scaffold configurations tested, as was the production of lactate, a byproduct of glucose metabolism (see FIG. 17).

Example 5

Isolation of Heterogeneous Population of Unfractionated Mixture of Renal Cells (Test Article #1)

An enriched population of unfractionated mixture of renal cells (UNFX), which are comprised predominantly of tubular cells, but also comprise smaller subpopulations of collecting duct, glomerular, endocrine, vascular, and other cell types, were isolated from whole kidney as follows:

Cell Donors Twenty (20) 2 week old male Lewis rats were sacrificed and their kidneys harvested. Freshly excised kidneys were placed into 50 mL conical tubes (10 kidneys per tube) containing 50 mL of cold (4° C.) Hypothermasol (Bi-olife Solutions, Inc. Bothell, Wash.) and kept on ice. The following day, the tubes containing kidneys were rinsed with 70% ethanol and placed in a Biological Safety Cabinet (BSC) for processing.

Kidney Cell Isolation Process: Kidneys were rinsed with 1×PBS (Gibco, Grand Island, N.Y.) containing 50 ug/ml of gentamycin (Sigma, St. Louis, Mo.) and connective tissue an calyx were manually removed using forceps and scalpels. Kidneys were minced manually into a cell/tissue slurry using sterile forceps and scalpels.

The cell/tissue preparation was enzymatically digested in Kreb's buffer containing dispase (4 U/mL) (#07193 Stem Cell Technologies, Vancouver, BC)+5 mM CaCl2+collagenase type IV (300 U/mL) (Worthington, Newark, N.J.) for 30 minutes at 37° C. on a rocking platform. The resulting cell suspension was then filtered through a cell strainer with 70 µm pores (BD Biosciences, Franklin Lakes N.J.) into a 50 mL sterile conical polypropylene tube containing 50:50 kidney cell growth medium (1:1 High Glucose DMEM: KSFM). Suspension was then centrifuged at 300× g for 5 minutes and resuspended in 10 mls of 50:50 kidney cell growth medium.

The 10 mL cell suspension was aliquoted into two 15 conical tubes (5 mls each). 5 mls of 30% w/v Optiprep (Sigma, St. Louis, Mo.) was added to each tube and inverted 6 times. After mixing, one milliliter of 1×PBS was carefully layered on top of each suspension. Tubes were centrifuged for 15 minutes at 800× g (room temp) with no brake. Cell bands (containing viable NeoKidney Cell Prototype#1) were removed via sterile 10 ml pipet, diluted 5× with 50:50 kidney cell growth medium (made with low-glucose DMEM), and centrifuged at 300× g for 5 minutes. After centrifugation, supernatant was carefully removed and cell pellets were resuspended in 10 mls of 50:50 (low glucose) kidney cell growth medium and enumerated. 500K cells were sampled for gene expression testing. The total yield of viable cells was $230×10^6$ (94% viability).

A total of $46.8×10^6$ cells were plated ($1.17×10^6$ cells per plate) into (40) p100 tissue-culture treated polystyrene plates (BD Biosciences, Franklin Lakes N.J.), in 50:50 (low glucose) media and placed in standard CO2 incubator (21% O2). After 48 hours, cultures were fed with a 100% media change, using 50:50 (low glucose) media, and placed into a 2% O2 environment at 37° C. After 24 hours at 2% O2 cells were harvested for transplantation. Each plate was washed 1× in sterile PBS, followed by the addition of 5.0 mL of warmed 0.25% Trypsin w/EDTA (Sigma), and returned to 37° C. for 5-7 minutes. Growth media was added (5.0 mL) to each plate, and cell suspensions were removed and pooled into 50 mL sterile conical polypropylene tubes. Cells were pelleted via centrifugation at 300× g for 5 minutes, washed 2× in sterile PBS, resuspended in cold (4° C.) PBS, and counted via hemacytometer. Aliquots were prepared at $10×10^6$ cells/100 µL, in sterile cold PBS. The Post-culture yield of viable cells was $91×10^6$ (90% viability). Fold Expansion (plated→harvested) was 3.91×.

Example 6

Isolation of Heterogeneous Population of Unfractionated Mixture of Renal Cells and Scaffold-Seeding (Test Article #2)

Cell Donors: Ten (10) 2 week old male Lewis rats were sacrificed and their kidneys harvested. Freshly excised kidneys were placed into 50 mL conical tubes (10 kidneys per tube) containing 50 mL of cold (4° C.) Hypothermasol (Biolife Solutions, Inc. Bothell, Wash.) and kept on ice. The following day, the tubes containing kidneys were rinsed with 70% ethanol and placed in a Biological Safety Cabinet (BSC) for processing.

Kidney Cell Isolation Process: Kidneys were rinsed with 1×PBS (Gibco, Grand Island, N.Y.) containing 50 ug/ml of gentamycin (Sigma, St. Louis, Mo.) and connective tissue was manually removed using forceps and scalpels. Kidneys were minced manually into a cell/tissue slurry using sterile forceps and scalpels.

The cell/tissue preparation was enzymatically digested in Kreb's buffer containing dispase (4 U/mL) (#07193 Stem Cell Technologies, Vancouver, BC)+5 mM $CaCl_2$+collagenase type IV (300 U/mL) (Worthington, Newark, N.J.) for 30 minutes at 37° C. on a rocking platform. The resulting cell suspension was then filtered through a cell strainer with 70 µm pores (BD Biosciences, Franklin Lakes N.J.) into a 50 mL sterile conical polypropylene tube containing 50:50 kidney cell growth medium (1:1 High Glucose DMEM: KSFM). The cell suspension was then centrifuged at 300× g for 5 minutes and resuspended in 10 mls of 50:50 kidney cell growth medium.

The 10 mL cell suspension was aliquoted into two 15 conical tubes (5 mls each). 5 mls of 30% w/v Optiprep (Sigma, St. Louis, Mo.) was added to each tube and inverted 6 times. After mixing, one milliliter of 1×PBS was carefully layered on top of each suspension. Tubes were centrifuged for 15 minutes at 800× g (room temp) with no brake. Cell bands (containing viable NeoKidney Cell Prototype#1) were removed via sterile 10 mL pipet, diluted 5× with 50:50 kidney cell growth medium (made with low-glucose DMEM), and centrifuged at 300× g for 5 minutes. After centrifugation, supernatant was carefully removed and cell pellets were resuspended in 10 mls of 50:50 (low glucose) kidney cell growth medium and enumerated. The total yield of viable cells was $71×10^6$ (97% viability).

24 sterile packaged Open-Cell Polylactic Acid (OPLA®) scaffolds (BD Biosciences, Franklin Lakes N.J.) were prewet with 50:50 (low glucose) medium, and each scaffold was seeded with $1×10^6$ RK42 NeoKidney Cell Prototype#1 in 50 µL of 50:50 (low glucose) medium. Scaffolds were allowed to acclimate for 2 hours at 37° C./21% $O_2$, then transferred to a charged MPS (Multiwell Perfusion System) unit (BD Technologies, RTP NC) and maintained in 50:50 (low glucose) media with continuous flow at 2% $O_2$ for 5 days. Medium was changed (50% volume change) every 2 days. On day 5, scaffolds were carefully removed from the MPS, rinsed in sterile PBS, and kept at ambient temperature for approximately 2 hours as they were transported in preparation for implantation.

Example 7

Transplantation of an Unfractionated Mixture of Renal Cells into a Rat Model of Renal Failure and Anemia To evaluate the therapeutic potential and safety of NeoKidney Cell Prototype#1 (UNFX), which contains a heterogeneous mixture of cells including EPO-producing interstitial fibroblasts, proximal and distal tubular epithelial cells, glomerular cells, and endothelial cells, isolated from rat kidney, as described supra, the ability of NeoKidney Cell Prototype#1 to slow or reverse renal failure and/or anemia was evaluated in surgically nephrectomized rodents. The study design is shown below in Table 1. Non-limiting success factors included the following:

1) significant positive effects on HCT and/or RBC number
2) significant reduction of serum BUN and/or Creatinine
3) histological evidence of erythroid stimulation
4) histological evidence of kidney regeneration
5) organism-level improvements (weight gain, survival)

According to the study design, twenty-four (24) adult female Lewis rats (8-10 weeks old) were procured from Charles River Laboratories (Wilmington, Mass.) and assigned to the study as recipients shown in Table 1 below. A subset from each group was monitored for onset of the disease state by daily health assessment and weekly hematology and serology. All recipient animals achieved a disease state of anemia/uremia prior to being treated with the neo-kidney prototypes. Two consecutive weeks of elevated serum creatinine (2× control level) in the nephrectomized rats were required prior to study initiation. Nephrectomized rats were assigned to one of four groups (see Table 1 below). Group 1 rats received 10 million NeoKidney Cell Prototype#1 (Test Article 1), suspended in sterile PBS, and delivered via direct injection to the corticomedullary region of the kidney. Group 2 rats were treated by attachment of NeoKidney Construct Prototype#1 (OPLA scaffold seeded with $1×10^6$ NeoKidney prototype#1 cells and cultured for 4 days) to the distal pole of the remnant kidney. Group 3 rats were treated by attachment of an empty OPLA scaffold to the distal pole of the remnant kidney. Group 4 rats received no treatment. Unmanipulated, age-matched control rats were designated Group 5, and age-matched controls that underwent sham nephrectomies and no further manipulations were designated as Group 6.

Blood (500 μL) was drawn weekly from all animals via the tail vein for evaluation of kidney function (creatinine & BUN) and erythropoiesis (HCT, RBC, & nucleated RBC (nRBC)). Health observations were made and body weights were collected weekly over the course of the study. At the end of the study (84 days) surviving rats were subjected to a swim endurance test. At necropsy, the femur, kidney, liver, spleen, heart and lungs were collected, weighed, and processed for histology by formalin-fixation & paraffin embedding (FFPE). A portion of the kidney was embedded in OCT media, frozen, and processed via cryosectioning. The FFPE tissues were processed and H&E stained.

TABLE 1

Study Design

| Grp | Name | NX | Treatment | N | Animal ID #'s | | Endpoints |
|---|---|---|---|---|---|---|---|
| 1 | NE-Cell | ✓ | NE-Cell Implant | 2 | 14, 16 | In-life | Body weight Hemotology & Serology: |
| 2 | NE-Construct | ✓ | NE Construct Implant | 6 | 18, 19, 21, 23, 24, 30 | | RBC, HCT, CREAT, BUN |
| 3 | OPLA | ✓ | Scaffold only implant | 1 | 15 | Pre-necropsy | Full Serum Panel Full Hematology Panel |
| 4 | NX | ✓ | None | 4 | 17, 25, 28, 20 | | |
| 5 | SHAM | no | None | 6 | 7, 8, 9, 10, 11, 12 | Post-necropsy | Bone Marrow Smears/Differential |
| 6 | HEALTHY | no | None | 5 | 1, 3, 4, 5, 6 | | Organ Weights Histopathology |

Time Points

Day 0, First nephrectomy (50%)

Day 7, Second partial nephrectomy (2/3 of remaining kidney removed)

Day 43, Date of first bleed/serology/hematology

Days 83-91, Date of treatment

Day 170, Date of sacrifice/study end

Test Articles:

Test Article #1—NeoKidney cell prototype #1 (UNFX), which comprises a heterogeneous mixture of cultured renal cells containing a subpopulation of EPO-producing cells, isolated as described supra in Example 3.

Test Article #2—NeoKidney construct prototype #1, which comprises OPLA® scaffold seeded with the heterogeneous mixture of cultured renal cells containing a subpopulation of EPO-producing cells, as described supra in Example 4.

Test Article #3—OPLA® scaffold

Recipient 5/6 Nephrectomized Female Lewis Rats: Thirteen (13) female Lewis rats (8-10 weeks of age) were subjected to a 2-step 5/6 surgical nephrectomy at Charles Rivers Laboratories (Wilmington, Pa.) as previously described.

Briefly, during phase 1 of the procedure, a ventral midline incision into the abdomen was made and sterile drape was applied. The intestine was retracted laterally to expose the animal's right kidney. The kidney was freed from the surrounding tissue. A piece of suture was placed around each pole of the kidney at its 1/3 position. The sutures were gently ligated around the kidney. The 1/3 kidney on each end was excised right beyond the ligatures. The abdominal incision was closed with suture and wound clips. During phase 2 of the procedure, and one week after the first step, the animal was anesthetized and prepared as described earlier. The hair on the back of lumbar area was shaved. A cranial-caudal skin incision was made on the animal's left lateral to the spine with its cranial terminus just behind the rib cage. The abdominal cavity was entered. The kidney was freed from the surrounding tissue and was pulled out of the incision gently. The adrenal gland, which was attached loosely to the anterior pole of the kidney by connective tissue and fat, was gently freed by tearing the attachments, and was put back into the abdominal cavity. The renal blood vessels and the ureter were cauterized. The kidney was then removed by transecting the vessels and ureter just distal to the cauterized spot. The incision was closed with suture and wound clips.

As controls, sham nephrectomies (surgical anesthesia, open, & close for both procedures) were also performed on (6) age-matched controls. In addition, (5) age-matched unmanipulated controls were obtained. Upon retrieval, all rats were held in quarantine for (5) days. Each rat was assigned to a group and given a numerical identifier, which was placed on a cage card along with study number, vendor, and study director. Rats were housed (1) per cage and fed Purina Certified Regular Rodent Chow, #5002. Water was provided ad libitum.

In-Life Assessment of Clinical Parameters: Body weights were observed and recorded weekly using a calibrated analytical balance.

Hematology/Clinical Chemistry: Beginning on day 43, blood and serum were collected weekly to Antech to determine hematocrit (HCT), red blood cell number (RBC), nucleated red blood cell number (nRBC), creatinine (CRE), and blood urea nitrogen (BUN). Blood was drawn aseptically from tail or saphenous vein and placed into blood- or serum-collection tubes (both from BD, Franklin Lakes, N.J.). Blood was collected between 8:00 AM and 12:00 PM to control for diurnal variation.

Surgical Treatment Procedures:

Anesthesia/Sedation/Analgesia: Rats were sedated prior to surgical preparation by first giving 0.05 cc (0.3 mg/ml) of buprenorphine (Buprenex) with a syringe fitted with a 26 gauge needle (IP). Rats were then anesthetized via isoflurane inhalant anesthetic by first placing in isoflurane chamber at 4-5% then maintaining anesthesia with isoflurane inhalant (3%) via nose-cone throughout the procedure. Each rat was given a second dose of Buprenex after surgery, and a third dose the following day.

Surgical Preparation: After adequate plane of anesthesia was achieved (assessed by toe-pinch), the animal was placed in dorsal recumbency and the right dorsolateral area was shaved using a number 5 clipper and application of betadine (3 times) and ethanol (4 times) in concentric circles. The area was prepared for aseptic surgery using sterile transparent adhesive drapes to enable accurate monitoring of respiration.

Direct Injection of NeoKidney Cell Prototype#1 (Test Article #1, or UNFX): A longitudinal incision was made in the right dorsolateral area, exposing the peritoneal cavity. The remnant right kidney was isolated and partially extracted from the peritoneal space using sterile gauze and blunt surgical forceps. NeoKidney Cell Prototype#1 (prep RK40, Test Article 1) were gently resuspended and loaded into a single sterile 1 cc syringe (BD, Franklin Lakes, N.J.), which was then fitted with a 23 G needle. 100 µL of cell suspension (10 million cells) was delivered slowly through the needle into the kidney parenchyma, attempting to target the corticomedullary junction area. A new sterile 23G needle was used for each animal. A collagen disk (GelFoam, 2 mm×2 mm) was placed onto the injection site as the needle was withdrawn to slow bleeding. The kidney was placed back into the abdominal cavity and 1 ml of warm sterile saline was added for hydration. The muscle wall was closed using 4.0 Vicryl sutures and the skin was closed using wound clips (Ethicon Inc., Somerville, N.J. for both items). Oxygen was administered post surgery (via inhalation/nose cone) and the animals were monitored until alert and conscious.

Surgical Delivery of Scaffold-based Test Articles (#2 & #3): A longitudinal incision was made in the right dorsolateral area, exposing the peritoneal cavity. The remnant right kidney was isolated and partially extracted from the peritoneal space using sterile gauze and blunt surgical forceps. The distal pole of the remnant kidney was located, and the adhered abdominal fat was teased from the area using blunt surgical techniques or forceps until the deep-red tissue of the kidney was observed. A Sklar #10 scalpel (Sklar Scientific, West Chester, Pa.) was used to expose the kidney, which was debrided with the scalpel until a ~4×4 mm area of the kidney parenchyma was exposed and bleeding slightly. A single NeoKidney Construct Protoype#1 (Test Article #2) or scaffold alone (Test Article #3) was bisected (to provide a large, flat point of contact with the exposed kidney parenchyma) and attached (cut surface onto the debrided area) to the debrided area via fibrin glue (Ethicon Inc. Somervile, N.J.). Attached scaffolds were provided a supplementary blood supply by folding abdominal fat over the scaffolds and sealing the fat to the kidney surface with additional fibrin glue. The kidney was then observed for ~1 minute for evidence of bleeding; any bleeds were staunched with fibrin glue, and the kidney remnant with scaffold attached was then returned to a neutral position in the peritoneal cavity. 1.0 ml of warm sterile saline was then added to the IP cavity to aide hydration. The muscle wall was closed using 4.0 Vicryl sutures and the skin was closed using wound clips (Ethicon Inc., Somerville, N.J. for both items). Oxygen was administered post surgery (via inhalation/nose cone) and the animals were monitored until alert and conscious.

Surgical Recovery: All animals were recovered after surgical procedure in the surgical suite with a cage containing an absorbent pad (but no loose bedding) placed onto a heating pad. Once the rats were mobile and awake, they were returned to their respective cages and observed for the remainder of the day and the first thing the following morning.

Pre-Necropsy Procedures:

Swim Endurance Test: 1 large circular metal tub (140 cm diameter×45 cm depth) was filled with water and maintained at 32° C. Rats (1 at a time) were gently lowered into the water facing the side of the tank and released. The time between release and the time that the rat stopped swimming and could not stay above water was measured with a stopwatch and recorded. Rats were dried off using cotton towels and recovered on heating pads before being returned to cages. Between animals, pool was cleared of fecal matter and temperature was checked and recorded.

Final Body Weight: Animals were transferred to necropsy suite. Final body weight was obtained using analytical balance and recorded in grams.

Euthanasia: Rats were placed into $CO_2$ chamber. Death was confirmed using absence of deep pain reflex and ocular test.

Necropsy Procedures:

Cardiac Puncture/Blood Collection: Euthanized rats were placed onto necropsy table and blood collected directly into serum- and blood-collection tubes. Serum samples were spun and serum collected for full serum chemistry panel. Blood samples were collected for full hematology panel.

Tissue Harvest: Kidney remnant (or, for controls and shams, whole right kidney) was carefully removed, weighed, and bisected longitudinally. One half was placed in 10% buffered formalin and processed for paraffin embedding and H&E staining. The other half was placed in a pre-chilled mold on dry ice, with OCT embedding media, and frozen. The frozen kidney halves were maintained on dry ice and stored at −80° C. until frozen sections were prepared for Y chromosome analysis. At necropsy, the spleen, liver, heart, and lungs were removed, weighed, and a small slit cut in each as they were placed in 10% buffered formalin for paraffin-embedding and H&E staining. Finally, the femur was removed and associated stromaltissue was removed. The proximal condyle was shaved with a scalpel blade to expose the marrow and the whole femur then placed into 10% buffered formalin before paraffin-embedding and H&E staining procedures.

Results

Figure 18:
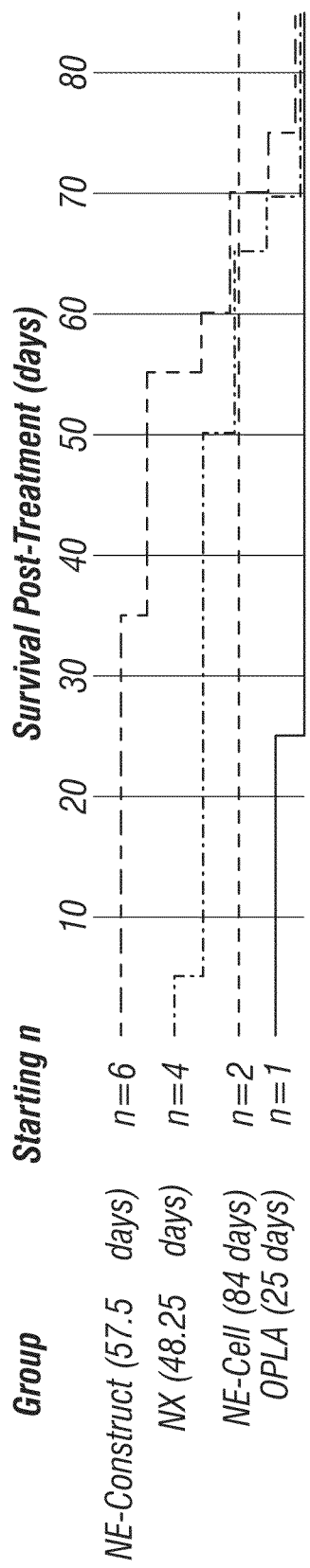
FIG. 18 depicts average survival (Days) of rodents Post-Treatment.

Survival: The majority of the nephrectomized rats did not survive the full length of the study. Groups 1, 5, & 6 survived until sacrifice at day 84. The average survival time (in days) of the Group 4 nephrectomized untreated rats was 48.25±29.8. The nephrectomized rat receiving scaffold only (Group 3) survived 25 days beyond treatment. The rats receiving the NeoKidney Construct Protoype#1 (Group 2) survived an average 57.5±14.3 days, or 9.25 days longer than the untreated nephrectomized rats. The Group 1 rats treated with NeoKidney Cell Prototype#1 survived the duration of the study and were sacrificed on Day 84 (arrow) with Groups 5 & 6 (FIG. 18).

Figure 19:
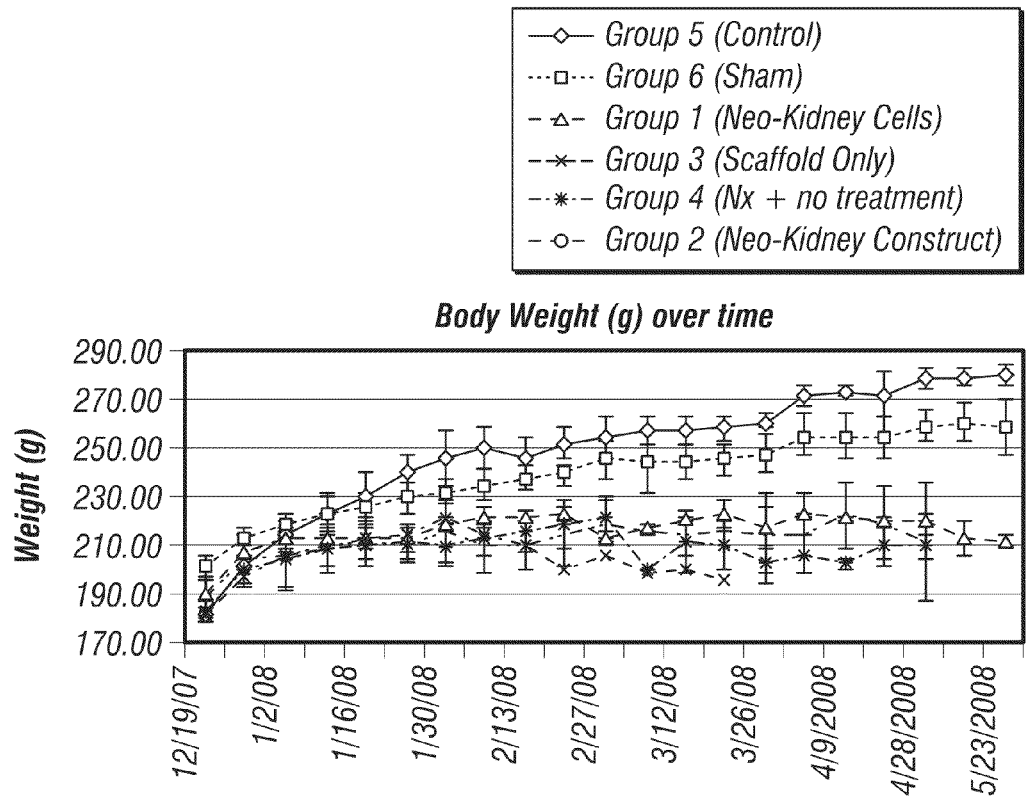
FIG. 19 shows rodent body weights throughout study.
Figure 20:
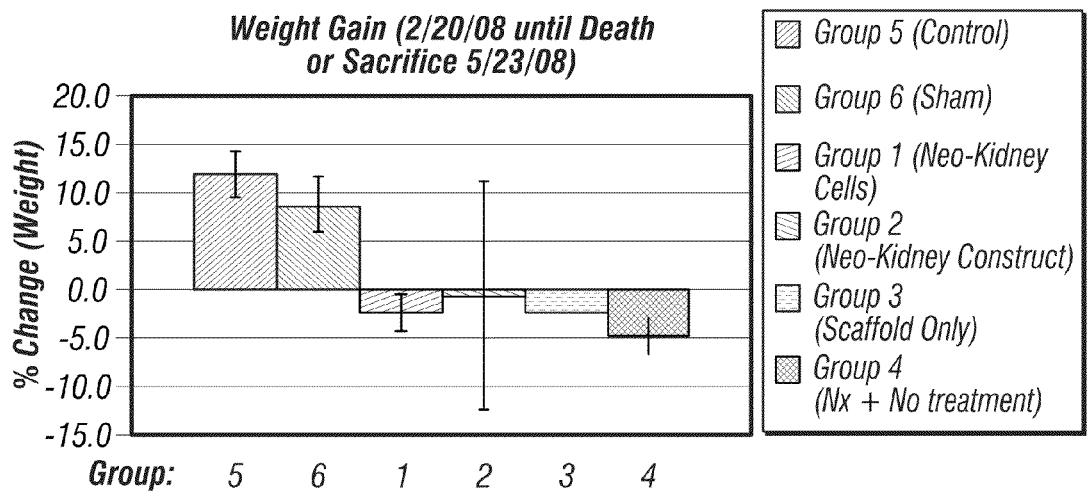
FIG. 20 graphically depicts Pre-Treatment to Sacrifice weight gain.

Body Weight: Body weight was measured weekly from study initiation (Day 14) to sacrifice (Day 170). Body weight data (g) are presented in FIG. 19 for each group. Group 5 (Control) rats had an average 56% (±5.5%) gain throughout the study, and Group 6 (Sham) rats had an average 30.3% (±5.3%) gain. All nephrectomized rats (Groups 1-4) had significantly less % weight gain over the study, with Group 1 (NeoKidney Cell Prototype#1) gaining an average 13.5%, Group 2 (NeoKidney Construct Protoype#1) gaining an average 13.3%, Group 3 (empty scaffold) gaining 7.8%, and Group 4 (No treatment) gaining 13.7%. When the weight gain is examined between the time of treatment and time of sacrifice or death, differences among groups become more apparent (FIG. 20). While Group 5 & 6 rats gained 11.9% & 8.8% body weight during the treatment period (Day 83-Day 170), nephrectomized rats that remained untreated (Group 4) lost an average of 4.8% body weight. Rats receiving NeoKidney Cell Prototype#1, constructs, or scaffold only (Groups 1, 2, &

3) also lost weight during the treatment period, but not as much as the Group 4 untreated nephrectomized rats.

Figure 21:
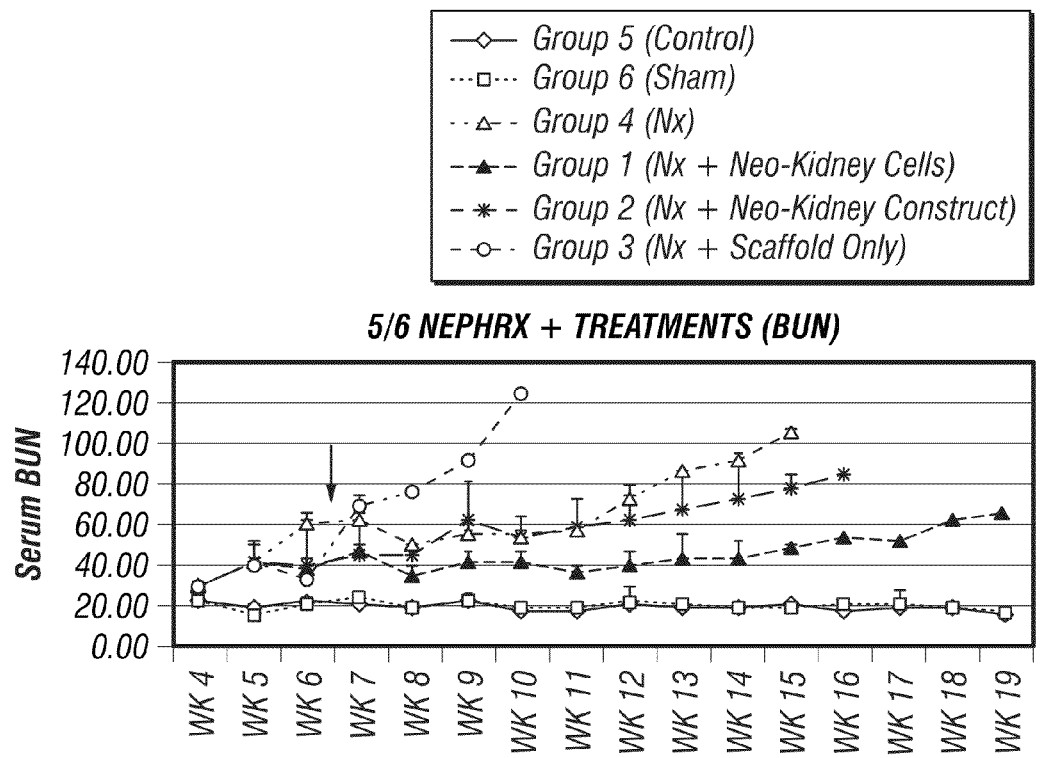
FIG. 21 depicts weekly average serum BUN concentration.
Figure 22:
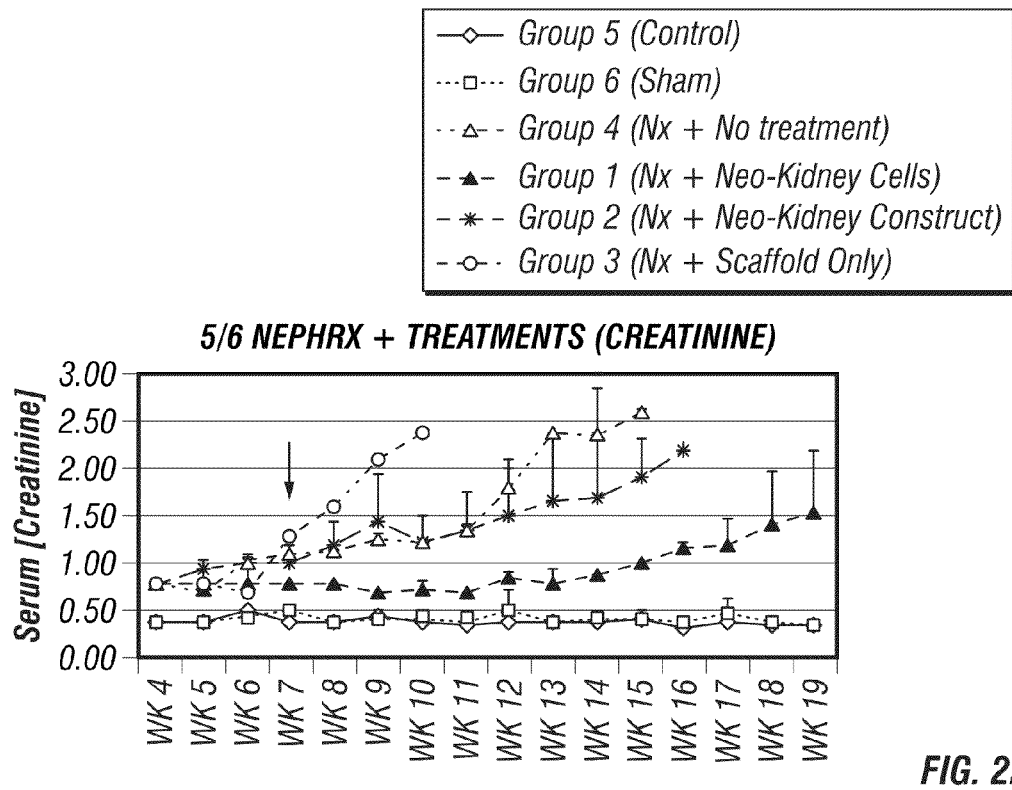
FIG. 22 shows weekly average serum creatinine concentration.

Weekly Assessment of Kidney Function (BUN & Creatinine): Both BUN and Creatinine measurements were taken from serum weekly throughout the study, beginning on week 4 through sacrifice on Day 170. Averaged data from individual rats is presented below in Tables 2 and 3. FIGS. 21 & 22 show BUN and Creatinine, respectively, measurements over time among the groups as a weekly average. Control and Sham [BUN] averaged 19.1±1.9 throughout the study. At the time of implantation (between Weeks 7 & 8 on the graph, arrow) the serum BUN was elevated in all nephrectomized rats, with an average [BUN] among the nephrectomized rats of 53.3±19.9. During the course of study, the Group 4 untreated nephrectomized rats displayed continuously rising [BUN], reaching values>100 before death. After treatment with NeoKidney Cell Prototype#1, Group 1 rats demonstrated stabilization of serum [BUN] through week 14, at which time [BUN] increased weekly through Week 19, the time of sacrifice. Group 2 rats receiving NeoKidney Construct Protoype#1 had lower serum [BUN] than Group 4, but did not show the same degree of stabilization as Group 1. The Group 3 rat receiving scaffold only declined rapidly after the procedure, as demonstrated by the rapidly elevated [BUN] and death by week 10.

began the study with an average [creatinine] of 1.38±0.75 at week 7, reaching a maximum value of 2.7 and an average of 2.6±0.15 at the time of death. The average [creatinine] in the seeded scaffold animals at the time of their death was 2.3 (std. 0.92), representing a minor improvement over Group 4. Interestingly, the nephrectomized rats receiving NeoKidney Cell Prototype#1 (Group 1) maintained stable [creatinine] levels from the time cells were implanted (week 7) at 0.8±0.0 through week 15 at 1.0±0.0, only climbing slightly towards the end of the study (weeks 16-19) with an average of 1.3±0.18.

Figure 23:
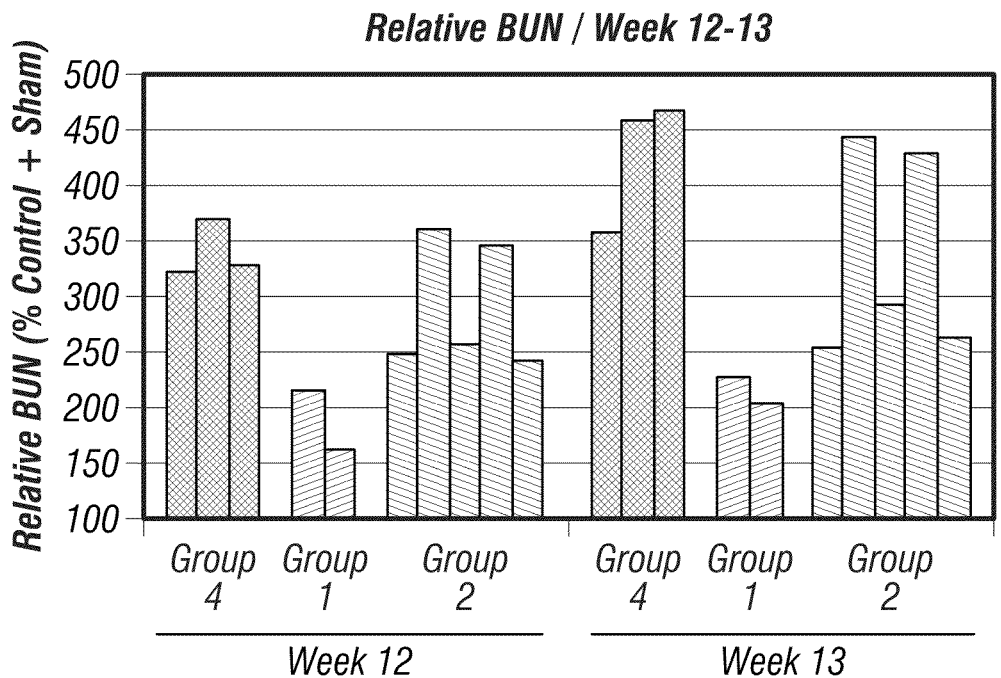
FIG. 23 depicts relative BUN at Midpoint/Individual Rat Data.
Figure 24:
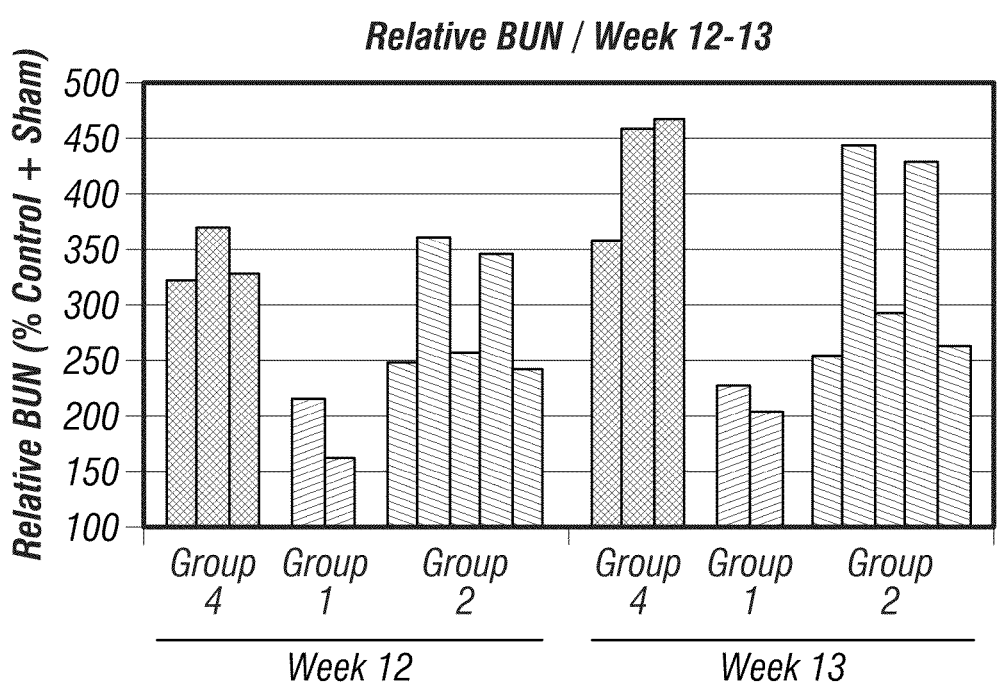
FIG. 24 shows relative serum creatinine at Midpoint/Individual Rat Data.

Examination of BUN and Creatinine values at the midpoint of the study (Weeks 12 & 13), with each individual rat's data expressed as % of (Controls+Shams−Groups 5 & 6), provides a means to examine the variability among rats in each group (FIGS. 23 & 24). At both weeks 12 & 13, 3/5 of the Group 2 NeoKidney Construct Protoype#1 rats have significantly lower BUN and creatinine than the Group 4 untreated nephrectomized rats. Both (2/2) Group 1 NeoKidney Cell-treated rats had significantly lower BUN and Creatinine than Groups 2 or 4.

TABLE 2

Weekly BUN Data

| Group | 1 | 2 | 3 | 4 | 5* | 6# | 7 | 8 | 9 | 10 | 11 | 12 | 13 | 14 | 15 | 16 |
|---|---|---|---|---|---|---|---|---|---|---|---|---|---|---|---|---|
| Control | 22 | 19.50 | 22.33 | 21 | 19.33 | 22.60 | 17.20 | 17.80 | 20.40 | 19.60 | 18.60 | 20.40 | 17.80 | 19 | 19.40 | 15.20 |
| Sham | 22.5 | 16 | 20.80 | 23.5 | 18.8 | 22.67 | 19.50 | 18.83 | 22.17 | 20.50 | 19.33 | 19.17 | 21.67 | 21.17 | 19.67 | 17.50 |
| NephRx | 29 | 41 | 59.67 | 68.50 | 49 | 56.33 | 54.67 | 56.33 | 72.67 | 86 | 92 | 105.5 | | | | |
| Cell injection | 29 | 41 | 37.5 | 47 | 34.5 | 41.5 | 41 | 36 | 40.5 | 43.5 | 42.5 | 48.5 | 53 | 52.5 | 62.5 | 65.5 |
| Seeded saffold | 29 | 38.67 | 40.33 | 43.60 | 46.75 | 61.00 | 53.83 | 58.67 | 62.20 | 67.60 | 74.20 | 77.50 | 84 | | | |
| Empty scaffold | 29 | 41 | 33 | 69 | 76 | 91 | 124 | | | | | | | | | |

*1st bleed post cell injection;
1st bleed post scaffold implantation

TABLE 3

Weekly Creatinine Data

| Group | 1 | 2 | 3 | 4 | 5* | 6# | 7 | 8 | 9 | 10 | 11 | 12 | 13 | 14 | 15 | 16 |
|---|---|---|---|---|---|---|---|---|---|---|---|---|---|---|---|---|
| Control | 0.4 | 0.4 | 0.5 | 0.4 | 0.4 | 0.44 | 0.4 | 0.36 | 0.38 | 0.38 | 0.38 | 0.42 | 0.32 | 0.38 | 0.34 | 0.36 |
| Sham | 0.4 | 0.4 | 0.46 | 0.5 | 0.4 | 0.43 | 0.42 | 0.37 | 0.5 | 0.4 | 0.42 | 0.42 | 0.4 | 0.48 | 0.38 | 0.35 |
| NephRx | | 0.65 | 1.33 | 1.38 | 1.17 | 1.30 | 1.27 | 1.37 | 1.77 | 2.4 | 2.33 | 2.55 | | | | |
| Cell injection | 0.8 | 0.8 | 0.8 | 0.8 | 0.8 | 0.7 | 0.75 | 0.7 | 0.85 | 0.8 | 0.9 | 1 | 1.15 | 1.2 | 1.4 | 1.55 |
| Seeded saffold | 0.8 | 0.9 | 1 | 0.96 | 1.15 | 1.38 | 1.22 | 1.35 | 1.52 | 1.66 | 2.16 | 1.9 | 2.2 | | | |
| Empty scaffold | 0.8 | 0.8 | 0.7 | 1.3 | 1.6 | 2.1 | 2.4 | | | | | | | | | |

*1st bleed post cell injection;
1st bleed post scaffold implantation

Figure 25:
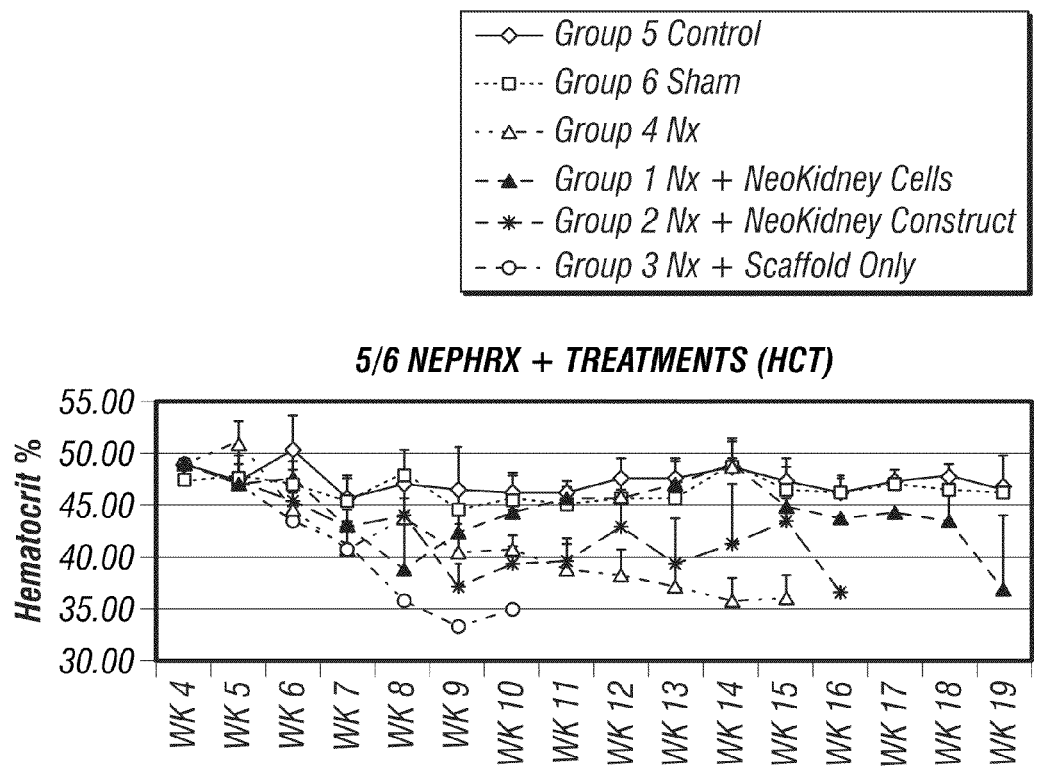
FIG. 25 shows Weekly Average HCT Relative HCT at Midpoint (Individual rat data).
Figure 26A:
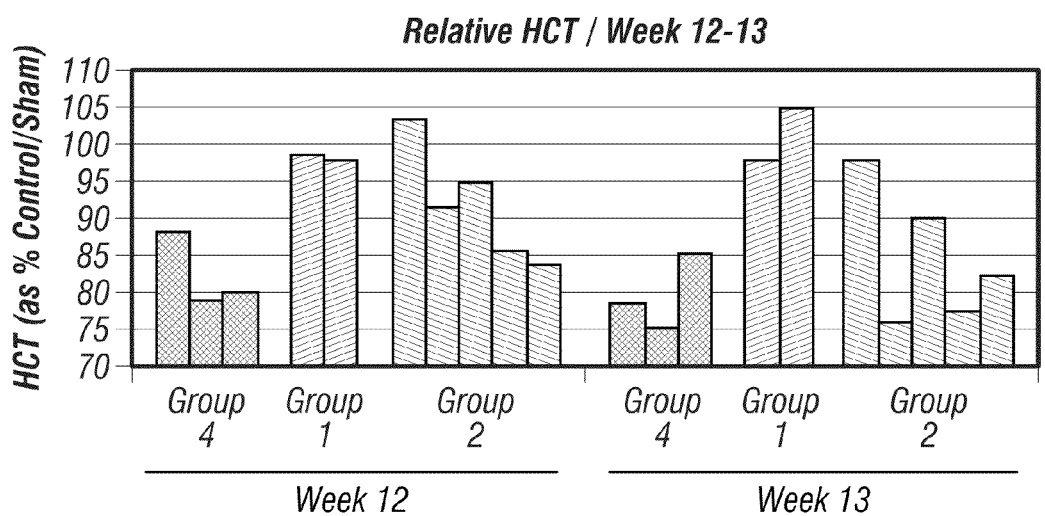
FIG. 26A depicts Relative HCT at Midpoint (Individual rat data).

Serum creatinine results for each group show the same trend of treatment effect as noted for [BUN] (FIG. 22). Throughout the study (Week 7-Week 19), Serum [creatinine] of Group 5 Control and Group 6 Sham animals was stable at 0.4±0.5. In contrast, Group 4 nephrectomized untreated rats Weekly Assessment of Erythropoiesis (HCT, RBC, nRBC): All data are presented below in Tables 4 and 5 below. From week 7 (time of treatment) through week 19 (study end), the average HCTs for Group 5 Controls and Group 6 Shams were 46.9±0.8 and 46.2±1.2, respectively. In contrast, the Group 4 nephrectomized animals receiving no treatment had an average HCT at week 7 of 40±2.6, and declined rapidly thereafter until they were sacrificed due to morbidity, with an average HCT at the time of sacrifice of 35.6±1.8. The average HCT in the Group 2 NeoKidney Construct Protoype#1 animals at the time of their death was 38.4±4.3, representing an improvement over Group 4, but not approaching HCT of Group 5 controls. Interestingly, Group 1 animals receiving NeoKidney Cell Prototype#1 showed improvement in HCT from a pre-implant average (week 7) of 42.8±0.2 to a value equivalent to Groups 5 & 6 through week 14 (48.9±0.4). Group 1 HCT values declined gradually from weeks 15-19, reaching an average of 36.8±7.1 at the time of sacrifice. Weekly average data are shown in FIG. 25. Because variability among rats in individual treatment groups was sometimes high, it is helpful to view the HCT data in an additional format so that individual rat data can be appreciated. FIG. 26A provides data from all treatment groups on weeks 12 & 13, expressed as % control (% control=averaged values from all control & sham animals on those dates).

Figure 27:
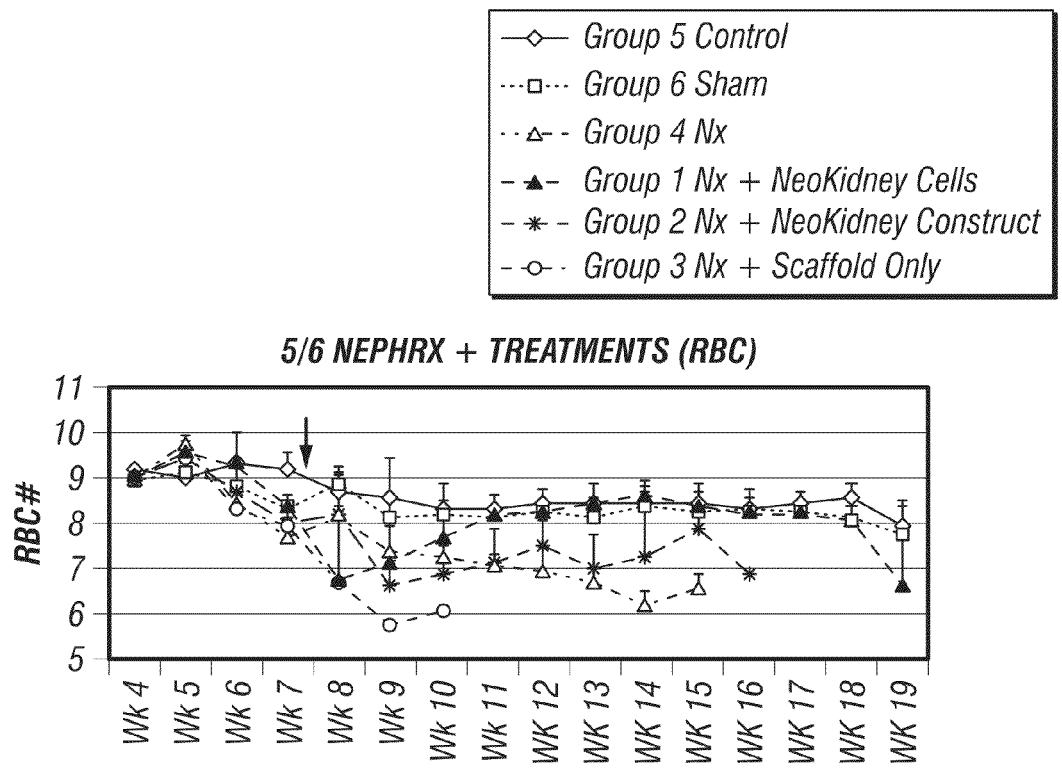
FIG. 27 shows Weekly Average RBC#.
Figure 28:
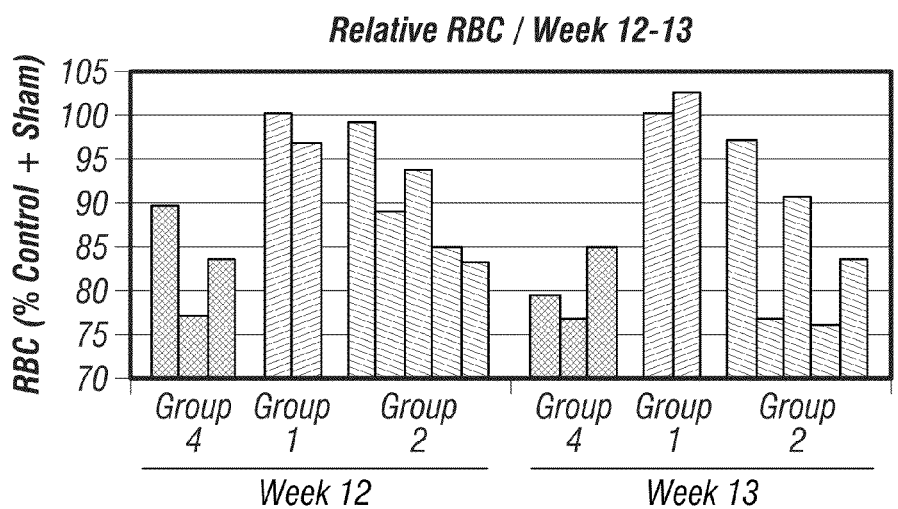
FIG. 28 depicts Relative RBC# at Midpoint/Individual Rat Data.
Figure 29A:
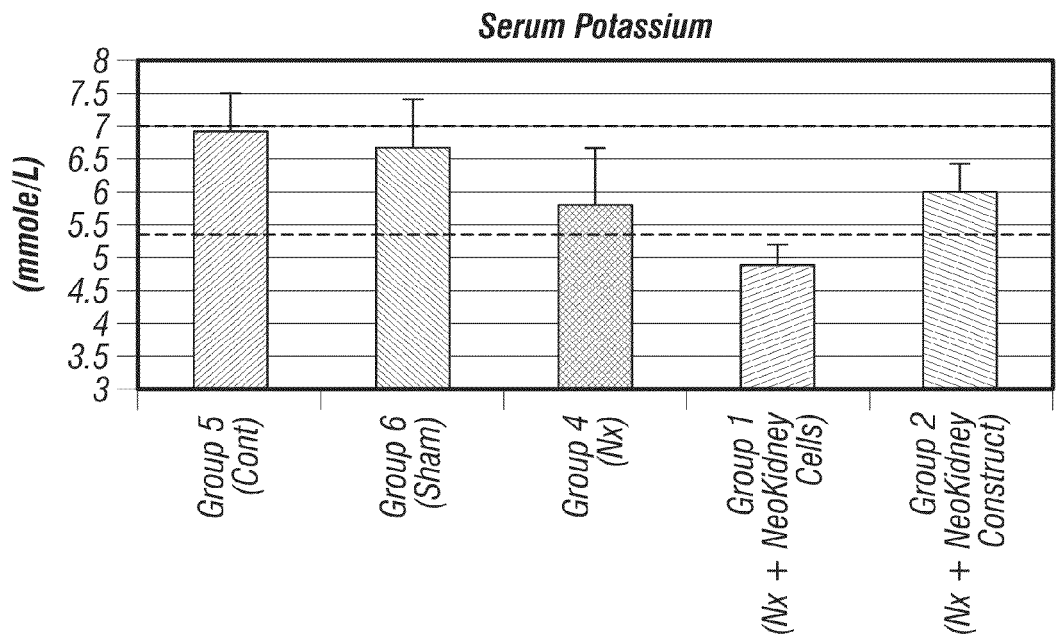
FIG. 29A-E depicts Terminal Serum Electrolyte Concentrations.
Figure 29B:
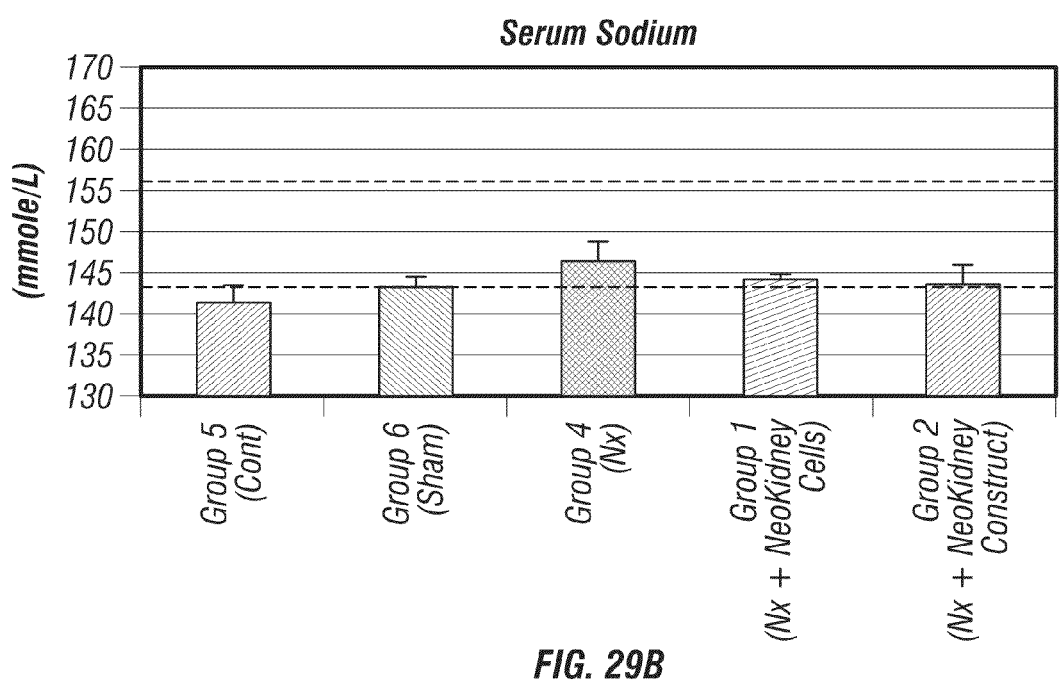
Figure 29C:
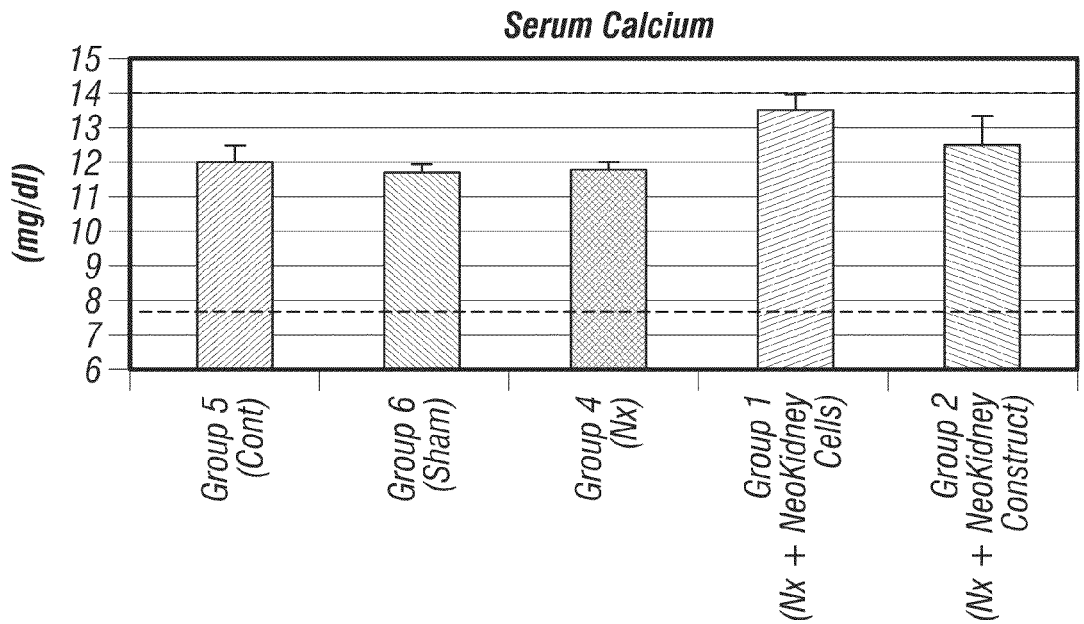
Figure 29D:
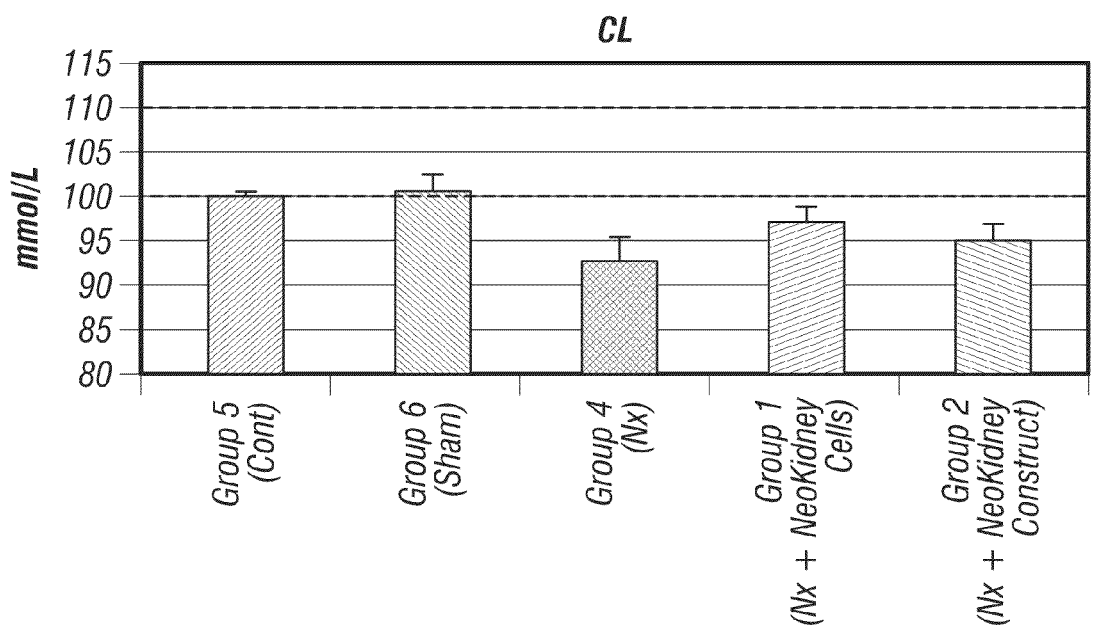
Figure 29E:
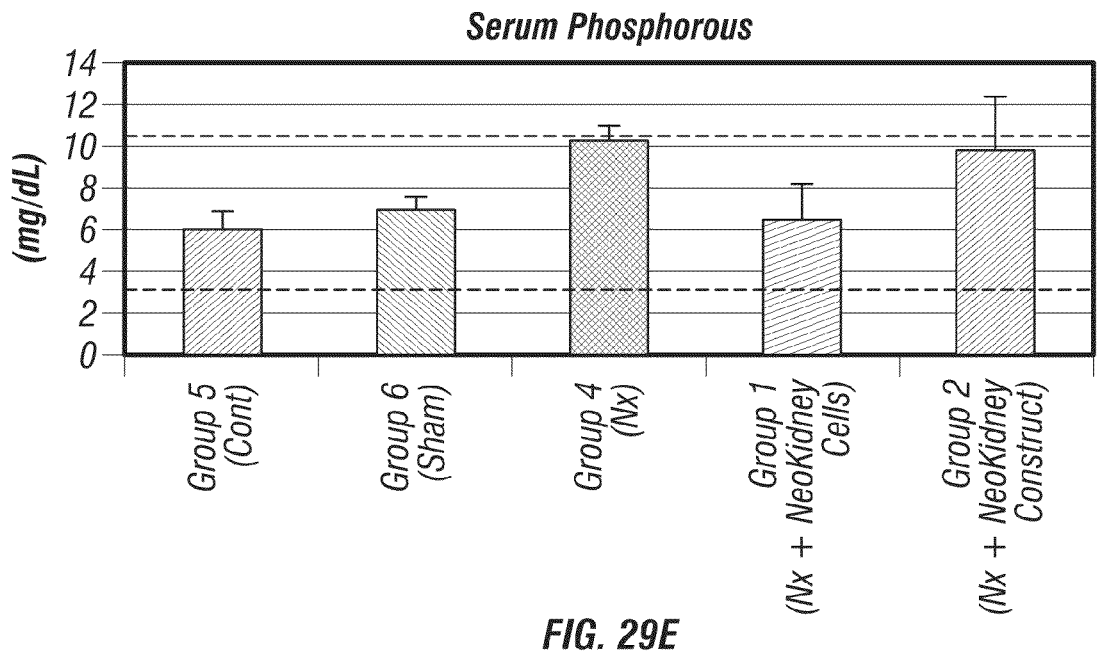

NeoKidney Cell Prototype#1 displayed a steady and consistent improvement in RBC# from 6.71±2.53 at week 8 to 8.03±0.32 at week 18. A sharp decline in average RBC# at week 19 (end of study) was noted, 6.6±1.15. In general, weekly average RBC number tracked with HCT (FIG. 27). Likewise, variability among animals in the various treatment groups makes the addition of a midpoint graph useful, whereby the RBC# in individual animals (Weeks 12-13) are expressed as % control (FIG. 28).

Hematology and Clinical Chemistry at Sacrifice

Electrolyte Balance: Serum levels of calcium, potassium, chloride, and phosphate were measured at the time of sacrifice (exception is animals found dead, from which blood could not be collected). All data are shown below in Tables 7a-7c. Results are summarized in FIG. 29. Normal range of each parameter measured is represented by two dotted lines on the graphs (Normal reference range is taken from Gad (ed.), Animal Models in Toxicology, $2^{nd}$ edition, (2008), Informa Healthcare USA, New York, N.Y.)).

TABLE 4

Weekly HCT Data

| Group | Week | | | | | | | | | | | | | | | |
|---|---|---|---|---|---|---|---|---|---|---|---|---|---|---|---|---|
| | 1 | 2 | 3 | 4 | 5* | 6# | 7 | 8 | 9 | 10 | 11 | 12 | 13 | 14 | 15 | 16 |
| Control | 49 | 47.2 | 50.15 | 45.7 | 46.9 | 46.3 | 46.12 | 46.22 | 47.52 | 47.44 | 48.64 | 47.22 | 45.98 | 47.2 | 47.7 | 46.43 |
| Sham | 47.1 | 47.6 | 46.85 | 45.4 | 48 | 44.43 | 45.55 | 44.87 | 45.73 | 45.65 | 48.73 | 46.35 | 46.12 | 46.92 | 46.47 | 46.25 |
| NephRx | 49 | 49.6 | 43.73 | 40.03 | 43.10 | 40.37 | 40.3 | 38.67 | 38.27 | 36.93 | 35.67 | 36.05 | | | | |
| Cell injection | 49 | 47 | 47.45 | 42.85 | 38.65 | 42.15 | 44.25 | 45.6 | 45.6 | 47 | 48.95 | 44.85 | 43.55 | 44.3 | 43.3 | 36.8 |
| Seeded saffold | 49 | 49.27 | 45.63 | 42.88 | 44.2 | 37.18 | 39.6 | 39.45 | 42.7 | 39.3 | 41.33 | 43.3 | 36.5 | | | |
| Empty scaffold | 49 | 47 | 43.3 | 41.3 | 35.7 | 33.3 | 34.9 | | | | | | | | | |

*1st bleed post cell injection;
1st bleed post scaffold implantation

TABLE 5

Weekly RBC Data

| Group | Week | | | | | | | | | | | | | | | |
|---|---|---|---|---|---|---|---|---|---|---|---|---|---|---|---|---|
| | 1 | 2 | 3 | 4 | 5* | 6# | 7 | 8 | 9 | 10 | 11 | 12 | 13 | 14 | 15 | 16 |
| Control | 9.16 | 9.02 | 9.33 | 8.5 | 8.71 | 8.53 | 8.31 | 8.32 | 8.43 | 8.45 | 8.42 | 8.44 | 8.28 | 8.47 | 8.55 | 7.92 |
| Sham | 8.95 | 9.12 | 8.81 | 8.32 | 8.86 | 8.11 | 8.18 | 8.11 | 8.24 | 8.14 | 8.34 | 8.27 | 8.35 | 8.27 | 8.11 | 7.75 |
| NephRx | 9 | 9.62 | 8.42 | 7.58 | 8.07 | 7.35 | 7.34 | 7.09 | 6.95 | 6.67 | 6.18 | 6.57 | | | | |
| Cell injection | 9 | 9.58 | 9.23 | 8.34 | 6.71 | 7.13 | 7.70 | 8.18 | 8.22 | 8.43 | 8.62 | 8.35 | 8.16 | 8.16 | 8.03 | 6.60 |
| Seeded saffold | 9 | 9.56 | 8.61 | 7.99 | 8.21 | 6.64 | 6.88 | 7.13 | 7.5 | 7.03 | 7.29 | 7.87 | 6.86 | | | |
| Empty scaffold | 9 | 9.58 | 8.3 | 7.94 | 6.7 | 5.78 | 6.06 | | | | | | | | | |

*1st bleed post cell injection;
1st bleed post scaffold implantation

Figure 30:
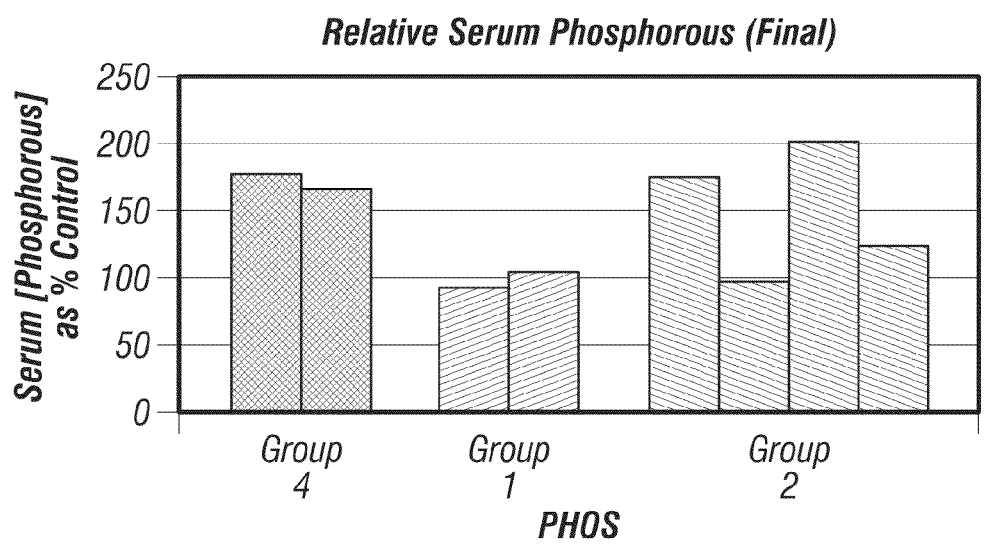
FIG. 30 shows Relative Serum Phosphorous (Final)/Individual rat data.
Figure 31A:
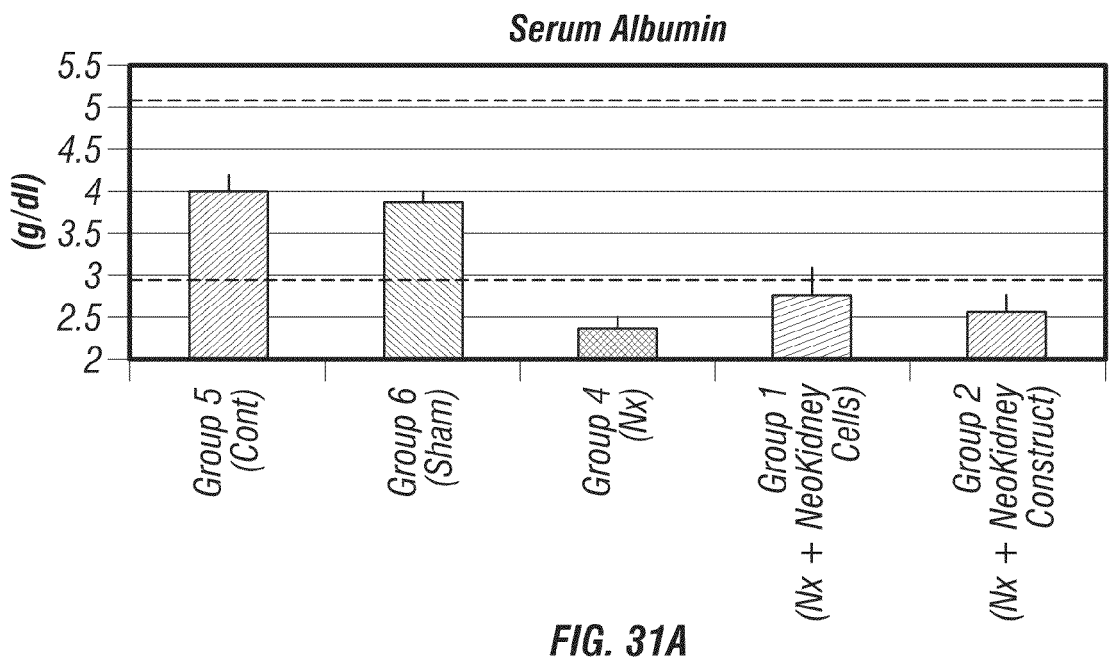
FIG. 31A-D depicts Terminal Serum Protein Concentrations.
Figure 31B:
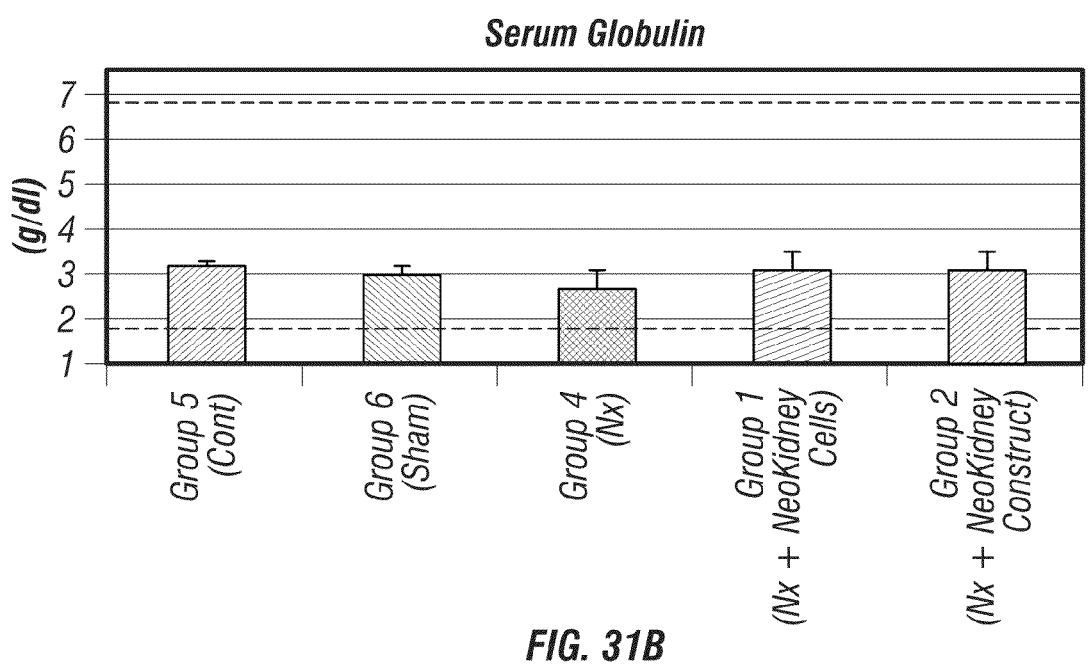
Figure 31C:
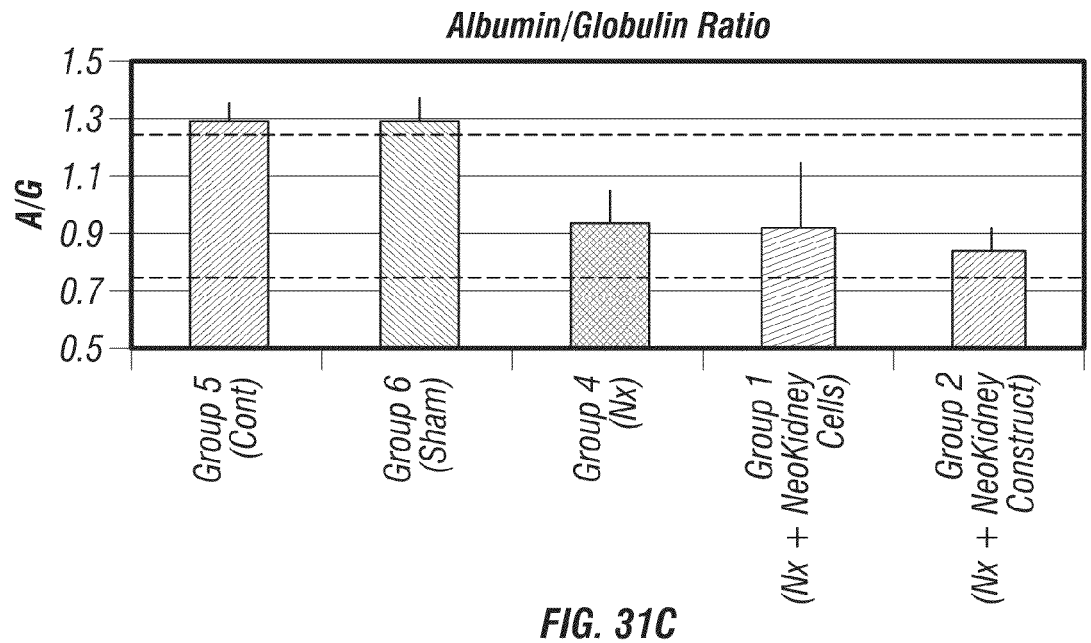
Figure 31D:
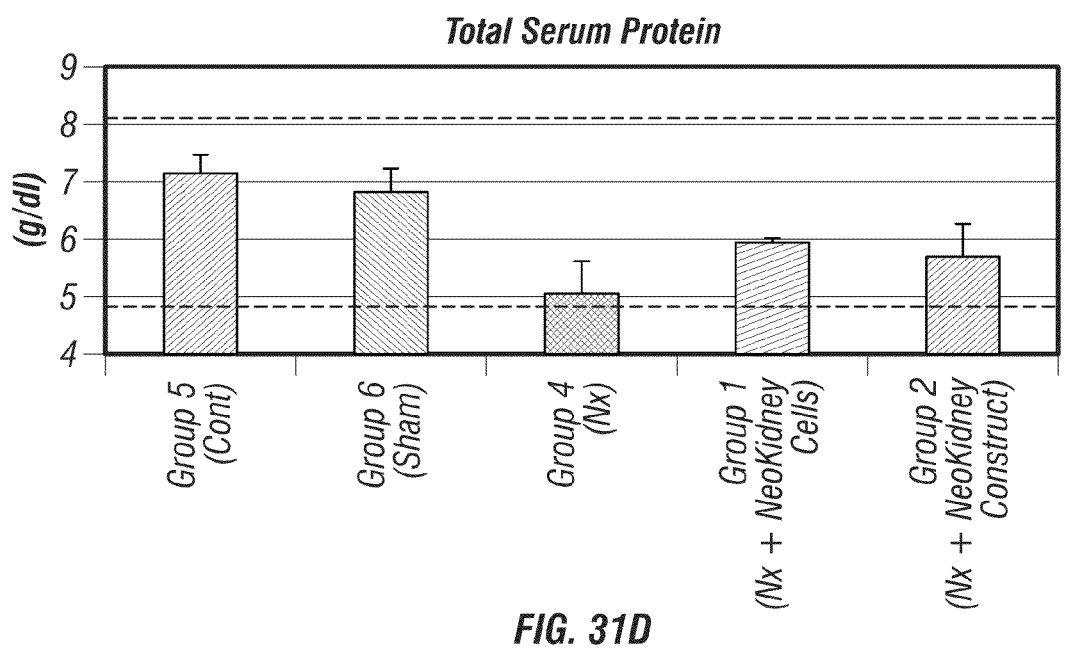

RBC and nucleated RBC (nRBC) were also measured weekly. Nucleated RBC were not detected throughout the study, and are not shown in graphical form. Averaged data are presented in Table 5 below. From week 7 (time of treatment) through week 19 (study end), the average RBC# for Group 5 controls and Group 6 shams was 8.32±0.2. Nephrectomized rats receiving no treatment began week 7 with an average RBC# of 7.58±0.58, and rapidly declined until death, with the average RBC# at death being 6.5±0.5 Group 2 NeoKidney Construct Prototype#1 animals had an average RBC# of 6.94±0.7 at the time of death. Group 1 animals that received Renal failure is typically associated with elevated potassium, sodium, and phosphorous, and declining levels of calcium and chloride. The Group 4 nephrectomized rats did show elevated sodium and phosphate (but not potassium) compared to controls, as well as lower chloride levels. The most consistent electrolyte changes in the nephrectomized rats were reduced chloride and elevated phosphorous levels. Treatment with NeoKidney Cell Prototype#1 (Group 1) resulted in a reduction in phosphorous and calcium, and a slight elevation in chloride compared to Group 4 (see FIG. 30).

If serum phosphorous levels are considered individually in the rats that were analyzed, it is clear that, like the BUN, Creatinine, HCT, and RBC values, the Group 2 rats were heterogeneous in response, with 2/4 rats exhibiting phosphorous levels as low as the Group 5 & 6 controls and shams, and the Group 1 NeoKidney Cell-treated rats.

Figure 32A:
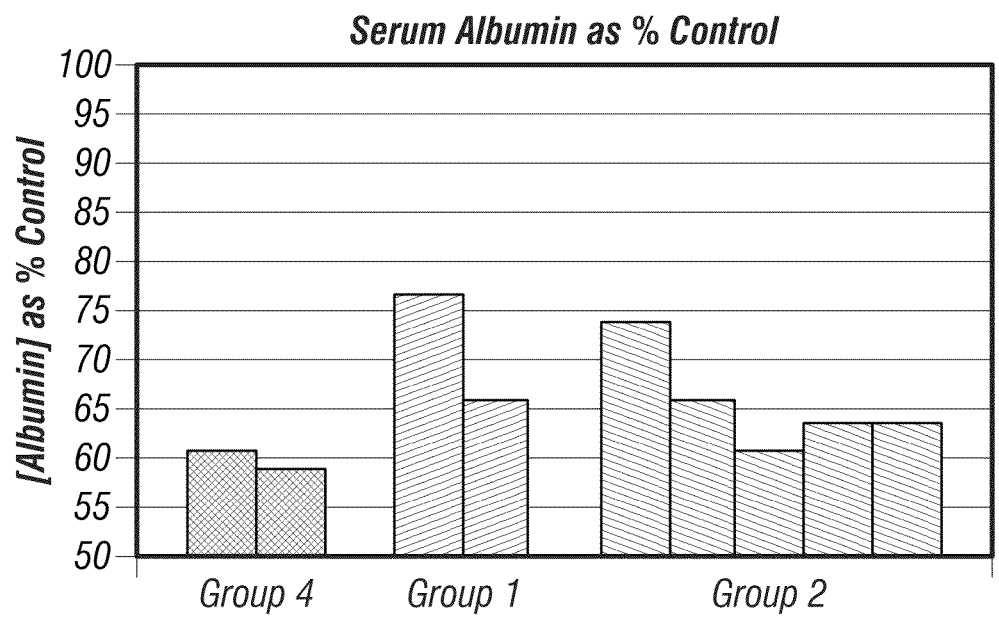
FIG. 32A-B shows Relative Serum Albumin & Total Protein (Final)/Individual Rat Data.
Figure 32B:
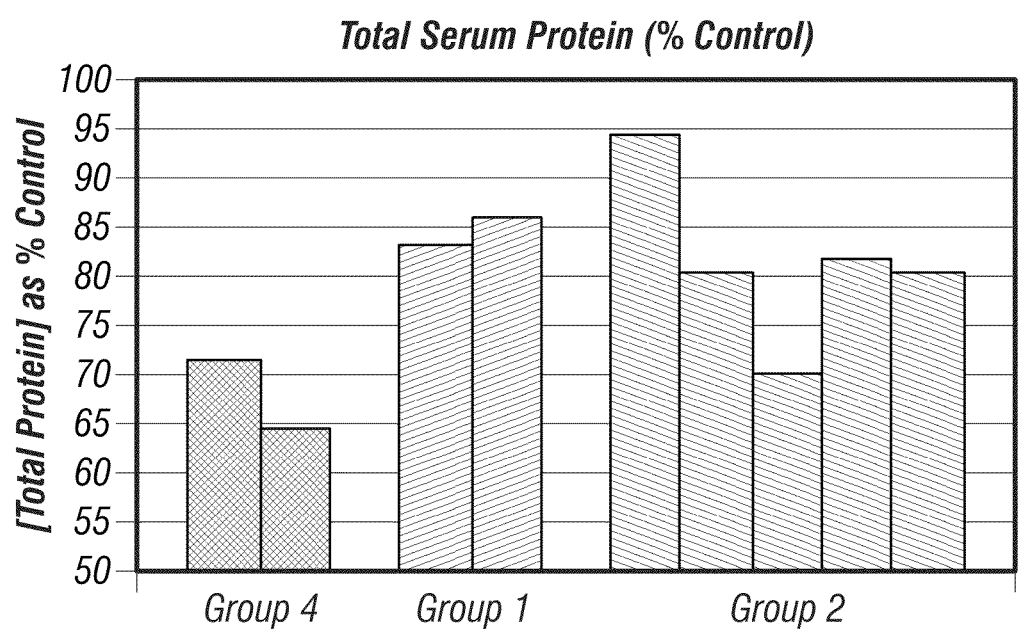
Figure 33A:
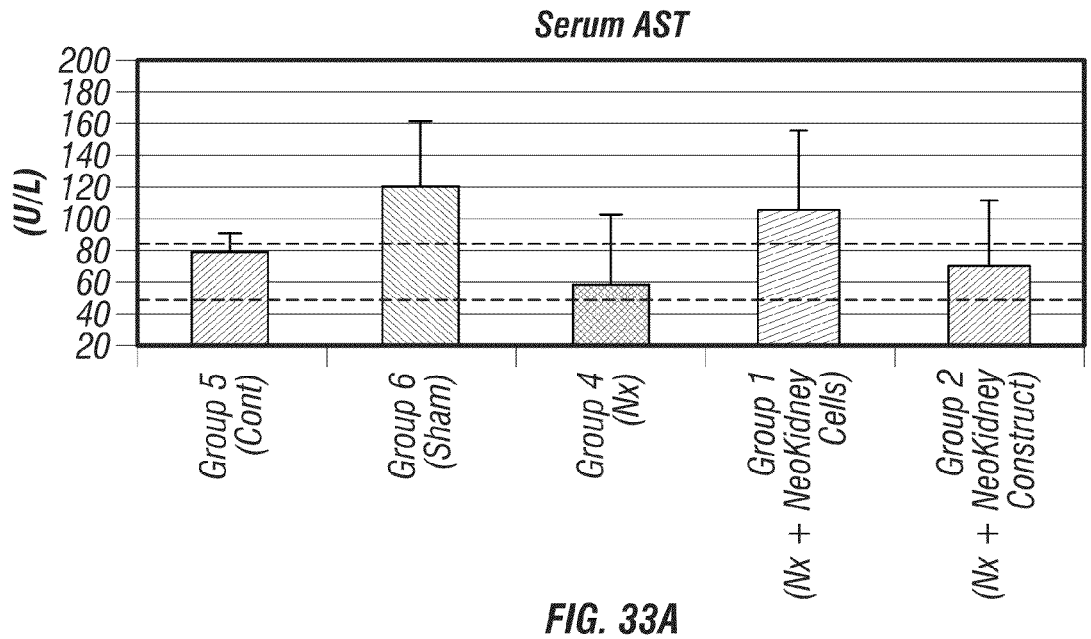
FIG. 33A-D depicts terminal serum liver function.
Figure 33B:
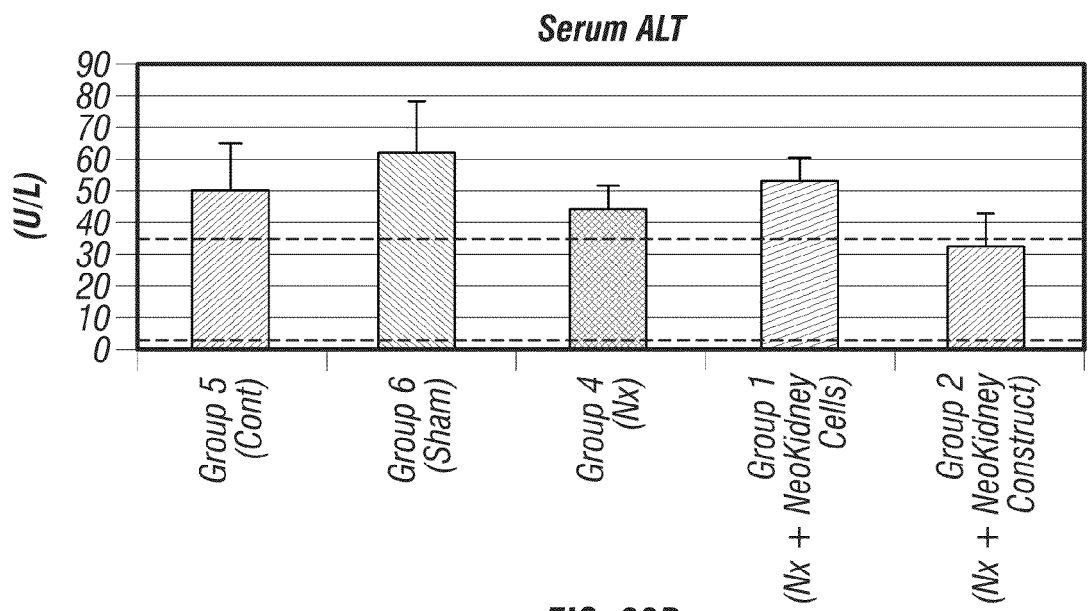
Figure 33C:
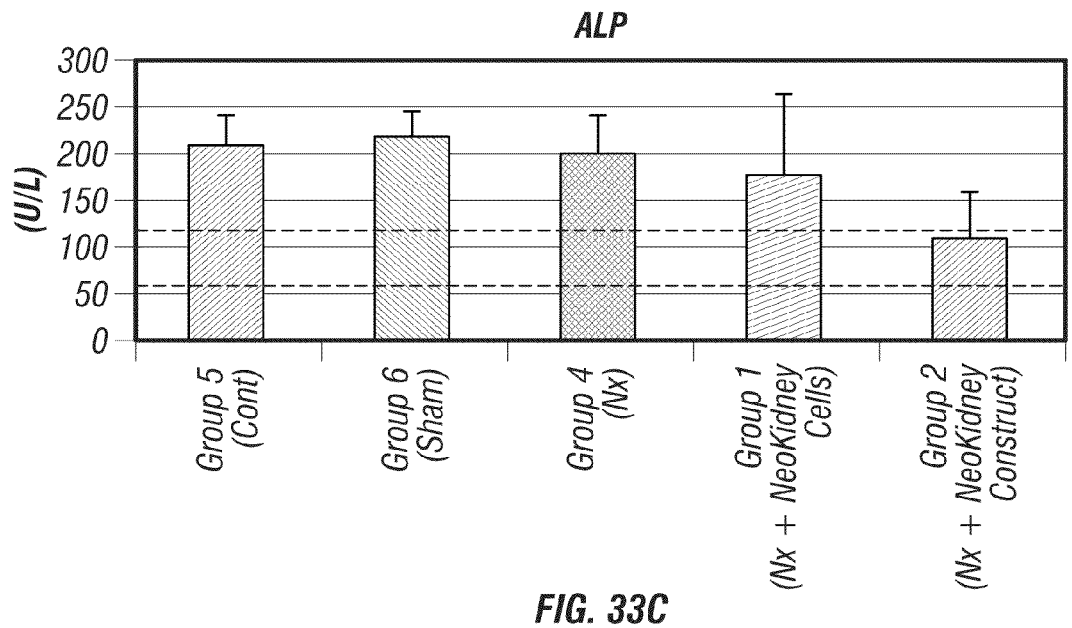
Figure 33D:
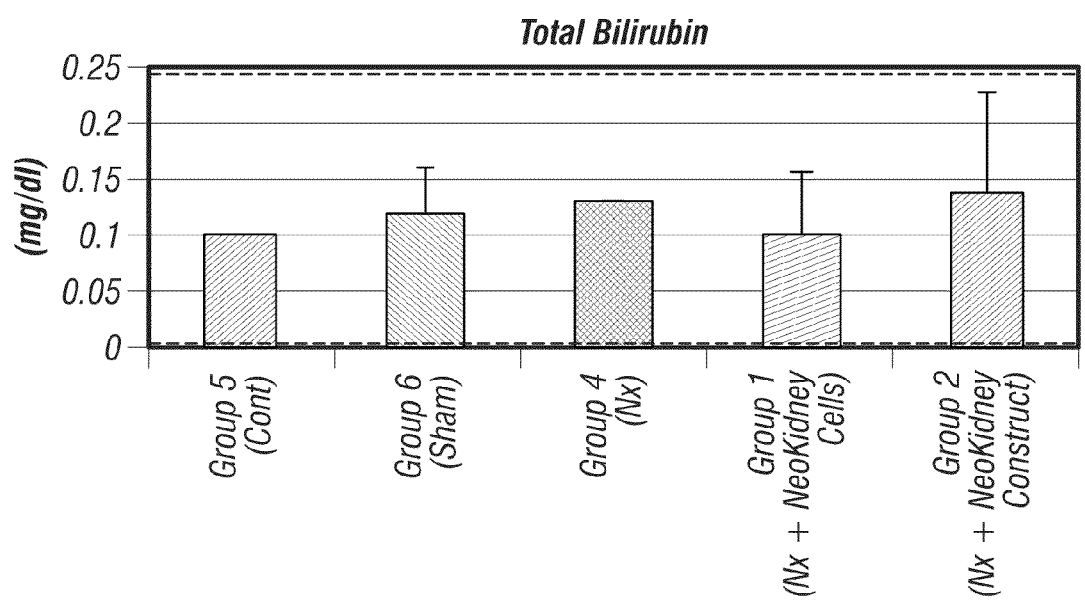

Serum Proteins: Total serum protein, serum albumin, and serum globulin levels were measured in all rats at sacrifice, with the exception of rats found dead from which blood was not taken. Serum albumin and globulin were within normal range for rat in Groups 5 & 6, controls and shams. Group 4 nephrectomized untreated rats had a significant reduction in serum albumin and total protein compared to controls and shams. Treatment with NeoKidney Cell Prototype#1 (Group 1) resulted in mild recovery of serum albumin and total serum protein (FIG. 31). Treatment with NeoKidney Construct Protoype#1 (Group 2) also resulted in mild recovery of total serum protein. Individual rat data for serum albumin and total protein are presented as % control in FIG. 32.

Liver Function: Liver function was assessed by measuring bilirubin, AST, ALT, GGT, & ALP. All data for these tests are presented in Tables 7a-7c. Average serum AST was above reported normal range in Group 6 Shams and Group 1 Nx+NeoKidney Cell Prototype#1-treated rats (FIG. 33). Group 5 controls fell within normal range, as did Groups 4 and 2, although with a high degree of variability. With the exception of Group 2 (NeoKidney Construct Protoype#1) all Groups had a higher average serum ALT and ALP than reported normal ranges for rat. Bilirubin levels were within reported normal range and were not different among treatment groups.

Figure 34A:
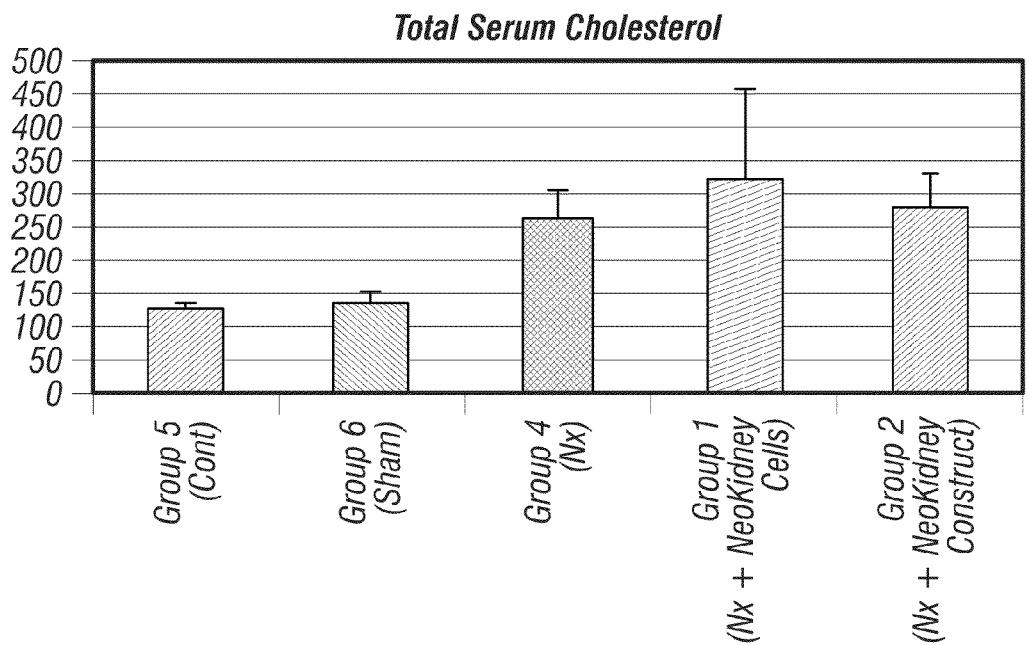
FIG. 34A-C shows Terminal Serum Cholesterol, Triglycerides, & Glucose.
Figure 34B:
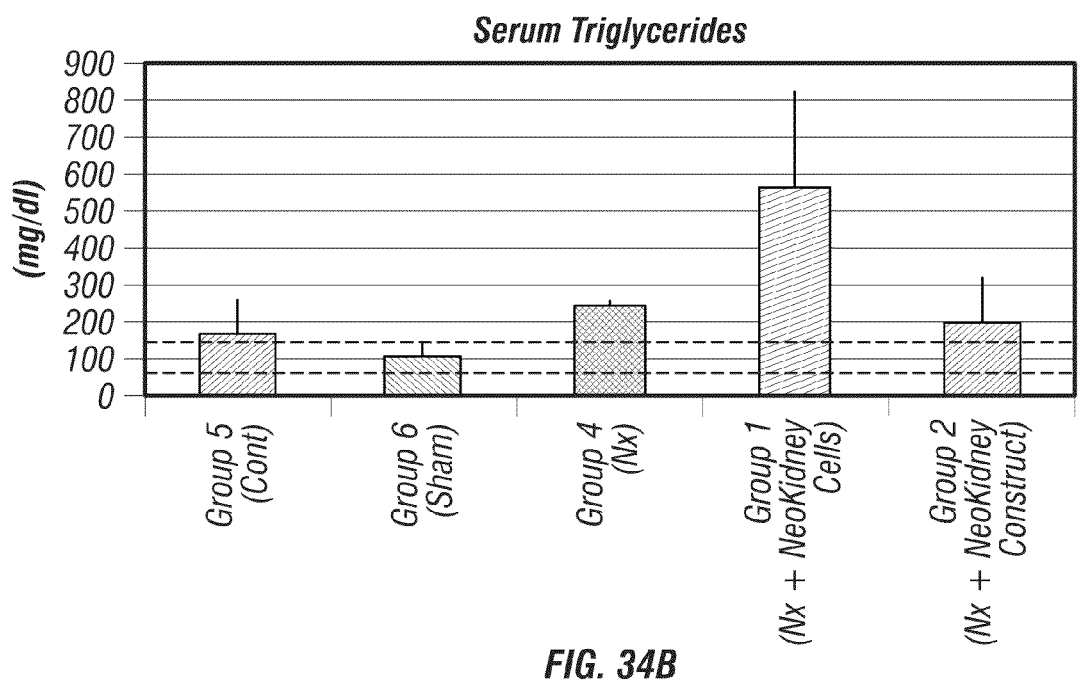
Figure 34C:
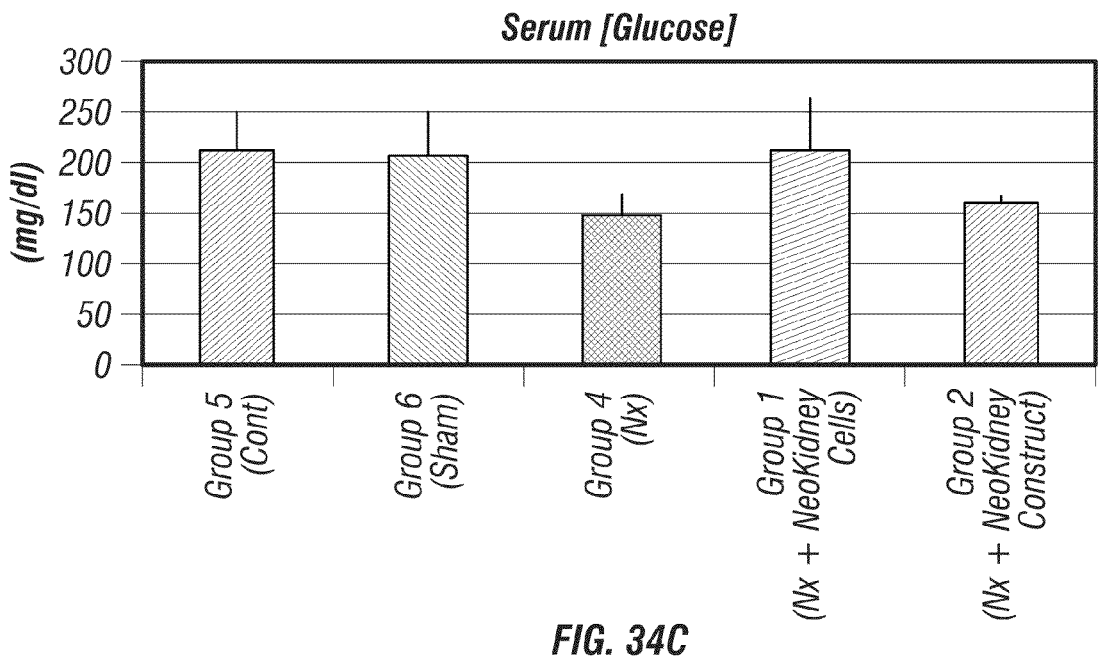
Figure 35A:
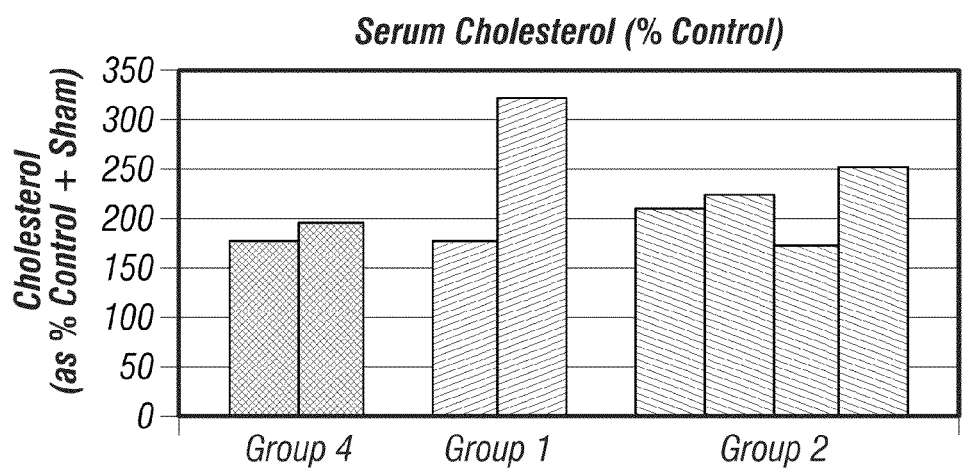
FIG. 35A-C shows Relative Serum Cholesterol, Triglycerides, Glucose (FINAL)/Individual Rat data.
Figure 35B:
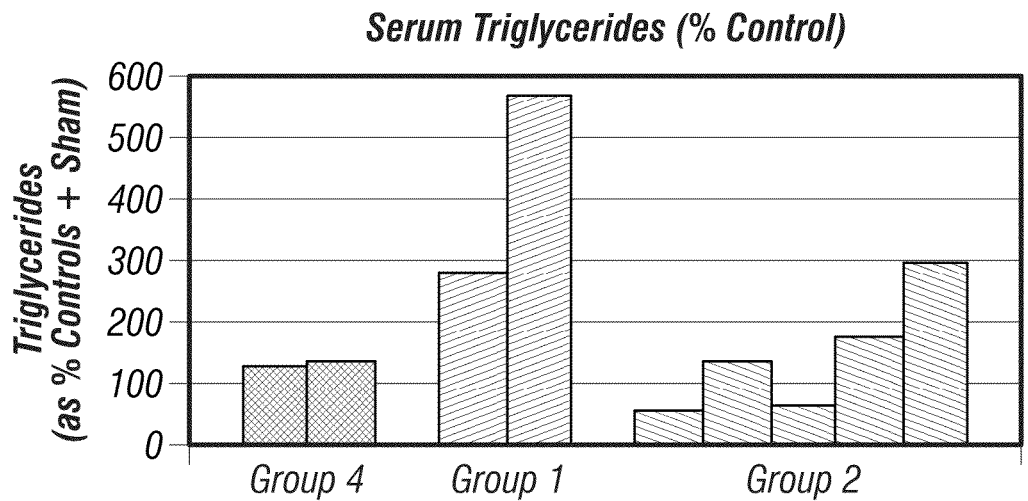
Figure 35C:
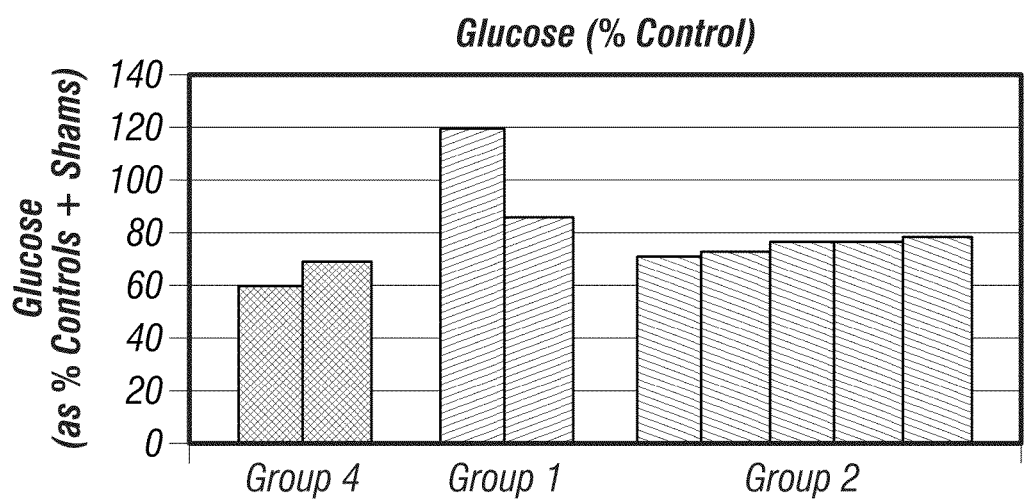

Lipids & Sugar: Cholesterol, triglycerides and glucose were also measured in serum collected from animals at time of sacrifice. All data are presented in tabular form in Appendix F. Both the average serum cholesterol and triglyceride levels were significantly elevated in the nephrectomized groups (1, 2, & 4), regardless of treatment. Of note was the Group 1 NeoKidney Cell Prototype#1-treated triglyceride average, which was significantly higher than the Controls and Shams (Groups 5 & 6) but also higher than Groups 4 & 2 (FIG. 34). Average serum glucose levels were higher than reported normal range for all groups. Group 1 NeoKidney Cell-treated rats had a serum [glucose] equivalent to controls & shams, while the Group 4 and Group 2 rats had slightly lower serum [glucose]. Individual rat data, expressed as % control+sham, are presented in FIG. 35 so that variability among rats in each group can be appreciated.

TABLE 7a

Final Serum Chemistry and Hematology

| Group | ALB (g/dl) | ALP (U/L) | AL (U/L) | AST (U/L) | A/G ratio | CA (mg/dl) | CHOL | GGT (U/L) | GLOB (g/dl) | GLU (mg/dl) |
|---|---|---|---|---|---|---|---|---|---|---|
| Control | 4.04 | 207.4 | 50.2 | 78.8 | 1.3 | 11.86 | 129.2 | 0 | 3.12 | 215.8 |
| Sham | 3.85 | 215.83 | 62.33 | 120.33 | 1.3 | 11.68 | 129.83 | 0 | 2.97 | 210.67 |
| Cell injection | 2.8 | 179 | 53.5 | 107.5 | 0.92 | 13.5 | 320.5 | 0 | 3.1 | 217 |
| NephRx | 2.4 | 199 | 43.67 | 58.17 | 0.93 | 11.8 | 262.33 | 0 | 2.63 | 146.33 |
| Seeded saffold | 2.58 | 107.2 | 33.2 | 70.7 | 0.84 | 12.52 | 282.8 | 0 | 3.1 | 159.6 |

| Group | K (mmole/L) | NA (mmole/L) | PHOS | TBIL (mg/dl) | TRPO (g/dl) | TRIG (mg/dl) | CL |
|---|---|---|---|---|---|---|---|
| Control | 6.92 | 141.6 | 6 | 0.1 | 7.16 | 159.8 | 99.8 |
| Sham | 6.67 | 142.5 | 6.8 | 0.12 | 6.82 | 105.33 | 100.67 |
| Cell injection | 4.9 | 144.5 | 6.35 | 0.1 | 5.9 | 553 | 97 |
| NephRx | 5.83 | 146.67 | 10.03 | 0.13 | 5.03 | 166 | 92.33 |
| Seeded saffold | 5.92 | 144.4 | 9.7 | 0.14 | 5.68 | 186.4 | 94.6 |

TABLE 7b

Final Serum Chemistry and Hematology

| Group | BAS ($10^3$/ul) | BAS % | EOS ($10^3$/ul) | EOS % | HB | LUC ($10^3$/ul) | LUC % | LYM ($10^3$/ul) | LYM % | MCH (pg) | MCHC (g/dl) |
|---|---|---|---|---|---|---|---|---|---|---|---|
| Control | 0.06 | 1.3 | 0.03 | 0.55 | 13.75 | 0.09 | 1.75 | 3.85 | 76.45 | 17.4 | 29.65 |
| Sham | 0.08 | 1.33 | 0.03 | 0.43 | 13.78 | 0.17 | 2.63 | 4.91 | 75.93 | 17.85 | 29.78 |
| Cell injection | 0.06 | 0.95 | 0.05 | 0.70 | 11.15 | 0.12 | 2 | 4.24 | 72.95 | 16.85 | 30.3 |
| NephRx | 0.01 | 0.35 | 0 | 0.2 | 5.88 | 0.02 | 0.85 | 0.97 | 42.55 | 17.5 | 32 |
| Seeded saffold | 0.04 | 0.68 | 0.17 | 1.63 | 13.48 | 0.09 | 1.63 | 2.49 | 45.93 | 18.23 | 31.88 |

TABLE 7c

Final Serum Chemistry and Hematology

| Group | MCV (fl) | MON ($10^3$/ul) | MON % | MPV (fl) | NEU ($10^3$/ul) | NEU % | PLT ($10^3$/ul) | RDW (%) | RET ($10^9$/L) | RET % | WBC ($10^3$/ul) |
|---|---|---|---|---|---|---|---|---|---|---|---|
| Control | 58.6 | 0.19 | 3.85 | 9.23 | 0.82 | 16.08 | 664.25 | 11.93 | 353.28 | 4.51 | 5.04 |
| Sham | 59.88 | 0.24 | 3.7 | 9.13 | 1.03 | 16 | 691.5 | 12.75 | 457.5 | 6.16 | 6.47 |
| Cell injection | 55.7 | 0.35 | 5.8 | 8.65 | 1.03 | 17.6 | 841 | 11.75 | 238.3 | 3.56 | 5.83 |
| NephRx | 54.65 | 0.16 | 7.9 | 8.4 | 1.02 | 48.15 | 858.5 | 10.8 | 147.8 | 3.03 | 2.17 |
| Seeded saffold | 57.2 | 0.19 | 3.45 | 9.55 | 2.58 | 46.65 | 715.25 | 11.68 | 247.87 | 3.65 | 5.5 |

Hematology at Sacrifice

Figure 36A:
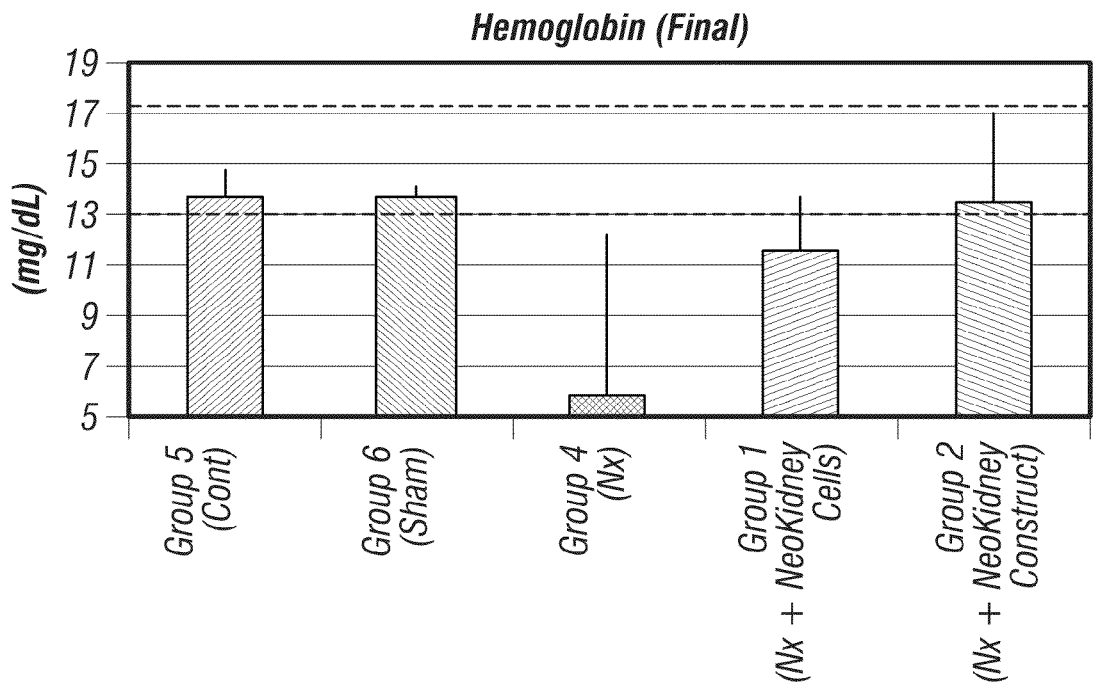
FIG. 36A-C depicts Terminal Hb, MCH, & MCHC.
Figure 36B:
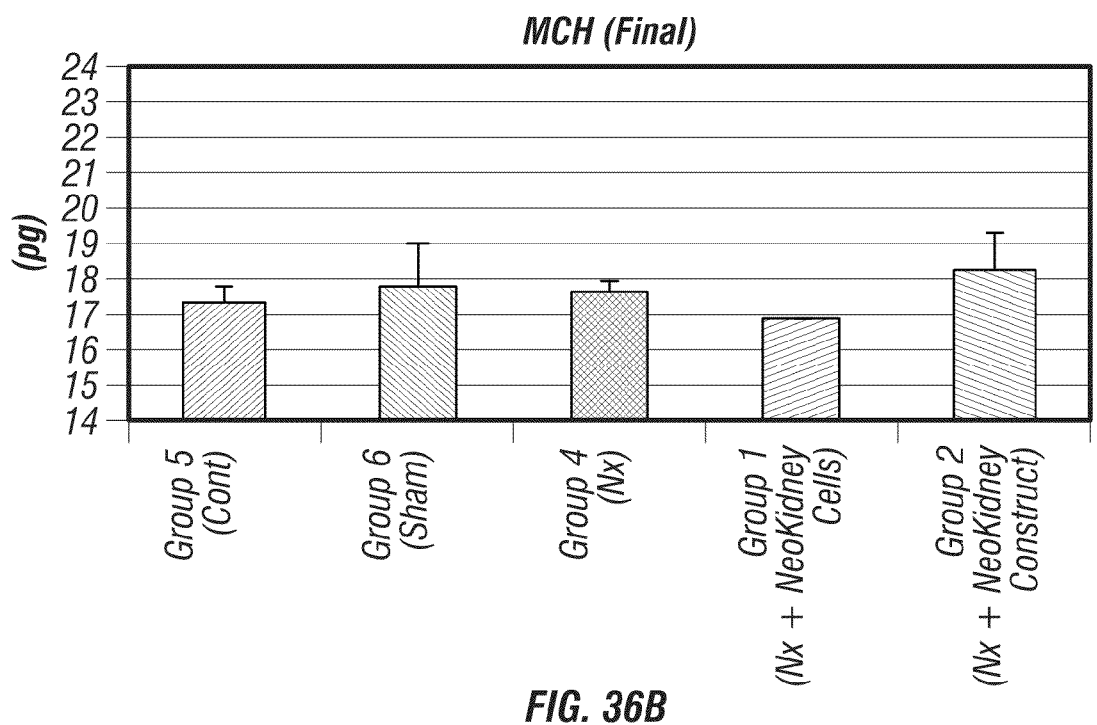
Figure 36C:
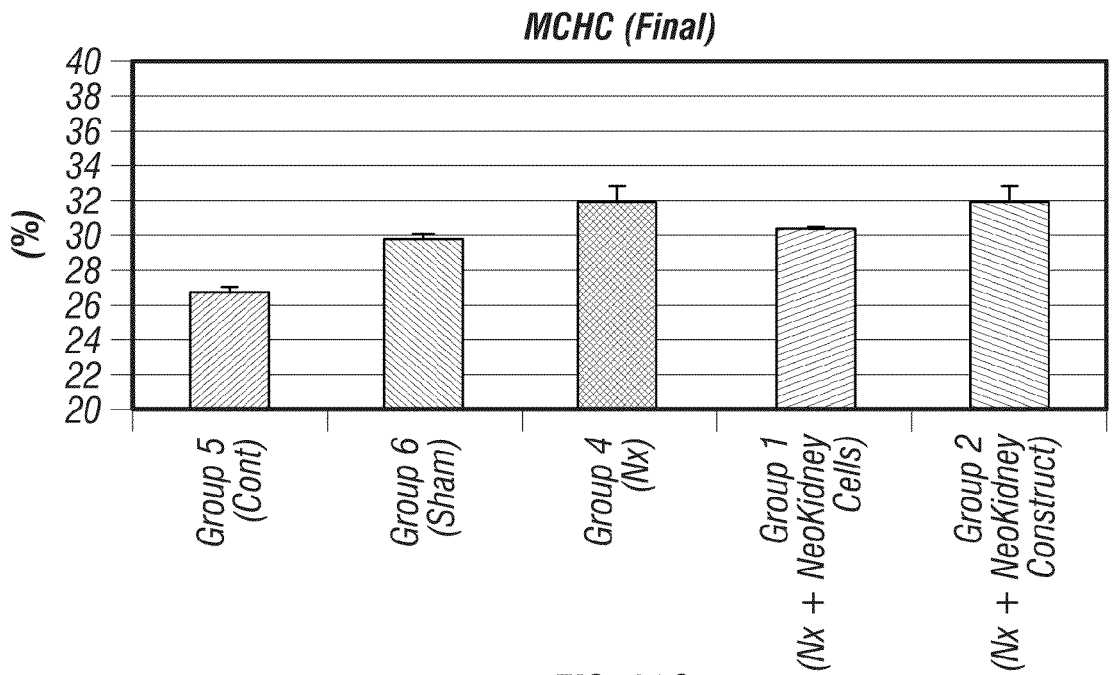
Figure 37:
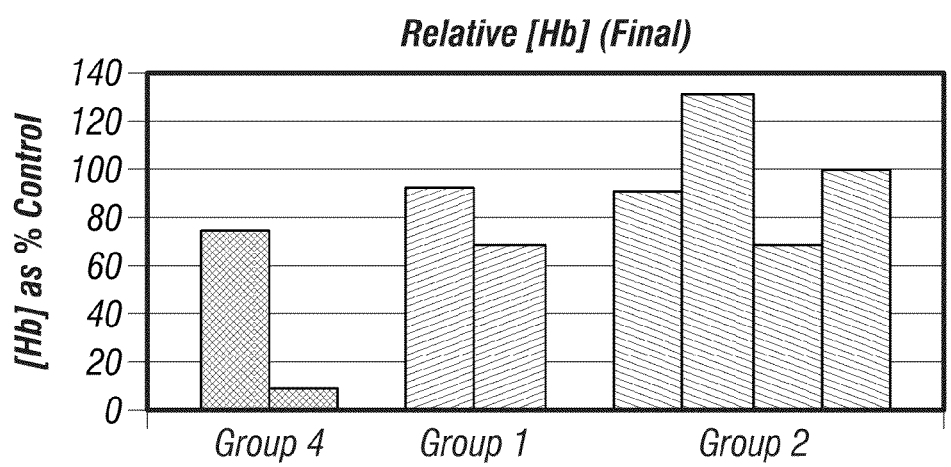
FIG. 37 shows Terminal Relative/Individual Rat Data.

Hemoglobin: At the time of sacrifice, blood was collected and used to measure hemoglobin (Hb), mean corpuscular hemoglobin (MCH), and mean corpuscular hemoglobin concentration (MCHC). All data are presented in Tables 7a-7c. Group 4 nephrectomized untreated rats had a significantly low [Hb] when compared to controls and shams (FIG. 36), as would be expected given both the depressed HCT and RBC# in Group 4. Both Group 1 and Group 2 average [Hb] was higher, with many rats returning to normal range (see individual data in FIG. 37). The MCH was relatively equivalent for all rats, indicating that the concentration of hemoglobin per RBC was similar among treatments. The observation of increased [Hb] in Group 1 & Group 2 rats treated with NeoKidney Cell Prototype#1 or NeoKidney Construct Protoype#1 is concordant with the observation of increased RBC# & Hematocrit in these rats. Taken together, the data suggest stimulation of erythropoiesis and oxygen-carrying capacity in the treated rats.

Figure 38:
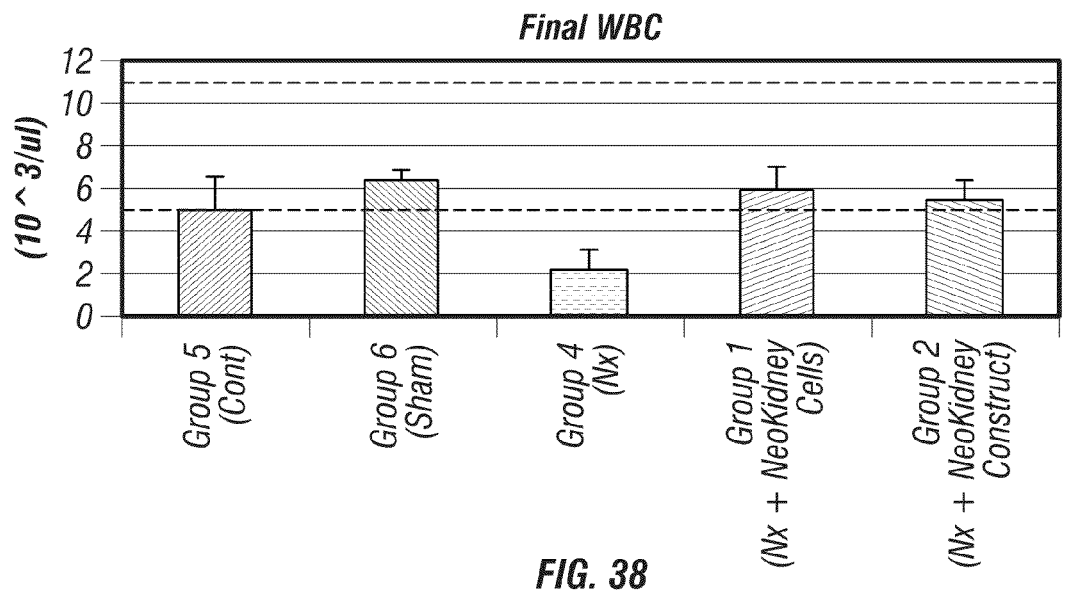
FIG. 38 depicts Terminal WBC Count.
Figure 39:
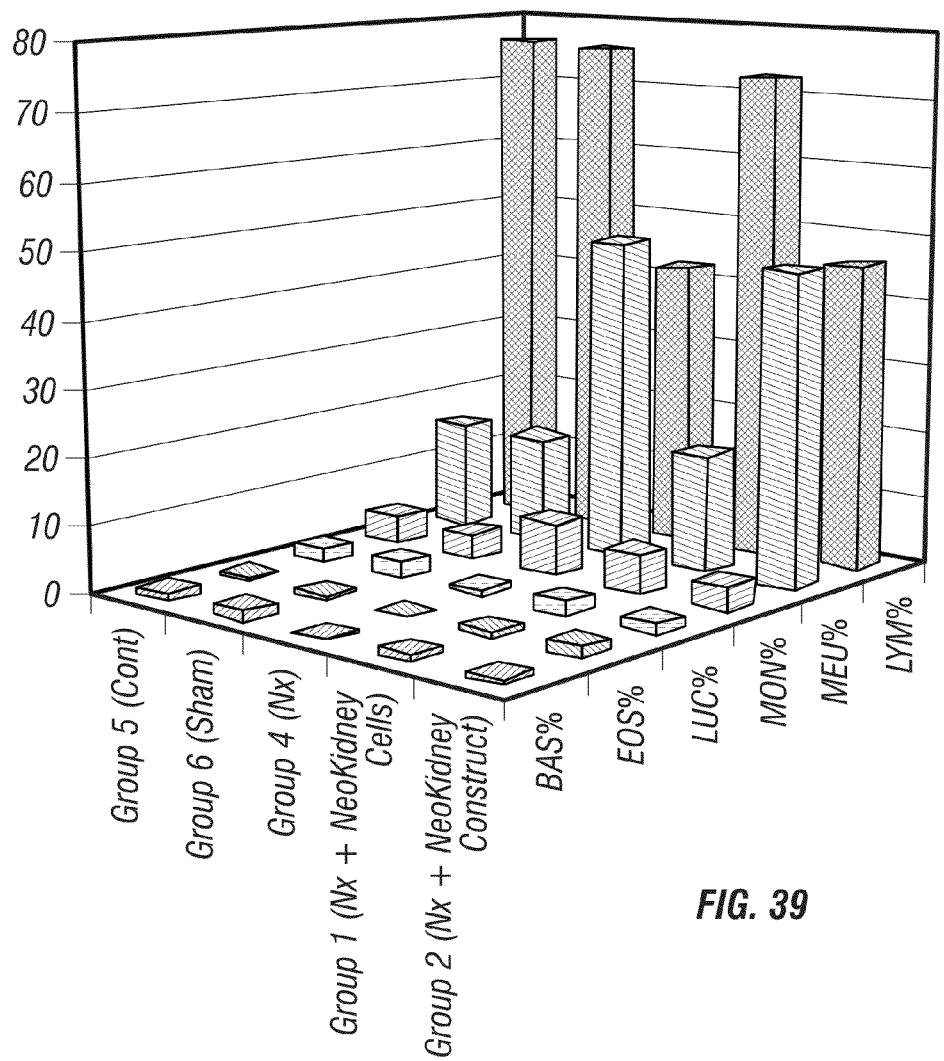
FIG. 39 shows Terminal WBC Composition.

WBC & RBC Counts & Composition: White blood cell counts (WBC) and red blood cell counts (RBC) were taken from all rats at sacrifice, with the exception of rats found dead from which blood could not be taken. All hematology data are presented in Tables 7a-7c. In addition, the total WBC population from each rat was evaluated for relative percentage of lymphocytes, monocytes, basophils, neutrophils, eosinophils, and large unstained cells (LUCs). As shown in FIG. 38, average WBC was in normal range for all groups except Group 4 nephrectomized untreated rats, in which WBC was depressed. FIG. 39 highlights differences in WBC composition among groups. Note the relatively low lymphocyte % and relatively high neutrophil % in both the Group 4 nephrectomized untreated rats and in the Group 2 nephrectomized rats that received NeoKidney Construct Prototype#1.

Figure 40A:
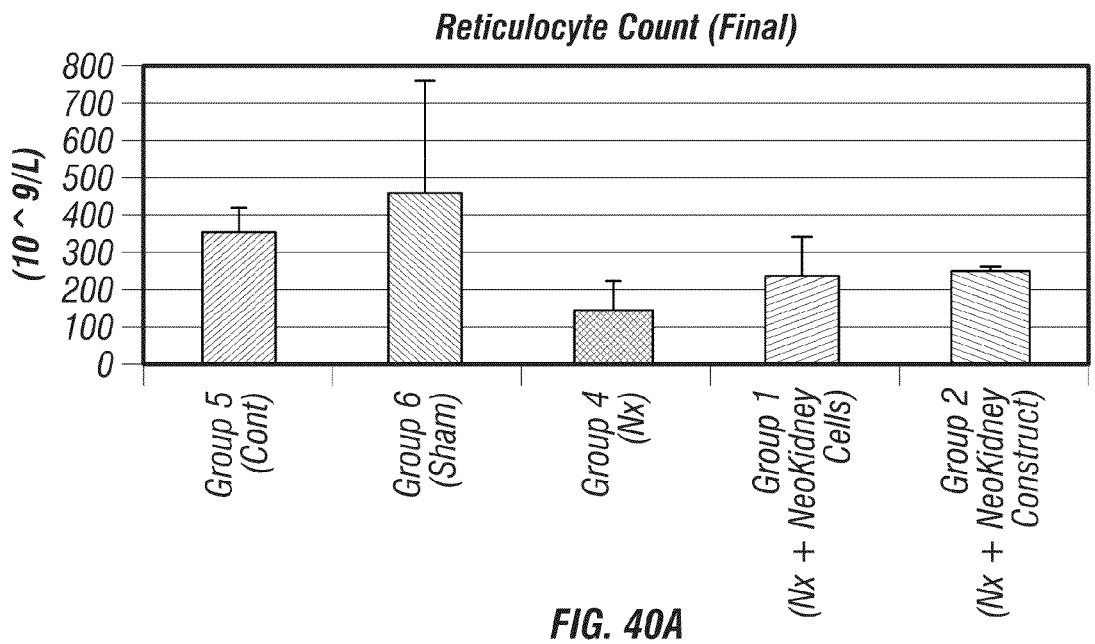
FIG. 40A-B depicts Terminal Reticulocyte.
Figure 40B:
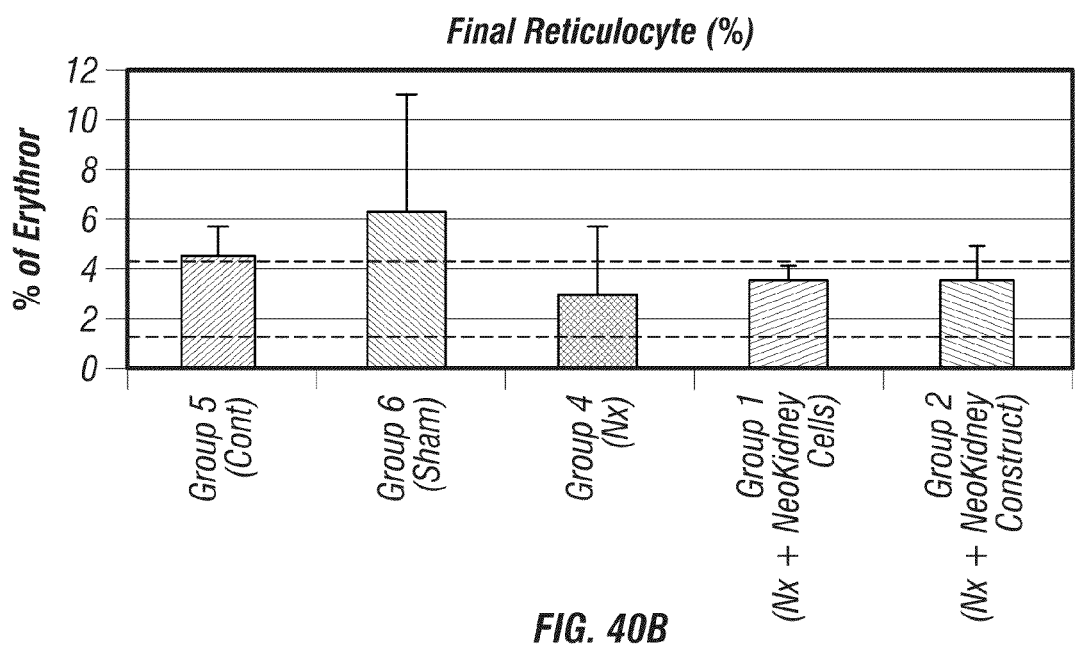

With respect to the erythroid population, reticulocyte number and percent were measured in the final blood draw (see FIG. 40). RBC and HCT have already been reported (see FIGS. 26-29). Reticulocyte number and percentage were depressed in the Group 4 nephrectomized untreated rats compared to Groups 5 & 6 controls & shams. Both treatment groups (1 & 2) show slight improvement compared to Group 4, but the difference is not significant statistically. RDW was also assessed (measures variability of RBC width) as well as MCV (mean corpuscular volume), but no significant differences were seen among groups (data not shown). All hematology data are presented in Tables 7a-7c.

Figure 41A:
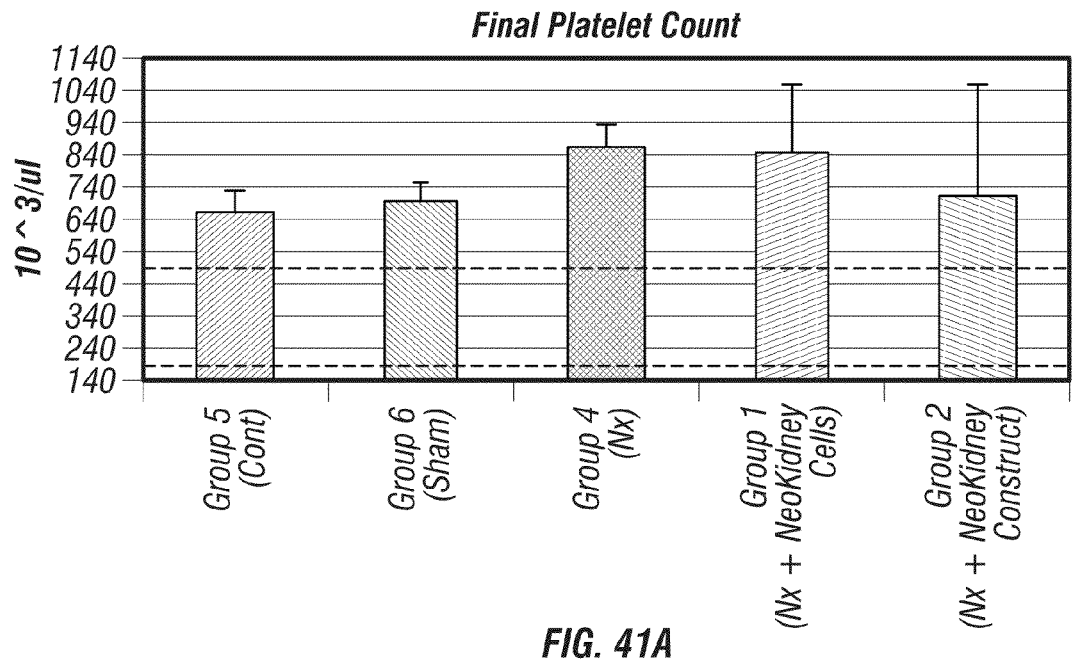
FIG. 41A-B shows Terminal Platelet Data.
Figure 41B:
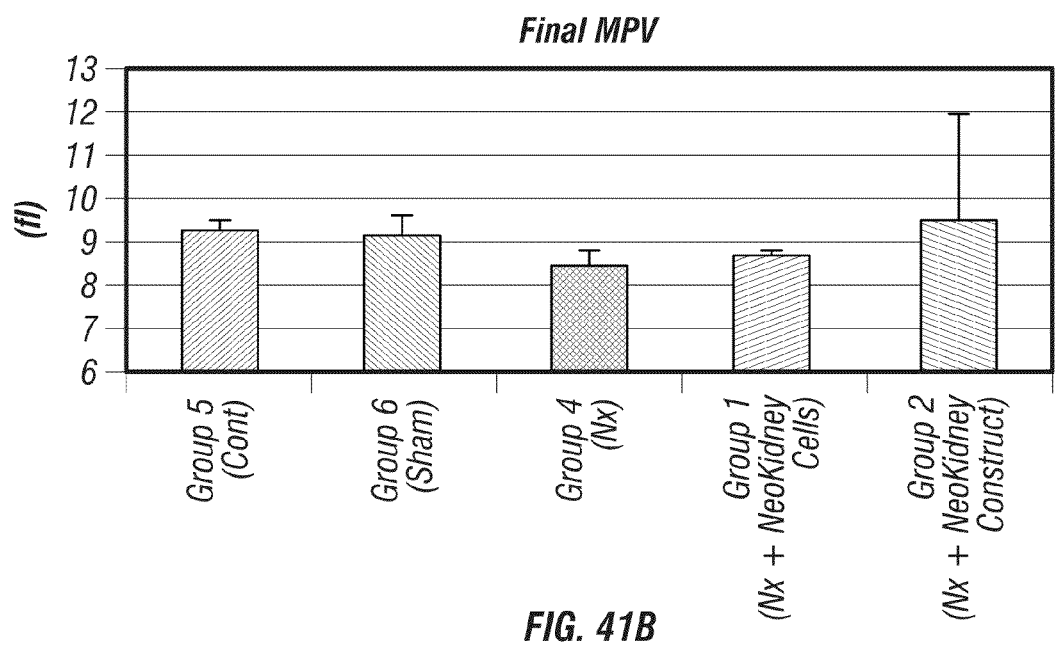

Platelets: Platelet counts and mean platelet volume (MPV) were measured in blood taken at sacrifice. Platelet counts were slightly above normal reported range in all groups. There were no significant differences in platelet counts or MPV among treatment groups (see FIG. 41).

Figure 42:
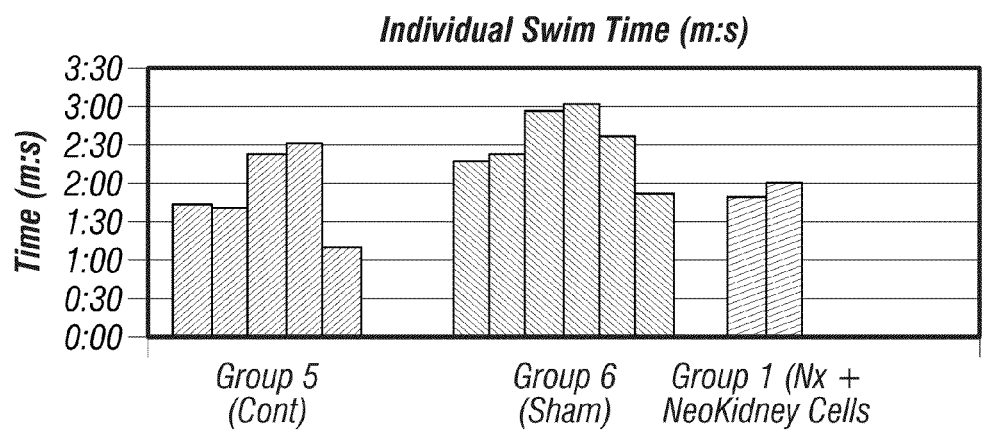
FIG. 42 shows swim test results.
Figure 43:
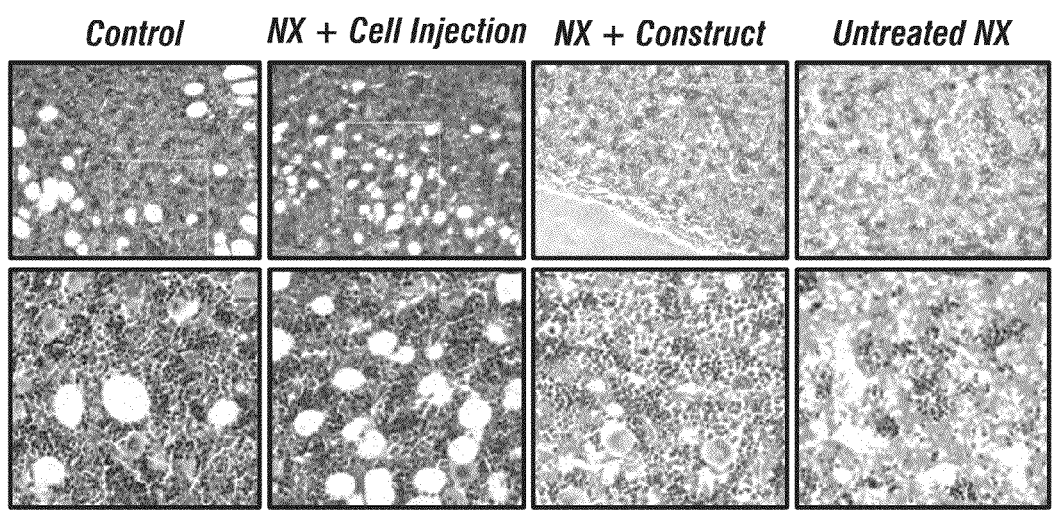
FIG. 43 depicts representative H&E-stained histological section of bone marrow from each test group. The top panel shows that compared to control, NX+ cell injection bone marrow cellularity and myeloid to erythroid ratios appeared to be equivalent. In contrast, the bone marrow in the NX+ Construct and untreated animals showed moderate and marked, decreased marrow celluarity, respectively (magnification 200×). The bottom panel shows a higher view of boxed views in the top panel (magnification unknown).
Figure 44A:
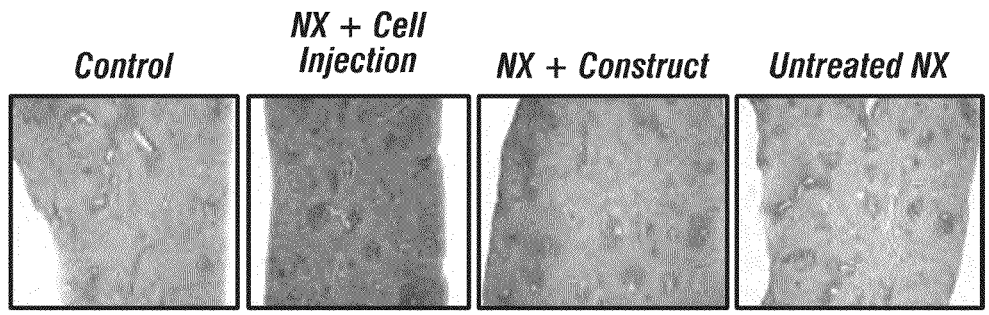
FIG. 44A-B shows representative H&E-stained histological section of spleen from each test group. The top panel shows no major histological differences or changes were observed between the Control and NX+ Cell Injection groups. In contrast, the immediate subcapsular red pulp space in NX+ Construct and untreated animals showed moderate and marked, respectively, decreases in adult red blood cells (RBC) and in RBC precursors (magnification 200×). The bottom panel shows a higher view of boxed views in the top panel (magnification unknown).
Figure 44B:
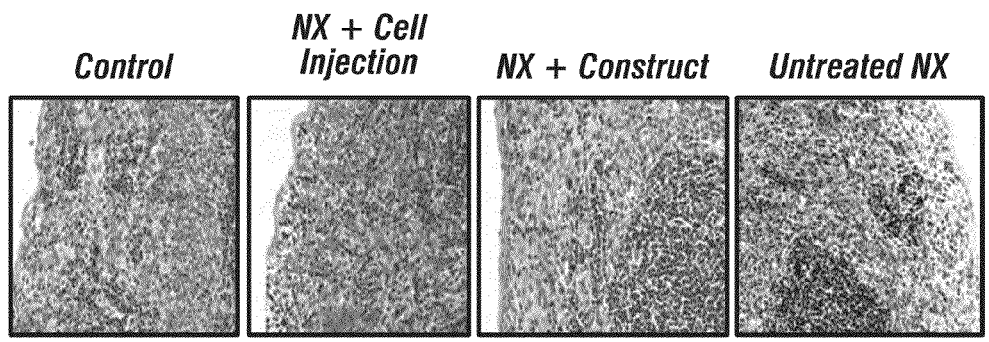
Figure 45A:
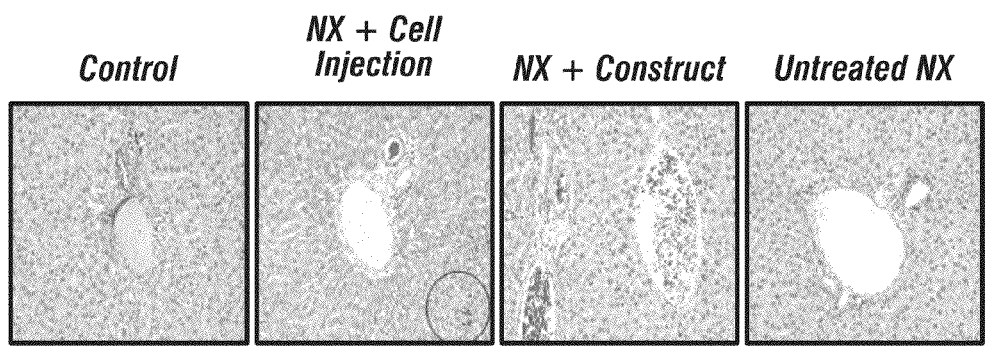
FIG. 45A-B shows representative H&E-stained histological section of liver from each test group. No appreciable changes were observed in the hepatic parenchyma and/or in the portal triads in NX+ Construct or untreated NX animals when compared to the control group. In contrast, focal areas of sinusoidal hematopoiesis (circle) were noted in the NX+ cell injection group (magnification 200×) (A). The bottom panel (B) shows a higher view of the portal triads shown in the top panel (magnification unknown).
Figure 45B:
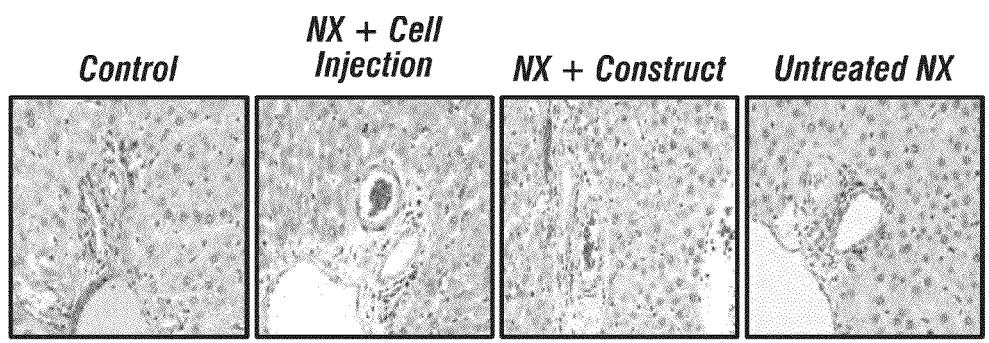
Figure 46A:
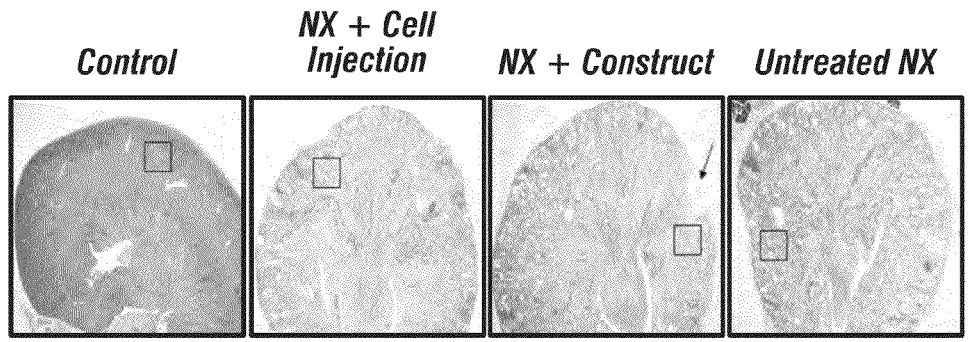
FIG. 46A-B depicts representative H&E-stained histological section of kidney from each test group (magnification 1×). The top panel shows that compared to control, renal sections of the other three groups showed progressive glomerular and tubular degeneration with loss of architecture, in all groups, characterized by poor hemosiderin pigment, and multifocal tubular regeneration (magnification 200×). Arrow points to construct treatment site. The bottom panel shows a higher view of boxed views in the top panel (magnification unknown).
Figure 46B:
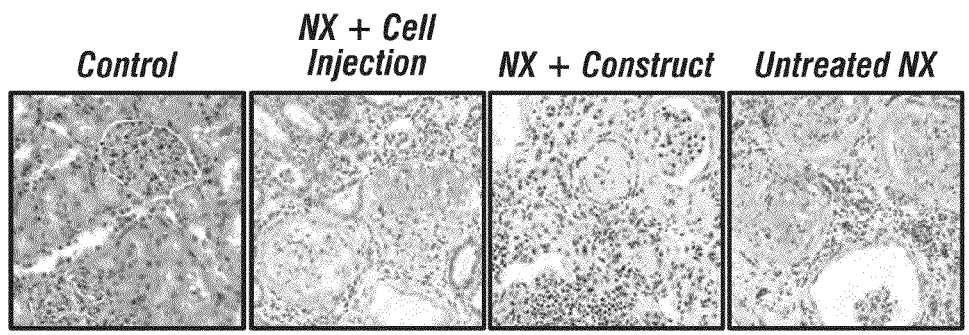

Swim Endurance: At the end of study, just prior to sacrifice on Day 84, remaining rats were subjected to a swim endurance test as described in Methods section. The swim test was conducted between the Group 1 NeoKidney Cell-treated rats and the Controls & Shams (Groups 5 & 6). As shown in FIG. 42, healthy rats swam for an average of 2 minutes and 12 seconds, with a reasonable degree of variability among rats (±33 seconds). This test also confirmed the performance level of the Group 1 NeoKidney Cell treated rats to be equivalent to the Control group.

Histopathology

Representative pictures can be found from each tissue examined in FIGS. 43-46. The following provides a summary of findings for each tissue among groups.

Liver: No appreciable changes were observed in the hepatic parenchyma and/or in the portal triads in Group 4 (Nx) or Group 2 (Nx+Neo-Kidney Construct) when compared to the Group 5 & 6 Controls & Shams. In contrast, focal areas of sinusoidal hematopoiesis were noted in the Group 1 (Nx+Neo-Kidney Cells) rats.

Kidney: Compared to Groups 5 & 6, all other test groups showed progressive glomerular and tubular degeneration of kidney with loss of architecture, characterized by poor demarcation between cortex and medulla, cystic spaces, periglomerular fibrosis, replacement of glomerular tufts with avascular hyaline material, hemosiderin pigment, and multifocal tubular regeneration.

Spleen: No major histological differences or changes were observed between the Groups 5 & 6 Controls & Shams and the Group 1 (Nx+Neo-Kidney cells injection). Examination of the immediate subcapsular red pulp space in Groups 2 and 4 animals showed moderate and marked, respectively, decreases in adult red blood cells (RBC) and in RBC precursors.

Figure 26B:
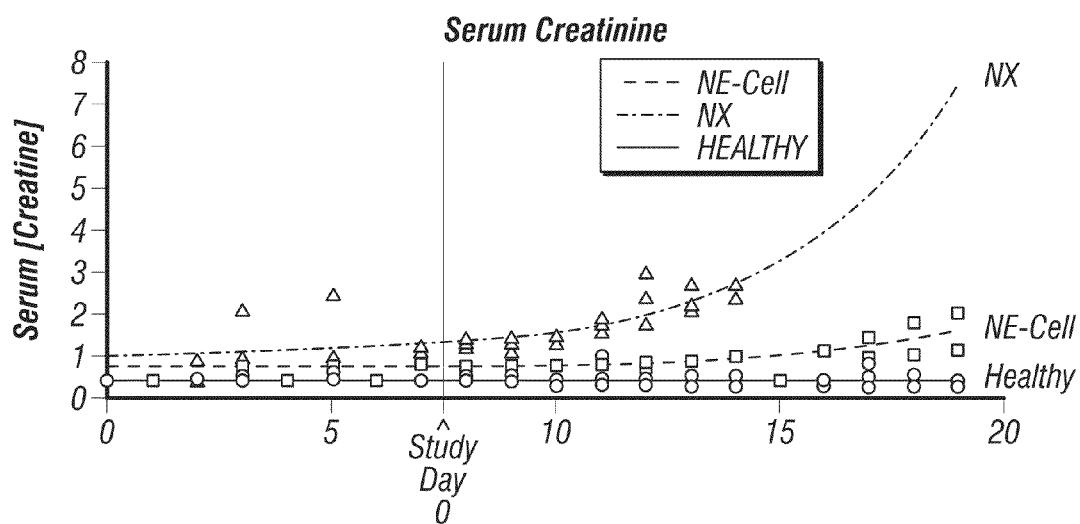
FIG. 26B-C shows serum creatinine (B) and hematocrit (C) post-nephrectomy.
Figure 26C:
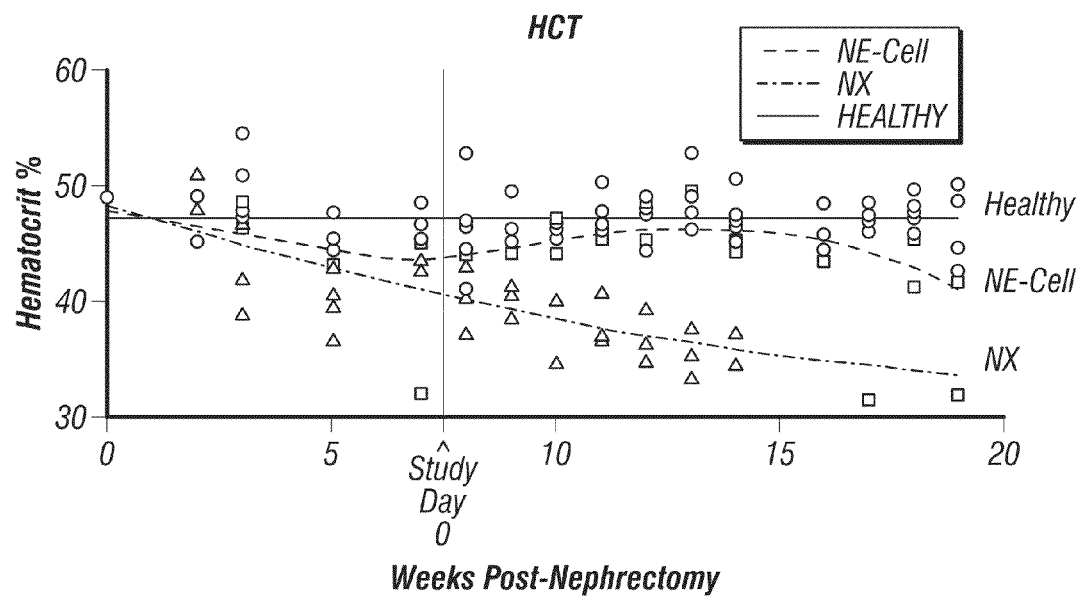

Marrow: Compared to Groups 5 & 6 controls & shams, Group 1 rats' bone marrow cellularity and myeloid to erythroid ratios appeared to be equivalent. In contrast, the bone marrow in Group 2 and Group 4 animals were characterized by moderate and marked decreases in marrow cellularity, respectively. As shown in FIG. 26, delivery of the Neo-Kidney cells in vivo to uremic/anemic rats had a stimulatory effect on the bone marrow, and in particular, on the erythroid population. FIG. 26 further shows that delivery of the Neo-Kidney cells in vivo to uremic/anemic rats also stimulated an increase in general cellularity, which was still persistent at least three months post-delivery.

Figure 47:
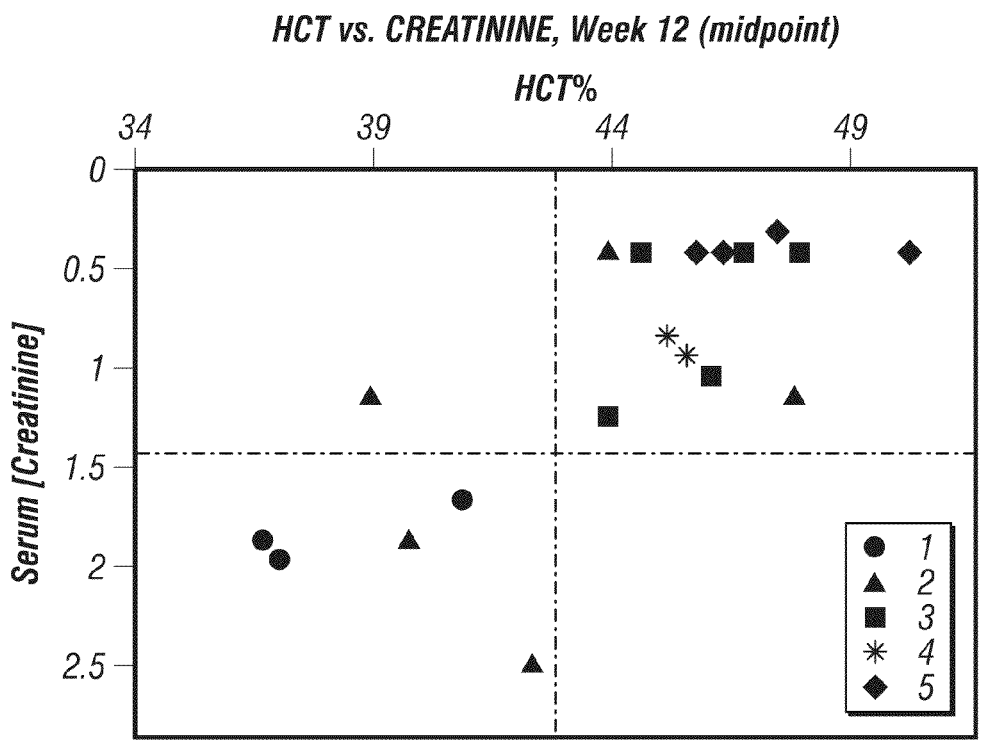
FIG. 47 shows Individual Rat Data/HCT % vs. Serum Creatinine. Group 5=solid circle; Group 6=encircled "3"; Group 4=encircled "1"; Group 1=encircled "4"; Group 2=encircled "2".

As shown above, NeoKidney Cell Prototype#1 (UNFX) delivered alone or in 3D scaffolding had restorative effects on erythropoiesis and erythroid homeostasis in the 5/6 surgical nephrectomy model, as determined by temporal analysis of RBC# & HCT and confirmed in the terminal bloodwork by other parameters (Hb, MHC, Reticulocytes). The effects were somewhat variable from animal to animal, especially in the Group 5 NeoKidney Construct Protoype#1-treated rats, which may have been due to variability in retention of the scaffold by the kidney or due to unidentified complications of scaffold breakdown within the kidney parenchyma. Importantly, in any one given rat, improvements in HCT or Creatinine also translated into improved values for RBC# and BUN, lending further strength to the observations that treatments had a positive overall effect. FIG. 47 plots the HCT data against the serum [creatinine] for each rat. All Group 5 & 6 controls and shams cluster to the upper right quadrant, with higher HCT and lower creatinine 2/2 and 2/5 of the Group 1 and Group 2 rats segregate into the upper right quadrant with Groups 5 & 6. ⅓ of the Group 2 treated rats demonstrates an improved creatinine when compared with Group 4, but not an improved HCT, thus it appears in the upper left quadrant. The remaining (2) Group 2 rats had little or no improvement in either parameter, thus they cluster with Group 4 rats in the lower left quadrant (high creatinine, low HCT).

In conclusion, the above results show that NeoKidney Cell implants (Group 1) improved survival of the 5/6 nephrectomized rats. 2/2 Group 1 rats reached the 3-month post-treatment timepoint and were sacrificed alongside controls and shams at day 84. NeoKidney Cell implants (Group 1) reversed anemia in this model for a duration of approximately 12 weeks, as evidenced by a return of HCT and RBC to normal value ranges. Further, FIG. 47 shows that delivery of NeoKidney Cell Prototype#1 in vivo to uremic/anemic rats restored hematocrit to normal levels and facilitated survival beyond that of untreated uremic/anemic rats. Also, as shown above, NeoKidney Cell implants regulated erythroid homeostasis during the 12 week period, as evidenced by the failure of the treatment to overcorrect the anemia and result in polycythemia vera. Interestingly, NeoKidney Cell implants provided stabilization of renal function, as evidenced by a stabilization of serum BUN and CREA from the time of treatment through 12 weeks. NeoKidney Construct Protoype#1 provided improvement in both HCT and stabilization of renal function in 2/5 rats at the midpoint of the study. At the time of death of the rats due to morbidity, the renal functions and erythroid functions were still measurably better than those of the Group 4 nephrectomized untreated rats at the time of their death due to morbidity. The observed heterogeneous nature of the cultured NeoKidney cells used in these experiments, paired with the clear observations of therapeutic benefit after transplant, provided impetus for identifying the specific cellular component(s) within the population responsible for delivering the therapeutic effects.

The above results also show that clear and significant positive effects were observed upon delivery of NeoKidney Cell Prototype#1 (2/2) and NeoKidney Construct Protoype#1 (3/5) on HCT and RBC numbers. Positive effects of NeoKidney Cell Prototype#1 were rapid (within 1 week of treatment) and sustainable up to 3 months post-treatment. This study also shows that NeoKidney Cell Prototype#1 (2/2) and NeoKidney Construct Protoype#1 (3/5) provided stabilization of renal function and slower progression of disease compared to nephrectomized rats that remained untreated. Further, clear histological evidence suggests that NeoKidney Cell Prototype#1 (2/2) provided stimulation of erythroblasts in the bone marrow sufficient to result in normal cellularity and M:E ratio at the time of sacrifice (3 months post-treatment). Furthermore, while the NeoKidney Construct Protoype#1 (Group 2) rats did not present normal bone marrow histology at the time of sacrifice, the cellularity and presence of erythroid lineage cells was superior to Group 4 untreated nephrectomized rats. The histological evidence obtained in this study also suggest that the Group 2 Neo-Kidney cells stimulated mild histological improvement in some aspects of the kidney, as determined by small pockets of tubular regeneration near the transplantation site. However, these changes are mild and not widespread throughout the kidney. Although not wishing to be bound by theory, it is hypothesized that any improvements seen systemically in renal function are due to effects at the individual cellular level in the Group 2 rats and may not be fully appreciable at the level of the tissue histologically. Finally, the above study shows that NeoKidney Cell Prototype#1 and NeoKidney Construct Protoype#1 extended lifespan, with NeoKidney Cell Prototype#1-treated rats living for the duration of the study (3 months). While all groups of nephrectomized rats failed to gain weight between treatment date and date of sacrifice during the study, weight loss was lesser in the groups treated with NeoKidney Cell Prototype#1.

Example 8

Kidney Cell Isolation and Enrichment of Specific Bioreactive Renal Cells from Heterogeneous Cell Population Kidney cell isolation: Briefly, batches of 10, 2-week-old male Lewis rat kidneys were obtained from a commercial supplier (Hilltop Lab Animals Inc.) and shipped overnight in Viaspan preservation medium at a temperature around 4° C. All steps described herein were carried out in a biological safety cabinet (BSC) to preserve sterility. The kidneys were washed in Hank's balanced salt solution (HBSS) 3 times to rinse out the Viaspan preservation medium. After the third wash the remaining kidney capsules were removed as well as any remaining stromaltissue. The major calyx was also removed using micro dissection techniques. The kidneys were then finely minced into a slurry using a sterile scalpel. The slurry was then transferred into a 50 ml conical centrifuge tube and weighed. A small sample was collected for RNA and placed into an RNAse-free sterile 1.5 ml micro-centrifuge tube and snap frozen in liquid nitrogen. Once frozen, it was then transferred to the −80 degree freezer until analysis. The tissue weight of 10 juvenile kidneys equaled approximately 1 gram. Based on the weight of the batch, the digestion medium was adjusted to deliver 20 mls of digestion medium per 1 gram of tissue. Digestion buffer for this procedure contained 4 Units of Dispase 1 (Stem Cell Tech) in HBSS, 300 Units/ml of Collagenase type IV (Worthington) with 5 mM $CaCl_2$ (Sigma).

The appropriate volume of pre-warmed digestion buffer was added to the tube, which was then sealed and placed on a rocker in a 37° C. incubator for 20 minutes. This first digestion step removes many red blood cells and enhances the digestion of the remaining tissue. After 20 minutes, the tube was removed and placed in the BSC. The tissue was allowed to settle at the bottom of the tube and then the supernatant was removed. The remaining tissue was then supplemented with fresh digestion buffer equaling the starting volume. The tube was again placed on a rocker in a 37° C. incubator for an additional 30 minutes.

After 30 minutes the digestion mixture was pipetted through a 70 μm cell strainer (BD Falcon) into an equal volume of neutralization buffer (DMEM w/10% FBS) to stop the digestion reaction. The cell suspension was then washed by centrifugation at 300× g for 5 min. After centrifugation, the pellet was then re-suspended in 20 mls KSFM medium and a sample acquired for cell counting and viability assessment using trypan blue exclusion. Once the cell count was calculated, 1 million cells were collected for RNA, washed in PBS, and snap frozen in liquid nitrogen. The remaining cell suspension was brought up to 50 mls with KSFM medium and washed again by centrifugation at 300× g for 5 minutes. After washing, the cell pellet was re-suspended in a concentration of 15 million cells per ml of KSFM.

Five milliliters of kidney cell suspension were then added to 5 mls of 30% (w/v) Optiprep® in 15 ml conical centrifuge tubes (BD Falcon) and mixed by inversion 6 times. This formed a final mixture of 15% (w/v) of Optiprep®. Post inversion, tubes were carefully layered with 1 mL PBS. The tubes were centrifuged at 800× g for 15 minutes without brake. After centrifugation, the tubes were removed and a cell band was formed at the top of the mixing gradient. There was also a pellet containing red blood cells, dead cells, and a small population of live cells that included some small less granular cells, some epo-producing cells, some tubular cells, and some endothelial cells. The band was carefully removed using a pipette and transferred to another 15 ml conical tube. The gradient medium was removed by aspiration and the pellet was collected by re-suspension in 1 ml KSFM. The band cells and pellet cells were then recombined and re-suspended in at least 3 dilutions of the collected band volume using KSFM and washed by centrifugation at 300× g for 5 minutes. Post washing, the cells were re-suspended in 20 mls of KSFM and a sample for cell counting was collected. Once the cell count was calculated using trypan blue exclusion, 1 million cells were collected for an RNA sample, washed in PBS, and snap frozen in liquid nitrogen.

Pre-Culture 'Clean-up' to Enhance Viability and Culture Performance of Specific Bioactive Renal Cells Using Density Gradient Separation: To yield a clean, viable population of cells for culture, a cell suspension was first generated as described above in "Kidney Cell Isolation". As an optional step and as a means of cleaning up the initial preparation, up to 100 million total cells, suspended in sterile isotonic buffer were mixed thoroughly 1:1 with an equal volume of 30% Optiprep® prepared at room temperature from stock 60% (w/v) iodixanol (thus yielding a final 15% w/v Optiprep solution) and mixed thoroughly by inversion six times. After mixing, 1 ml PBS buffer was carefully layered on top of the mixed cell suspension. The gradient tubes were then carefully loaded into the centrifuge, ensuring appropriate balance. The gradient tubes were centrifuged at 800× g for 15 minutes at 25° C. without brake. The cleaned-up cell population (containing viable and functional collecting duct, tubular, endocrine, glomerular, and vascular cells) segmented between 6% and 8% (w/v) Optiprep®, corresponding to a density between 1.025-1.045 g/mL. Other cells and debris pelleted to the bottom of the tube.

Kidney Cell Culture: The combined cell band and pellet were then plated in tissue culture treated triple flasks (Nunc T500) or equivalent at a cell concentration of 30,000 cells per cm2 in 150 mls of a 50:50 mixture of DMEM (high glucose)/KSFM containing 5% (v/v)FBS, 2.5 µg EGF, 25 mg BPE, 1×ITS (insulin/transferrin/sodium selenite medium supplement) with antibiotic/antimycotic. The cells were cultured in a humidified 5% CO2 incubator for 2-3 days, providing a 21% atmospheric oxygen level for the cells. After two days, the medium was changed and the cultures were placed in 2% oxygen-level environment provided by a CO2/Nitrogen gas multigas humidified incubator (Sanyo) for 24 hrs. Following the 24 hr incubation, the cells were washed with 60 mls of 1×PBS and then removed using 40 mls 0.25% (w/v) trypsin/EDTA (Gibco). Upon removal, the cell suspension was neutralized with an equal volume of KSFM containing 10% FBS. The cells were then washed by centrifugation 300× g for 10 minutes. After washing, the cells were re-suspended in 20 mls of KSFM and transferred to a 50 ml conical tube and a sample was collected for cell counting. Once the viable cell count was determined using trypan blue exclusion, 1 million cells were collected for an RNA sample, washed in PBS, and snap frozen in liquid nitrogen. The cells were washed again in PBS and collected by centrifugation at 300× g for 5 minutes. The washed cell pellet was re-suspended in KSFM at a concentration of 37.5 million cells/ml.

Enriching for Specific Bioactive Renal Cells Using Density Step Gradient Separation:

Cultured kidney cells, predominantly composed of renal tubular cells but containing small subpopulations of other cell types (collecting duct, glomerular, vascular, and endocrine) were separated into their component subpopulations using a density step gradient made from multiple concentrations w/v of iodixanol (Optiprep). The cultures were placed into a hypoxic environment for up to 24 hours prior to harvest and application to the gradient. A stepped gradient was created by layering four different density mediums on top of each other in a sterile 15 mL conical tube, placing the solution with the highest density on the bottom and layering to the least dense solution on the top. Cells were applied to the top of the step gradient and centrifuged, which resulted in segregation of the population into multiple bands based on size and granularity.

Briefly, densities of 7, 11, 13, and 16% Optiprep® (60% w/v Iodixanol) were made using KFSM medium as diluents. For example: for 50 mls of 7% (w/v) Optiprep®, 5.83 mls of stock 60% (w/v) Iodixanol was added to 44.17 mls of KSFM medium and mixed well by inversion. A peristaltic pump (Master Flex L/S) loaded with sterile L/S 16 Tygon tubing connected to sterile capillary tubes was set to a flow rate of 2 ml per minute, and 2 mL of each of the four solutions was loaded into a sterile conical 15 mL tube, beginning with the 16% solution, followed by the 13% solution, the 11% solution, and the 7% solution. Finally, 2 mL of cell suspension containing 75 million cultured rodent kidney cells was loaded atop the step gradient (suspensions having been generated as described above in 'Kidney cell Culture'). Importantly, as the pump was started to deliver the gradient solutions to the tube, care was taken to allow the fluid to flow slowly down the side of the tube at a 45° angle to insure that a proper interface formed between each layer of the gradient. The step gradients, loaded with cells, were then centrifuged at 800× g for 20 minutes without brake. After centrifugation, the tubes were carefully removed so as not to disturb each interface. Five distinct cell fractions resulted (4 bands and a pellet) (B1–B4, +Pellet) (see FIG. 48, left conical tube). Each fraction was collected using either a sterile disposable bulb pipette or a 5 ml pipette and characterized phenotypically and functionally (See example 10). When rodent kidney cell suspensions are subjected to step-gradient fractionation immediately after isolation, the fraction enriched for tubular cells (and containing some cells from the collecting duct) segments to a density between 1.062-1.088 g/mL. In contrast, when density gradient separation was performed after ex vivo culture, the fraction enriched for tubular cells (and containing some cells from the collecting duct) segmented to a density between 1.051-1.062 g/mL. Similarly, when rodent kidney cell suspensions are subjected to step-gradient fractionation immediately after isolation, the fraction enriched for epo-producing cells, glomerular podocytes, and vascular cells ("B4") segregates at a density between 1.025-1.035 g/mL. In contrast, when density gradient separation was performed after ex vivo culture, the fraction enriched for epo-producing cells, glomerular podocytes, and vascular cells ("B4") segregated at a density between 1.073-1.091 g/mL. Importantly, the post-culture distribution of cells into both the 'B2' and the "B4" fractions was enhanced by exposure (for a period of about 1 hour to a period of about 24 hours) of the cultures to a hypoxic culture environment (hypoxia being defined as <21% (atmospheric) oxygen levels prior to harvest and step-gradient procedures (additional details regarding hypoxia-effects on band distribution are provided in Example 9).

Figure 49A:
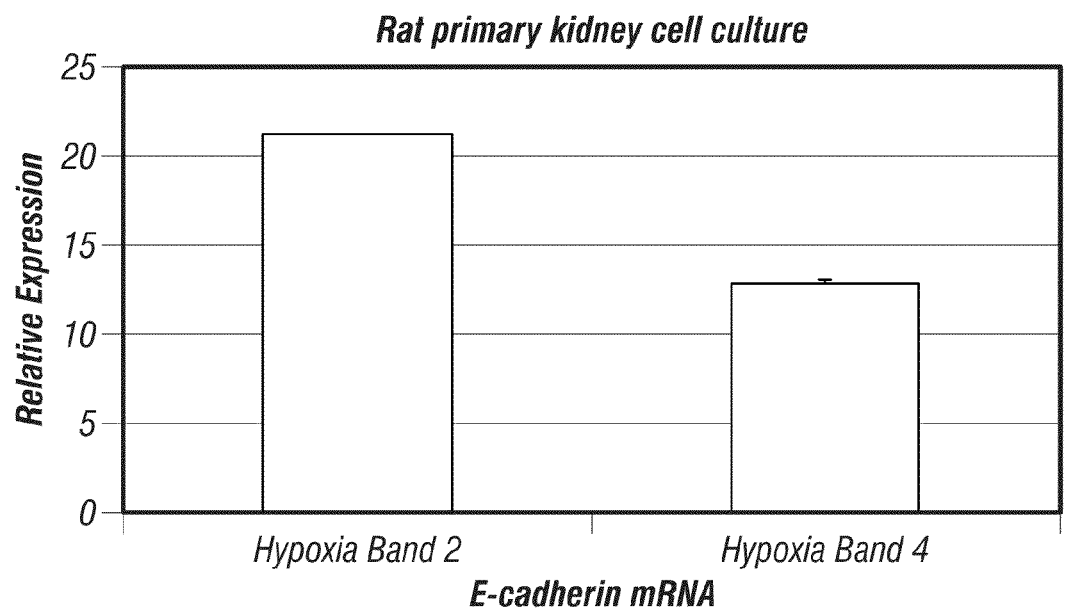
FIG. 49A shows quantitative real-time PCR (QRTPCR) results confirming E-cadherin expression.
Figure 49B:
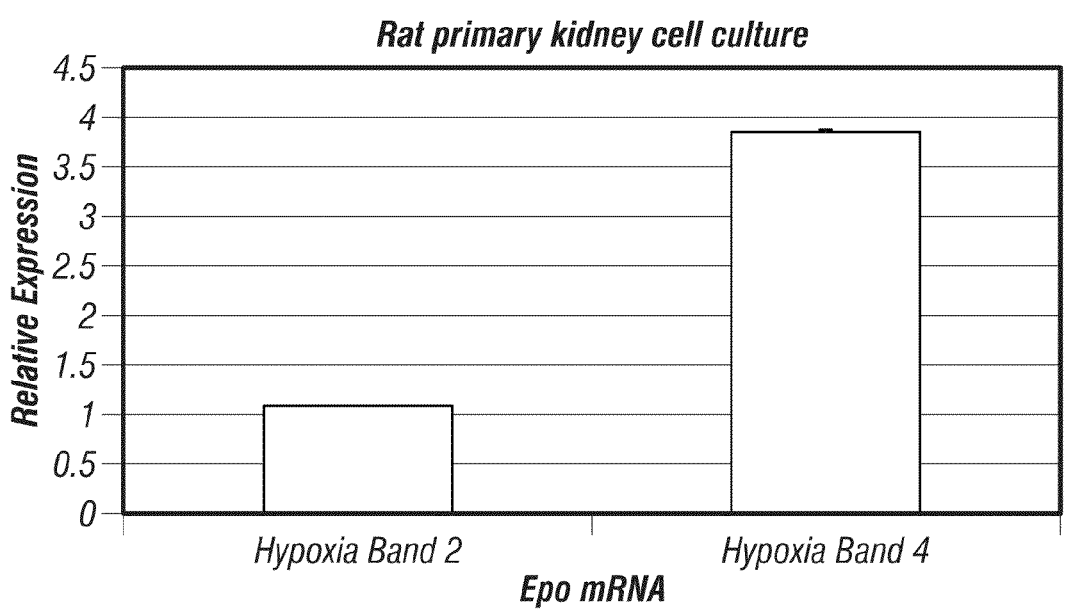
FIG. 49B shows quantitative real-time PCR (QRTPCR) results confirming Epo enrichment using the density step gradient.

Each band was washed by diluting with 3× the volume of KSFM, mixed well, and centrifuged for 5 minutes at 300× g. Pellets were re-suspended in 2 mls of KSFM and viable cells were counted using trypan blue exclusion and a hemacytometer. 1 million cells were collected for an RNA sample, washed in PBS, and snap frozen in liquid nitrogen. The cells from B2 and B4 were used for transplantation studies into uremic and anemic female rats, generated via a two-step 5/6 nephrectomy procedure at Charles River Laboratories. Characteristics of B4 were confirmed by quantitative real-time PCR, including oxygen-regulated expression of erythropoietin and vEGF, expression of glomerular markers (nephrin, podocin), and expression of vascular markers (PECAM). Phenotype of the 'B2' fraction was confirmed via expression of E-Cadherin, N-Cadherin, and Aquaporin-2. See FIGS. 49A and 49B.

Figure 50A:
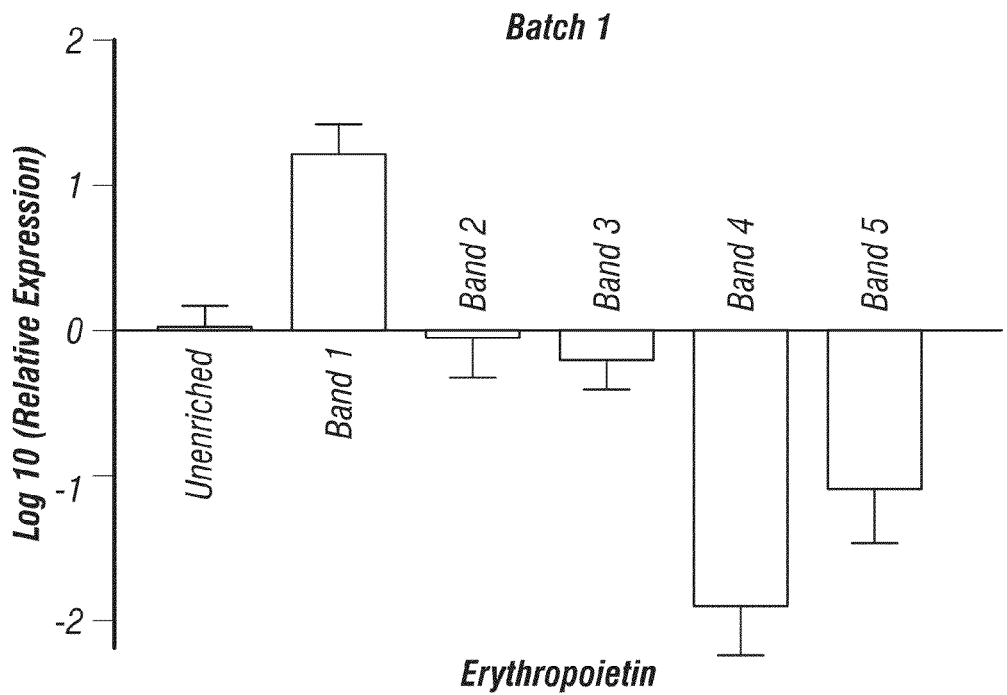
FIG. 50A-C graphically depicts relative gene expression of step gradient fractions at the time of isolation and in culture. Panels (A) and (B) show two independent batches of primary kidney cells that were subjected to density gradient fractionation immediately after tissue dissociation. Erythropoietin (Epo) mRNA expression is reproducibly enriched in Band 1 of the step gradient in both batches. Expression of Epo in all samples is normalized to freshly-digested heterogeneous kidney cell population. Panel (C) shows clearly that Band 1, in addition to being enriched for epo expression, is relatively depleted of tubular cells, as demonstrated by low expression of tubular markers, N-cadherin, E-cadherin, Aquaporins 1 and 2. In contrast, the tubular markers are enriched in Bands 2 and 3, highlighting an added feature of the step gradient—concomitant enrichment of tubular cell fractions.
Figure 50B:
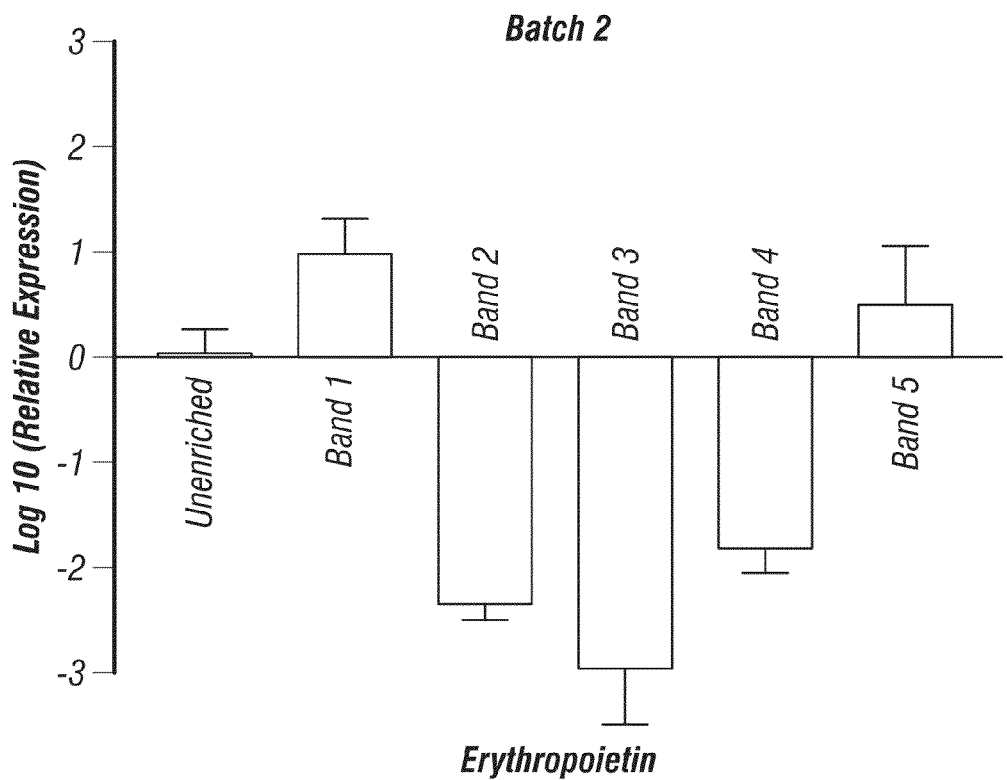
Figure 50C:
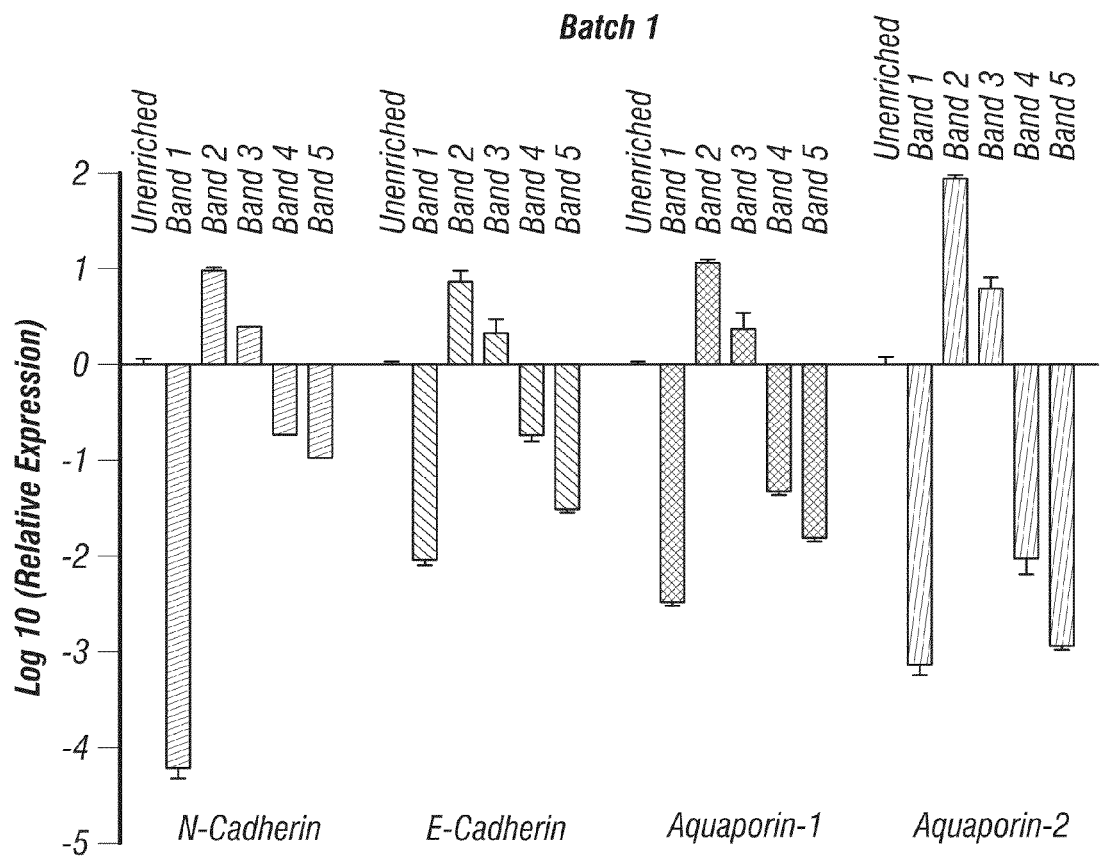
Figure 51:
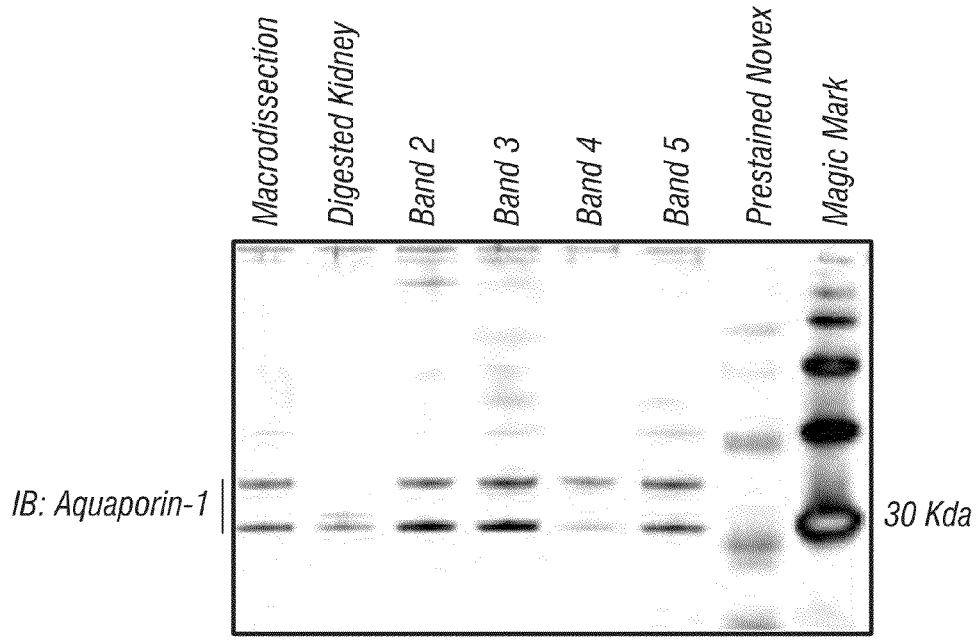
FIG. 51 shows Western Blot analysis of Aquaporin-1, a tubular cell marker. In further support of the tubular cell enrichment of fractions 2 & 3, as described in FIG. 2, panel (d), this western blot shows clear and specific enrichment of Aquaporin 1 protein in Bands 2 & 3.

Thus, use of the step gradient strategy allows not only the enrichment for a rare population of epo-producing cells (B4), but also a means to generate relatively enriched fractions of functional tubular cells (B2) (see FIGS. 50 & 51). The step gradient strategy also allows EPO-producing and tubular cells to be separated from red blood cells, cellular debris, and other potentially undesirable cell types, such as large cell aggregates and certain types of immune cells.

The step gradient procedure may require tuning with regard to specific densities employed to provide good separation of cellular components. The preferred approach to tuning the gradient involves 1) running a continuous density gradient where from a high density at the bottom of the gradient (16-21% Optiprep, for example) to a relatively low density at the top of the gradient (5-10%, for example). Continuous gradients can be prepared with any standard density gradient solution (Ficoll, Percoll, Sucrose, iodixanol) according to standard methods (Axis Shield). Cells of interest are loaded onto the continuous gradient and centrifuged at 800× G for 20 minutes without brake. Cells of similar size and granularity tend to segregate together in the gradients, such that the relative position in the gradient can be measured, and the specific gravity of the solution at that position also measured. Thus, subsequently, a defined step gradient can be derived that focuses isolation of particular cell populations based on their ability to transverse the density gradient under specific conditions. Such optimization may need to be employed when isolating cells from unhealthy vs. healthy tissue, or when isolating specific cells from different species. For example, optimization was conducted on both canine and human renal cell cultures, to insure that the specific B2 and B4 subpopulations that were identified in the rat were isolatable from the other species. The optimal gradient for isolation of rodent B2 and B4 subpopulations consists of (w/v) of 7%, 11%, 13%, and 16% Optiprep. The optimal gradient for isolation of canine B2 and B4 subpopulations consists of (w/v) of 7%, 10%, 11%, and 16% Optiprep. The optimal gradient for isolation of human B2 and B4 subpopulations consists of (w/v) 7%, 9%, 11%, 16%. Thus, the density range for localization of B2 and B4 from cultured rodent, canine, and human renal cells is provided in Table 8.

TABLE 8

Species Density Ranges.

| Step Gradient Band | Species Density Ranges g/ml | | |
|---|---|---|---|
| | Rodent | Canine | Human |
| B2 | 1.045-1.063 g/ml | 1.045-1.058 g/ml | 1.045-1.052 g/ml |
| B4 | 1.073-1.091 g/ml | 1.063-1.091 g/ml | 1.063-1.091 g/ml |

Example 9

Low-Oxygen Culture Prior to Gradient Affects Band Distribution, Composition, and Gene Expression To determine the effect of oxygen conditions on distribution and composition of prototypes B2 and B4, neokidney cell preparations from different species were exposed to different oxygen conditions prior to the gradient step.

Figure 71:
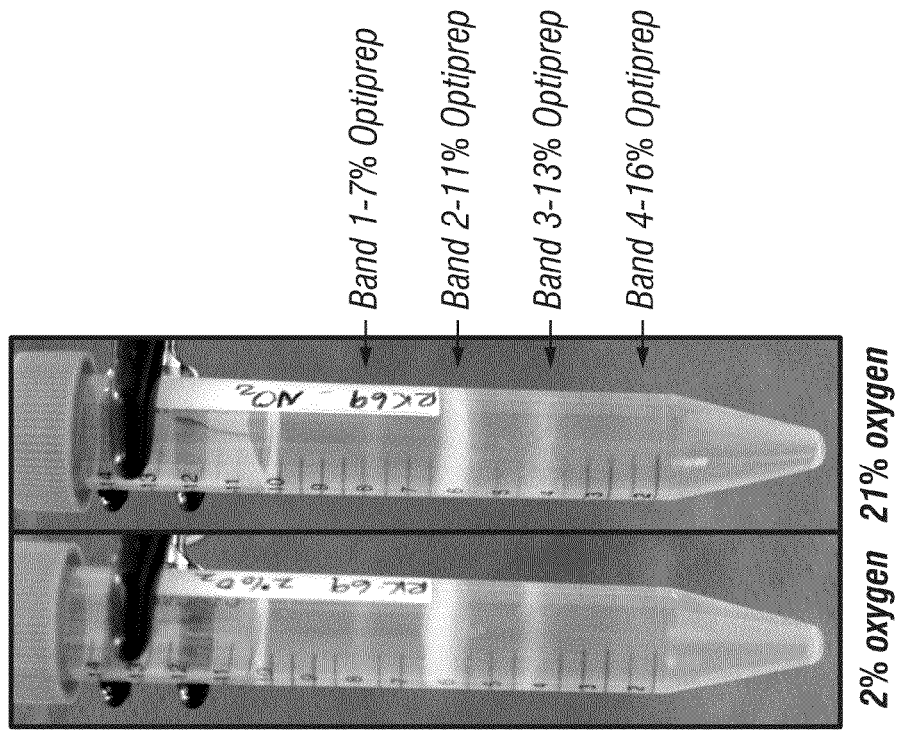
FIG. 71 shows step gradients of "normoxic" (21% oxygen) and "hypoxic" (2% oxygen) rodent cultures that were harvested separately and applied side-by-side to identical step gradients step gradients.
Figure 73:
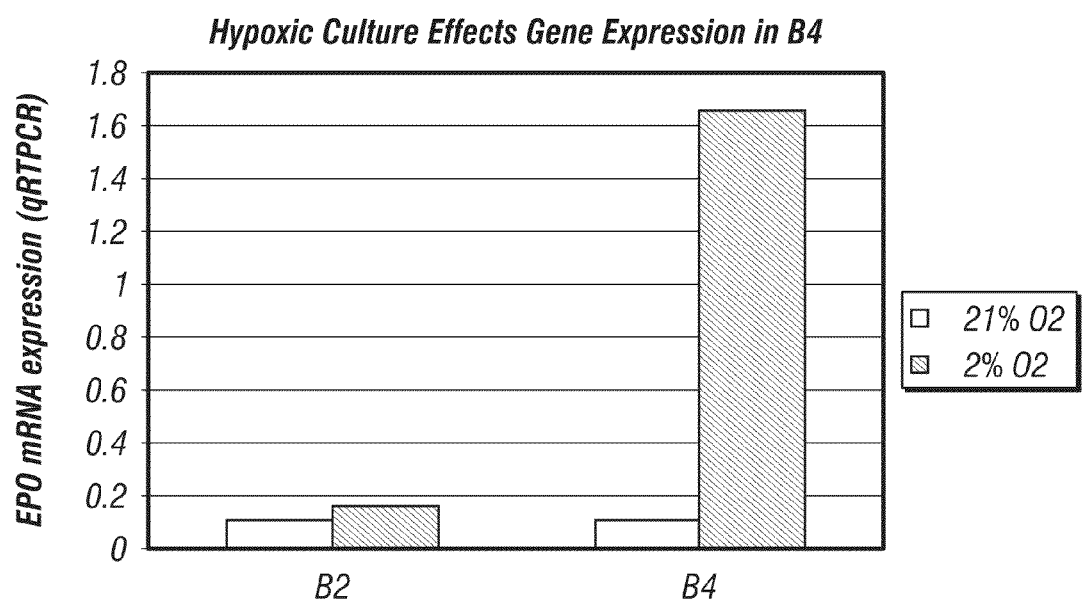
FIG. 73 depicts hypoxic culture effects on gene expression in B4.

A rodent neo-kidney augmentation (NKA) cell preparation (RK069) was established using standard procedures for rat cell isolation and culture initiation, as described supra. All flasks were cultured for 2-3 days in 21% (atmospheric) oxygen conditions. Media was changed and half of the flasks were then relocated to an oxygen-controlled incubator set to 2% oxygen, while the remaining flasks were kept at the 21% oxygen conditions, for an additional 24 hours. Cells were then harvested from each set of conditions using standard enzymatic harvesting procedures described supra. Step gradients were prepared according to standard procedures and the "normoxic" (21% oxygen) and "hypoxic" (2% oxygen) cultures were harvested separately and applied side-by-side to identical step gradients. (FIG. 71). While 4 bands and a pellet were generated in both conditions, the distribution of the cells throughout the gradient was different in 21% and 2% oxygen-cultured batches (Table 1). Specifically, the yield of B2 was increased with hypoxia, with a concomitant decrease in B3. Furthermore, the expression of B4-specific genes (such as erythropoietin) was enhanced in the resulting gradient generated from the hypoxic-cultured cells FIG. 73).

Figure 72:
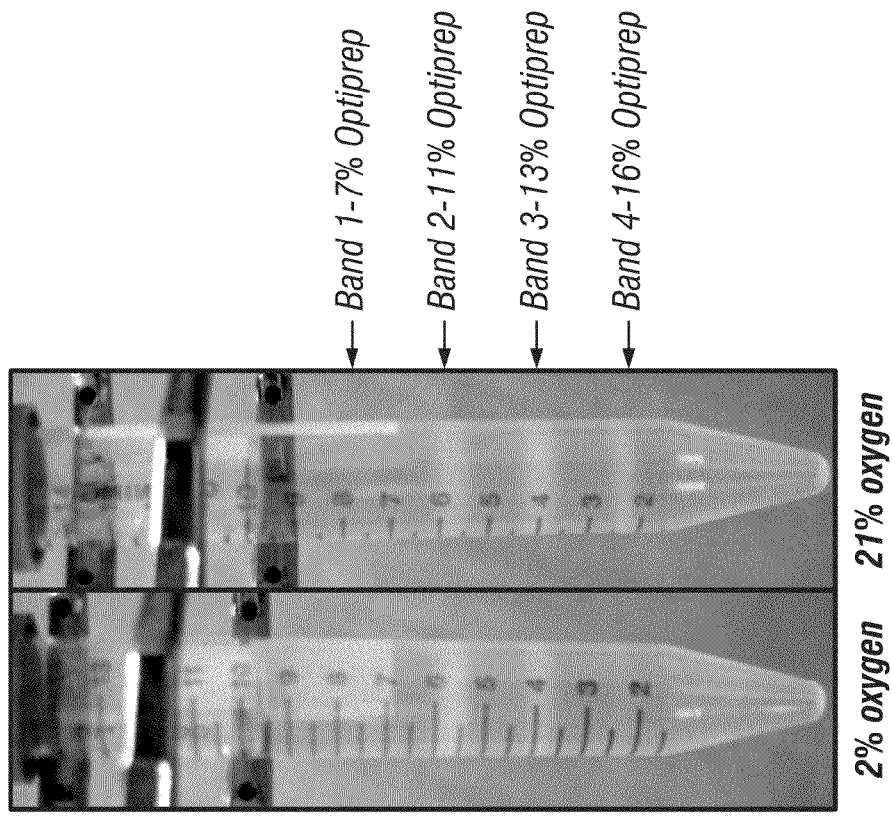
FIG. 72 shows step gradients of "normoxic" (21% oxygen) and "hypoxic" (2% oxygen) canine cultures that were harvested separately and applied side-by-side to identical step gradients step gradients.

A canine NKA cell preparation (DK008) was established using standard procedures for dog cell isolation and culture (analogous to rodent isolation and culture procedures), as described supra. All flasks were cultured for 4 days in 21% (atmospheric) oxygen conditions, then a subset of flasks were transferred to hypoxia (2%) for 24 hours while a subset of the flasks were maintained at 21%. Subsequently, each set of flasks was harvested and subjected to identical step gradients (FIG. 72). Similar to the rat results (Example 1), the hypoxic-cultured dog cells distributed throughout the gradient differently than the atmospheric oxygen-cultured dog cells (Table 9). Again, the yield of B2 was increased with hypoxic exposure prior to gradient, along with a concomitant decrease in distribution into B3.

TABLE 9

| | Rat (RK069) | | Dog (DK008) | |
|---|---|---|---|---|
| | 2% O2 | 21% O2 | 2% O2 | 21% O2 |
| B1 | 0.77% | 0.24% | 1.20% | 0.70% |
| B2 | 88.50% | 79.90% | 64.80% | 36.70% |
| B3 | 10.50% | 19.80% | 29.10% | 40.20% |
| B4 | 0.23% | 0.17% | 4.40% | 21.90% |

The above data show that pre-gradient exposure to hypoxia enhances composition of B2 as well as the distribution of specific specialized cells (erythropoietin-producing cells, vascular cells, and glomerular cells) into B4. Thus, hypoxic culture, followed by density-gradient separation as described supra, is an effective way to generate 'B2' and 'B4' cell populations, across species.

Example 10

Transplantation of Neo-Kidney Prototypes into a Rat Model of Renal Failure and Anemia Isolation and propagation of Epo-producing cells from native tissue was first described in 2008 when primary cultures of mouse kidney cells were shown to express Epo mRNA and protein (Aboushwareb, T, et al. World J Urol, 26: 295-300, 2008). Subsequently, similar cell isolation and culture methods were applied to rat, swine, and human kidney tissue, and it was found that the cultures from all species examined were comprised of a variety of cell types, including the small subpopulation of Epo-expressing cells described by Aboushwareb et al., but predominantly comprised of tubular cells, and including populations of glomerular cells, collecting duct cells, and vascular cells. Preliminary experiments demonstrated that in vivo transplantation of the heterogeneous cell cultures into uremic/anemic rats stabilized renal filtration, restored erythroid homeostasis, and improved overall survival. These data indicated collectively that bioactive cellular component(s) resided within the heterogeneous primary kidney cultures and were capable of delivering significant therapeutic benefits.

The objective of the present study was to identify the bioactive cellular components contained within a heterogeneous renal cell culture, based on both specialized functional characteristics in vitro and translational evidence in vivo. It was found that both a tubular-enriched subfraction (B2) and a subfraction containing oxygen-regulated Epo-producing cells, glomerular cells, and vascular cells (B4) were more efficacious and more durable than the heterogeneous mixture (UNFX) across a spectrum of clinical parameters assessing filtration, erythropoiesis, and organism-level functions. The specific in vitro characteristics and in vivo performance of each subfraction are presented herein.

To determine the particular effects of specific components of the heterogeneous population of neo-kidney cells, the B4 (enriched for EPO-producing, glomerular, and vascular cells) and B2 (enriched for tubular cells and depleted of EPO-producing, glomerular, and vascular cells) fractions were generated and transplanted into a rat model of renal failure and anemia. The study plan is found below in Table 10.

Tissue procurement and primary cell culture

Primary kidney cell cultures were established from male donor Lewis rats purchased from Hilltop Labs. Specimens were shipped at 4° C. in Hypothermasol (BioLife Solutions) and received within 24 hours of harvest. Primary kidney cells were isolated according to previously published methods (Aboushwareb, T, et al. World J Urol, 26: 295-300, 2008), and cultured on tissue-culture treated polystyrene flasks or dishes at a density of 30,000 cells per cm2 in a 50:50 mixture of high glucose DMEM containing 5% (v/v) FBS, 2.5 µm EGF, 25 mg BPE, 1×ITS (insulin/transferrin/sodium selenite medium supplement), antibiotic/antimycotic (all from Invitrogen), in a 37° C., humidified 5% $CO_2$ under atmospheric oxygen conditions (21% oxygen). For experiments involving exposure to hypoxia, cultures were transferred to low-oxygen (2%) conditions at 37° C. for 24 hours prior to harvest of cells for analyses. For harvest or serial passage, cultured cells were detached with 0.25% Trypsin EDTA. Samples harvested for gene expression analysis were snap-frozen in liquid nitrogen and stored at −80° C. prior to RNA isolation. Standard density gradient techniques were adapted to fractionate cells post-culture (14, 28, 36), in order to generate subtractions enriched for specific renal cell types including tubular, vascular, collecting duct, glomerular, and oxygen-regulated Epo-producing cells. Briefly, multi-stepped gradients were prepared using iodixanol (Optiprep™) at concentrations ranging from 7-16% (v/v) in sterile isotonic buffer. Hypoxia-exposed cells were layered on top of step gradients and centrifuged at 800× g for 20 minutes at 25° C. with no brake. Cell fractions (apparent as bands in the gradient after centrifugation) were collected sequentially from the top (B1) to the bottom (B4). Viability was assessed via trypan blue exclusion and numeration was performed manually using a hemacytometer.

Test Articles: The cellular prototypes delivered to the kidney are listed below. Doses for subpopulations B2 and B4 were chosen based on their relative quantitative contribution to the heterogeneous mixture of cells that was tested above in Example 7.

UNFX is comprised of an unfractionated, heterogeneous mixture of renal cells generated via dissociation and in vitro culture of kidney tissue. The isolation and culture conditions favor establishment of cell strains comprised predominantly of tubular cells, but also containing smaller subpopulations of collecting duct, glomerular, endocrine, vascular, and other cell types.

B2 is a relatively abundant subpopulation of UNFX, which contains proximal tubular cells capable of robust albumin-uptake in vitro, contains some distal tubule and collecting duct epithelial cells, and only trace quantities of other cell types.

B4 is a rare subpopulation of UNFX, which is enriched for hypoxia-responsive EPO-expressing cells, as well as glomerular podocytes, specialized vascular cells, and a population of cells characterized by low forward- and side-scatter (size and granularity), compared to B2 or UNFX.

Immunocytochemistry

Cells from B2 and B4 were sub-cultured post-gradient and characterized by expression of distal and proximal tubular markers using immunocytochemistry. Cells were seeded at a density of 10,000 cells/well and cultured to 85% confluence in a 96-well tissue culture treated plate (BD Falcon 353219), then fixed for 10 minutes at room temperature in a 1:1 mixture of ice-cold Acetone/Methanol. Fixed cells were washed twice in PBS (Gibco) and were blocked for 10 minutes in PBS containing 0.5% BSA (Sigma). Blocked cells were co-labeled simultaneously with primary mouse monoclonal antibodies to N-Cadherin IgG1 (BD Biosciences 610921) and E-Cadherin IgG2a (BD Biosciences 610182), both at 3 µg/ml/ 4° C./overnight. Isotype-matched controls (mouse myeloma IgG1 (Zymed 02-6100) and mouse myeloma IgG2a (Zymed 02-6200) respectively), were also applied at 3 µg/ml/4° C./overnight. Primary-labeled cells were washed 3 times in PBS and labeled with secondary antibodies: goat anti-mouse IgG1 Alexa488 (Molecular Probes A21121) and goat anti-mouse IgG2a Alexa 647 (Molecular Probes A21241), both at concentrations of 1 µg/ml for 30 minutes at room temperature protected from light. Cells were subjected to 3 washes in PBS and imaged using a BD Pathway 855 BioImager (Becton Dickinson).

Gene Expression

The expression levels of target genes were examined via quantitative real-time PCR (qRTPCR) using catalogued Taqman Probes and Primer sets from ABI and an ABI-Prism 7300 Real Tim PCR System (Applied Biosystems; Foster City, Calif.). 18s rRNA was utilized as an endogenous control for abundantly-expressed genes, and Peptidylprolyl isomerase B (PPIB) was used to normalize low-abundance transcripts. Multiple calibrators were used to compare the relative quantity of target transcripts, including whole kidney tissue and Origene kidney cDNA purchased from OriGene Technologies (Rockville, Md.). The following Taqman primer and probe sets were purchased from ABI (Foster City, Calif.). Erythropoietin, Rn01481376_m1; Hypoxia Inducible Factor 2 alpha (HIF2α) Rn00576515_1; Kdr, Rn00564986_1; E-cadherin, Rn00580109_1; Cubilin, Rn00584200_1; CYP2R1, Rn01423150_1; Nephrin, Rn00575235_1; Podocin, Rn00709834_1; Custom SRY: Forward Primer AAGCGCCCCATGAATGC: Reverse Primer AGCCAACTTGCGCCTCTCT: Probe TTTATGGTGTGGTCCCGTG-MGB.

Surgical procedures and in vivo analyses

Female Lewis rats, subjected to a two-step 5/6 Nephrectomy (5/6 Nx), were purchased from Charles River Laboratories (CRL) and shipped to Research Triangle Institute, International (RTI), where rats were housed, monitored, and subjected to various treatment procedures (see Table 10 for Treatment groups and details). Following the surgical procedures, uremia was confirmed prior to treatment via weekly serologic analyses. Animal well being was governed by the respective Institutional Animal Care and Use Committees (IACUC) of CRL and RTI while under their care. Rats were sedated prior to anesthesia in an isoflurane chamber (4-5%) and maintained throughout surgical procedures under isoflurane inhalant (3%) administered via nose-cone. Cells were delivered directly to kidney remnants through a right dorsolateral incision. Cells (5×106 UNFX or B2; 1×106 B4) were implanted intra-parenchymally in a volume of 100 µL of sterile saline via a sterile 1 cc syringe fitted with a 23G needle (Becton Dickinson, Franklin Lakes N.J.) and followed for up to six months post-implant. After cell delivery, 1 ml of warm sterile saline was added to the intraperitoneal cavity for hydration, the muscle layer was closed using 4.0 Vicryl sutures, and the skin was closed using wound clips (Ethicon Inc., Somerville, N.J. for both items). Oxygen was administered post surgery (via inhalation/nose cone) and the animals were monitored until alert and conscious. Rats received 0.5 cc of (0.3 mg/ml) of buprenorphine (Buprenex) intraperitoneally, immediately after surgery. The following day, rats were administered (via oral gavage) 0.6 ml (1 mg/ml) of Tramadol for pain management. Rats receiving recombinant human Epo (R&D Systems) were dosed twice weekly at either 100 IU/kg or 500 IU/kg via intraperitoneal injection. Blood was drawn via tail vein or orbital bleed weekly for serological and hematological analyses throughout the study. BUN, sCREAT, HCT, and RBC# were tracked weekly, while complete serum and hematology panels were conducted at baseline (pre-treatment), at the study midpoint (12-14 weeks), and at the time of necropsy. At necropsy, kidney(s), heart, liver, and spleen were weighed and utilized for frozen and formalin-fixed/paraffin-embedded sections. Femurs and sternums were also collected for histopathologic analyses, taking care to expose the marrow prior to fixation. Body weights were collected weekly.

Surgeries/blood draws were performed in Group 1 RK 68 rats with the following rat numbers: 66, 36, 59, 46, 63, 34, 32, 79, 54, 43, 67, 52, 76, 51, 78, 44, 62, 48, 69, 71, 74, 33, 77, 81, 82, 83, 86 and 87. Surgeries/blood draws were performed in Group 2 RK 69 rats with the following rat numbers: 68, 38, 70*, 37, 31, 65, 45, 41, 64, 42, 50, 35, 58, 80, 56, 57, 72, 75, 49, 61, 39, 55, 84, 85, 88, 89 and 90. RK 70 surgery was performed in the following rat numbers: 70 and 65.

Histolopathological Assessment of Kidney and Bone.

Following necropsy, the remnant kidney was weighed and bisected longitudinally. One half was utilized for preparation of frozen sections and isolation of DNA and RNA, and the other half was placed in 10% buffered formalin for 24 hours, then transferred to 70% ethanol for transport to histopathology lab (Premier Laboratories, Colorado). Tissues were dehydrated, embedded in paraffin, cut into 5 micron sections, and stained with hematoxylin and eosin (H&E), Masson's trichrome and Periodic Acid Schiff (PAS), all according to standard laboratory procedures. The left femur was collected and submitted for histology using the procedure described above and stained with H&E. Glomerular injury was characterized by an increase in mesangial matrix to segmental mesangial sclerosis and/or hyalinosis with adhesions of the glomeruluar tuft and/or with thickening of Bowman's capsule. Tubular injury was characterized by tubular atrophy, dilatation, accumulation of lymphocytes, accumulation of intralumenal protein casts, tubular necrosis and interstitial fibrosis. Microscopic assessment of femoral sections was performed using H&E stains. Sections were examined at 200× and 400× original magnification for any increase/decrease in bone marrow cellularity and myeloid to erythroid ratios.

Measurements: Animals were weighed weekly. Bi-weekly serological and hematological analyses provided in-life assessments of kidney function (BUN & CREAT) and erythropoiesis (HCT & RBC) pre- and post-implantation. Complete serum and hematology panels were conducted at baseline, 6 weeks, 12 weeks, and pre-necropsy. At the time of necropsy, organs (kidney, liver, spleen, heart, lungs) were weighed and collected for histology. Femoral bone marrow was collected for histology and bone marrow smear analysis.

Results

Generation and Compartmental Characterization of Candidate Bioactive Cell Populations (B2 & B4). In vivo pilot studies indicated clearly that bioactive cells capable of enhancing renal functions were contained within the heterogeneous population (UNFX) of cultured kidney cells (see Example 7). Based on the clinical parameters affected by the delivery of the UNFX population in previous studies, logical candidate cell populations for affecting renal homeostasis were functional tubular cells (based on improvements in creatinine excretion and protein retention), glomerular cells (based on improvement in protein retention), and the highly-specialized oxygen-responsive Epo-producing cells of the corticomedullary junction (based on restoration of erythropoiesis) (Maxwell, P H, et al. Kidney Int, 52: 715-24, 1997, Obara, N, et al. Blood, 111: 5223-32, 2008). The presence of tubular, glomerular, and Epo-producing cells was confirmed in renal cultures established and propagated from rat as well as other species.

TABLE 10

Study Plan

| Grp | Name | NX | Treatment | N | Animal ID #'s | Endpoints |
|---|---|---|---|---|---|---|
| 1 | UNFX | ✓ | UNFX | 5 | 31, 34, 45, 63, 65 | In-life |
| 2 | B4 | ✓ | B4 (HIGH) | 5 | 32, 41, 42, 64, 79 | Body weight Survival Hematology & Serology: |
| 3 | B4(b) | ✓ | B4 (LOW) | 4 | 35, 43, 50, 54 | RBC, HCT, CREAT, BUN Baseline & Midpoint: |
| 4 | B2 | ✓ | B2 | 3 | 52, 58, 80 | Full Serum Panel |
| 5 | NX | ✓ | None | 8 | 33, 39, 49, 55, 61, 71, 74, 77 | Full Hematology Panel Pre-necropsy Full Serum Panel |
| 6 | NX + rEPO | ✓ | 100 IU/kg rEPO 2x weekly | 4 | 44, 72, 75, 78 | Full Hematology Panel Post-necropsy Bone Marrow Smears/Differential |
| 7 | NX + rEPO | ✓ | 500 IU/kg rEPO 2x weekly | 4 | 51, 56, 57, 76 | Organ Weights Histopathology |
| 8 | NX + Vehicle | ✓ | Cell-Free Implant | 2 | 48, 69 | |
| 9 | Sham Nx | NO | None | 5 | 86, 87, 88, 89, 90 | |
| 10 | HEALTHY | NO | None | 5 | 81, 82, 83, 84, 85 | |

Density gradient methods (Qi, W, et al. Nephrology (Carlton), 12: 155-9, 2007, Gesek, F A, et al. Am J Physiol, 253: F358-65, 1987, McLaren, J, et al. Hum Exp Toxicol, 14: 916-22, 1995) were adapted and optimized to enable reproducible generation of distinct cellular subfractions (B1-B4) from established cultures of the UNFX heterogeneous cell population. The subfractions were distinguished from one another and from UNFX based on functional, molecular, and phenotypic characteristics, and two subfractions (B2 & B4) were selected as bioactive candidates for further in vitro and in vivo studies.

Subfraction B2, which represents a prominent (from about 20% to about 50%) component of the UNFX mixture, was selected based on relative enrichment for tubular cells, a predominant cell type in established and expanded cultures of UNFX. Targeted gene expression analyses were performed to assess the relative contribution of major cellular compartments of the kidney to subfractions B2 and B4. Subfraction B2 was relatively depleted of vascular cells (kdr+), glomerular cells (nephrin+, podocin+), and Epo-producing cells (FIG. 74D-H). Two proximal tubular markers associated with clinically-relevant tubular cell functions were enriched significantly in B2, Vitamin D Hydroxylase (CYP21R) (4.3× enrichment) and Cubilin (3.0× enrichment). The majority (>75%) of distal tubular cells (E-cadherin+) and collecting duct cells (D. bonus agglutinin+, Aquaporin-2+) were localized to subfraction B1, which was not selected for further evaluation in these studies due to the relative absence of albumin-transporting cubilin+ cells and the existence of other undesired characteristics. However, expression of the distal tubular marker, E-cadherin, was relatively enriched in B2 (1.6×) compared to B4 (FIG. 74 C).

Quantitative differential gene expression data are presented in table form (FIG. 74 I). Relative distribution of proximal and distal cellular components of B2 and B4 were confirmed qualitatively at the protein level via immunofluorescent staining for N-cadherin (proximal) and E-cadherin (distal) (FIG. 74 J, K). A key function associated with proximal tubular cells is receptor-mediated resorption of albumin from the glomerular filtrate, thus reducing proteinuria and contributing to serum protein homeostasis(7). A functional assay to capture cubilin/megalin-mediated albumin uptake (45) was adapted to confirm robust protein transport activity in cubilin-expressing cells of the B2 subfraction (FIG. 75A). In contrast, cubilin protein expression and albumin uptake were detected infrequently in the B4 subfraction (FIG. 75A), confirming the differential cellular compositions of B2 and B4 observed at the gene expression level. Receptor-mediated transport of albumin by the tubular cells was reduced significantly by hypothermic inhibition of active transport (data not shown), and specificity of the uptake was confirmed by blocking cubilin/megalin-mediated endocytosis with a competitive inhibitor, receptor associated protein (RAP)(30) (FIG. 75 A).

Figure 74A:
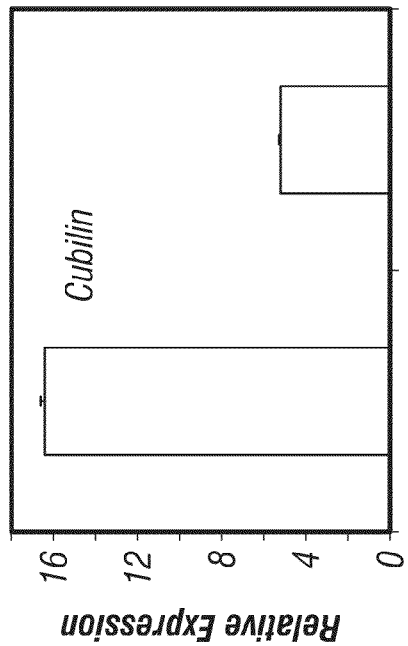
Figure 74B:
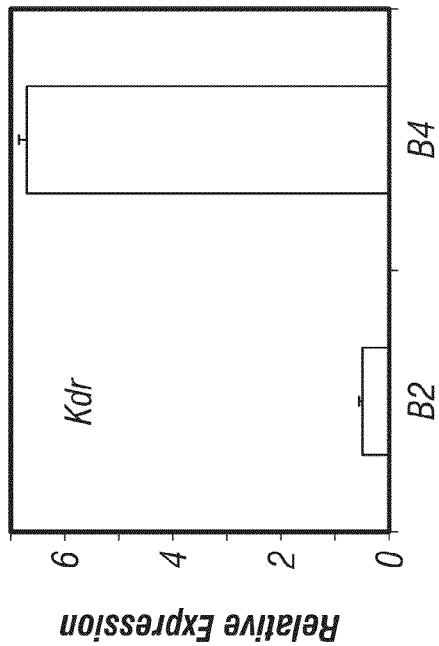
Figure 74C:
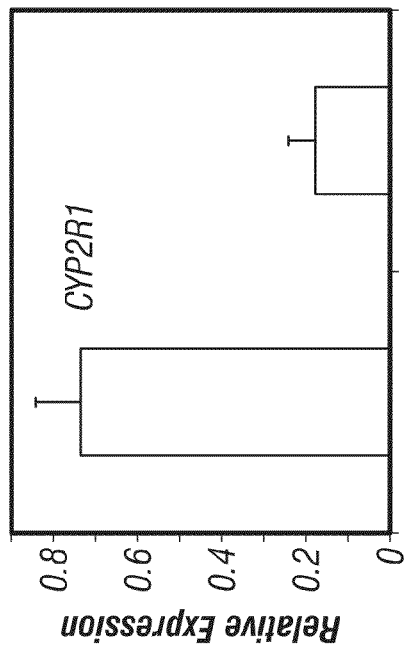
Figure 74D:
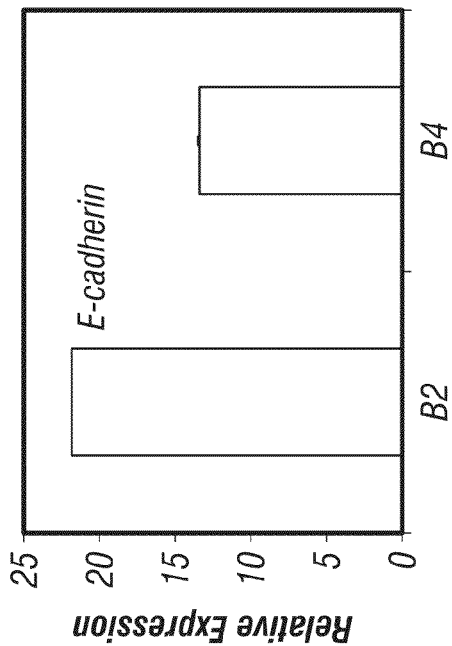
Figure 74E:
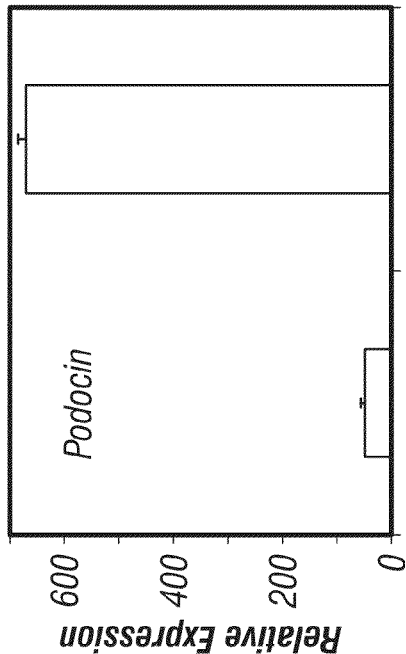
Figure 74F:
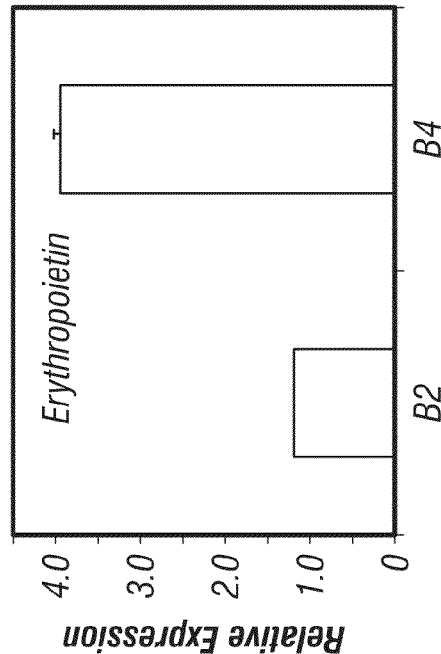
Figure 74G:
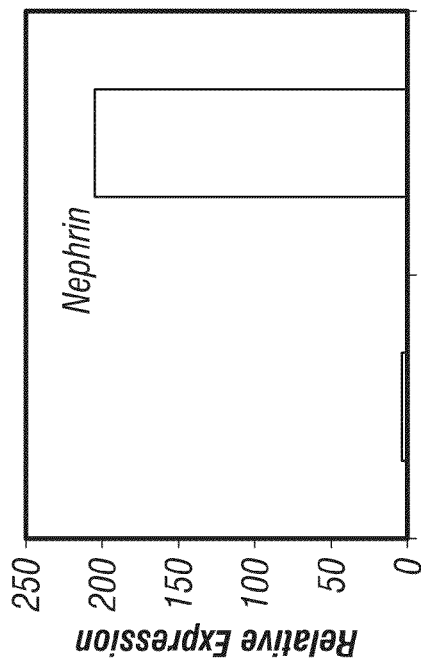
Figure 74H:
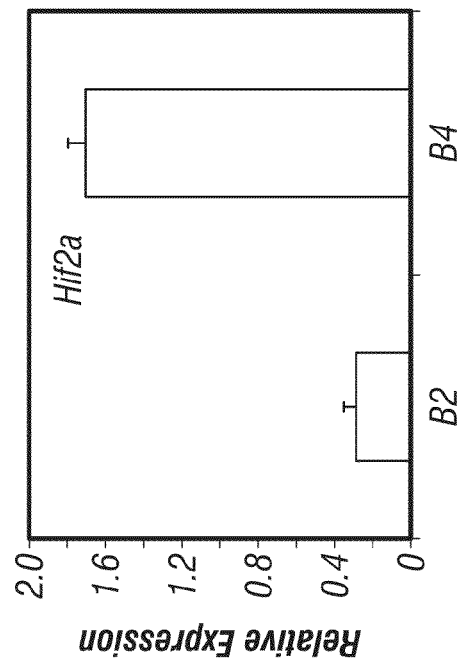

The B4 subfraction represented a rare component of the unfractionated (UNFX) cell population (<10%) and was comprised of several specialized cell types, all with clear theoretical therapeutic value based on in vitro characteristics. The B4 subfraction was selected based on relative enrichment of the hypoxia-responsive Epo-producing cells, glomerular podocytes and cells of vascular origin (FIG. 74-76). Flow cytometric analyses of the UNFX population showed previously that the Epo-expressing cells were distinct from tubular cells in the UNFX population, and were further characterized as small cells (low forward scatter) with low granularity (low side scatter)(34). The B4 subfraction was enriched ~15× for small, low-granularity cells that upregulated Epo expression significantly in response to a hypoxic stimulus (FIG. 74G, H, I, FIG. 75 B). The B4 subfraction was also ~200× enriched for glomerular podocytes (nephrin and podocin) and ~15× for vascular cells (Kdr) (FIG. 74 I).

Comparative in vivo Function of B2 and B4 in Rats with Progressive Renal Failure.

Figure 53:
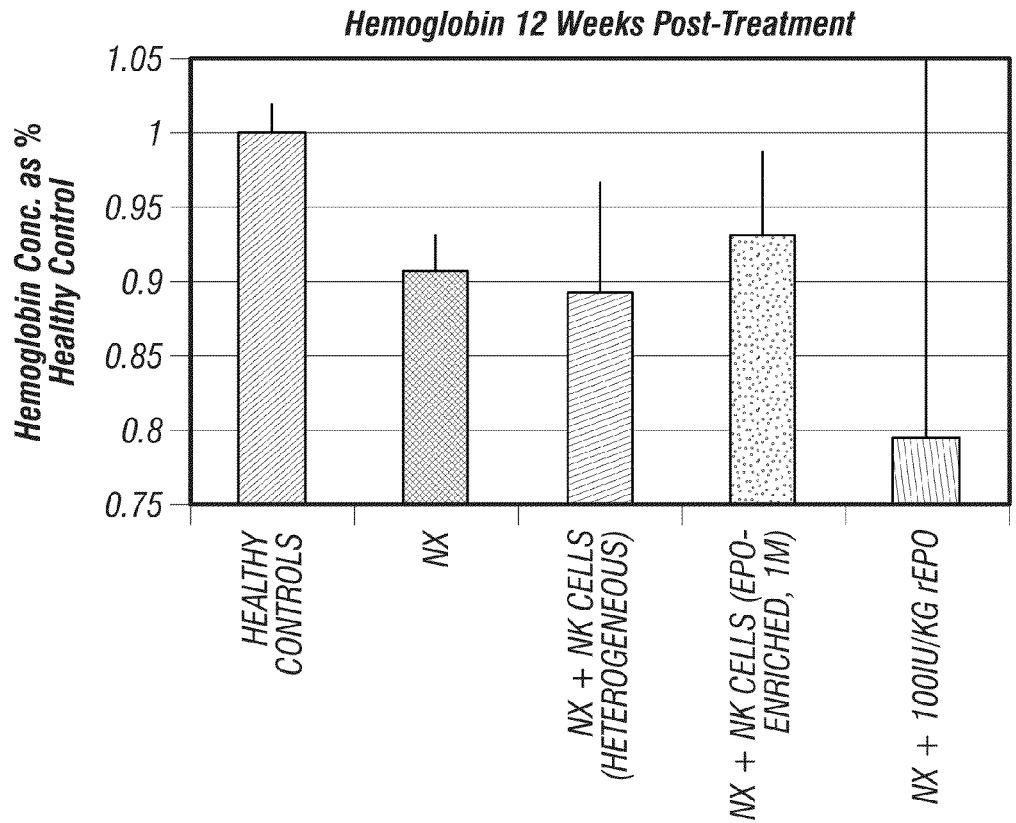
FIG. 53 shows hemoglobin levels at 12 weeks post-treatment.
Figure 54:
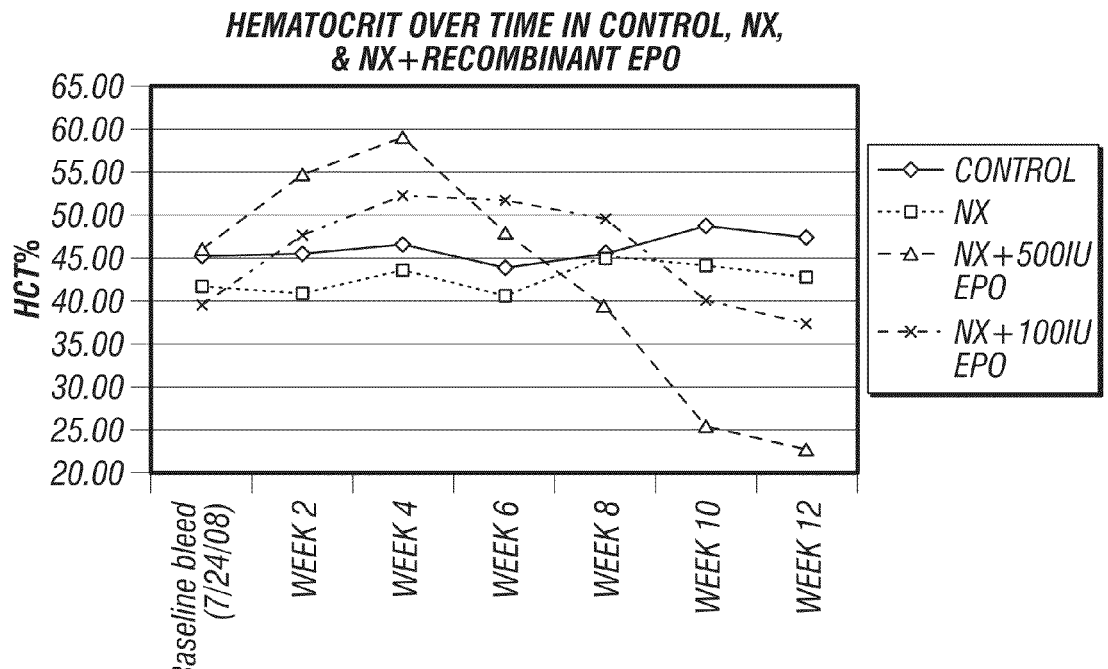
FIG. 54 shows hematocrit levels over time in 5/6 nephrectomized rats treated with two different doses of rEPO as compared to a control group and an untreated group.
Figure 55:
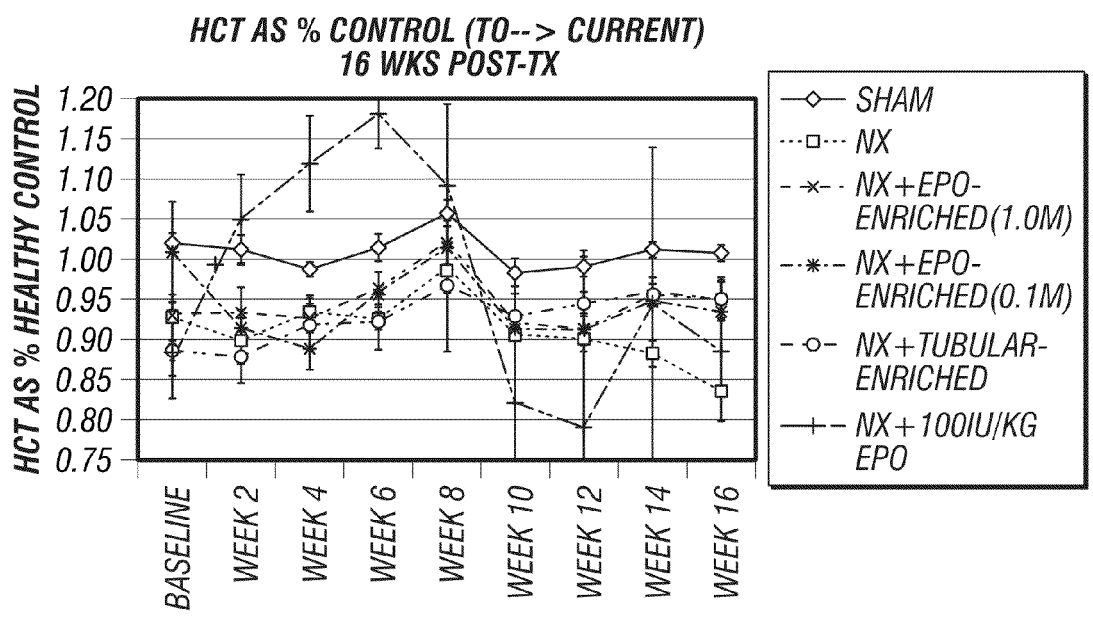
FIG. 55 shows hematocrit levels over time in 5/6 nephrectomized rats treated with high and low doses of EPO-enriched cells as compared to tubular-enriched cells and rEPO.
Figure 56A:
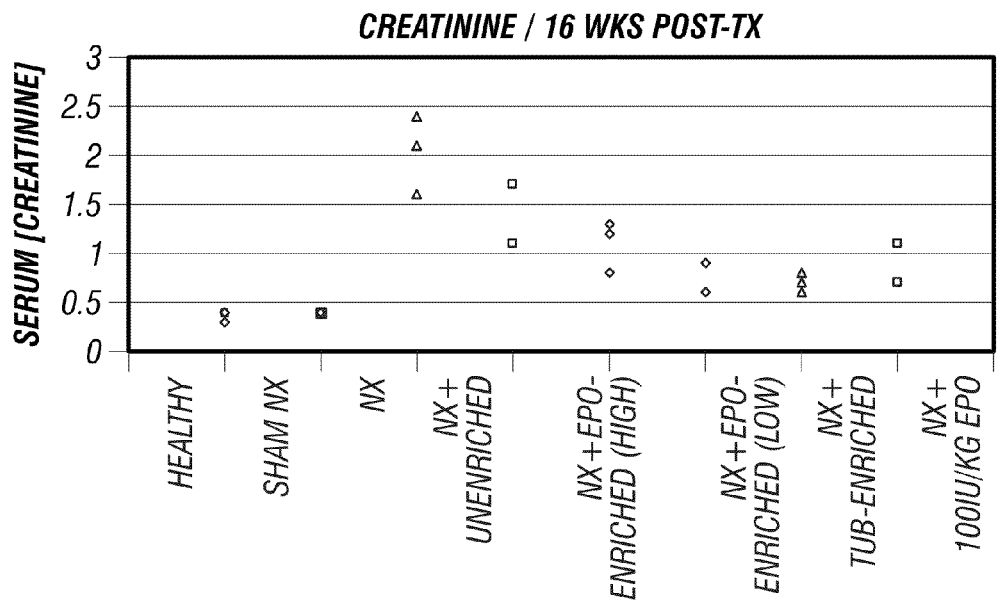
FIGS. 56A and 56B depict serum creatinine concentration at 16 weeks post-treatment and creatinine as percent control from pre-treatment to 16 weeks post-treatment.
Figure 56B:
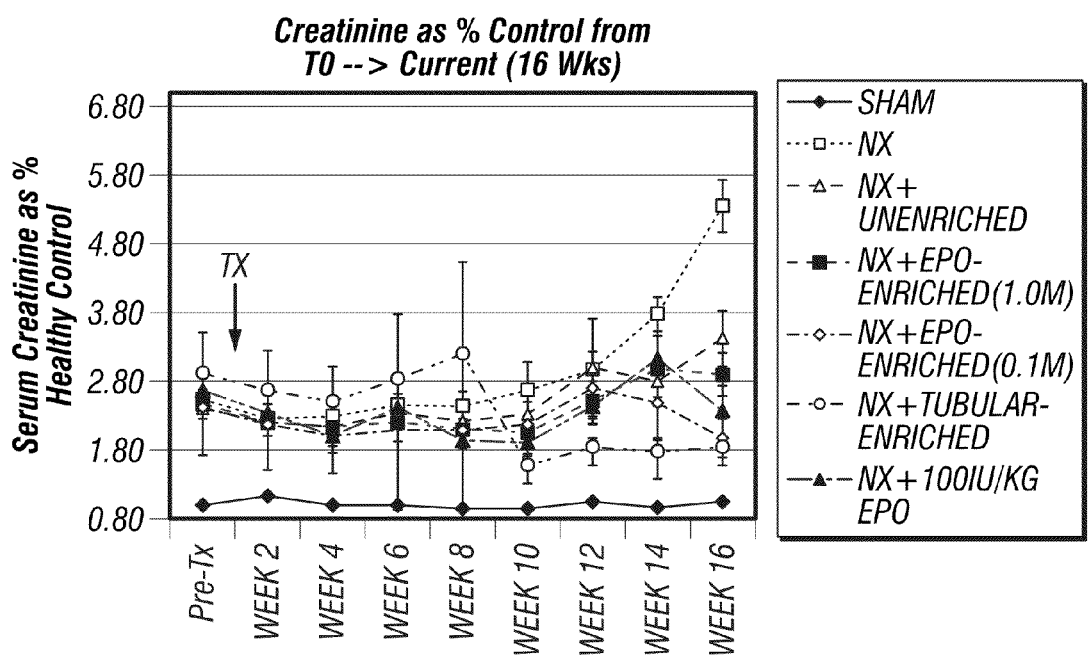
Figure 76A:
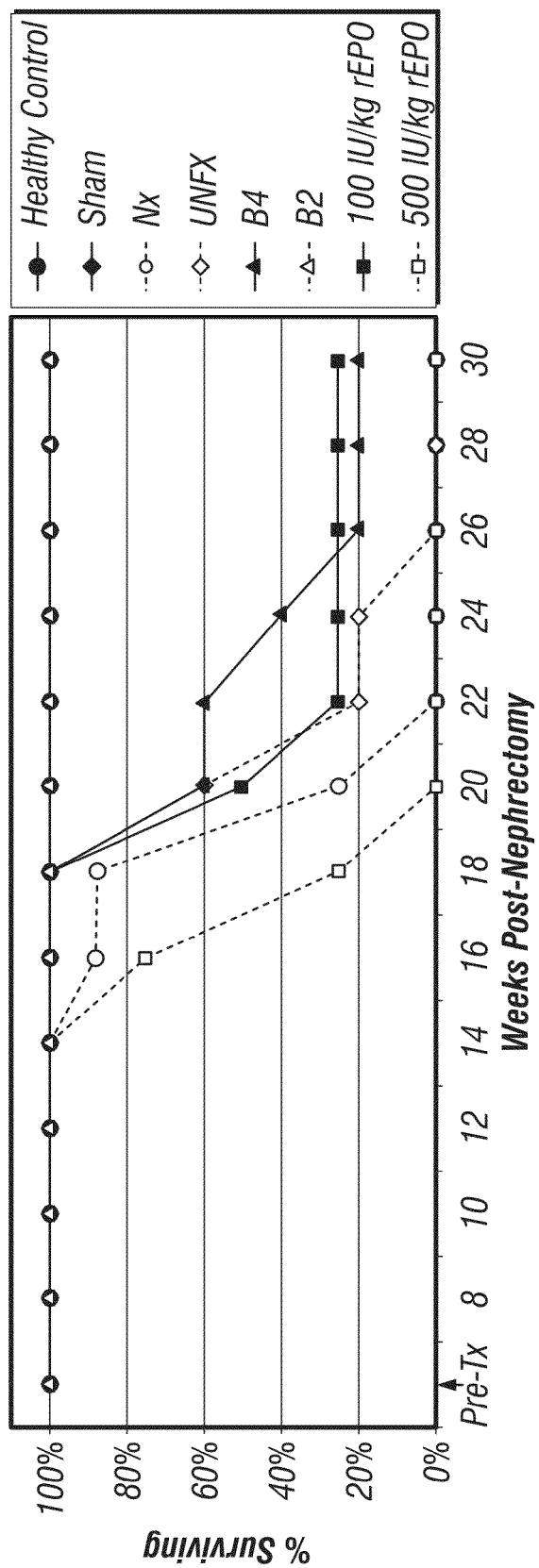
FIG. 76A-C shows the effects of in vivo transplantation of B2 and B4 on survival, body weight, and heart weight in uremic/anemic rats. (A) Rate of survival is presented for each control and treatment group for study duration (30 weeks post-nephrectomy, 6 months post-treatment). Among treatment groups, only B2-treated rats had 100% survival, equivalent to healthy controls. (B) The % change in body weight over time was calculated for each rat individually as: ((weight at sacrifice)−(weight at study initiation))/(weight at study initiation). The 14.3% gain in body weight of the B2 treated animals was considered extremely significant (P value<0.0001) compared to the 5% loss in body weight of the Nx control animals. B4 (P value=0.0239) and vehicle (P value=0.0125) also showed weight gains significantly higher than Nx animals. (C) Relative heart weight was calculated as % body weight at time of necropsy. Untreated Nx rats had significantly enlarged hearts at the time of necropsy (150% of healthy controls). B2 exhibited only a 25% increase in relative heart weight six months post-treatment (FIG. 3C) compared to Nx animals (P value<0.0001). B4 (P value=0.0002) and vehicle (P value<0.0001 were also statistically significant from Nx controls.

Survival and weight gain. A pilot study involving intrarenal transplantation of UNFX cells suggested that the UNFX population contained bioactive cells that were able to stabilize filtration/urine production and restore erythroid homeostasis for 3 months after orthotopic transplantation. The cellular composition and functional attributes of B2 (albumin uptake) and B4 (oxygen-regulated Epo production) made both subfractions logical candidates for further investigation as bioactive components of the UNFX population, potentially responsible for the observed in vivo effects of improved filtration and enhanced erythropoiesis, respectively. Female uremic/anemic rats were generated via two-step 5/6 nephrectomy, and syngeneic male cells were delivered orthotopically after the progressive disease state was established, 5-6 weeks post-injury, when serum creatinine levels in the nephrectomized rats were already>250% of healthy controls (0.76±0.02 vs. 0.3±0.00) and the hematocrit was reduced by 8% (41.8±0.67 vs. 45.6±0.70). UNFX cells were delivered as in the previous study, and the B2 and B4 subfractions were delivered at doses approximating their relative contribution to the UNFX population; B2 at $5 \times 10^6$/rat and B4 at $1 \times 10^6$/rat. Additional controls included delivery vehicle only (PBS), and twice-weekly dosing with recombinant human Epo protein (rEpo) at 100 IU/kg and 500 IU/kg. All unmanipulated Healthy Controls and Sham Nx rats survived the duration of the study (30 weeks post-nephrectomy). As anticipated by previous studies, 100% of the untreated Nx rats died within 22 weeks of the nephrectomy procedure (FIG. 76A). Among the treatment groups, 100% of B2-treated rats survived 6 months post-treatment; 6-month survival of B4-treated and UNFX-treated groups was 20% and 0%, respectively. Rats treated with 100 IU/kg rEpo had a 25% survival rate 6 months post-treatment, similar to treatment with B4 (the Epo-producing cell fraction). In contrast, treatment with 500 IU/kg rEPO resulted in accelerated death; 100% of the treated rats died within 14 weeks of initiation of the dosing regimen, most with severe anemia at the time of death. Specifically, high dose (500 IU/kg) rEPO elevated HCT and RBC to levels>125% of healthy controls for 1 month, followed by profound anemia and death, whereas low dose (100 IU/kg) rEPO maintained HCT and RBC within high normal range for 1 month, followed by anemia in 75% of rats by 3 months. (see FIGS. 53-55). It should also be noted that recombinant EPO failed to support erythropoiesis in 6/8 rats beyond 4 weeks of repeated dosing. Poor survival following rEpo treatment was likely due to a combination of bone marrow exhaustion and the development of antibodies against rEpo, consistent with previously described immunity against human Epo (Campeau, P M, et al. Mol Ther, 17: 369-72, 2009).

Figure 52:
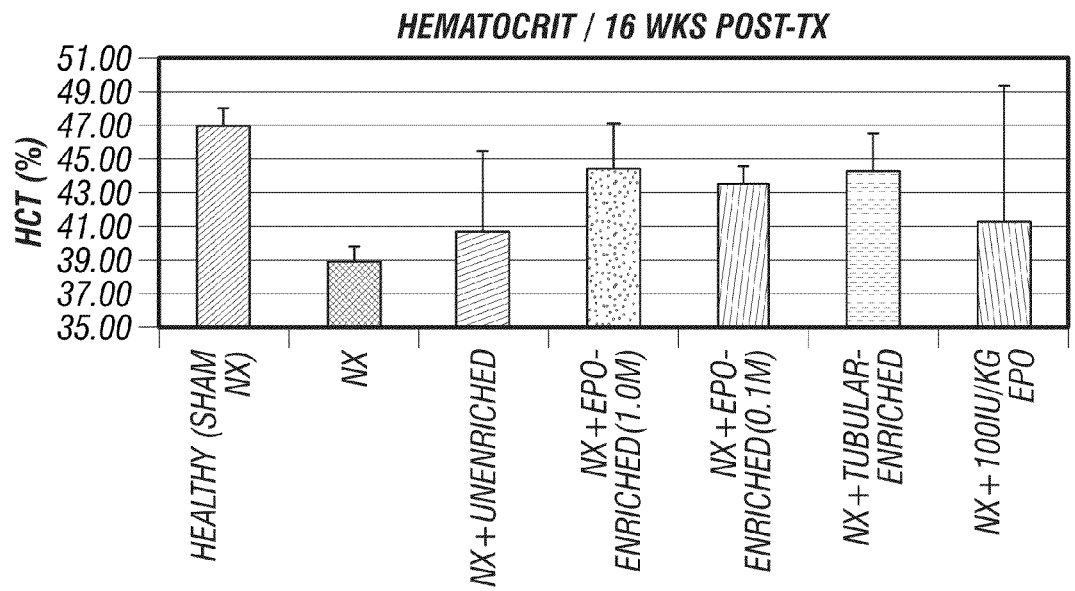
FIG. 52 shows hematocrit levels at 16 weeks post-treatment.

As shown in FIG. 52, the EPO-enriched (B4) cells performed at two different doses (high and low, 1M and 0.1M, respectively) and exceeded the recombinant EPO arm at 16 weeks. Specifically, and as also shown in Table 11 below, the hematocrit was restored to 95% normal healthy level by the EPO-enriched cells. Further, it was found that much less variability in the outcome existed when the EPO-enriched cells were delivered as compared to recombinant EPO protein.

Figure 58:
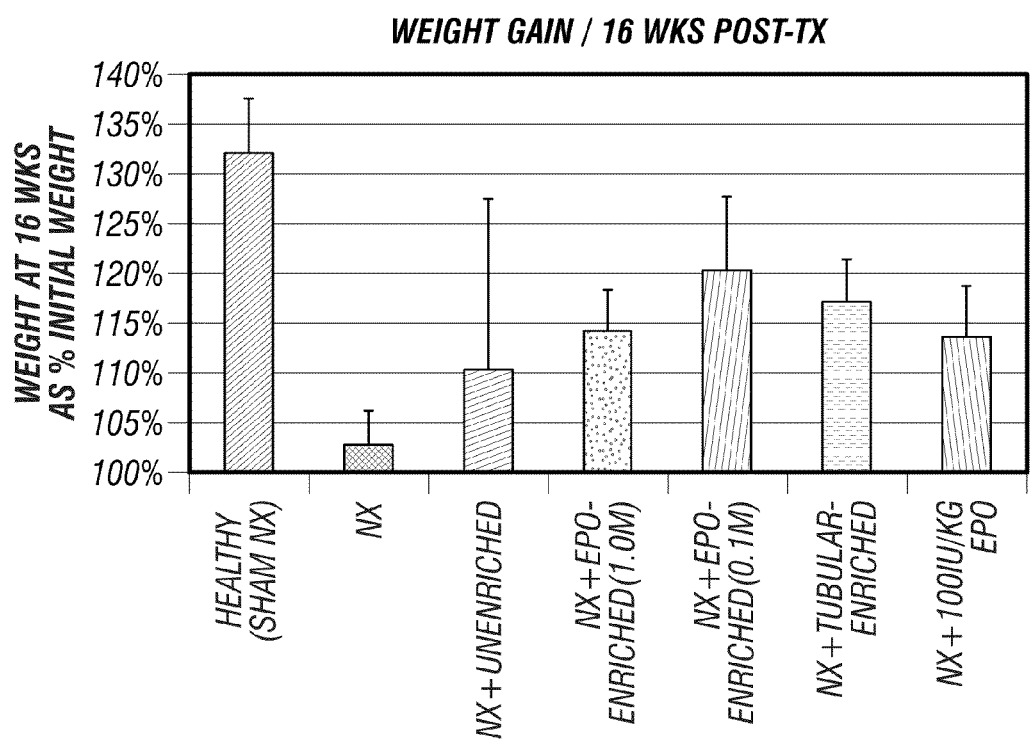
FIG. 58 shows weight gain at 16 weeks post-treatment as percent of initial weight.
Figure 76B:
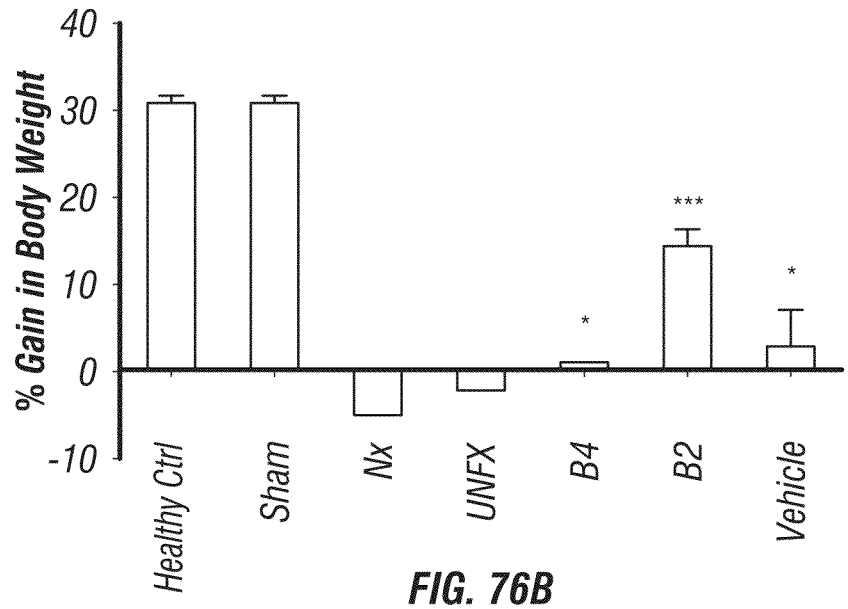
Figure 76C:
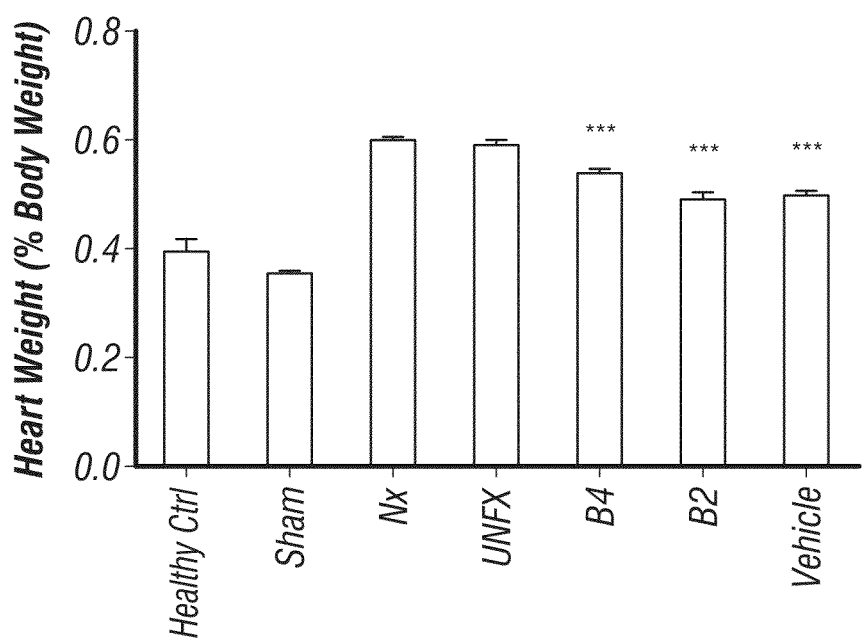

Weight gain measured at 16 weeks post-treatment also was improved in the EPO-enriched treated group than in the non-EPO-enriched treated group (see FIG. 58). While Healthy Control and Sham Nx rats gained an average of 30% body weight over the course of the entire study, the untreated Nx rats lost an average of 5% of their initial weight at the time of their death (FIG. 76B). In contrast, B2-treated rats gained an average of 14.3% body weight during the 6-months post-treatment (p<0.0001) (FIG. 76B), indicative of significant organism-level improvements in feeding and general well-being. B4 and vehicle also showed weight gain significantly higher than Nx animals (B4: p=0.0239; Vehicle: p=0.0125). Chronic hypertension can be both a cause and an effect of CKD; regardless of etiology, prolonged systemic hypertension places an excess load on the heart and results in relative cardiomegaly due to substantial left ventricular hypertrophy (LVH) (Foley, R N, et al. Kidney Int, 47: 186-92, 1995). Hypertension and LVH have been confirmed in rodent models of nephrectomy (Amann, K, et al. Nephrol Dial Transplant, 13: 1958-66, 1998). In the present study, heart weight and body weight data were collected at necropsy to determine whether cardiomegaly/LVH was a feature of two-step 5/6 nephrectomy-induced renal failure in Lewis rats, and to determine whether any of the treatment(s) reduced or eliminated this hypertrophic response. Relative to normal animals, heart weight was increased by 50% in the Nx rats, while rats treated with B2 exhibited only a 25% increase in relative heart weight six months post-treatment (P<0.0001) (FIG. 76C). Although not as pronounced as the treatment effects of B2, both B4 and vehicle treatments yielded heart weights that were significantly less than untreated Nx controls. These data collectively support treatment-dependent enhancement of kidney-regulated cardiovascular function.

Progression of uremia and anemia.

As described above, rats that underwent a two-step 5/6 nephrectomy were uremic and anemic at 5-6 weeks post-nephrectomy, when various treatments were delivered. At baseline (pre-transplant) and weekly throughout the study, uremia was assessed via sCREAT and BUN, and erythropoiesis was evaluated via HCT and RBC#.

Figure 77A:
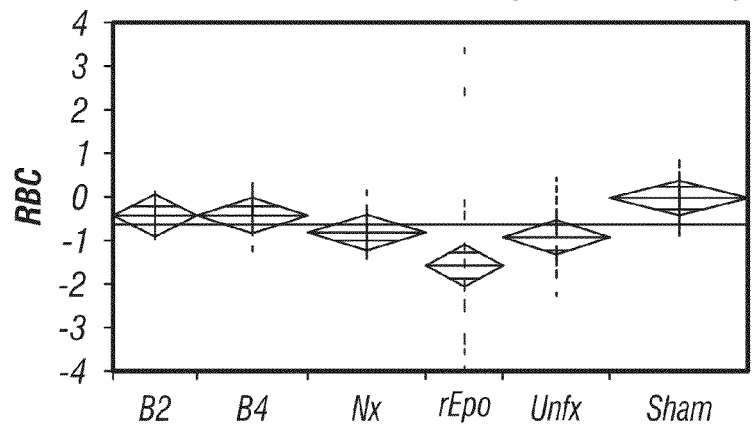
FIG. 77A-F depicts temporal and statistical assessment of treatment effects on filtration and erythropoiesis. A one-way Analysis of Variance (ANOVA) was performed on serum chemistry results from all 10 to 20 week data using JMP version 7.0 from SAS Institute Inc (Cary, N.C.). (a,b,c) Significant differences in erythropoiesis were observed among the treatment groups (HCT, p=0.0005; RBC, p=0.0029), with B2- and B4-treated rats showing the greatest improvement over untreated Nx, UNFX-treated, and rEPO-treated. (d,e,f) Significant differences in filtration function were observed among the treatment groups (sCREAT, p<0.0001); BUN, p<0.0001), with the effects of B2 treatment being most significant, followed by B4.
Figure 77B:
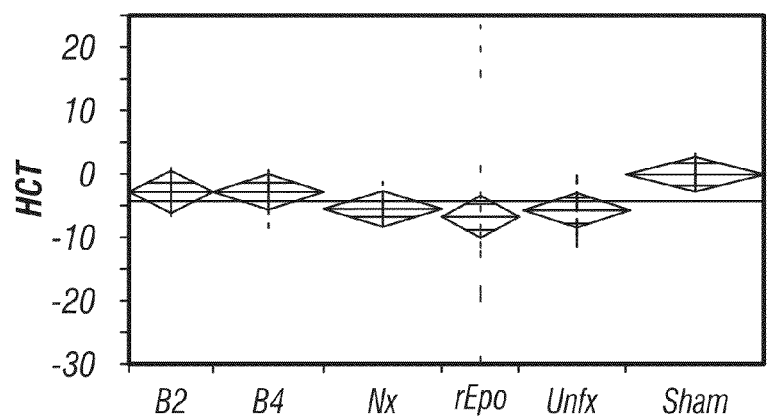
Figure 77C:
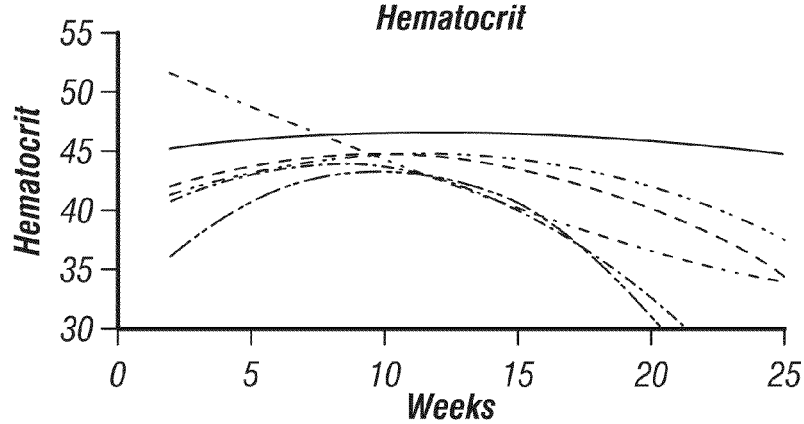
Figure 77D:
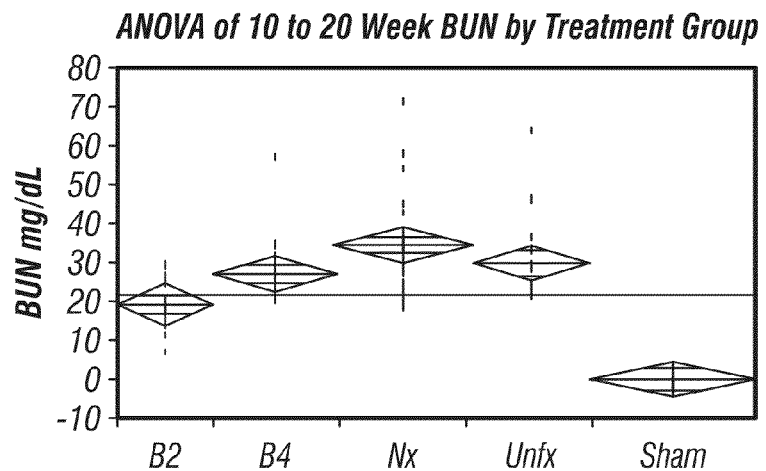
Figure 77E:
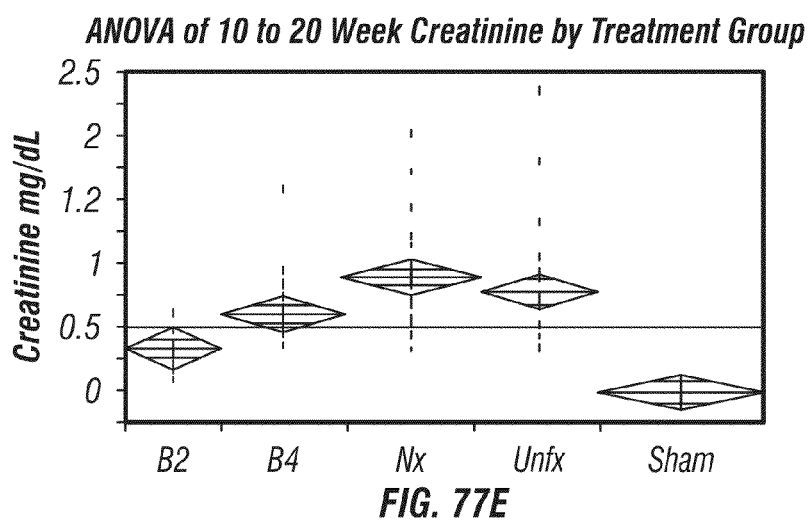
Figure 77F:
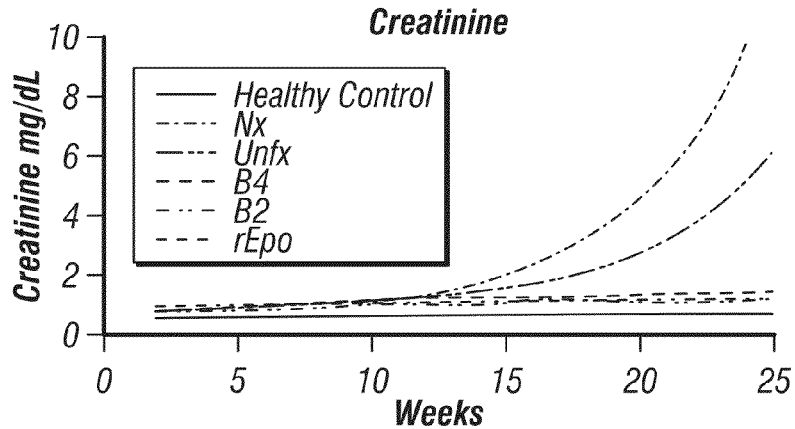

Statistical assessment of performance among groups was conducted with all data from 10-20 weeks post-treatment, when a sufficient number of rats were alive from each group to enable robust comparison. A one-way Analysis of Variance was performed on serum chemistry results from the 10 to 20 week samples using JMP version 7.0 from SAS Institute Inc (Cary, N.C.). Significant differences were observed among the treatment groups in this time range: upper panel, BUN (p<0.0001); (FIG. 77D), Creatinine (p<0.0001) (FIG. 77E). ANOVA of 10 to 20 week measurements of BUN and CREAT levels showed that Nx rats treated with B2 and B4 cells demonstrated stabilization of renal filtration and lower BUN and CREAT levels compared to Nx alone and Nx+Unfx cells, suggesting a general renoprotective effect of the treatments. Nx rats treated with B2 and B4 prototypes also demonstrated improvement in hematological parameters. Significant differences were observed among the treatment groups in this time range: RBC (p<0.0029) (FIG. 77A); HCT (p=0.0005) (FIG. 77B). The data showed clearly that B2-treated rats had higher average HCT and RBC number (FIGS. 77A-C) and lower average CREAT and BUN levels (FIG. 77D-F) compared to Nx and UNFX, indicating that B2 was a potent bioactive component of UNFX, and that delivery of the B2 subtraction (without other components of UNFX) extended both the magnitude and durability of the therapeutic response. This organism observation was supported by histological evidence of native-like glomeruli, tubules, and nephron structures in the B2 treated animals that were not observed in other groups. While B4 did not affect filtration function significantly, erythropoiesis was stimulated by B4 treatment, as exemplified by significant enhancement of RBC# and HCT (FIG. 77A-C). Regular dosing with recombinant Epo resulted in short-term stimulation of erythropoiesis, with an initial period of polycythemia followed by severe anemia and, ultimately, death in the majority (7/8) of rats receiving the drug. The poor overall performance of recombinant EPO in this study is likely due to the development of antibodies to the human EPO protein in the immune-competent rats.

Figure 57:
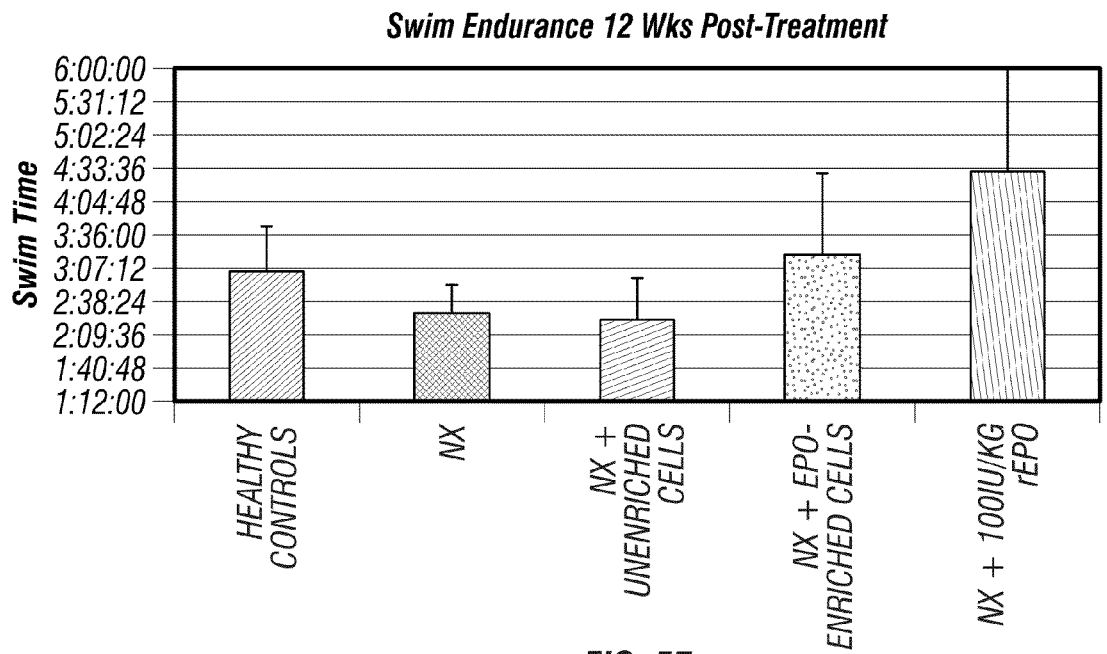
FIG. 57 shows swim endurance results at 12 weeks post-treatment.

As shown in FIG. 57, when subjected to a swim endurance test at 12 weeks post-treatment, nephrectomized (NX) rats swam for a shorter time on average than healthy rats. The rats treated with unenriched neo-kidney cells swam longer on average than the NX rats but with a great deal of variability. By contrast, the rats treated with high dose B4 cells swam nearly as long as the control group and with the least variability among treatment groups. Survival in all of the treated groups is better than nephrectomized, untreated rats. Table 11 (see below). Clinical value as % healthy control at 12-14 weeks post-treatment.

Tubule-Associated Functions Enhanced in Treated vs. Untreated Uremic Rats

Figure 78B:
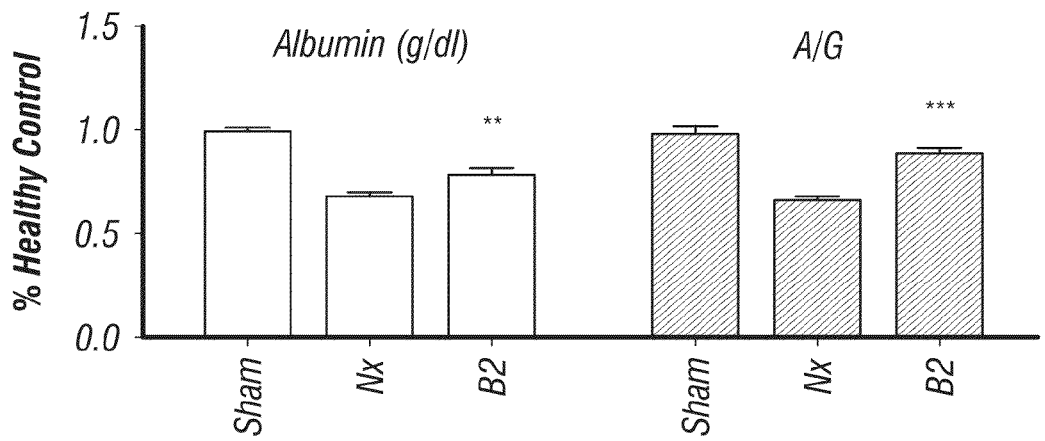
Figure 78C:
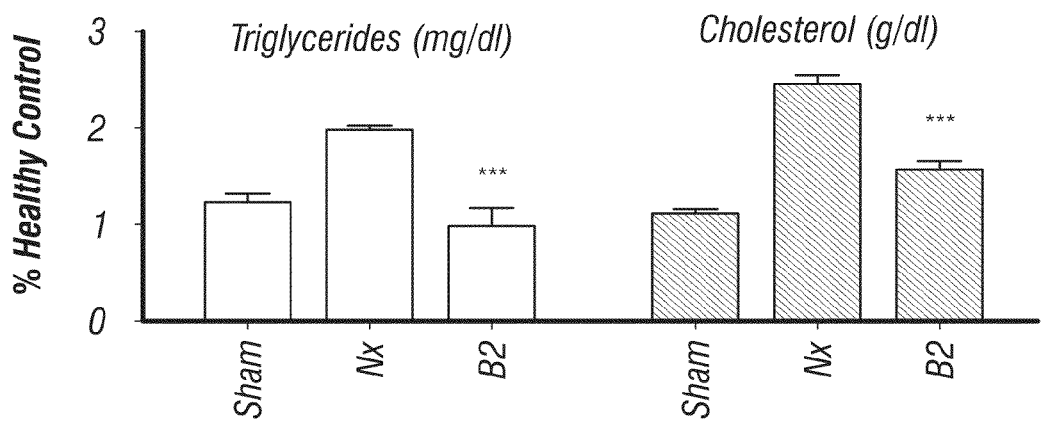

Protein Handling and Lipid Metabolism. Comprehensive clinical chemistry analyses were completed at the study midpoint (12-14 weeks post-treatment) so that additional comparisons could be made among treatment groups at a time when the majority of rats were still alive and available for sample collection (FIG. 78A). As shown in FIG. 78, B2 treatment enhances protein handling by the kidney and ameliorates dyslipidemia in the 5/6 Nx model of progressive renal failure. Sham NX, NX, NX+VEH, NX+UNFX, NX+B2, and NX+B4 were normalized to healthy controls and compared at 12-14 weeks (see Table 11 above). Serum albumin and albumin/globulin (A/G) ratios were reduced by 30% and 34%, respectively, in the untreated Nx rats relative to Healthy Controls, demonstrating that significant protein loss is a feature of the 5/6 Nx model of CKD (FIG. 78). Treatment with B2 increased serum albumin levels significantly ($p<0.05$), suggesting improved integrity of glomerular filtration mechanisms and/or enhanced resorption of albumin by the tubular epithelium (FIG. 78A, B). This observation was confirmed further by a significant increase in the serum A/G ratio in B2-treated vs. Nx animals ($p<0.001$) (FIG. 78A, B).

| CLINICAL VALUE AS % HEALTHY CONTROL (12-14 WKS POST-TX) | HEALTHY (SHAM NX) | NX | NX + SHAM TX | NX + UN-ENRICHED CELLS (UNFX) | NX + EPO-ENRICHED CELLS (1M) (B4) |
|---|---|---|---|---|---|
| SERUM ALBUMIN | 1.0 +/− 0.01 | 0.69 +/− 0.01 | 0.73 +/− 0.05 | 0.63 +/− 0.02 | 0.71 +/− 0.021 |
| A:G RATIO | 0.99 +/− 0.02 | 0.66 +/− 0.01 | 0.77 +/− 0.05 | 0.62 +/− 0.05 | 0.74 +/− 0.04 |
| SERUM PHOSPHOROUS | 1.07 +/− 0.03 | 1.09 +/− 0.05 | 1.19 +/− 0.12 | 1.36 +/− 0.28 | 1.12 +/− 0.08 |
| SERUM CALCIUM | 1.00 +/− 0.03 | 1.01 +/− 0.08 | 0.72 +/− 0.13 | 0.97 +/− 0.15 | 1.07 +/− 0.03 |
| PHOS:CALCIUM RATIO** | 0.52 +/− 0.03 | 0.59 +/− 0.08 | 0.81 +/− 0.09 | 0.72 +/− 0.13 | 0.50 +/− 0.025 |
| SERUM POTASSIUM | 0.98 +/− 0.07 | 1.04 +/− 0.03 | 1.15 +/− 0.03 | 1.03 +/− 0.03 | 1.10 +/− 0.05 |
| SERUM CREATININE | 0.96 +/− 0.07 | 3.78 +/− 0.24 | 2.84 +/− 1.02 | 2.80 +/− 0.23 | 2.99 +/− 0.48 |
| BUN | 0.94 +/− 0.04 | 3.08 +/− 0.18 | 2.49 +/− 0.38 | 2.07 +/− 0.30 | 2.51 +/− 0.26 |
| CHOLESTEROL | 1.11 +/− 0.03 | 2.47 +/− 0.09 | 1.67 +/− 0.10 | 2.07 +/− 0.3 | 1.96 +/− 0.28 |
| TRIGLYCERIDES | 1.20 +/− 0.09 | 1.97 +/− 0.19 | 1.02 +/− 0.21 | 1.69 +/− 0.63 | 1.44 +/− 0.09 |
| HEMOGLOBIN | 1.00 +/− 0.03 | 0.90 +/− 0.01 | 0.89 +/− 0.02 | 0.87 +/− 0.04 | 0.93 +/− 0.03 |
| HEMATOCRIT | 1.01 +/− 0.01 | 0.88 +/− 0.01 | 0.91 +/− 0.02 | 0.90 +/− 0.03 | 0.96 +/− 0.01 |
| RBC# | 1.01 +/− 0.02 | 0.90 +/− 0.01 | 0.93 +/− 0.06 | 0.92 +/− 0.03 | 0.96 +/− 0.02 |
| MCH | 1.00 +/− 0.01 | 0.99 +/− 0.00 | 0.98 +/− 0.01 | 0.97 +/− 0.01 | 0.98 +/− 0.01 |
| RETICULOCYTE# | 0.90 +/− 0.04 | 0.94 +/− 0.05 | 0.98 +/− 0.08 | 1.14 +/− 0.14 | 0.98 +/− 0.04 |
| RETICULOCYTE % | 0.90 +/− 0.04 | 1.03 +/− 0.06 | 1.08 +/− 0.10 | 1.30 +/− 0.19 | 1.04 +/− 0.04 |
| MCV | 1.00 +/− 0.01 | 0.98 +/− 0.01 | 0.99 +/− 0.03 | 0.98 +/− 0.01 | 0.97 +/− 0.01 |
| RDW | 0.99 +/− 0.01 | 1.00 +/− 0.01 | 1.00 +/− 0.01 | 1.07 +/− 0.03 | 1.02 +/− 0.02 |
| SWIM ENDURANCE | ANALYSIS IN PROGRESS | | | | |
| % SURVIVAL** | 100% | 38% | 66% | 80% | 60% |
| % WEIGHT GAIN PRE-TX - 14 WKS** | 25% +/− 2% | 4% +/− 1% | 5% +/− 2% | 9% +/− 7% | 8% +/− 2% |

| CLINICAL VALUE AS % HEALTHY CONTROL (12-14 WKS POST-TX) | NX + EPO-ENRICHED CELLS (0.1M) (B4) | NX + TUBULAR-ENRICHED CELLS (B2) | NX + 100 IU/KG RECOMBINANT EPO |
|---|---|---|---|
| SERUM ALBUMIN | 0.72 +/− 0.04 | 0.80 +/− 0.02 | 0.73 +/− 0.03 |
| A:G RATIO | 0.76 +/− 0.06 | 0.87 +/− 0.05 | 0.77 +/− 0.06 |
| SERUM PHOSPHOROUS | 1.05 +/− 0.12 | 1.02 +/− 0.02 | 1.14 +/− 0.09 |
| SERUM CALCIUM | 0.94 +/− 0.13 | 1.02 +/− 0.00 | 1.04 +/− 0.03 |
| PHOS:CALCIUM RATIO** | 0.55 +/− 0.06 | 0.48 +/− 0.02 | 0.50 +/− 0.07 |
| SERUM POTASSIUM | 1.09 +/− 0.06 | 0.97 +/− 0.04 | 1.08 +/− 0.04 |
| SERUM CREATININE | 2.49 +/− 0.55 | 1.78 +/− 0.20 | 3.13 +/− 0.70 |
| BUN | 2.42 +/− 0.49 | 1.92 +/− 0.31 | 2.56 +/− 0.36 |
| CHOLESTEROL | 1.8 +/− 0.2 | 1.57 +/− 0.08 | 1.85 +/− 0.79 |
| TRIGLYCERIDES | 1.66 +/− 0.54 | 0.95 +/− 0.18 | 1.76 +/− 0.42 |
| HEMOGLOBIN | 0.91 +/− 0.01 | 0.94 +/− 0.04 | 0.79 +/− 0.23 |
| HEMATOCRIT | 0.95 +/− 0.00 | 0.96 +/− 0.02 | 0.94 +/− 0.19 |
| RBC# | 0.93 +/− 0.01 | 0.96 +/− 0.01 | 0.90 +/− 0.19 |
| MCH | 0.98 +/− 0.01 | 0.99 +/− 0.03 | 0.99 +/− 0.02 |
| RETICULOCYTE# | 1.02 +/− 0.04 | 0.89 +/− 0.03 | 1.39 +/− 0.22 |
| RETICULOCYTE % | 1.10 +/− 0.04 | 0.94 +/− 0.06 | 1.90 +/− 0.18 |
| MCV | 0.98 +/− 0.01 | 0.99 +/− 0.04 | 1.00 +/− 0.02 |
| RDW | 1.02 +/− 0.02 | 1.00 +/− 0.02 | 1.35 +/− 0.06 |
| SWIM ENDURANCE | | | |
| % SURVIVAL** | 50% | 75% | 75% |
| % WEIGHT GAIN PRE-TX - 14 WKS** | 13% +/− 4% | 12% +/− 2% | 8% +/− 8% |

**Not expressed as % Control

Interestingly, these in vivo observations associated with B2 treatment are aligned with key in vitro characteristics of B2, namely the strong expression of protein transport receptors (cubilin/megalin) and robust receptor-mediated albumin uptake (described in FIG. 75A). Hyperlipidemia is a well-documented feature of human CKD (23) and in the rat 5/6 nephrectomy model of CKD (Kasiske, B L, et al. Circ Res, 62: 367-74, 1988) (FIG. 78A, C). Midpoint clinical chemistry showed that B2 treatment ameliorated the Nx-induced elevation in serum triglycerides, returning levels to normal (FIG. 78A, C). Serum cholesterol was also reduced in B2-treated rats, achieving levels at 150% of Healthy Controls, compared to >250% of Healthy Controls in the Nx group (FIG. 78A, C). Improvements in serum cholesterol may be attributed indirectly to greater elimination of cholesterol through improvements in kidney filtration function with B2 treatment. The midpoint clinical analyses support the observation that B2 is bioactive with regards to improving kidney functions across a wide spectrum of relevant clinical parameters, including those associated with urine production (sCREAT, BUN, serum Albumin, A:G ratio), erythropoiesis (HCT, RBC#), mineral balance (Calcium:Phosphorous), and lipid metabolism (Triglyceride, Cholesterol).

Figure 59:
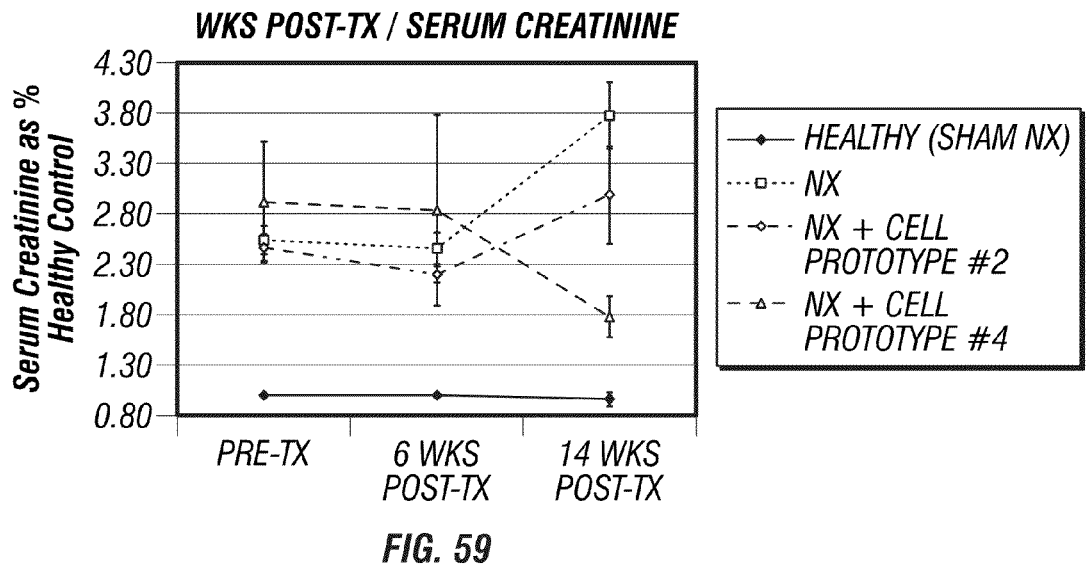
FIG. 59 depicts serum creatinine as percent healthy control between untreated uremic rats and uremic rats treated with a high dose of EPO-enriched cells (Prototype #2) or tubular enriched cells (Prototype #4).
Figure 60:
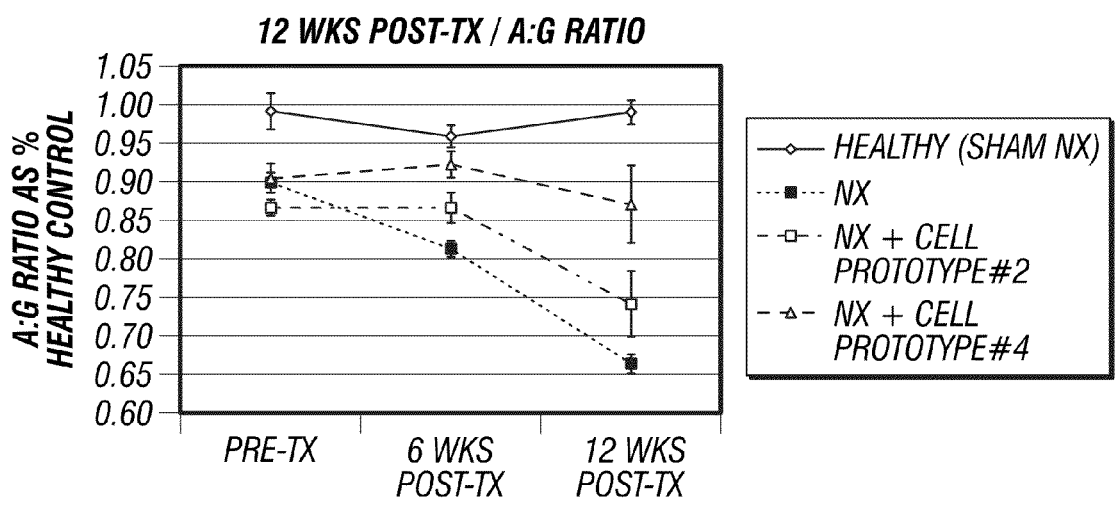
FIG. 60 shows albumin/globulin ratio in untreated uremic rats and uremic rats treated with a high dose of EPO-enriched cells (Prototype #2) or tubular enriched cells (Prototype #4) 12 weeks post-treatment.
Figure 61:
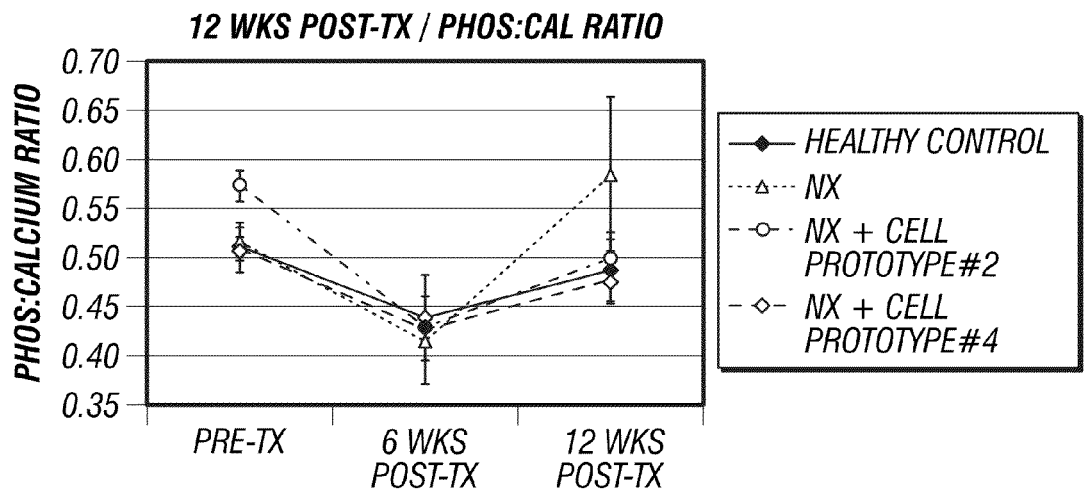
FIG. 61 depicts phosphorus:calcium ratios in untreated uremic rats and uremic rats treated with a high dose of EPO-enriched cells (Prototype #2) or tubular enriched cells (Prototype #4) 12 weeks post-treatment.
Figure 62:
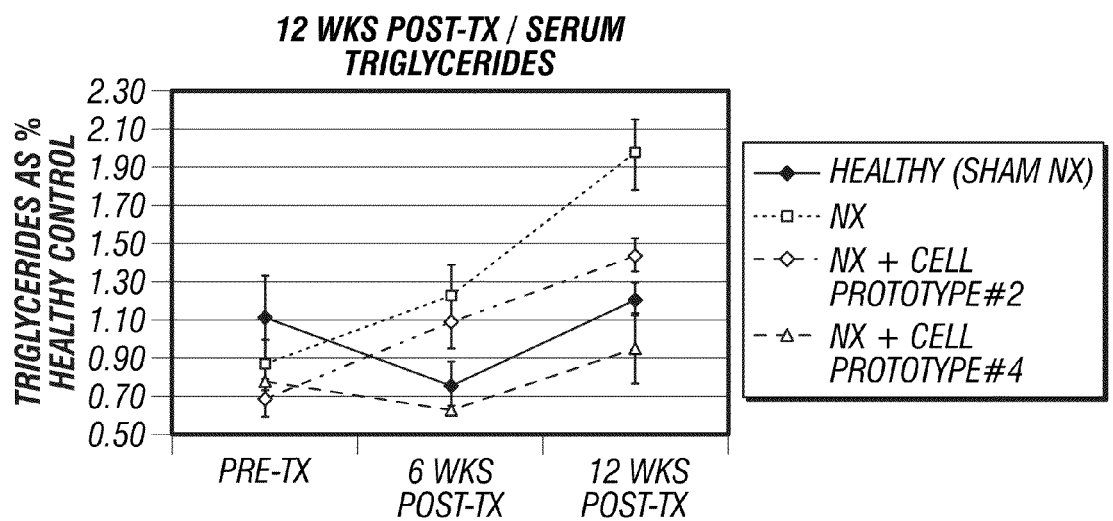
FIG. 62 shows serum triglyceride levels in untreated uremic rats and uremic rats treated with a high dose of EPO-enriched cells (Prototype #2) or tubular enriched cells (Prototype #4) 12 weeks post-treatment.
Figure 63:
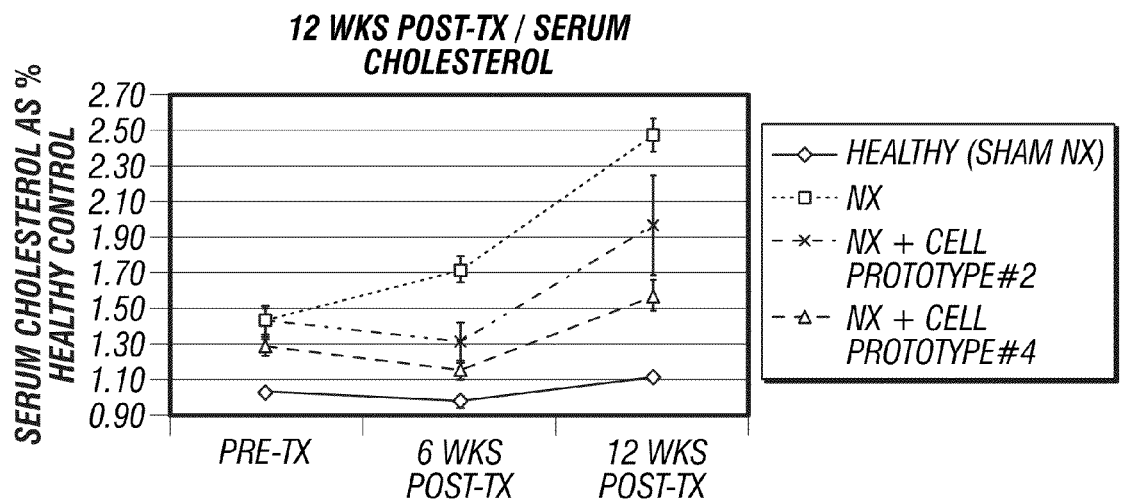
FIG. 63 depicts serum cholesterol levels in untreated uremic rats and uremic rats treated with a high dose of EPO-enriched cells (Prototype #2) or tubular enriched cells (Prototype #4) 12 weeks post-treatment.
Figure 64:
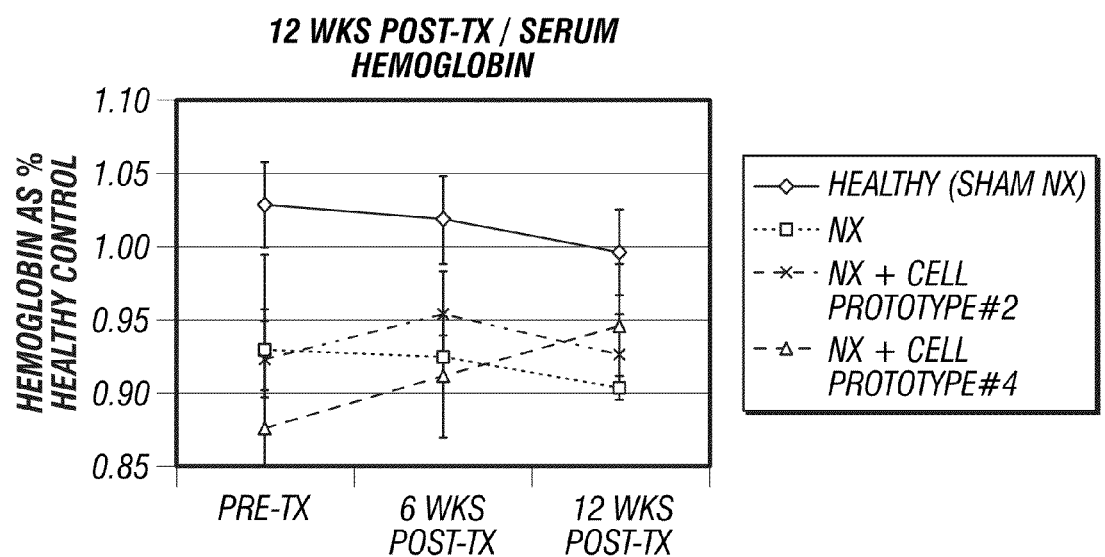
FIG. 64 shows serum hemoglobin levels in untreated uremic rats and uremic rats treated with a high dose of EPO-enriched cells (Prototype #2) or tubular enriched cells (Prototype #4) 12 weeks post-treatment.
Figure 65:
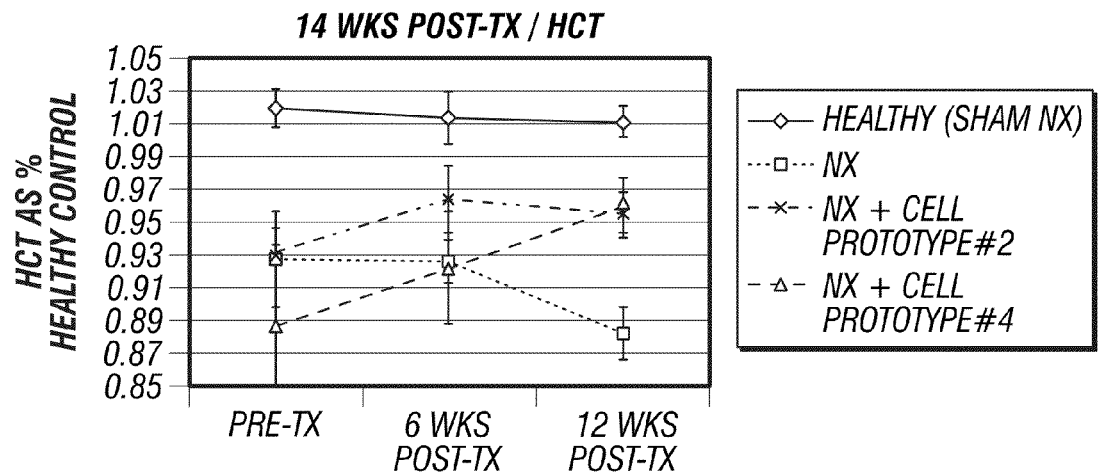
FIG. 65 shows hematocrit levels in untreated uremic rats and uremic rats treated with a high dose of EPO-enriched cells (Prototype #2) or tubular enriched cells (Prototype #4) 12 weeks post-treatment.

FIGS. 59-61 also show that, at the study midpoint, uremic rats treated with cell prototype #4 (B2) (tubular enriched cells) showed improved serum creatinine over time in, stabilized serum albumin and phosphorus:calcium ratios near normal compared to untreated uremic rats. FIG. 61 shows that uremic rats treated with cell prototype #2 (1M dose of EPO-enriched cells) also showed phosphorus:calcium ratios near normal. FIGS. 62-63 show the improvement in lipid metabolism in treated vs. untreated uremic rats. FIG. 11 shows that uremic rats treated with cell prototypes #2 (B4 HIGH) and #4 (B2) had lower serum cholesterol and lower serum triglycerides (see FIGS. 62-63). FIGS. 64 and 65 show the increased hemoglobin levels and hematocrit levels greater than 95% of normal rats in uremic rats treated with cell prototypes #2 (B4 HIGH) and #4 (B2), showing systemic evidence of erythroid stimulation.

Renal Mass Correlates with Renal Function.

Figure 79A:
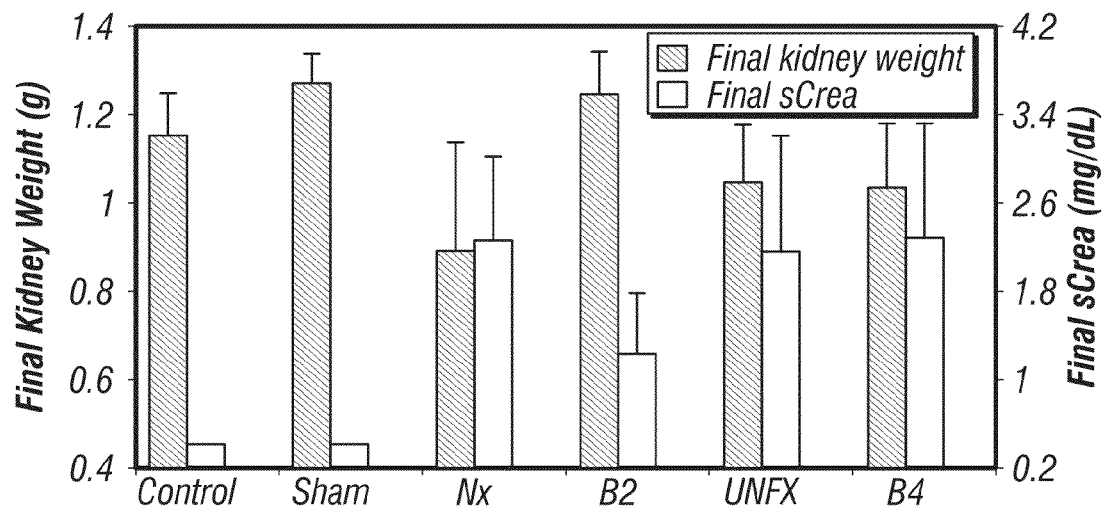
FIG. 79A-B shows that renal mass correlates with renal function. Weights of the (right) kidney were collected at the time of necropsy. (A) Unilateral renal mass in B2-treated kidneys was equivalent to healthy controls. Examination of sCREAT in serum collected at the time of necropsy revealed an apparent inverse relationship between renal mass and sCREAT (panel A, secondary axis). (B) Linear regression analysis of renal mass and sCREAT for all rats on study confirmed a significant inverse correlation of kidney weight and kidney function (r2=0.38; p value<0.001).
Figure 79B:
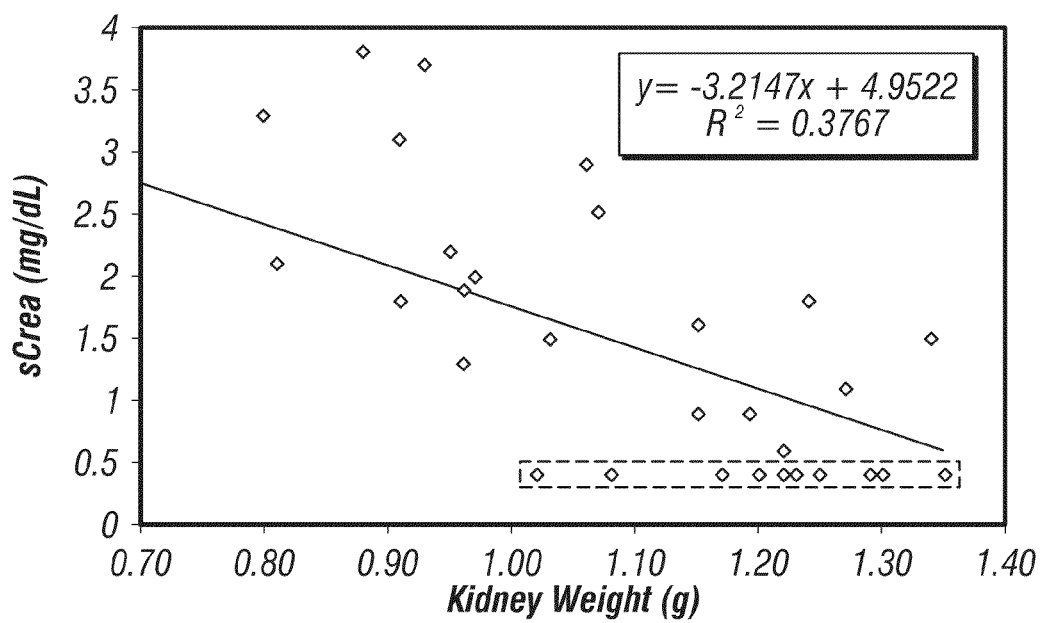
Figure 80:
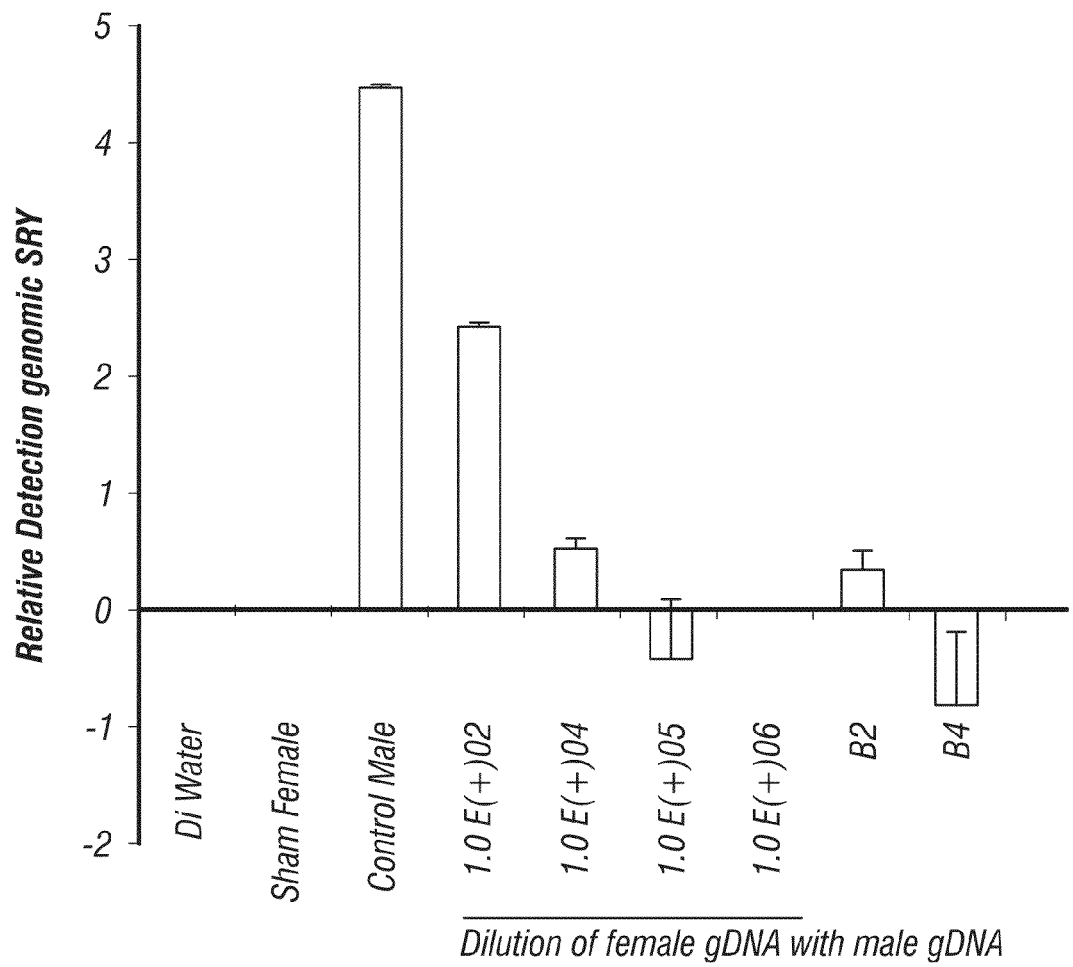
FIG. 80 depicts PCR-based DNA analysis with probes for SRY.

The long-term benefits of B2 cell delivery to the kidney were clear by systemic and histological analyses throughout the six months post-treatment (FIG. 76-79), suggesting that the cells may have directly or indirectly provided repair and/or regeneration resulting in preservation and/or neogenesis of functional kidney mass. PCR-based DNA analysis with probes for SRY, a gene localized to the Y chromosome, was employed to confirm retention of male B2 donor cells in female kidney tissue at the time of harvest (6 months post-treatment), and the contribution of male cells to the host kidney estimated by this method at this time point was relatively low (~1%) (see FIG. 80). Post-mortem kidney weights were collected from remnant (Nx, B2, B4, and UNFX) or intact (Healthy Controls & Sham Nx) right kidneys. Untreated Nx kidney remnants had an average 43% reduction in renal mass compared to Sham controls, while kidney remnants that received B2 cells orthotopically had an average renal mass equivalent to Sham controls (FIG. 79A). Interestingly, the average kidney mass in each group was inversely proportional to the average serum creatinine value for that group (FIG. 79A). The reciprocal relationship between kidney weight and serum creatinine was validated further by a linear regression analysis demonstrating a significant ($R2=0.38$) inverse correlation between the two parameters for each rat (FIG. 79B). These data illustrate the direct relationship between renal mass and renal function and highlight again the distinct therapeutic advantage of B2 over B4 and UNFX.

Histological Evaluation.

Figure 81A:
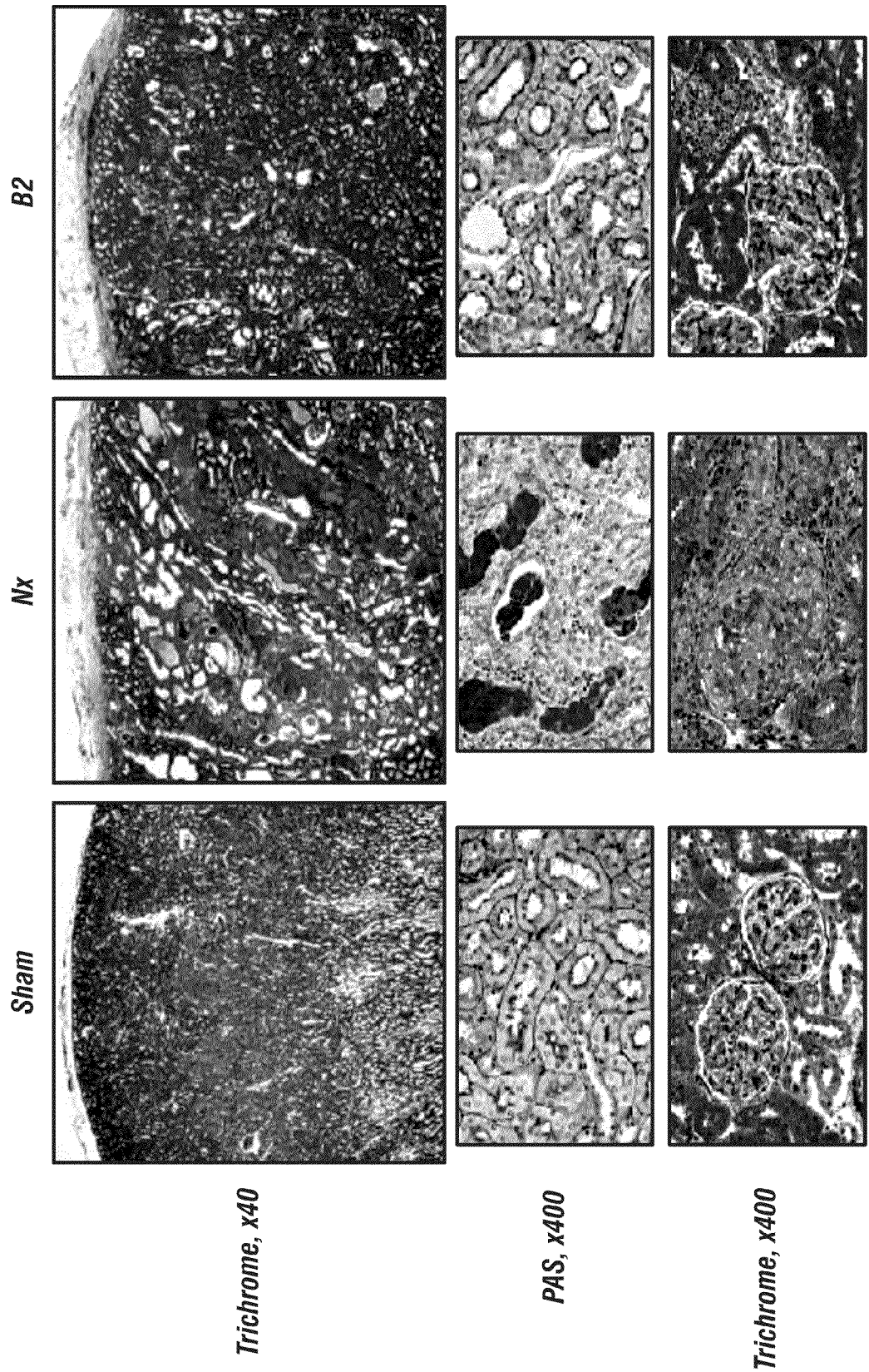
FIG. 81A-D shows histopathology analysis of the kidney and bone marrow. (A) Representative light micrographs of sham control and remnant kidney (Masson's Trichrome and PAS staining). Sham (control) kidneys have normal parenchymal architecture characterized by well demarcated cortical-medullary junction and the absence of tubular or glomerular injury. Nx untreated animals showed progressive glomerular and tubular degeneration consisting of moderate to marked tubulo-interstitial fibrosis and glomerular sclerosis (blue staining by Masson's trichrome), tubular dilatation with luminal casts (eosinophilic staining by PAS), and decreased bone marrow cellularity (myeloid to erythroid ratios). In contrast to Nx animals, B2-treated rats showed evidence of treatment effect characterized by reduction in tubulo-interstitial fibrosis and glomerular sclerosis, and near-normal of bone marrow cellularity with a myeloid-to-erythroid ratio equivalent to healthy controls. (B) H&E stained bone marrow revealed ample evidence of bone resorption in the untreated Nx rats, with prominent osteoclasts and the formation of lacunae with bone erosion. Like healthy controls, the endosteal surfaces of B2-treated rats were smooth, with no evidence of osteoclasts, lacunae, or bone erosion. (C, D) Terminal serum phosphorous (mg/dl), and calcium (mg/dl, corrected for total protein–0.4+3.3) provide systemic support for histologic observations of bone resorption in the model and amelioration of the resorption with B2 treatment.

The 5/6 nephrectomy procedure in rodents leaves in place a remnant kidney, which initially undergoes a hypertrophic response that partially restores renal mass via compensatory enlargement of existing nephrons, rather than forming new nephrons (Brenner, B M. Am J Physiol, 249: F324-37, 1985, Kaufman, J M, et al. Kidney Int, 6: 10-7, 1974). Despite the initial hypertrophic response, changes in renal hemodynamics associated with the loss of renal mass ultimately result in hypertension, uremia, anemia, and chronic morphologic disruptions of renal tissue architecture. Standard histologic techniques and stains (H&E, PAS and Masson's Trichrome) were employed to compare Sham Nx, Nx and B2 treatments, with a specific focus on the kidney, bone marrow and endosteal surfaces of B2 treated rats (FIG. 81A, B, C). Histopathologic changes observed in the untreated 5/6 Nx rat kidneys included moderate to marked glomerulo-tubular injury, consisting of multifocal to diffuse glomerular hypertrophy with segmental to global glomerular sclerosis, characterized by replacement of glomerular matrix with homogeneous eosinophilic material (protein) and moderate mesangial proliferation. There were multifocal glomerular tuft adhesions and focal glomerular atrophy associated with Nx animals. Furthermore, the Nx rat kidneys had mild to moderate tubulo-interstitial fibrosis with multifocal inflammation. Multifocal tubular hypertrophy and hyperplasia were observed, predominantly in the proximal tubules, and diffuse tubular dilatation affected both proximal and distal tubules. Most dilated tubules showed attenuated epithelium and thickened basement membrane, with many tubules containing hyaline casts indicating intraluminal protein accumulation.

Compared to the global morphologic disruptions observed in the surgical model, the comparative microanatomical features in B2-treated kidneys were more consistent morphologically with healthy control kidneys. Specifically, kidneys treated with B2 had proportionally more healthy glomeruli, tubules and nephron structures, a decrease in tubular dilatation, a reduction in tubular hyaline casts, a decrease in tubulo-insterstitial fibrosis and minimal glomerular sclerosis (FIG. 81A). Although B2 treated animals had occasional foci of injured renal tissue evident within the parenchyma, the predominant morphology was consistent with that of healthy controls. Conversely, B4-treated kidneys had proportionally more healthy glomeruli and less glomerular sclerosis than Nx animals, but tubular pathology, including dilatation and tubular casts, were similar to untreated Nx controls. Furthermore, B4-treated kidneys were characterized by predominant regions of injury, slightly improved compared to untreated Nx rats but not approximating healthy controls.

Figure 81B:
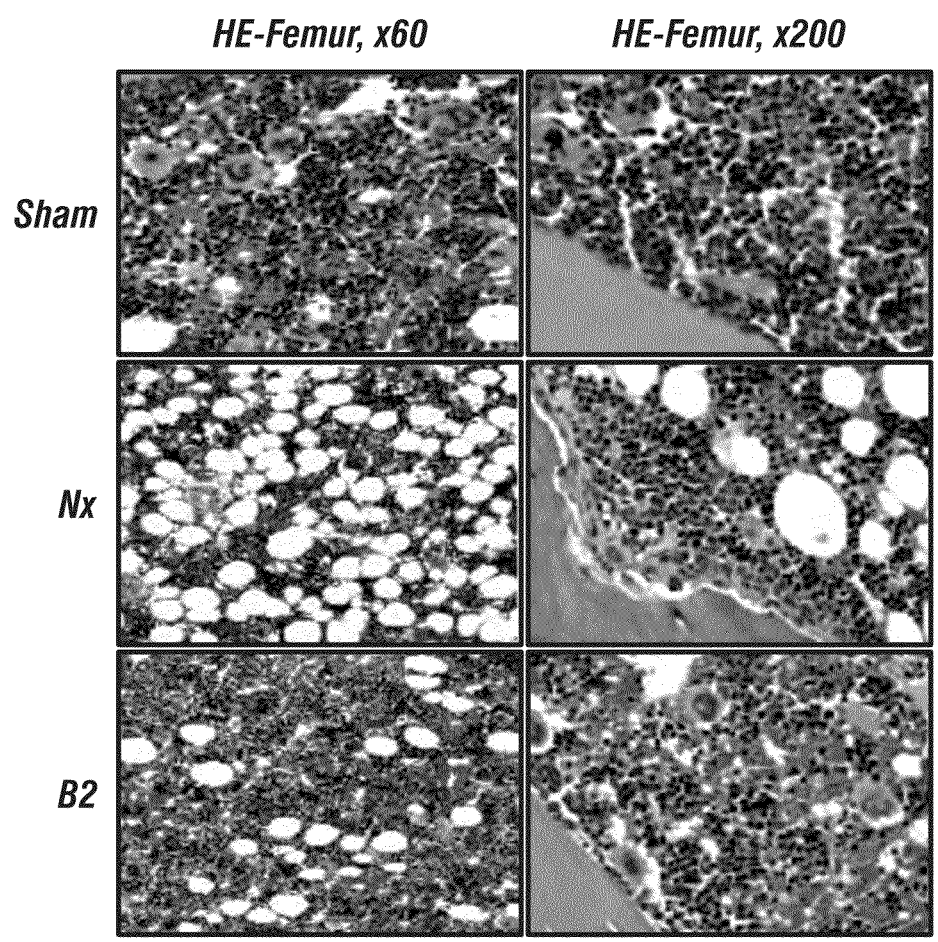

Femoral bone and marrow from the healthy Sham Nx rats were considered to be normal and without significant histological changes. Two histological features were present in the marrow and bone of untreated Nx rats: 1) reduced overall cellularity of the marrow with a paucity of red blood cells and increased myeloid:erythroid ratio (FIG. 81B; and 2) moderate bone resorption characterized by scalloping of endosteal surfaces with prevalent osteoclasts and the formation of lacunae (FIG. 81B). In the Nx animals there was thinning of the cortical and trabecular bone indicative of osteopenia. Compared to bone marrow from the Nx group, marrow from B2 treated animals had more free red blood cells, homeostatic myeloid:erythroid ratios, and absence (B2) of histological evidence of bone resorption. The magnitude of bone marrow response to B2 treatment was most prominent among the treatment groups, with bone marrow composition and morphology approximating that of healthy controls.

Figure 81C:
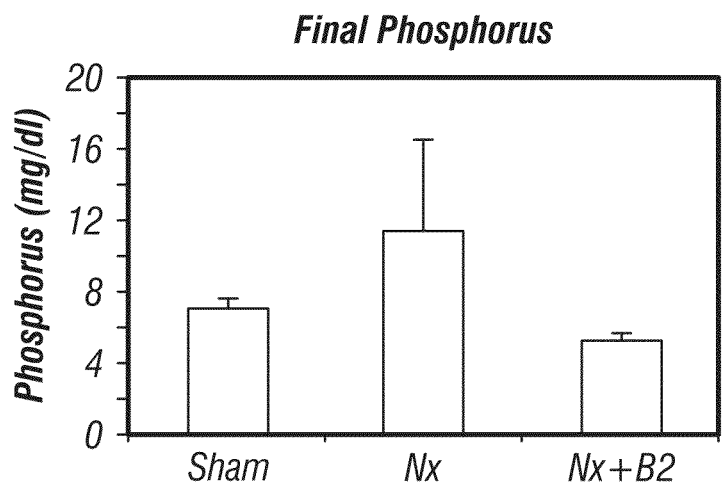
Figure 81D:
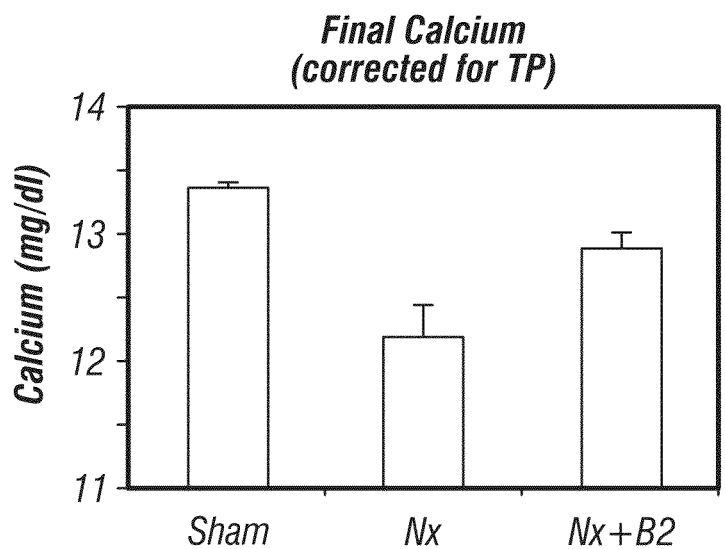

The histologic observation of bone erosion in the Nx rats paired with apparent lack of this phenomenon in the B2-treated rats led to additional assessments of serum calcium and phosphate levels. Consistent with the described osteodystrophy of end stage renal disease (37), hyperphosphatemia and hypocalcemia were observed in Nx animals (FIG. 81C). As was predicted by histopathological observations of the endosteal surfaces, B2-treated animals had phosphorus and calcium levels equivalent to healthy controls, suggesting systemic and homeostatic regulation of these minerals (FIG. 81C). Collectively, the histologic observations provide confirmation of systemic indicators that B2 enhances renal filtration function and restores erythroid homeostasis in a rodent model of progressive renal failure.

Discussion

A regenerative stimulus, initiated by the orthopic transplantation of selected kidney-derived cells with specific functional attributes in vitro, reduced mortality, augmented function, and slowed disease progression in vivo in a rodent model of CKD. The data presented herein provide systemic and histological evidence that specific cellular subfractions of a heterogeneous renal cell population provide a broader spectrum of clinically-relevant benefits, are more efficacious with regard to specific clinical parameters, and extend the durability of clinical effect by at least 50%, when compared to the unfractionated heterogeneous mixture. The two cell subfractions (B2 and B4) that were tested comparatively in these studies were generated by fractionation after in vitro propagation and shown to possess unique compositional and functional attributes related to filtration (B2) and erythropoiesis (B4). Subtraction B2, comprised of proximal and distal renal tubular cells (~90%) and some collecting duct cells (~10%), was enriched for specialized cubilin+/megalin+proximal tubular cells capable of robust receptor-mediated endocytosis of albumin. Given the cellular composition and functional attributes of B2, it was not surprising to observe that this subfraction augmented function across the nephron, via effects such stabilization of serum creatinine and BUN, resorption of protein, and electrolyte balance. The renal homeostatic effects of B2 were accompanied by significant whole organism level benefits, such as extended survival, improved weight gain, a normal blood lipid profile, and a reduction in bone catabolism. Taken together, the physiologic data presented herein reflect a broad and relevant stabilization of kidney function in a terminal model of CKD, via transplantation of the B2 cell subfraction.

Physiological evidence of stabilized kidney function was supported directly by histopathological analyses at 6 months, showing near-native tubular and glomerular morphology in the remnant kidneys of rats treated with B2. Restoration of renal mass by B2 treatment (FIG. 79) was accompanied by histologic evidence that glomerulosclerosis, tubulo-interstitial fibrosis, and intralumenal protein deposition were attenuated in the B2-treated vs. untreated Nx kidneys, and the erythropoietic response in the bone marrow was analogous to healthy controls (FIG. 81). Though less pronounced, B4 treatment did provide some clear tissue-level improvements including reduction in glomerulosclerosis and restoration of erythroid homeostasis in the bone marrow. The syngeneic male donor/female recipient approach enabled assessment of tissue chimerism via detection of male cells (SRY) in the genomic DNA of recipient female kidneys at the time of sacrifice. Male cells were still detectable in the female kidney six months after transplantation by this method at a frequency of approximately 1%. Using the historical estimate that approximately 100 million cells are present in a gram of tissue, and the estimate that, at the time of transplant, the remnant kidney weighed ~0.8 grams, the dose of B2 cells delivered to the kidney (5 million) represented ~6.25% of the remnant kidney. Since the B2 cell subfraction is comprised predominantly of functionally mature cells that have not, to date, been characterized as long-term engrafting stem or progenitors, it would not be expected that 100% of the implanted cells would be retained for six months in vivo, assuming a moderate rate of cell turnover in the kidney. The disease-attenuating effects of B2 cells may be due to repopulation of the host nephrons with functional cells (salvage), cytoprotective or regenerative effects of implanted cells on host cells (modulation), regeneration of new nephrons via combined actions of implanted donor cells and recruited host cells (nephronogenesis), or a combination of one or more of these mechanisms. It is also possible that an as-yet-unidentified component of B2 contributes to the observed therapeutic effects. For example, the presence or absence of immunomodulatory cells, such as tissue-specific macrophages, might modulate pathogenesis in the kidney, especially as it relates to mechanisms of fibrosis and tissue remodeling. Furthermore, kidney-specific stem or progenitor cells could feasibly facilitate regenerative mechanisms such as the nephronogenesis contemplated above. A well-controlled temporal study of the molecular and cellular components of the treated kidney tissue is required to develop a thorough understanding of the mechanism(s) of action of B2 and B4.

A primary measure of success for the present study was survival. B2 cells extended survival to approximately 6 months post treatment (30 weeks after nephrectomy), or 3 months longer than average survival in the untreated Nx rats, all of which died of renal failure by 22 weeks post-nephrectomy. The duration of survival observed with B2 treatment was greater than post-treatment survival observed in other published cell-based therapies for renal failure (Kim, S S, et al., Improvement of kidney failure with fetal kidney precursor cell transplantation. Transplantation, 83: 1249-58, 2007, Choi, S, et al. Stem Cells Dev, 18: 521-9, 2009, Zeisberg, M, et al. Am J Physiol Renal Physiol, 285: F1060-7, 2003, Eliopoulos, N, et al. J Am Soc Nephrol, 17: 1576-84, 2006). Prolonged survival in the B2 treatment arm was likely due to the positive effects on renal function delivered or elicited by the implanted cells: filtration (sCrea, BUN), tubular resorption (protein), electrolyte balance (calcium, phosphorus), and endocrine (Vit D, Epo). The hypothesis that B2 cells significantly impacted multiple cellular compartments in the kidney is supported further by: 1) the observed increase in kidney weight, with the weight of B2-treated kidneys reaching mass equivalent to a single healthy kidney from unmanipulated age-matched control rats (FIG. 79); and 2) the clear histological evidence of slower disease progression in B2-treated kidneys, including reduced tubulo-interstitial fibrosis, reduced glomerular sclerosis, and focal evidence of tubular regeneration with reduction in protein accumulation in the tubular lumens (FIG. 81), which corroborates the systemic evidence of improved protein resorption (FIG. 78), and pairs cognitively with the in vitro evidence of robust protein uptake function in B2 cells (FIG. 75A). Thus, stabilization of renal function by B2 reduced the uremia and wasting associated with the 5/6 nephrectomy model, and allowed the treated animals to survive and thrive via the metabolic and physiologic responses to nutrition (exemplified by the significant gain in body weight, FIG. 76B), normal blood oxygenation (erythropoiesis; FIG. 77A-C, FIG. 78A), and the elimination of waste (functional nephron; FIG. 77D-F, FIG. 78).

CKD in the 5/6 nephrectomy model is accompanied by multiple complications that further worsen the progression of sclerotic lesions in the glomeruli and tubulo-interstitial spaces. With the onset of uremia, organ systems involved in the production and regulation of circulating hormones often become dysfunctional. In the kidney, uremia disrupts the normal endocrine function of the kidney, such as Vitamin D activation and production and delivery of Epo to the erythroid precursors in the bone marrow. Normal mineralization of the serum and bone require kidney-regulated Vitamin D activation balanced with parathyroid hormone feedback. The bone erosion (FIG. 81B), hyperphosphatemia (FIG. 81C) and hypocalcemia (FIG. 81C) observed in the Nx rats were consistent with osteodystrophy and secondary hyperparathyroidism of end stage renal disease (Ritz, E. J Nephrol, 18: 221-8, 2005). Consistent with the multitude of benefits offered by B2 treatment in this study, a normal serum calcium/phosphorous balance was established and was equivalent to healthy controls a full 6 months after treatment, punctuating the long-term stabilizing therapeutic effects of B2. Anemia is another endocrine dysfunction associated with progression in human CKD and in the 5/6 nephrectomy model. Although B4 would have been predicted to have the greatest effect on anemia based on gene expression profiling and in vitro function characteristics (FIG. 74, 75), both B4 and B2 positively affected the Epo-dependent endocrine function of the kidney (FIG. 77, 78, 81). Interestingly, B2 treatment supported erythropoiesis more stably and durably than B4 when the study results are considered in entirety. While the mechanism(s) by which B2 affects erythropoiesis are not yet understood, when these results are paired with our previous observation that localized Epo production is robust in the kidneys of humans with severe CKD, it is feasible that the re-establishment of homeostatic tissue architecture observed in the kidney with B2 treatment has the ancillary benefit of providing microenvironmental elements that are required for effective release of Epo from the cortical fibroblasts into the bloodstream.

As reported in the literature and observed in this study, rats subjected to a 5/6 nephrectomy procedure become dyslipidemic (Kasiske, B L, et al. Circ Res, 62: 367-74, 1988). Unexpectedly, a normal serum lipid profile (cholesterol and triglycerides) was observed in B2-treated animals. Although the cellular mechanism(s) by which B2 improved serum triglyceride and cholesterol levels are not understood, improved dietary protein handling (FIG. 80) may directly affect the ability of the nephron to excrete dietary cholesterol, triglycerides and free fatty acids. These data suggest that B2 or other cell-based therapies that restore tissue homeostasis could potentially reduce or eliminate the need for pharmacological intervention for lipid control in the CKD patient population (Kasiske, B L, et al. Circ Res, 62: 367-74, 1988).

The pathogenesis of primary or essential hypertension is often linked to kidney disease (Brenner, B M, et al. Am J Hypertens, 1: 335-47, 1988, Hoy, W E, et al. J Am Soc Nephrol, 16: 2557-64, 2005, Silberberg, J S, et al. Kidney Int, 36: 286-90, 1989). The progressive form of hypertension that ensues shortly after renal ablation in the 5/6 nephrectomy model is related to high compensatory glomerular capillary pressure (Kaufman, J M, et al. Kidney Int, 6: 10-7, 1974) and disruptions to the renin-angiotensin II-aldosterone axis (Greene, E L, et al. J Clin Invest, 98: 1063-8, 1996). Kidneys of patients with chronic hypertension have been shown to have fewer glomeruli than normotensive controls (Keller, G, et al. N Engl J Med, 348: 101-8, 2003). Nephron loss in the 5/6 remnant kidney is associated with changes in renal hemodynamics that include increases in glomerular filtration rate (Kaufman, J M, et al. Kidney Int, 6: 10-7, 1974) and glomerular and tubular hypertrophy (Brenner, B M. Am J Physiol, 249: F324-37, 1985). CKD and the ensuing hypertension often lead to LVH (Zolty, R, et al. Am J Transplant, 8: 2219-24, 2008), an adaptation that may ultimately progress to congestive heart failure. Cardiac complications of CKD are caused by the compensatory left ventricular pressure required to overcome increased peripheral vascular resistance or hypertension. Augmentation of kidney function with B2 significantly attenuated the development of cardiac hypertrophy compared to untreated nephrectomized controls and those treated with unfractionated cells (FIG. 76C). These data provide another example whereby dependency on pharmacological interventions, in this case to control blood pressure (i.e. ACE inhibitors or ARBs) could potentially be reduced by selective cell-based regenerative therapies.

The functional outcomes reflect not only prevention of progressive renal disease in this model but, when coupled with the anatomical improvement in the nephron, suggest that the B2 fraction also promoted regeneration of normal renal compartments (e.g. glomeruli and tubules). These studies have demonstrated that B2 prototypes have the potential to protect and restore normal cellular and tissue function associated with the major compartments of the kidney (e.g. tubules, glomeruli, and interstitial compartments). Potential molecular and cellular mechanisms by which B2 cells prompted the regenerative outcome are currently under investigation. Collectively, these data indicate that specific renal cells with in vitro functional attributes can restore homeostatic tissue architecture and cellular milieu in order to prevent or delay the progression in terminal, progressive CKD. The cell-based regenerative medicine approach contemplated by the present study is analogous to treating a CKD patient after a clear progressive disease state is established, but before renal failure has progressed to end-stage disease requiring dialysis or whole organ transplantation. These results provide proof-of-concept that regenerative strategies could reduce dependency on dialysis and drugs in the CKD patient population, and may ultimately shift the treatment paradigm for CKD from palliative to curative.

Example 11

Isolation of Rodent Neo-kidney Cells Characterized by Tubular Function Attributes in Vitro and In Vivo Cells, isolated as described above, were seeded and cultured on OPLA scaffolds, with perfusion, for five days in vitro.

Figure 66:
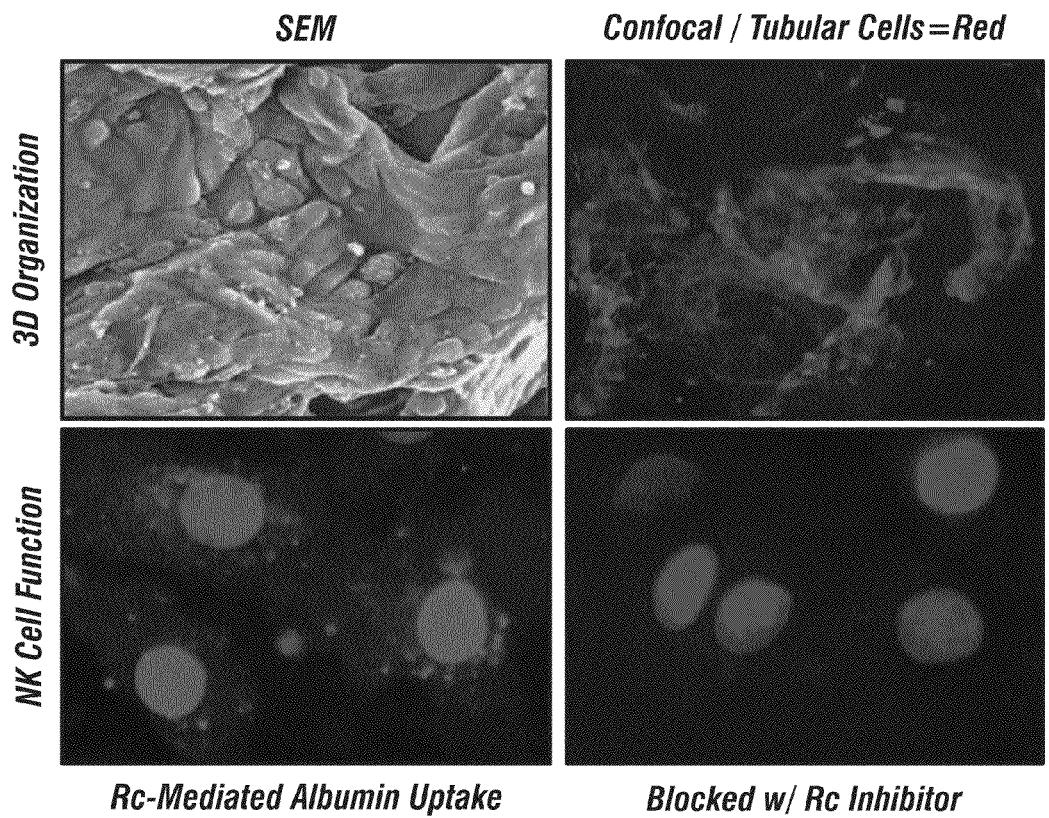
FIG. 66 depicts rhodamine-conjugated albumin uptake by functional rodent kidney tubular cells.

Tubular cells that maintain key features of tubular cell function were also isolated. As seen in FIG. 1, these functional features were enhanced in vitro by three-dimensional culture systems, where the cells interacted and formed tubular-like structures. FIG. 66 also shows that rhodamine-conjugated albumin is taken up by proximal tubular cells through a specific interaction with two receptors acting in concert: megalin and cubilin. The specificity of the albumin uptake was confirmed by addition of the competitive inhibitor, RAP protein, which prevented the rhodamine-conjugated albumin from being uptaken.

Figure 67:
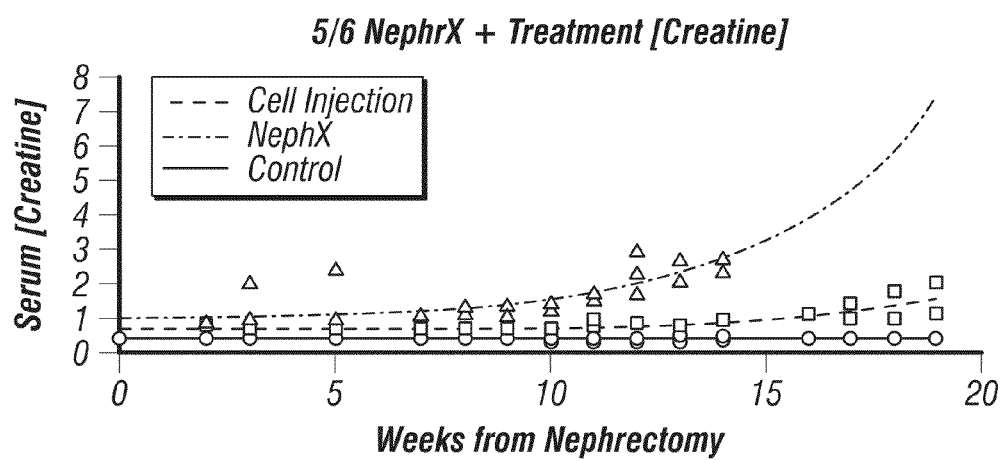
FIG. 67 shows maintenance of serum creatinine, a renal function indicator, at a level closer to normal levels in the neo-kidney cell (heterogeneous EPO-producing cells) treated uremic rats as compared to the untreated uremic rats.

The ability of the cultured tubular cells to stabilize renal function in vivo is demonstrated in FIG. 67, which shows serum creatinine, a renal function indicator, was maintained at a level closer to normal levels in the neo-kidney cell treated uremic rats as compared to the untreated uremic rats. 62% of the untreated rats died prior to the 16-week timepoint.

Example 12

Isolation of Tubular/Glomerular Cells from Human Kidney

Figure 68:
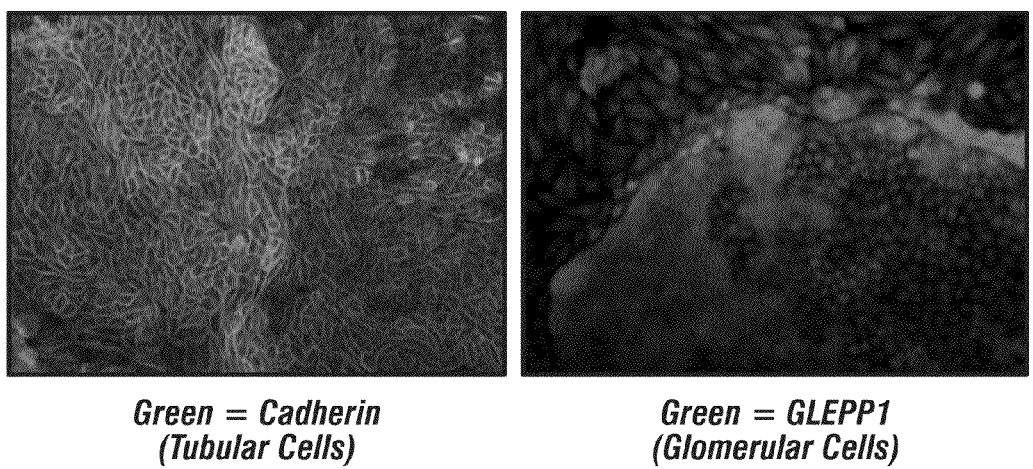
FIG. 68 depicts maintenance of phenotypic attributes of tubular and glomerular cells isolated and propagated from normal human kidney.
Figure 69:
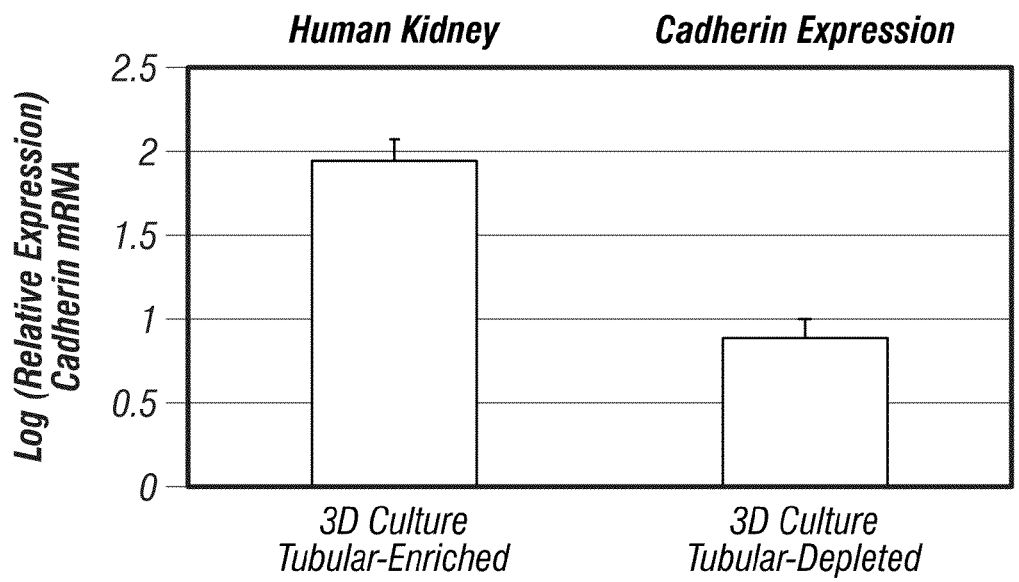
FIG. 69 depicts increased expression of tubular marker, cadherin, in tubular-enriched populations as compared to tubular-depleted populations cultured in 3D dynamic culture.

Tubular and glomerular cells were isolated and propagated from normal human kidney tissue by the enzymatic isolation methods described throughout. By the gradient method described above, the tubular cell fraction was enriched ex vivo and after culture. As shown in FIG. 68, phenotypic attributes were maintained in isolation and propagation. Tubular cell function, assessed via uptake of labeled albumin, was also retained after repeated passage and cryopreservation. FIG. 69 shows that when tubular-enriched and tubular-depleted populations were cultured in 3D dynamic culture, a marked increase in expression of tubular marker, cadherin, was expressed in the tubular-enriched population. This confirms that the enrichment of tubular cells can be maintained beyond the initial enrichment when the cells are cultured in a 3D dynamic environment.

Example 13

Further Separation of EPO-Producing Cells Via Flow Cytometry

Figure 70:
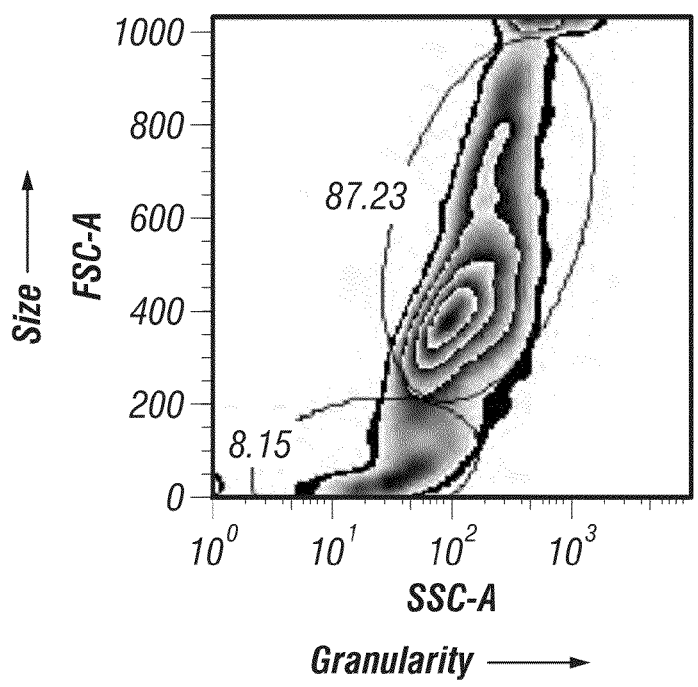
FIG. 70 shows separation of EPO-producing cells via flow cytometry.

The same cultured population of kidney cells described above in Example 8 was subjected to flow cytometric analysis to examine forward scatter and side scatter. The small, less granular EPO-producing cell population was discernable (8.15%) and was separated via positive selection of the small, less granular population using the sorting capability of a flow cytometer (see FIG. 70).

Example 14

Effects of Neo-Kidney (NK) Cellular Prototypes B2 and B4 in Delivery Systems in a Rat Model of Renal Failure with Anemia To determine the effects of the NeoKidney (NK) B2 and B4 cellular prototypes in various biomaterials-based delivery systems, the B2 and B4 prototypes were delivered in one of three delivery system prototypes (CP1, CP2 or CP3) to diseased rodent kidney parenchyma. The comparative ability of the Cellular Prototypes, delivered in one of three delivery system prototypes, to slow or reverse progression of renal failure and/or anemia in rats with established kidney disease was examined for 3 months post-transplantation and assessed across multiple systemic and histologic parameters, including CREAT, BUN, HCT, RBC#, serum proteins, body weight, and relative heart weight.

Non-limiting success factors included:

1) Prototype maintains/enhances erythropoiesis resulting in homeostatic HCT and/or RBC
2) Prototype yields histologic evidence of erythroid stimulation
3) Prototype provides measurable improvement or stabilization of renal function(s) as assessed by sCREAT and BUN
4) Prototype yields histologic evidence of repair and/or regeneration in the kidney, including (but not limited to):
   a. Glomerular repair, regeneration, or glomerulogenesis
   b. Tubular repair, tubular regeneration, tubulogenesis, or nephronogenesis
   c. Repair, regeneration, or morphogenesis of the collecting duct system
5) Prototype provides organism-level improvements (weight gain, survival) linked to improvement of one or more renal functions
6) Prototype provides comprehensive benefit across multiple relevant parameters, such that a concomitant tabular quantitative assessment of therapeutic features of all tested prototypes identifies the prototype as beneficial or neutral for all tested outcomes.

Cells: Primary kidney cell cultures were established from male donor Lewis rats and expanded using standard methodology. Prior to transplantation, B2 and B4 cellular prototype configurations were generated using population fractionation methods described supra.

Delivery Systems: Three construct prototype (CP) delivery systems were evaluated in the study. CP1 was comprised of hyaluronic acid (HA) in hydrogel form. CP2 was comprised of hyaluronic acid in porous foam form. CP3 was comprised of OPLA foam.

Test Articles: Test articles consisted of cells, or cells+ biomaterial delivery system. The B2 cell prototype contained a mixture of specific tubular cells and a very small fraction of other kidney cell types. The B4 cell prototype contained epo-expressing cells, glomerular cells, and specific tubular cells. For B4/CP1 and B2/CP1, cells were combined with CP1 2-4 hours prior to implant. For B4/CP2 and B2/CP2, cells were seeded onto the foam scaffolding 24 hours prior to implant. For B4/CP3 and B2/CP3, cells were seeded onto the foam scaffolding 24 hours prior to implant.

Animal Model Used for Testing: Adult female Lewis rats were obtained from Charles River Laboratories (CRL, Portage, Mich.), the majority of which underwent a two-step 5/6 nephrectomy (NX) (see Table 12 for Treatment groups and details). Rats, assigned randomly to the study groups, were housed and monitored for 5-8 weeks prior to treatment. The animal model and surgical procedures performed were identical to those utilized described in Examples 7 and 9. As in previous studies, rats were maintained post-nephrectomy for 5-8 weeks prior to implant to confirm uremia via weekly serologic analysis. Prototypes were delivered to diseased kidney parenchyma and followed for 3 months post-implant. This duration was chosen to enable histologic examination of the tissue at an optimal time to observe regeneration, and to enable comparative systemic analyses while the majority of treated rats were alive.

Surgery: Cell and cell/CP prototypes were delivered to the diseased kidney parenchyma via injection for B2, B4, B2/CP1, and B4/CP1. B4/CP2, B4/CP3, B2/CP2, and B4/CP3 were surgically implanted on the distal pole of the remnant kidney and wrapped with a small piece of abdominal fat.

TABLE 12

Study Design

| GROUP # | N = | DESCRIPTION | Rat Numbers | Group 1 (RK86) | Group 2 (RK87) | Substitutions (RK88) | Assessments |
|---|---|---|---|---|---|---|---|
| 1a | 4 | NX + B4 | 114, 113, 126 and 127 | 113 and 114 | 126 and 127 | | In-Life weekly HCT, RBC# |
| 1b | 4 | NX + B2 | 94, 131, 100 and 101 | 94 and 131 | 100 and 96 | 101 | weekly sCREAT, BUN weekly weight |
| 2a | 5 | NX + B4/CP1 | 104, 137, 123, 92 and 115 | 92 and 115 | 104 and 123 | 137 | baseline/6-/12-week full hematology panel |
| 2b | 5 | NX + B2/CP1 | 109, 125, 112, 117 and 128 | 112, 117 and 128 | 109, 138 and 125 | | full serology panel Terminal/3-month |
| 3a | 5 | NX + B4/CP2 | 107, 121, 118, 133 and 132 | 118, 132 and 133 | 107 and 121 | | full hematology panel full serology panel |
| 3b | 5 | NX + B2/CP2 | 102, 116, 140, 91 and 122 | 91 and 122 | 102, 116 and 140 | | organ weights histopathology |
| 4a | 5 | NX + B4/CP3 | 99, 124, 95.110 and 139 | 99 and 124 | 95, 110 and 139 | | |
| 4b | 5 | NX + B2/CP3 | 130, 93, 97, 111 and 108 | 97, 111 and 108 | 93 and 130 | | |
| 5 | 3 | NX | 129, 135 and 106 | | 135, 106 and 129 | No Treat. | |
| 6 | 5 | HEALTHY CONTROLS | 146, 147, 148, 149 and 150 | 146, 147, 148 | 149, 150 | No Treat. | |
| 7 | 5 | SHAM NX | 141, 142, 143, 144 and 145 | 141 and 142 | 143, 144 and 145 | No Treat. | |

Measurements: Animals were weighed weekly. Serological and hematological analyses provided in-life assessments of kidney function (serum BUN & serum creatinine (sCREAT)) and erythropoiesis (HCT & RBC#) pre- and post-implantation. Complete serum and hematology panels were conducted at baseline, 6 weeks post-implant, 12 weeks post-implant, and pre-necropsy (whether sacrificed moribund or at the end of the study). At the time of necropsy, organs (kidney, liver, spleen, heart, lungs) were weighed and collected for histology. Femoral bone marrow was collected for histology.

RESULTS. Recipient animals achieved a disease state of uremia within 4 weeks of the 5/6 nephrectomy procedure. Untreated NX animals all died within the timeframe of the experiment (3 months after transplantation). The anemia in this group of NX rats produced a<10% drop in HCT and no significant reduction in RBC#. Compared to NX rats, rats treated with cell or cell/CP prototypes survived longer. Serologic data collected throughout the study showed that the B2 prototype outperformed all other treatments with regard to stabilization of renal filtration function, finishing the study with an average serum CREAT of only 0.78±0.13 (compared to 1.77±0.7 in untreated NX), and a BUN of only 34±3.6 (compared to 64±17 in untreated NX). The CREAT and BUN levels for all treatments are shown below in Table 13. Although the anemia produced in these NX rats was mild, three prototypes (B2, B4/CP1, and B4/CP2) restored HCT % to levels equivalent to Healthy Controls. Considering all parameters and time points, the B2 prototype provided the most comprehensive therapeutic benefit throughout the duration of the study (see Table 13 below).

Figure 82A:
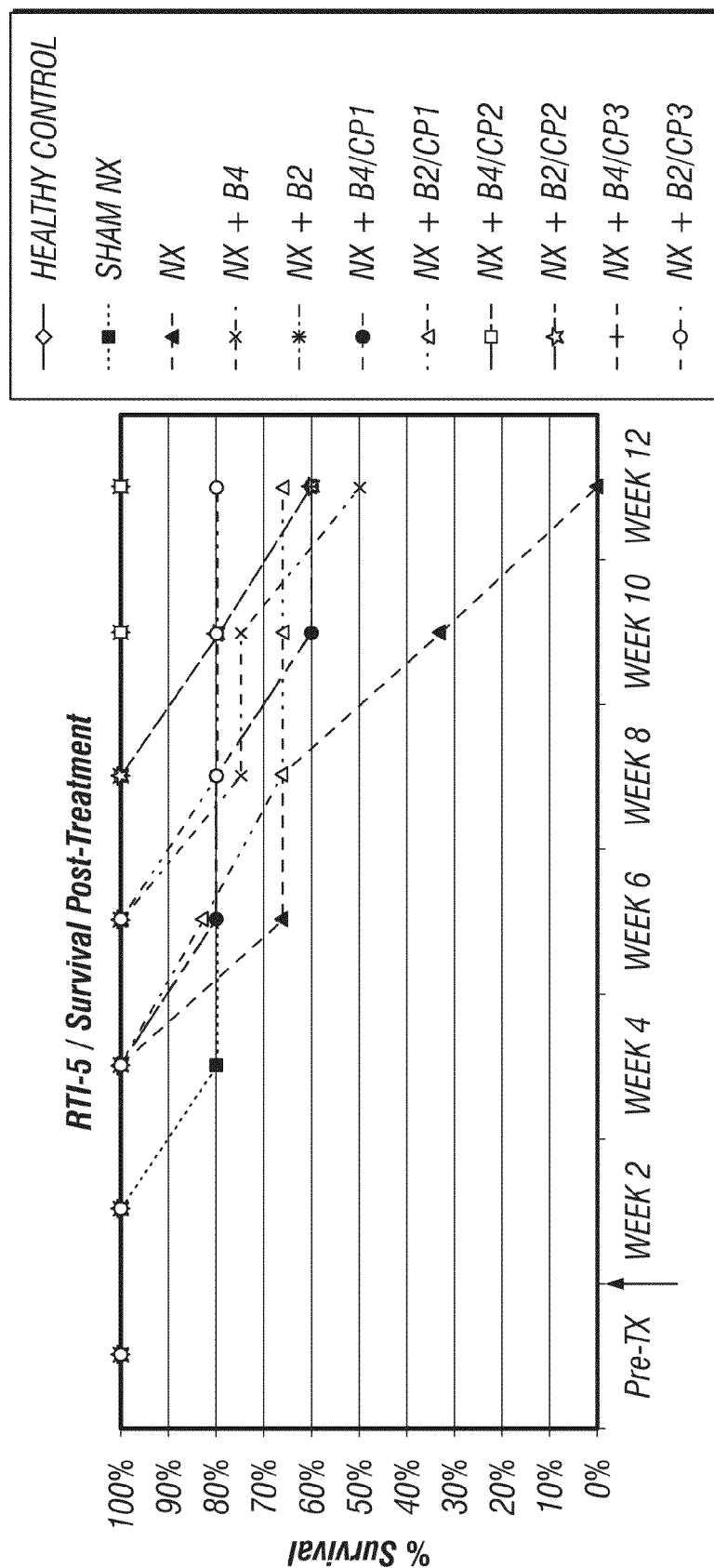
FIG. 82A shows survival through 12 weeks post-treatment.
Figure 82B:
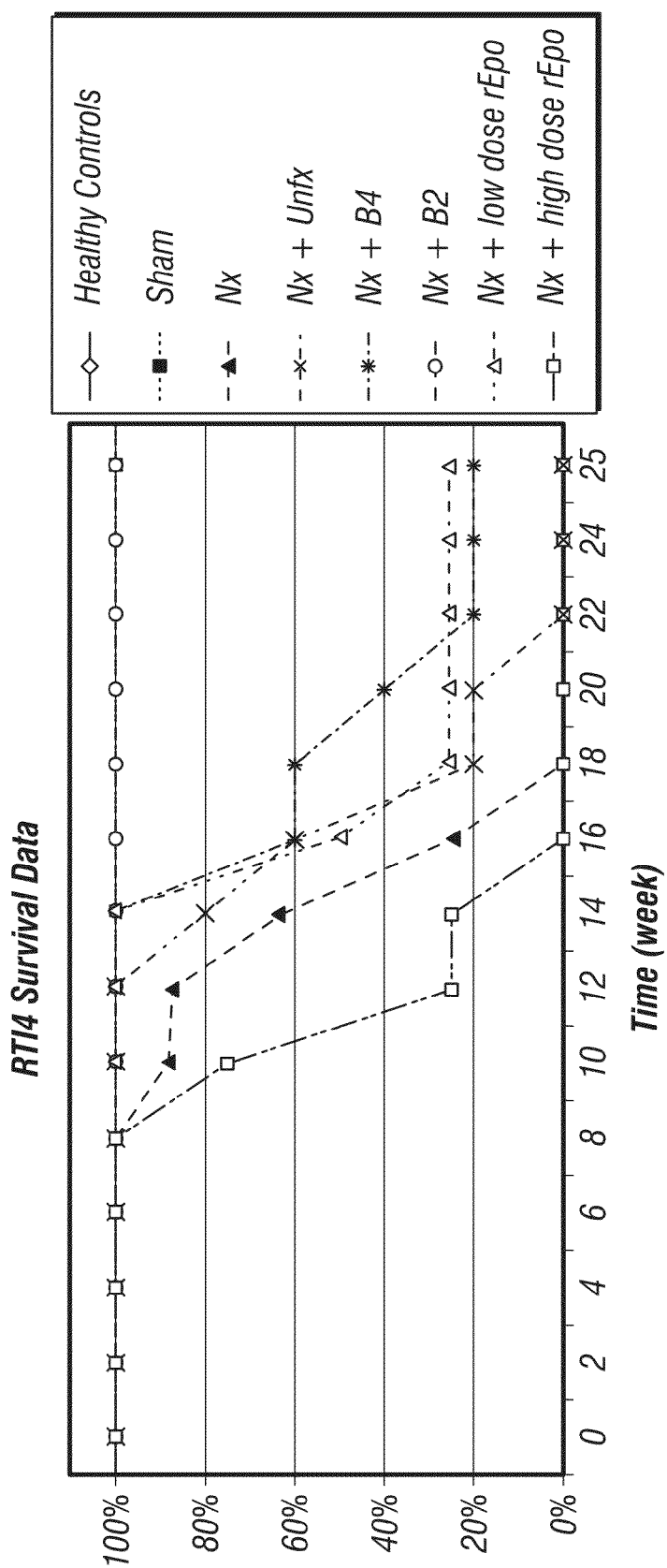
FIG. 82B shows survival through 25 weeks post-treatment.

Treatment with B2, B4/CP1 and B4/CP3 resulted in 100% survival from T0→3 months post-treatment (see FIG. 82). As expected from previous studies, 100% of untreated NX rats died within 12 weeks of transplant. As in Example 10, 100% of the rats treated with the B2 cell prototype survived to the study endpoint (3 months), as did the healthy controls. One SHAM NX rat died spontaneously during Week 4, of unknown cause. 50% of the rats treated with the B4 cell prototype survived to 3 months. The survival of rats treated with the B2 prototype was greatest (100%) when cells were delivered alone, followed by B2/CP3 (80%), B2/CP1 (66%), and B2/CP2 (60%). In contrast, the survival of rats treated with the B4 prototype (50%) was enhanced by all three biomaterial delivery systems tested, with survival increased to 60% in B4/CP1 and B4/CP3, and to 100% in B4/CP2.

Figure 83A:
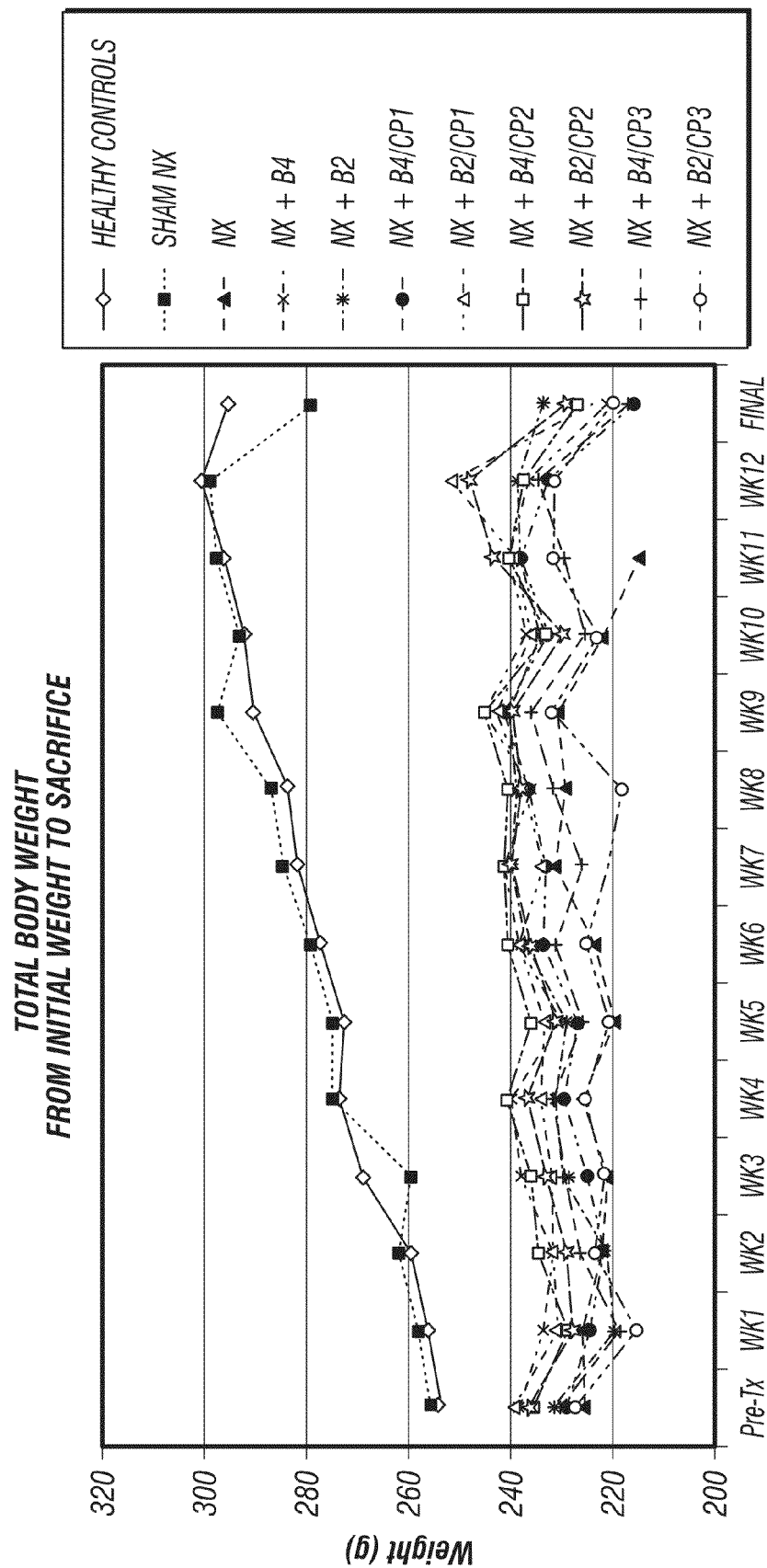
FIG. 83A shows total body weight from initial weight to sacrifice.
Figure 83B:
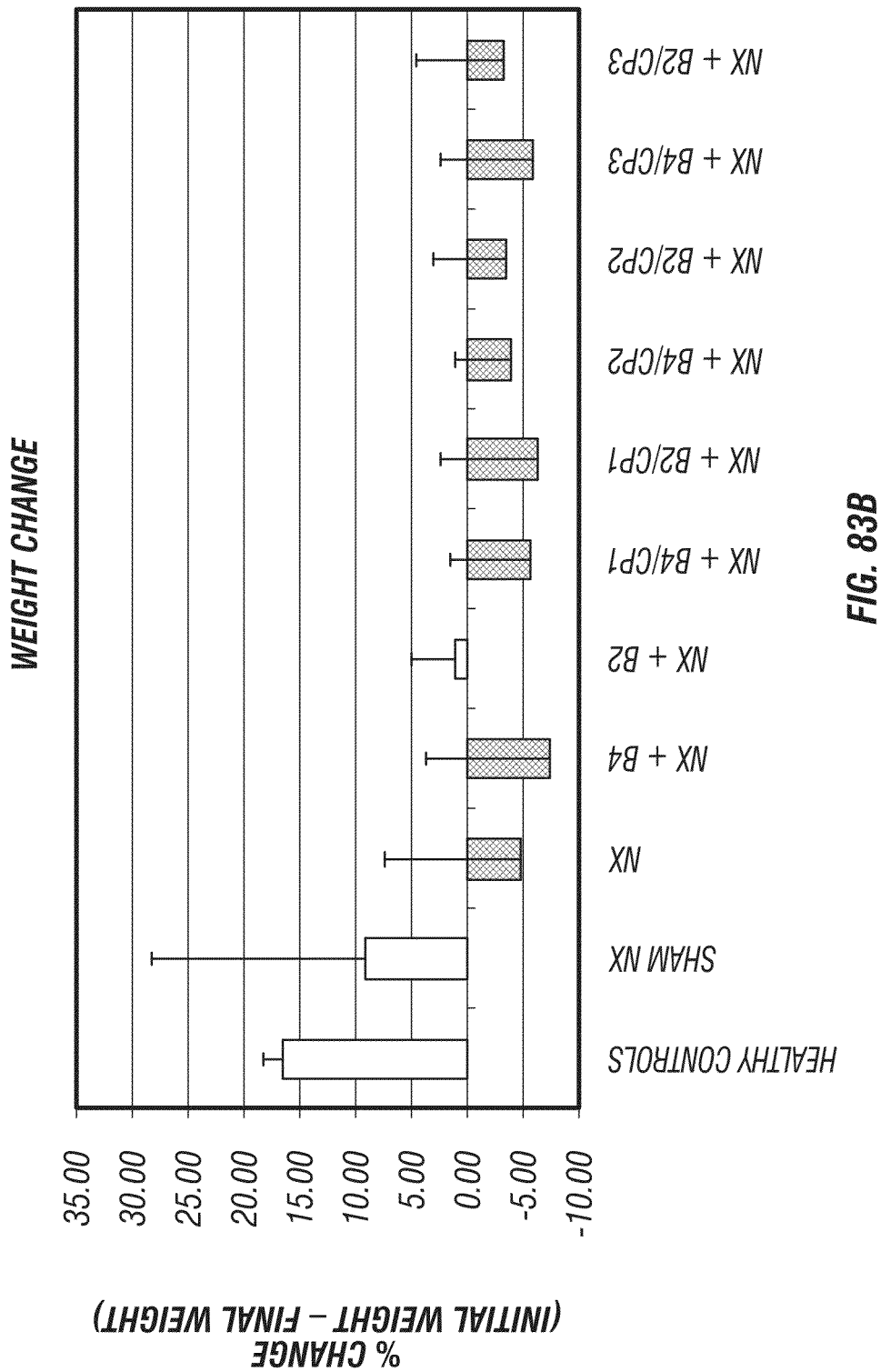
FIG. 83B shows percentage weight change from initial weight to sacrifice in rodents treated with cell populations in delivery systems.

As shown in FIG. 83, B2 treatment reduced weight loss and promoted weight gain throughout study (FIG. 83A, B). Body weights were measured for all rats weekly (panel 83a). Weight gain/loss was calculated for each rat separately via comparison of pre-treatment weight to weight at time of death (panel 83B). The weight gain noted in the Healthy Controls and Sham Nx rats is consistent with 3-month weight gain noted in previous studies in healthy Lewis female rats. The weight loss (~5%) noted for the untreated NX rats is consistent with the two-step 5/6 nephrectomy model, in which weight loss over time is typical. Only the healthy controls, Sham NX, and the NX+B2-treated groups exhibited a weight gain over time in this study. Other groups' weights were consistent with untreated NX rats.

Figure 84:
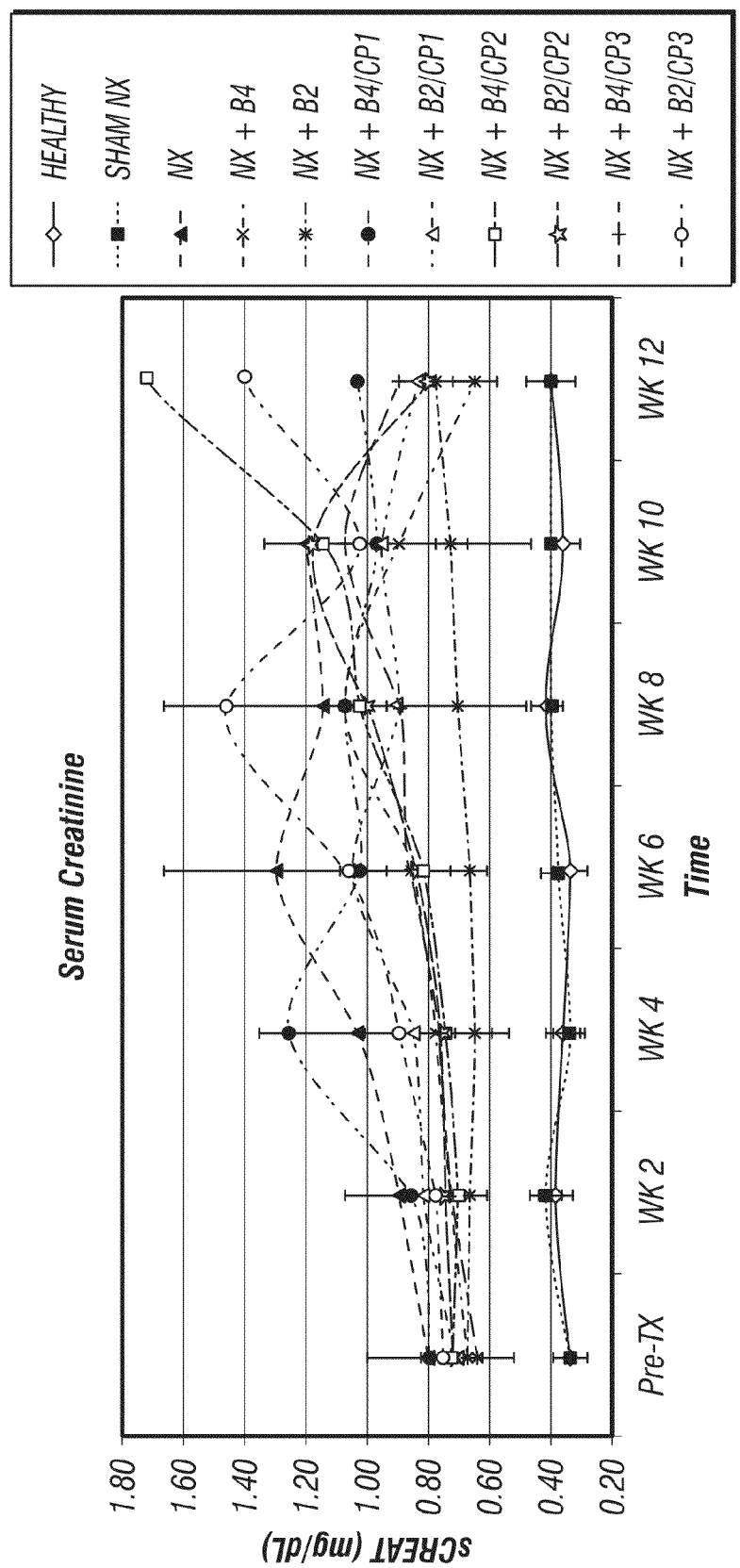
FIG. 84 shows serum creatinine levels through week 12 for all treatment groups.
Figure 85:
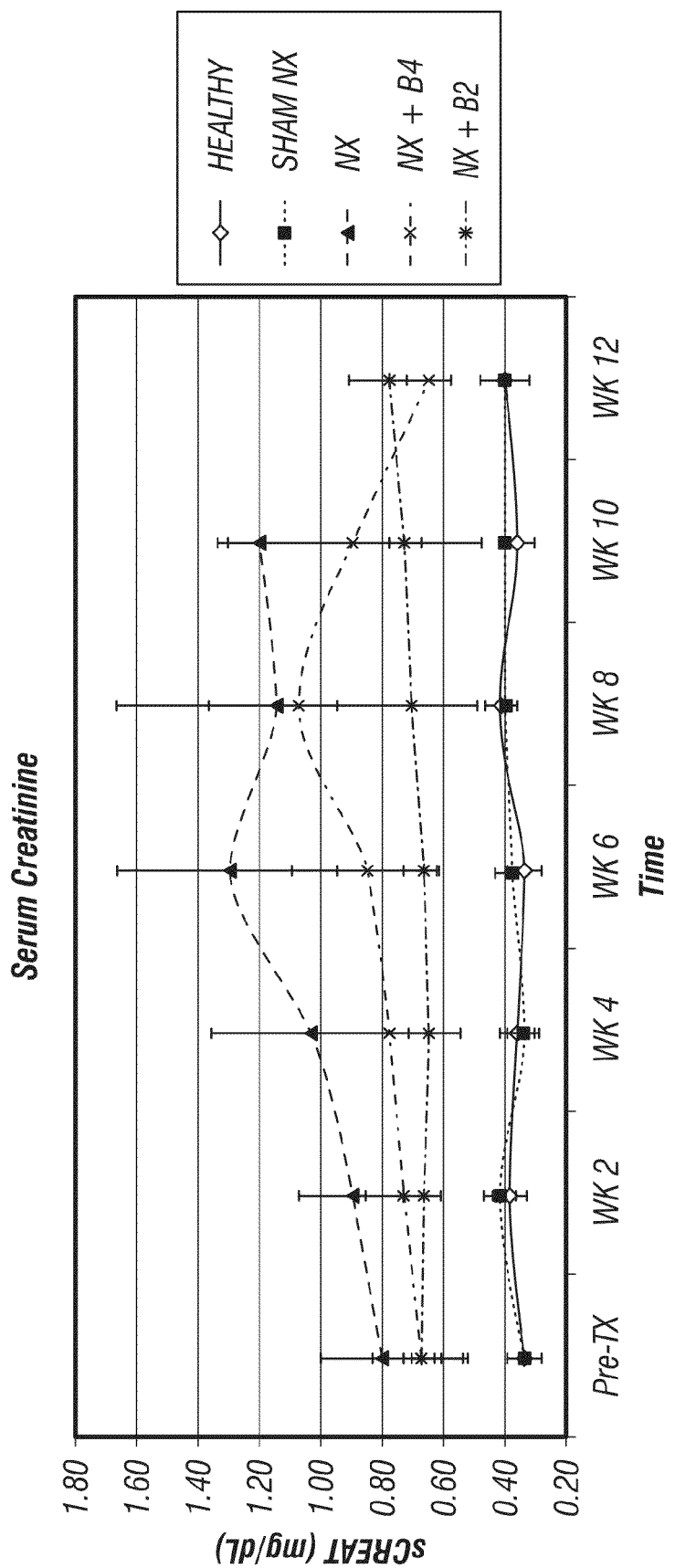
FIG. 85 shows serum creatinine levels through week 12 for the B2 and B4 treatment groups along with NX, Healthy Control, and Sham Nx.
Figure 86:
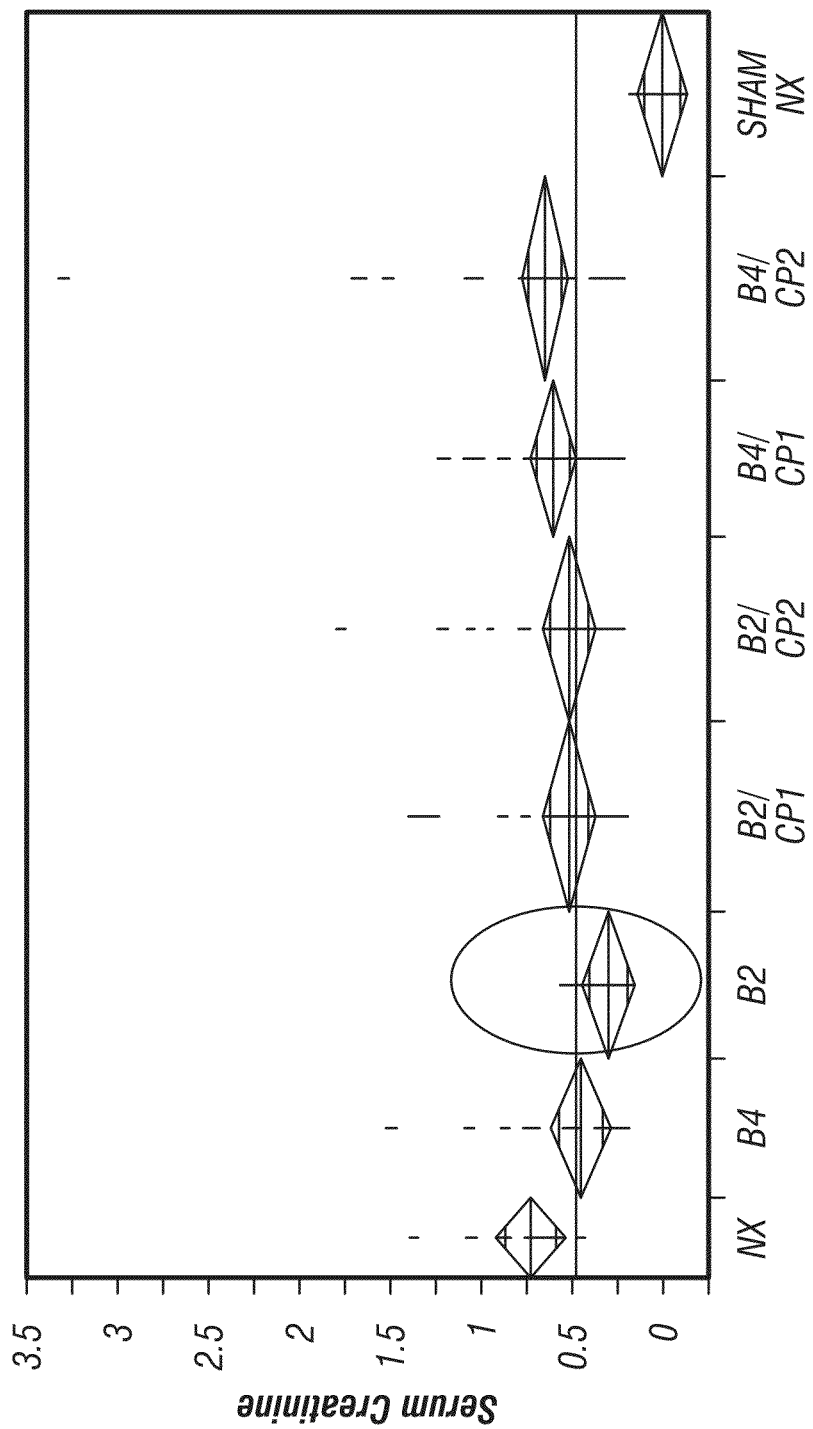
FIG. 86 depicts a oneway ANOVA analysis for serum creatinine across all timepoints.
Figure 87:
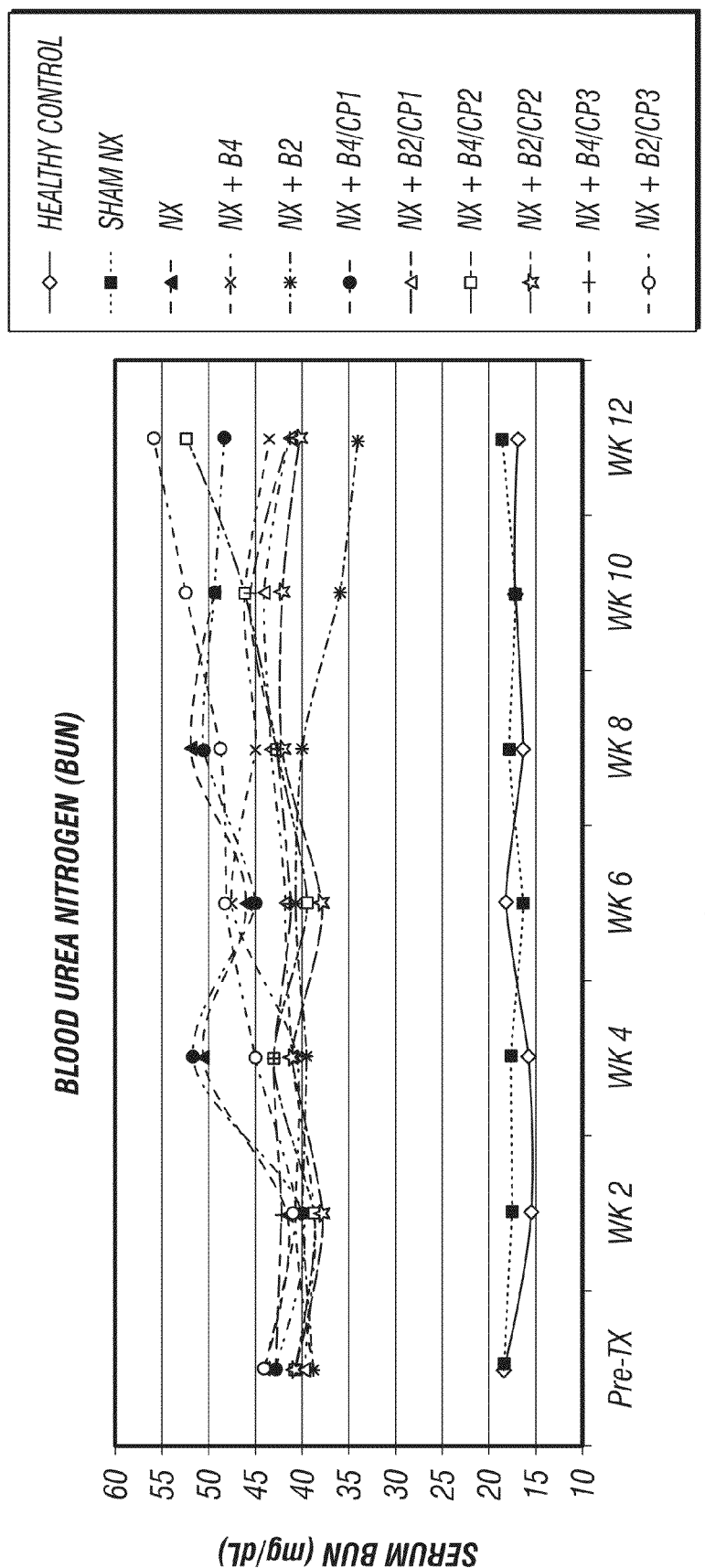
FIG. 87 shows blood urea nitrogen (BUN) levels.

As provided in FIG. 84-87, renal function stabilized with B2 treatment based on stabilization of renal tubular function based on serum creatinine and blood urea nitrogen (BUN). Both Healthy Control and Sham Nx rats maintained serum creatinine levels around 0.4 throughout the study, with low variability (FIGS. 84-86). The untreated NX rats' average serum creatinine climbed to >1.2 (a 300% increase), after which time the rats became moribund and were ordered to be sacrificed by the study veterinarian. All of the B2-treated rats survived the study and maintained a stable serum creatinine level throughout the study, from an average of 0.68±0.05 prior to treatment to an average of 0.78±0.13 at study termination (3 months post-treatment) (see FIGS. 84-85). While all treatment groups are shown in FIG. 84, the B2 and B4 treatment groups are shown along with NX, Healthy Control, and Sham Nx in FIG. 85 for further clarity. Error bars represent standard deviation. None of the delivery system prototypes (CP1, CP2, or CP3) improved the performance of the B2 or B4 cell prototypes with regard to stabilization of serum creatinine. However, the majority of prototypes outperformed the untreated NX group. Data from all timepoints were combined for each treatment group and subjected to a oneway ANOVA analysis (FIG. 86). As expected, the B2 treatment (circled)

outperformed other treatments for stabilization of serum creatinine, providing clear improvement over untreated NX as well as most of the other prototypes. Both the B2 and B4 cell prototypes performed in a similar manner in this study and that in Example 10. Serum BUN was also monitored throughout the study in all test groups, and these results support the creatinine data by showing a similar pattern of performance among treatment groups, with the B2 prototype characterized by the lowest serum BUN values over time (FIG. 87).

Figure 88:
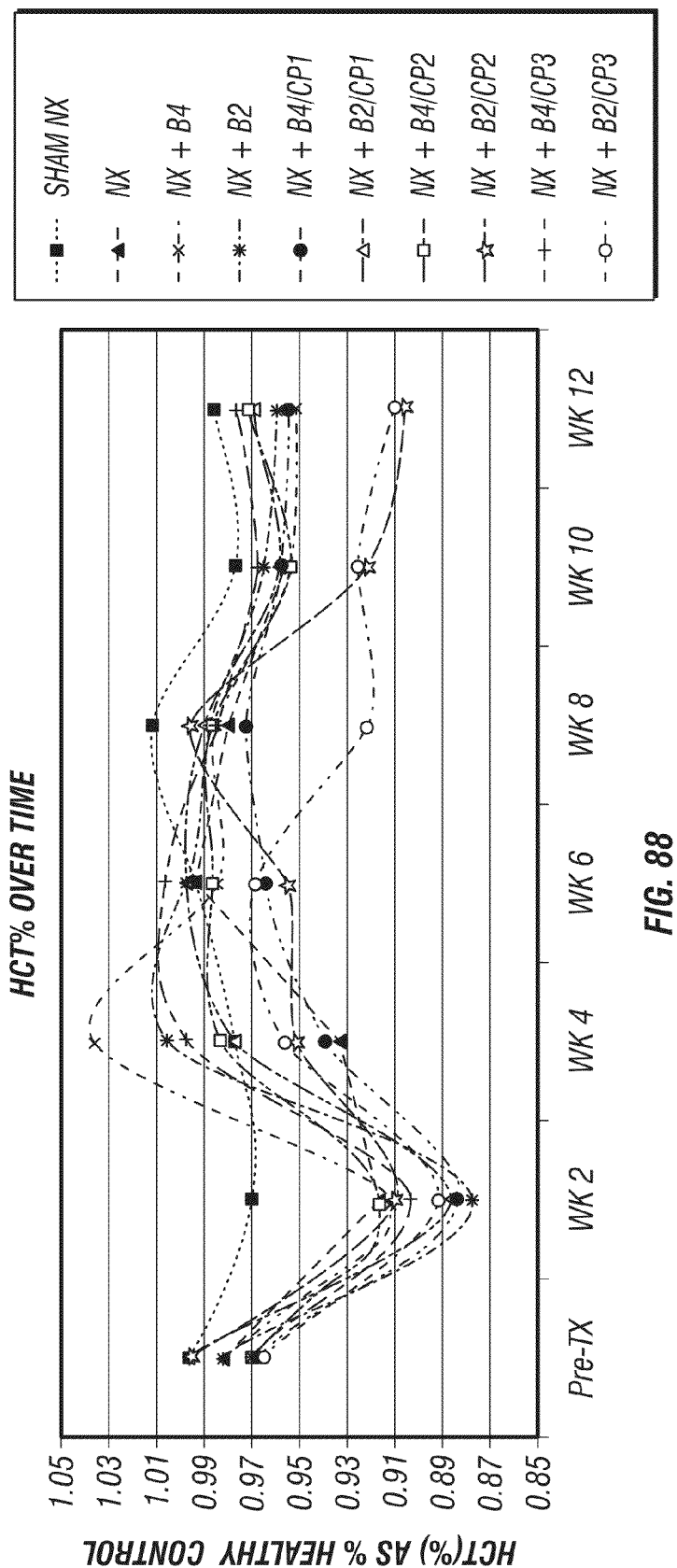
FIG. 88 shows HCT percent over 12 weeks for all treatment groups.
Figure 89:
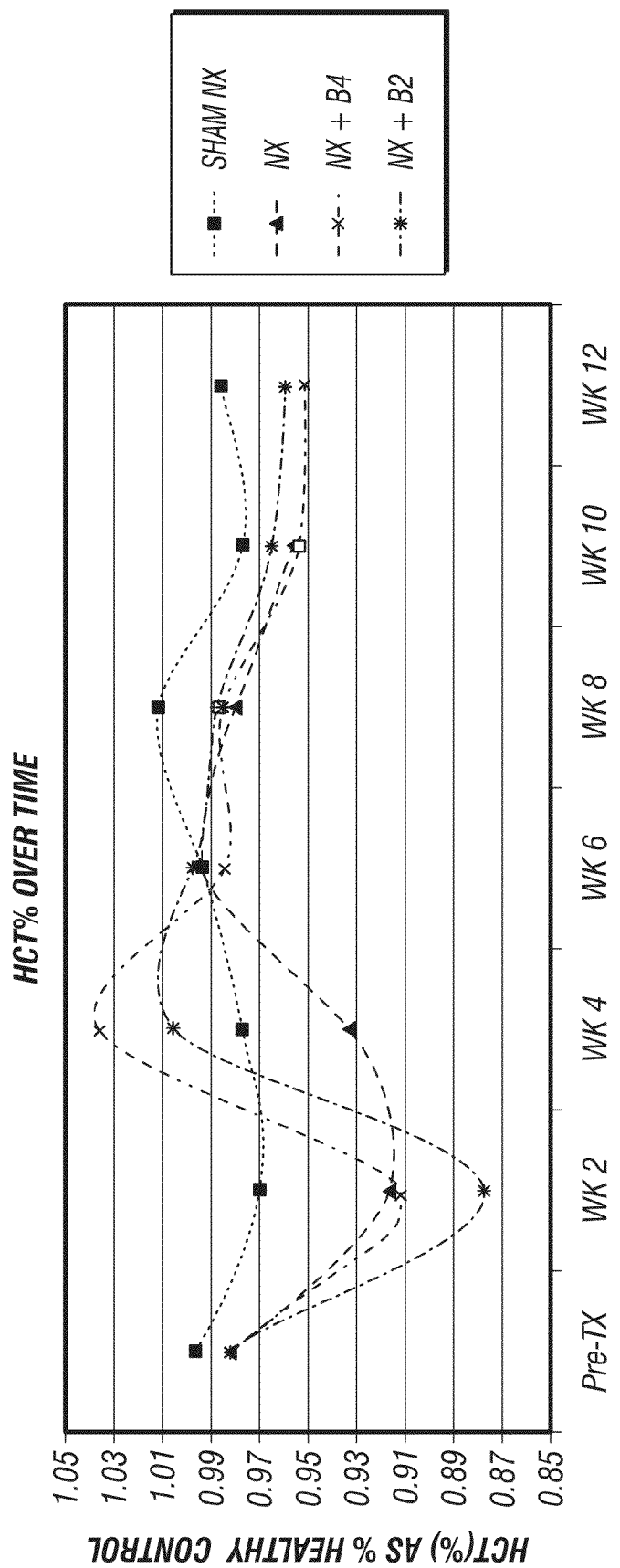
FIG. 89 shows HCT percent over 12 weeks for the B2 and B4 treatment groups along with NX, Healthy Control, and Sham Nx.
Figure 90:
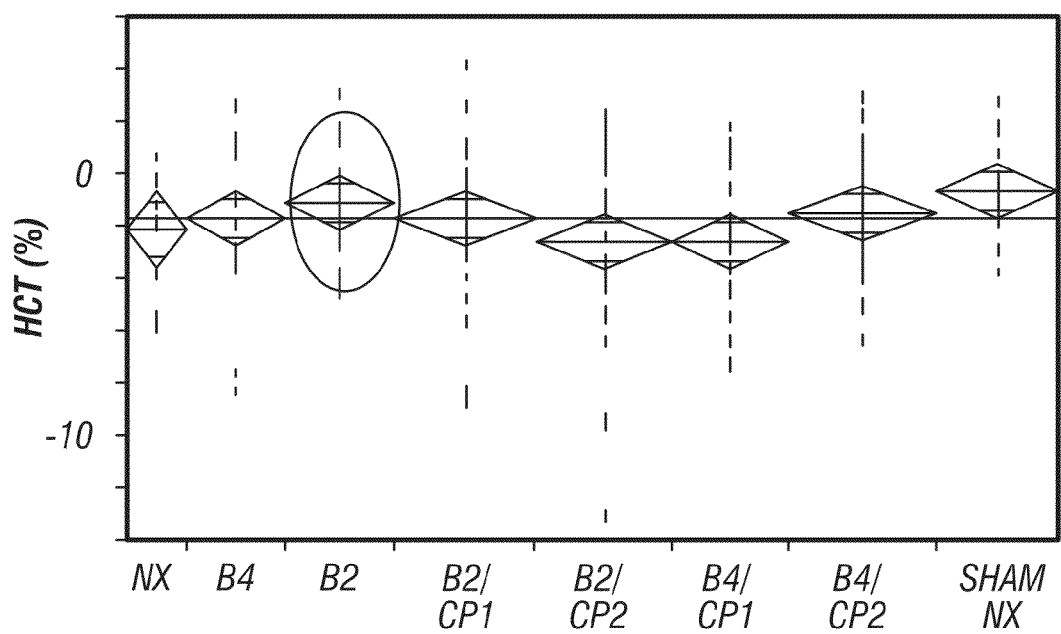
FIG. 90 depicts a oneway ANOVA analysis for HCT percent across all timepoints.

FIGS. 88-90 show that erythropoiesis was surprisingly improved by B2 prototype based on restoration of HCT. A mild decrease in HCT(%) was noted in the untreated NX rats, reflecting the anemia that develops in this model secondary to renal failure. However, it was noted that the anemia in this cohort of rats was mild and transient, producing a less pronounced effect than in previous studies. The HCT (reflected as % healthy control) is shown for all treatment groups (FIG. 88), and is shown for SHAM NX, B2, B4, and NX only in panel (FIG. 89) for clarity. When all data are considered together in a oneway ANOVA (FIG. 90), it is noted that the HCT was more similar to healthy rats (Sham Nx) in the B2 prototype (see FIG. 89, circled). Interestingly, the B4/CP2 prototype, which was also characterized by 100% survival at the 3-month time point, also displayed an improvement in HCT (see FIGS. 88 and 90).

Figure 91:
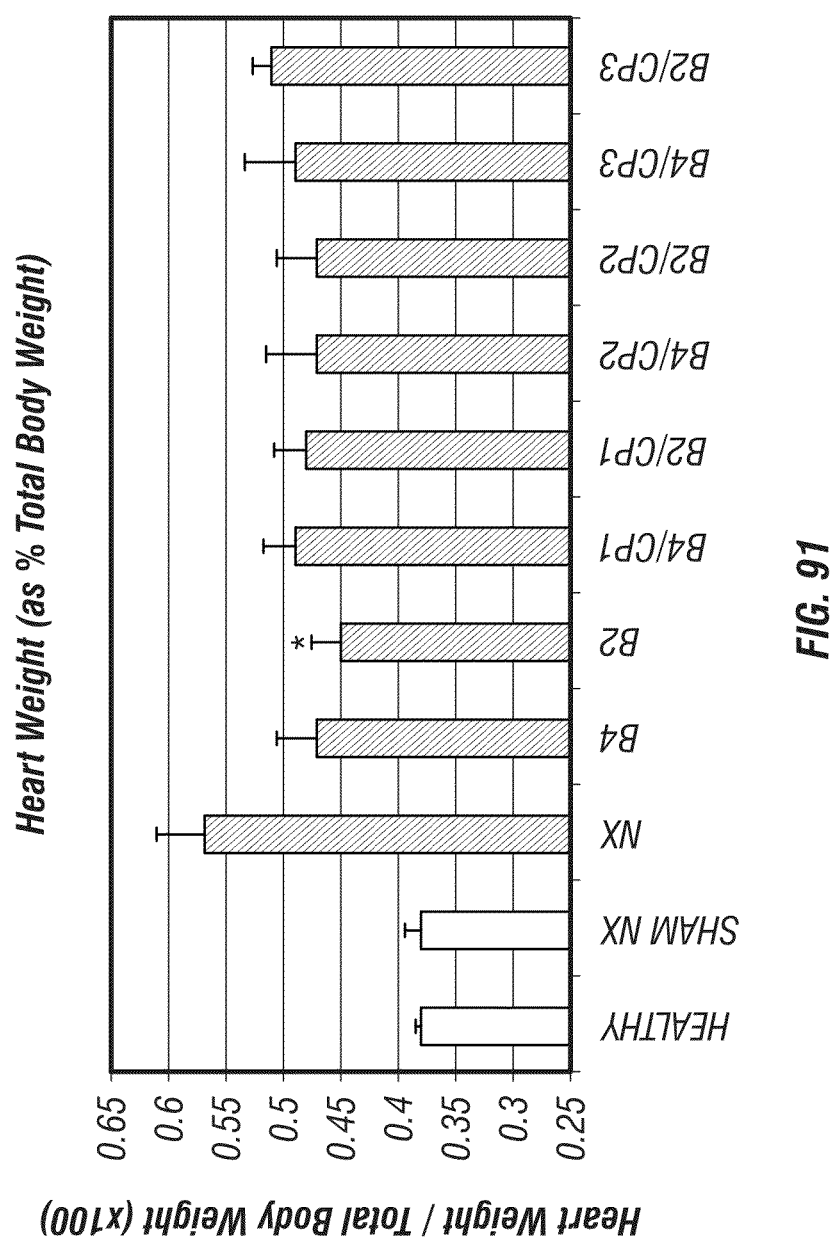
FIG. 91 shows heart weight as percentage of total body weight.

As shown in FIG. 91, treatment with B2 prototype led to a significantly lower relative heart weight. The 5/6 nephrectomy model is characterized by an increase in heart weight relative to body weight. Upon gross observation at the time of death, left ventricular wall hypertrophy was appreciable in the NX rats, and the average weight of the heart was 1.22±0.07 g (compared to 1.13±0.07 g in the healthy controls). All rats subjected to the 5/6 nephrectomy procedures had significantly higher heart weight/body weight ratios compared to health controls and SHAM NX rats (p<0.05; striped bars on graph). Rats treated with the B2 prototype had significantly reduced heart weight/body weight ratios compared to untreated NX rats (p<0.05*). This observation was consistent with previous results shown in Example 10. While all other prototypes had reductions in heart weight/body weight compared to untreated NX, none were statistically significant.

Figure 92:
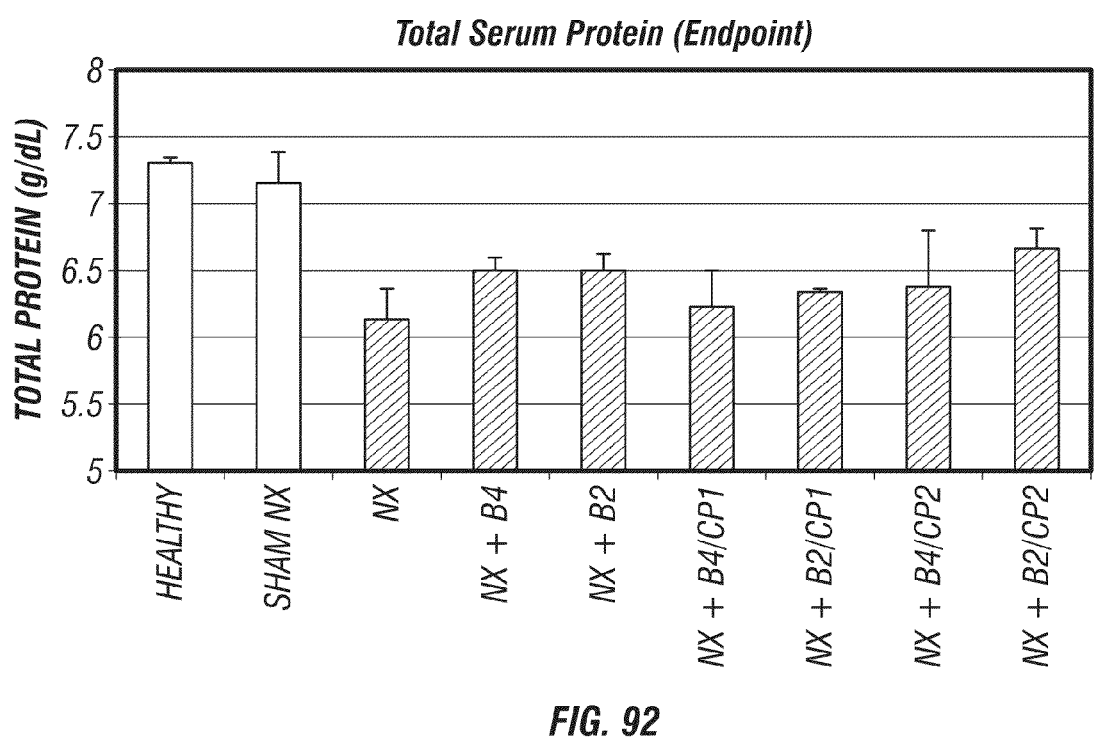
FIG. 92 shows total serum protein levels at study endpoint.

FIG. 92 shows that a trend of protein retention in rats treated with B2 and B4 prototypes. Significant reductions in total serum protein, albumin, and albumin/globulin (A/G) ratio are features of the 5/6 nephrectomy model. As expected, all rats receiving the nephrectomy procedure had significant reductions in total serum protein (striped bars, p<0.05). In previous studies it was noted that serum protein concentrations were increased slightly upon treatment with the B2 prototype. Trends toward improved protein retention were noted in rats treated with B2, and in surviving rats treated with B4 and B2/CP2 prototypes, although none were significant statistically.

Figure 93:
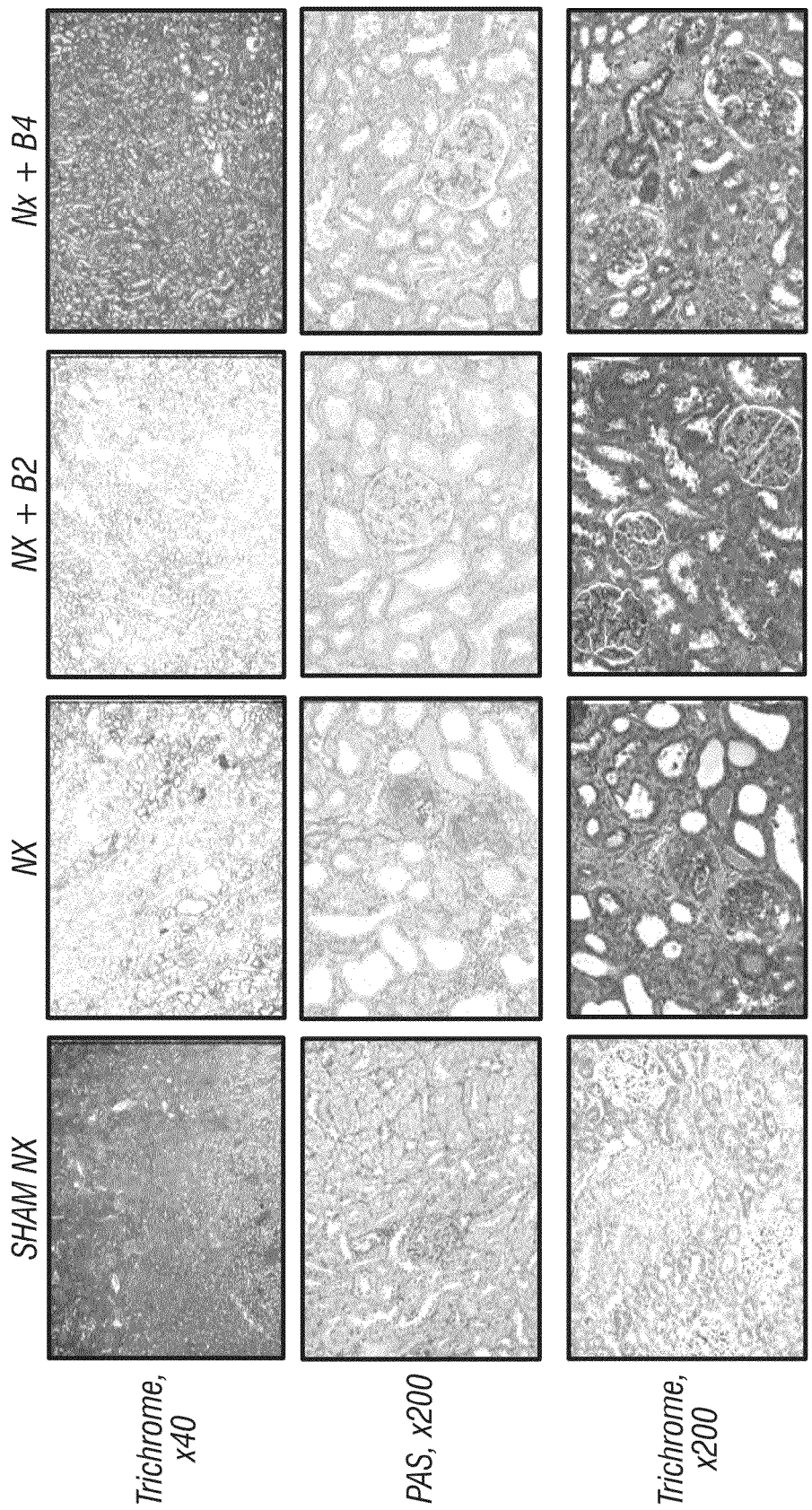
FIG. 93 shows histological assessment at the 3-month time point.

As shown in FIG. 93, histological assessment at the 3-month time point provides evidence of enhanced tubular & glomerular health in B2- and B4-treated rats. All rats that underwent the 5/6 nephrectomy procedure had kidneys at the time of death or sacrifice that were characterized by progressive glomerular and tubular injury. Tubules were dilated with an accumulation of proteinaceous casts (highlighted by the PAS stain in FIG. 7), and there was tubular atrophy and tubulo-interstitial fibrosis (highlighted by the Masson's Trichrome stain in FIG. 7). Glomerular injury evident in the model included periglomerular fibrosis, mesangial proliferation, glomerular hypertrophy, and some glomerular atrophy. Compared to NX and NX+B4, kidneys treated with NX+B2 were characterized by less severe glomerular injury, less tubular dilatation and protein accumulation, and markedly reduced tubulo-interstitial fibrosis. Treatment with B4 also provided some improvement in tubular dilatation and cast accumulation, but effects were less pronounced in comparison to kidneys treated with the B2 prototype. B4 treatment also resulted in reduced glomerular injury.

Multi-parameter comparison of prototypes enables selection of best prototype overall (see Table 13 below). Each major parameter (survival, weight change, HCT, CREAT, BUN, and heart weight) is displayed in tabular form from the final measurement taken from all rats in each treatment group. Since one SHAM NX rat died during the study, survival at 80% or greater was considered healthy. Values equivalent to healthy controls are in bold. Values equivalent or worse than NX are italicized. Values not reaching the mean level of healthy controls, but clearly better than NX, were considered improved and highlighted as bold and underlined. Taken together, the data provide impetus for further investigation into the use of the B2 cellular prototype as a component of regenerative therapies for CKD. In both the this study and the study described in Example 10, the B4 cellular prototype has yielded limited but significant therapeutic benefit. Interestingly, the implantation of the B4 cellular prototype in biomaterial-based delivery systems enhanced the effects of B4 across multiple parameters, including survival.

Based on terminal and in-life serologic/hematologic data, the B2 prototype (NX+B2) notably offered 100% survival, consistent with the results for the B2 prototype obtained in Example 10. NX+B4/CP2 also offered 100% survival, compared to 50% survival for B4 delivered alone, suggesting that the CP2 delivery system provides a milieu that enhances regeneration and/or repair specific to the B4 cellular prototype. Overall, the above data show that all prototypes yielded a higher % survival at 3 months than NX rats. The following prototypes improved HCT to levels close to SHAM NX: B2, B4/CP1, and B4/CP2, and these observations were confirmed by histologic analyses of the bone marrow. The erythropoietic effects of B4 were enhanced when the cells were delivered in CP1 or CP2—both of which are comprised of hyaluronic acid, thus suggesting that the erythropoietic effects of B4 may be enhanced by incorporating an extracellular milieu that recapitulates in part the milieu of the developing kidney during organogenesis.

TABLE 13

Multi-parameter comparison of prototypes.

| | Survival (%) | Weight Change | HCT(%) | CREAT | BUN | HEART WEIGHT AS % TOTAL BODY WEIGHT |
|---|---|---|---|---|---|---|
| HEALTHY CONTROL | 100% | 16.5 ± 1.6 | 45.7 ± 1.5 | 0.38 ± 0.08 | 16.6 ± 1.7 | 0.38 ± 0.01 |

TABLE 13-continued

Multi-parameter comparison of prototypes.

|  | Survival (%) | Weight Change | HCT(%) | CREAT | BUN | HEART WEIGHT AS % TOTAL BODY WEIGHT |
|---|---|---|---|---|---|---|
| SHAM NX | 80% | 17.6 ± 3.5 | 47.7 ± 5.3 | 0.38 ± 0.07 | 18.8 ± 2.6 | 0.38 ± 0.03 |
| NX | 0% | −3.9 ± 12.1 | 42.2 ± 2.2 | 1.77 ± 0.70 | 63.7 ± 17.2 | 0.57 ± 0.07 |
| NX + B2 | 100% | 1.0+3.9 | 44.2 ± 2.7 | 0.78+0.13 | 34.0+3.6 | 0.45+0.05 |
| NX + B2/CP1 | 66% | −4.9 ± 7.4 | 42.9 ± 2.4 | 1.28 ± 0.51 | 46.3+17.7 | 0.48 ± 0.07 |
| NX + B2/CP2 | 60% | −2.7 ± 5.9 | 41.8 ± 3.6 | 1.46 ± 1.05 | 45.6+26.8 | 0.47 ± 0.08 |
| NX + B2/CP3 | 80% | −3.1 ± 7.5 | 41.8 ± 2.8 | 1.70 ± 0.79 | 59.4 ± 22.9 | 0.51 ± 0.04 |
| NX + B4 | 50% | −4.6 ± 8.1 | 42.2 ± 2.2 | 1.60 ± 1.22 | 58.5 ± 41.6 | 0.47 ± 0.07 |
| NX + B4/CP1 | 60% | −0.3 ± 3.4 | 44.2 ± 2.7 | 1.34 ± 0.53 | 49.6+14.6 | 0.49 ± 0.06 |
| NX + B4/CP2 | 100% | −3.9 ± 4.9 | 44.8 ± 3.1 | 1.72 ± 1.20 | 52.4 ± 46.8 | 0.47 ± 0.10 |
| NX + B4/CP3 | 60% | −4.7 ± 7.3 | 42.8 ± 2.6 | 1.16 ± 0.51 | 39.2+12.6 | 0.49 ± 0.10 |

While the HCT response in this batch of nephrectomized rats was mild (<10% reduction in HCT) compared to previous studies it is still clear that three prototypes, B2, B4/CP1, and B4/CP2, supported erythropoiesis well, which was confirmed by histologic analysis of the bone marrow. In contrast, two prototypes (B2/CP3 and B2/CP2) resulted in reductions in HCT when compared to other treatment groups, suggesting that the erythroid homeostasis effects that B2 provided when delivered alone were inhibited when the cells were delivered in CP3 and CP2. Interestingly, both the CP3 and CP2 prototypes are solid porous foams which do not distribute throughout the kidney, while both the B2 alone and B2/CP1 (CP1 being a semi-solid gel) distribute throughout the kidney, indicating that the therapeutic actions of B2 may depend in part on distribution throughout the kidney and/or intimate contact with other cell types in the kidney—both of which are reduced or prevented by the use of fixed solid scaffolds.

The following prototypes provided some level of stabilization of renal function, as determined by sCREAT (in rank order): B2>B2/CP1>B4/CP3>B4/CP1>B2/CP2>B4; although, it should be noted that among these, the B2 prototype provided the most consistent stabilization (CREAT 0.78±0.13 at end of study) and was the only prototype in this group that provided 100% survival during the 3 months post-treatment.

Treatment with the B2 prototype reduced the relative heart weight in treated rats compared to the NX untreated group. This is consistent with observations in Example 10, and may indicate some level of performance pertinent to blood pressure control.

The following trends, consistent with the results obtained in Example 10, were noted with all B2 and B4 treatments (though not statistically significant): reduction in serum cholesterol and triglycerides; increase in serum total protein & albumin; and reduction in serum phosphorous.

When data are considered across multiple parameters tested (see Table 13 above), the B2 cellular prototype provides a significant and reproducible benefit across most parameters when delivered alone and is not enhanced significantly by delivery in any of the three delivery systems tested in this study. The B4 cellular prototype provides a significant survival benefit (50%) as well as support of erythroid homeostasis and glomerular repair. The performance of B4 was enhanced across most parameters by the addition of a biomaterials-based delivery system, with the hyaluronic acid-based materials (CP1 and CP2) being of greatest interest for further investigation.

In summary, the B2 cellular prototype offers consistent positive benefit across both renal filtration and erythropoiesis. Interestingly, the B4 prototype also provides substantial improvement in key areas, and this is enhanced when the cells are delivered in biomaterials-based delivery systems. Thus, experiments aimed at maximizing therapeutic benefit may involve testing combination(s) of cell- and delivery system-prototypes.

Example 15

Effects of Neo-Kidney Cellular Prototype Combinations in a Rat Model of Renal Failure with Anemia To evaluate the comparative ability of six NeoKidney (NK)-Cellular Combination Prototypes (B2, B3, B2/B4, B2/B3, B3/B4 and B1/B5), to slow or reverse progression of renal failure and/or anemia in rats, the six combination prototypes were delivered intra-renally to rats with established kidney disease. The study plan is shown below in Table 14. Non-limiting success factors included the following:
  1) Prototype(s) maintains/enhances erythropoiesis resulting in homeostatic HCT/RBC#
  2) Prototype(s) yields histologic evidence of erythroid stimulation
  3) Prototype(s) provides measurable improvement or stabilization of renal function(s) as assessed by sCREAT and BUN
  4) Prototype(s) yield histologic evidence of repair and/or regeneration in the kidney
  5) Prototype(s) deliver organism-level improvements (e.g., survival, weight gain, blood pressure)
  6) Combination prototype(s) provide benefit(s) above and beyond those offered by (B2) alone Cells: Primary kidney cell cultures were established from male donor Lewis rats and expanded as described supra. Prior to transplantation, the (6) cellular prototype configurations were isolated and combined as described below (Test Articles).

Test Articles: Test articles consisted of cultured primary cells, expanded, propagated, and subjected to fractionation/enrichment methods as described, supra., to establish specific cell subpopulations. The specific fractions were characterized molecularly and functionally to confirm their phenotype prior to implantation. Each fraction is characterized as follows:
  B2: comprised predominantly of tubular cells, containing mostly proximal tubular cells capable of robust albumin uptake, with some distal tubule and collecting duct cells present. Other confirmed cell types (endocrine, glomerular, vascular) are present only in trace quantities.

B4: comprised of endocrine, vascular, and glomerular cells, but including also some small tubular cells, predominantly proximal in nature. Some cells within this fraction also possess features consistent with a renal stem or progenitor cell population (i.e., low side- and forward-scatter as well as expression of markers associated with renal development).

B1: comprised predominantly of distal tubular and collecting duct cells, with trace amounts of other cell types present.

B3: comprised predominantly of proximal tubular cells, with a small quantity of endocrine, vascular, glomerular, and progenitor-like cells (defined by expression of specific developmental-associated markers and the presence of a low side- and forward-scatter population by flow cytometry) also present.

B5: comprised of very small cells, endocrine, vascular, and progenitor-like in nature; this fraction also contains cells with low viability, and represents a very small portion of the population overall.

Cells were combined for testing in ratios based on their naturally-occurring mixture (relative to each other) in normal healthy kidney.

B2: was tested alone, based on previous experiments demonstrating that this fraction provided superior survival and stabilization of renal functions, especially functions associated with restoration of the tubular cell compartment.

B3: was tested alone, based on the premise that it shares the tubular functional features of B2 as well as contains some of the endocrine, glomerular, and progenitor-like cells of B4, and thus might provide an admixture of both populations' benefits B2/B4: this combination was tested based on the premise that the substantial effects on renal filtration function provided by B2 in previous studies, and the less pronounced (but significant) benefits noted with B4 treatment (glomerular improvement, endocrine functions) might combine to provide a more comprehensive therapeutic effect.

B2/B3: this combination was tested based on past performance of B2 in previous studies and the shared B2 and B4 features of B3.

B3/B4: this combination was tested to determine whether delivering a greater relative dose of progenitor-like, endocrine, and glomerular cells would enhance therapeutic value.

B1/B5: this combination was tested in a small number of rats to determine if a mixture of collecting duct cells and small progenitor-like, endocrine, and vascular cells would offer therapeutic benefit across the various tested functions of the kidney (very few functional tubular cells are present in this mixture).

Animal Model Used for Testing: Adult female Lewis rats were obtained from Charles River Laboratories (CRL, Portage, Mich.), the majority of which underwent a two-step 5/6 nephrectomy (NX) prior to shipment. (See Table 14 below for treatment groups and details). For this study, hemi-nephrectomized controls were added, and were generated at CRL using the same whole-kidney removal procedure employed in generation of the 5/6-nephrectomized rats. All nephrectomized rats and controls were delivered to RTI International (Durham, N.C.), housed, and monitored for approximately 5 weeks prior to treatment. The animal model and surgical procedures performed at the vendor were identical to those utilized in Examples 7 and 9. As in previous studies, rats were maintained post-nephrectomy for 5-8 weeks prior to implant to confirm significant and persistent uremia via weekly serologic analyses. Prototypes were delivered to diseased kidney parenchyma and were followed for 3 months post-implant. The study continued until 6-months post-implant, so that differences in durability of the various combination prototypes could discerned.

Surgery: Cell prototypes were delivered into the kidney parenchyma, targeting the corticomedullary junction accessed via the distal pole of the remnant kidney.

Measurements: Animals were weighed weekly. Bi-weekly serological and hematological analyses are providing in-life assessments of kidney function (BUN & CREAT) and erythropoiesis (HCT & RBC), from baseline pre-treatment throughout study duration. Comprehensive serum and hematology panels were conducted at baseline (the week prior to treatment), at 6 weeks post-treatment, 12 weeks post-treatment, and were repeated at 6-week intervals for study duration. Blood pressure measurements were taken via tail-cuff at 6 weeks, 12 weeks, and every 6 weeks throughout the remainder of the study. Urinalysis was also performed at 10-11 weeks, and at intervals throughout the study. At the time of necropsy, organs (kidney, liver, spleen, heart, lungs) were weighed and collected for histology. Femoral bone marrow was collected for histology to assess erythropoiesis.

TABLE 14

Study Plan

| N = | DESCRIPTION | Rat Numbers | Group 1 Surgeries/ blood draw prep: RK 96 | Group 2 Surgeries/ Blood draw prep: RK 97 | Assessments |
|---|---|---|---|---|---|
| 7 | Nx + B2 (5 M) | 160, 162, 164, 179, 163, 185 and 186 | 162, 163, 185 and 186 | 160, 164 and 179 | In-Life Bi-weekly sCREAT, BUN, HCT, RBC |
| 7 | Nx + B3 (5 M) | 190, 194, 177, 158, 196, 153, and 165 | 190, 194, 177 and 158 | 196, 153, and 165 | Weekly body weights Full hematological and serological panel (6 wk intervals) |
| 7 | Nx + B2/B4 (5 M) | 159, 157, 174, 170, 171, 169 and 181 | 157, 159 and 174 | 170, 171, 169 and 181 | Blood pressure (6 wk intervals) |
| 7 | Nx + B2/B3 (5 M) | 173, 180, 187, 152, 155, 166 and 178 | 155, 166 and 178 | 180, 173, 187 and 152 | Urinalysis (~6 wk intervals) 7-day |

TABLE 14-continued

Study Plan

| N = | DESCRIPTION | Rat Numbers | Group 1 Surgeries/ blood draw prep: RK 96 | Group 2 Surgeries/ Blood draw prep: RK 97 | Assessments |
|---|---|---|---|---|---|
| 7 | Nx + B3/B4 (5 M) | 176, 154, 189, 191, 192, 175 and 184 | 191, 175, 184 and 192 | 176, 154 and 189 | (2) rats per group (see Appendix) sacrificed for early histopath |
| 3 | NX (untreated) | **183, **188 and 193 | | | 3 month (1-2) rats per group |
| 3 | Nx + B1/B5 (5 M) | 168, 182 and 195 | | 168, 182 and 195 | (see Appendix) sacrificed for 3-month |
| 4 | Nx + Vehicle (Diluent only) | 151, 156, 167 and 172* | 151, 156, 167 and 172* | | time point for histopath Terminal |
| 5 | Hemi-NX controls | 197, 198, 199, 200 and 201 | 197 and 198 | 199, 200 and 201 | Full hematological and serological panel |
| 3 | Healthy Controls (Unmanipulated) | 202, 203 and 204 | n/a | 202, 203 and 204 | Organ weights Histopath |
| 3 | Sham NX (matched controls that were surgically open/close on both dates of the 2-step nephrectomy) | 205, 206 and 207 | 205, 206 and 207 | n/a | |

178 replaced 183

Rats were assigned randomly to groups.

*#172 had a sCREAT >1.0 at time of transplantation (>2x healthy).

**#183 & 188 developed abscesses at the surgical site of nephrectomy which were discovered immediately after delivery from the vendor; they were treated with a 2-week course of Clavamox by the study veterinarian.

Results

Recipient animals achieved a disease state of uremia within 5 weeks of the 5/6 nephrectomy procedure, as confirmed by a doubling of the serum creatinine, a significant rise in the BUN, and a mild decrease in HCT. At 12 weeks post-treatment, the B2, B2/B4, B3, and B1/B5 groups had a 100% survival rate. Serologic and hematologic data showed that all cell treatment groups have lower average CREAT & BUN and higher HCT compared to NX untreated or NX vehicle-treated rats. Although variation persists among the different combinations for any given parameter, the B2/B4 combination provided the most comprehensive effects, with the data suggesting demonstrated therapeutic benefit towards survival (100% vs. 25% in untreated), weight gain (11% vs.-3.5% in untreated, filtration function (stabilization of CREAT & BUN), protein retention (confirmed by urine and serum protein levels), erythropoiesis (HCT % equivalent to healthy controls), and hypertension (mean systemic blood pressure only 10%>than healthy controls, compared to 30% increase in untreated). Post-3M and terminal serum chemistries, histopathology, urinalysis, and blood pressure measurements support 3-5M observations showing optimal performance of B2/B4 combination across all parameters.

As shown in Table 15 below, the B2/B4 prototype promoted 100% survival through week 20. B2, B3, and B2/B3 prototypes had 80% survival rates at 20 weeks post-treatment. No NX rats survived to Week 20. These results for the B2 prototype are consistent with previous observations as shown in Examples 9 and 13.

Figure 94:
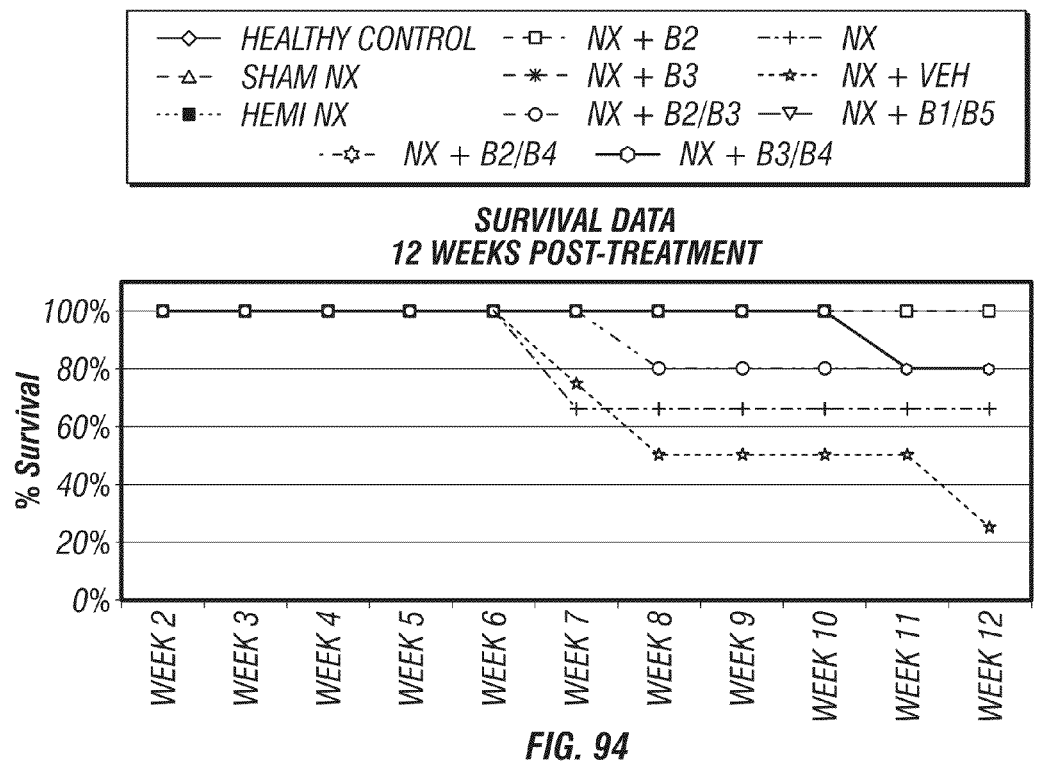
FIG. 94 shows survival data at 12 weeks post-treatment.
Figure 95:
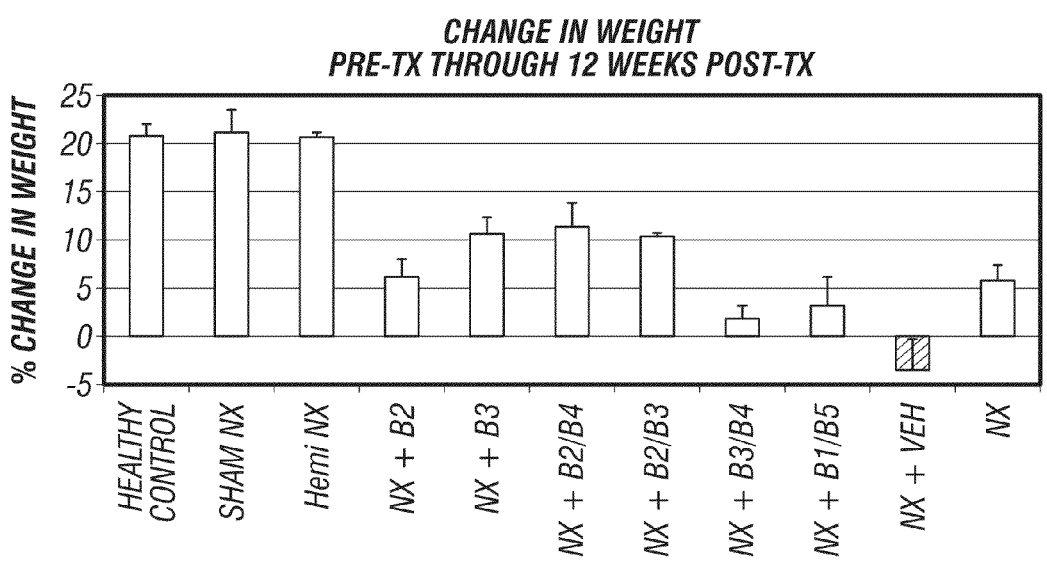
FIG. 95 depicts percent change in weight from pre-treatment through 12 weeks post-treatment.

FIG. 95 shows that multiple prototypes promoted weight gain through the 12-week time point. Weight gain (as % change) was calculated for each rat separately from baseline (pre-treatment) until the time that they were sacrificed moribund or the 12-week time point. Weight gain has been noted in previous studies upon treatment with the B2 prototype, and is seen again at the 12-week time point in this study, and is in-line with the % gain at the 3-month time point in Example 14 with B2 treatment. Unlike previous experiments, the untreated NX rats gained an average 5.81% weight between baseline (pre-treatment) and the 12-week time point, but only one NX rat survived to Week 12 (see FIG. 94). Interestingly, two of the three rats in the NX group were treated with Clavamox for incision-site abscesses, thus the rats were exposed to antibiotics during the sub-acute phase of renal injury post-nephrectomy. For this reason, the NX rats treated with vehicle (i.e., the cell-free sham treatment), may be considered more reliable controls for this study. The weight loss seen in the NX+VEH rats was similar to loss seen in previous studies with untreated or sham-treated rats. Three prototypes, B3, B2/B4, and B2/B3 have generated weight gain in the treated rats that is superior to B2; both B3 and B2/B4 prototypes have also yielded 100% survival (see FIG. 94).

Figure 96:
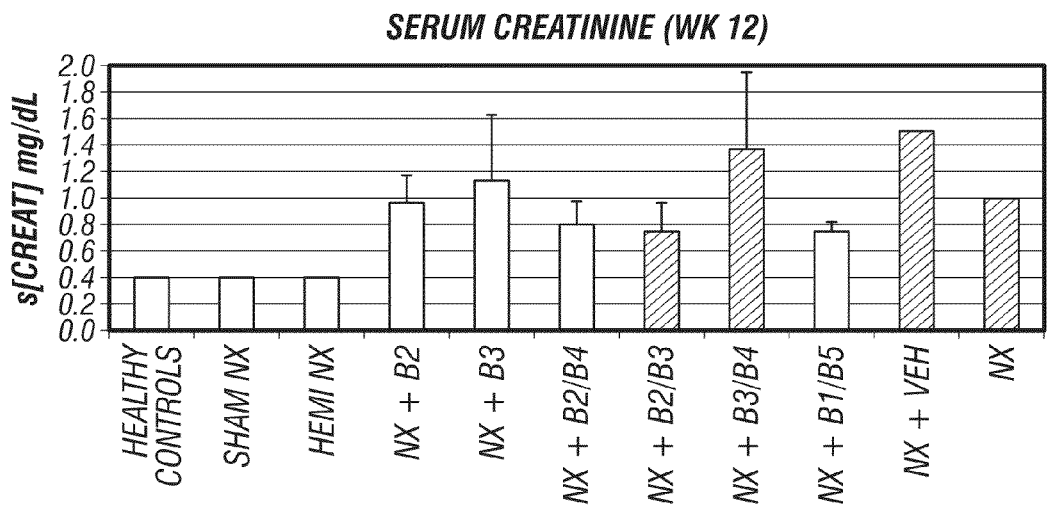
FIG. 96 shows serum creatinine levels at week 12.
Figure 97:
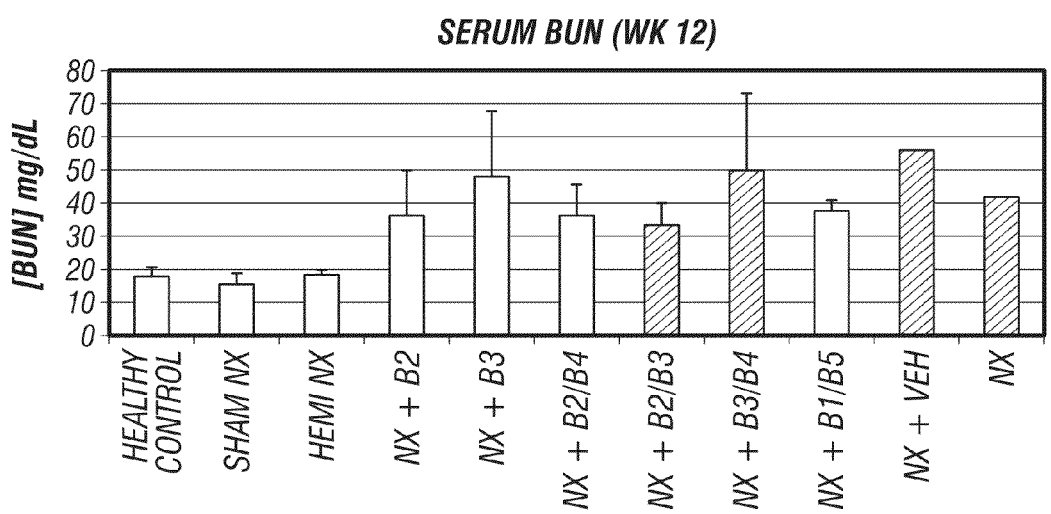
FIG. 97 shows serum BUN levels at week 12.

Renal filtration functions were stabilized by B2/B4 and B1/B5 prototypes through Week 12 (FIGS. 96-97). Previous studies demonstrated stabilization of renal functions (sCREAT & BUN) over time upon treatment with the B2 cell prototype. At the 12-week post-treatment time point, the group of rats treated with the B2 prototype exhibited a lower sCREAT (3a) and BUN (3b) compared to the NX+VEH and NX controls (although both of these control groups have reduced survival at the 12-week time point). Groups with 100% survival at 12 weeks are displayed as green bars; those with <100% survival are displayed as black bars. Error bars=STDEV. Both the B2/B4 and B1/B5 combination prototypes slightly outperformed the B2 prototype, while other prototypes (B3/B4, for example) performed poorly.

Figure 98:
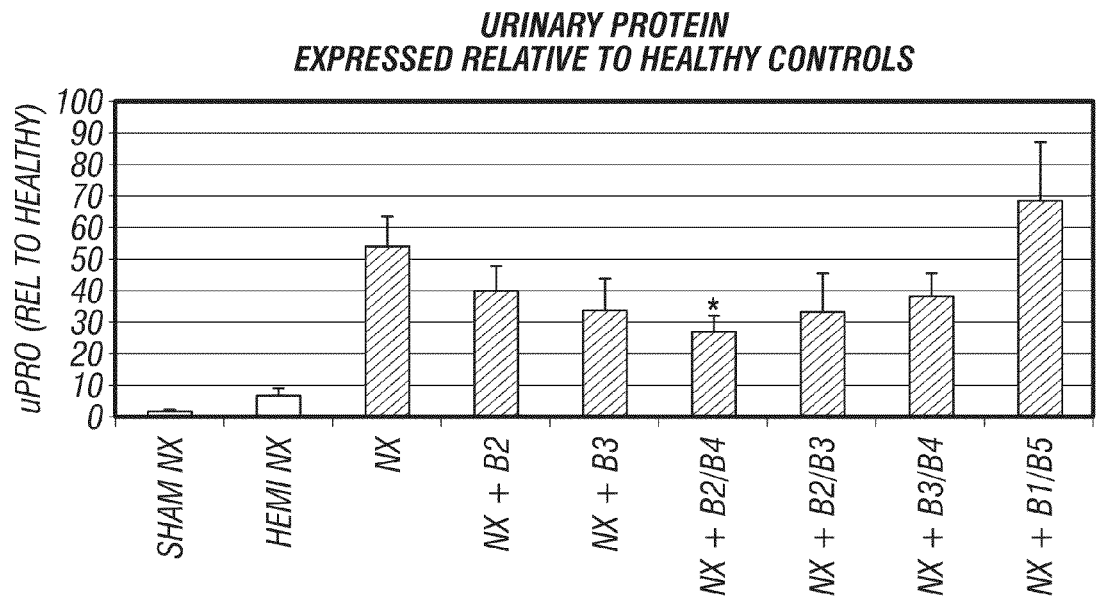
FIG. 98 depicts urinary protein levels expressed relative to healthy controls.
Figure 99:
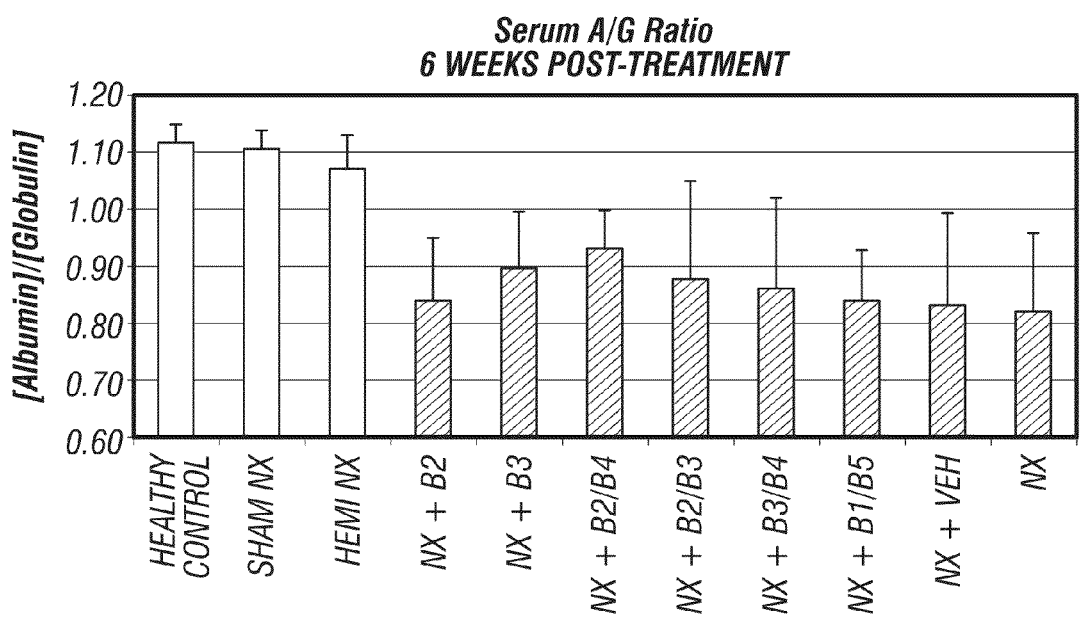
FIG. 99 shows serum A/G ratios at six weeks post-treatment.

Protein retention was also significantly enhanced in prototype B2/B4 through 11 weeks post-treatment (see FIG. 98). Improvements in serum total protein and albumin levels were noted in previous studies upon treatment with B2, and to a lesser degree, B4 prototypes. Consistent with past studies, serum total protein, albumin, and A/G ratio were increased slightly in treated rats compared to NX and NX+VEH, but the differences were not significant statistically. A 16-hr urine collection was conducted on all rats at 11 weeks post-treatment, and the urine was subjected to urinalysis for measurement of urinary protein (uPRO) and other parameters. While all NX rats had a significantly higher uPRO compared to SHAM NX and HEMI NX (p<0.01), and several prototypes exhibited trends in reduction of uPRO, only rats treated with the B2/B4 prototype had a significant reduction in uPRO compared to the untreated NX rats (p<0.05). Note: NX+VEH rats are not shown on the graph because their urine collection was completed (4) weeks earlier than all other groups. All urinalysis data are normalized to HEALTHY CONTROLS. Although not significant statistically, the serum A/G ratios of the treatment groups measured 6 weeks post-treatment follow a pattern that is inversely related to the uPRO levels (compare FIGS. 98 and 99 for each group). In the B2/B4 treatment group, the reduction in protein excretion upon treatment is accompanied by retention of that protein in the serum.

Figure 100:
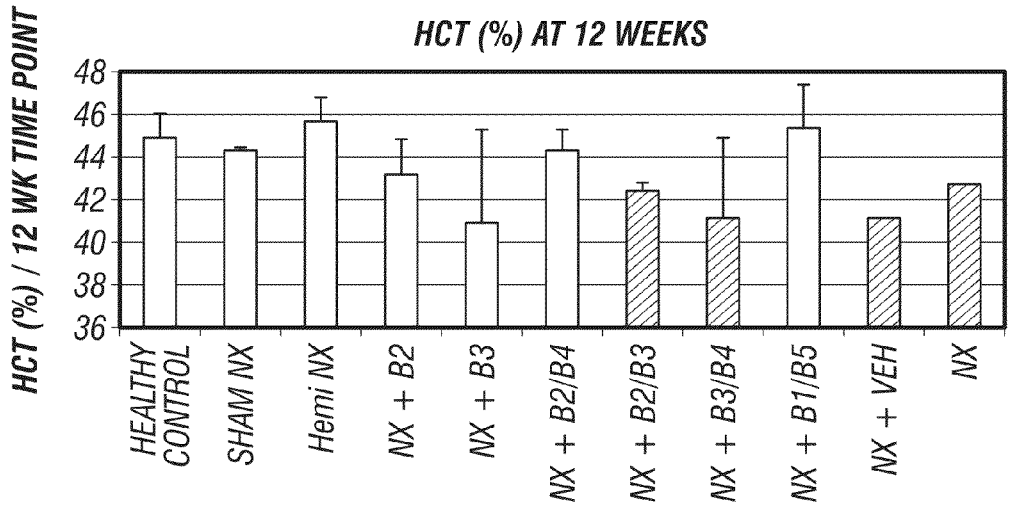
FIG. 100 shows HCT percent at 12 weeks.
Figure 101:
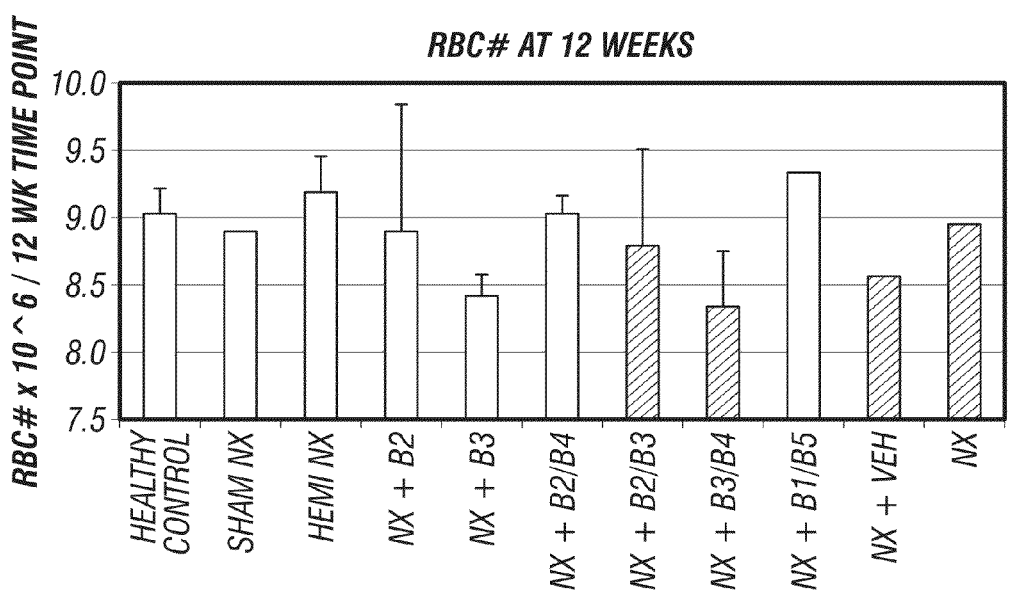
FIG. 101 shows RBC number at 12 weeks.

As shown in FIGS. 100-101, erythropoiesis is supported by B1/B5 and B2/B4 prototypes through Week 12. As noted in Example 14, the secondary anemia is mild in this cohort of nephrectomized rats. Black bars represent groups with <100% survival at 12 weeks, while green bars represent groups with 100% survival at 12 weeks. Data shown are group means+/−SDEV. The B1/B5 and B2/B4 prototypes provided the strongest erythropoiesis support at 12 weeks. This is logical given the relative enrichment of epo-producing cells in the B5 and B4 cellular fractions. Although less pronounced than HCT (5a), the RBC# mirrors the HCT in the various treatment groups (5b).

Figure 102:
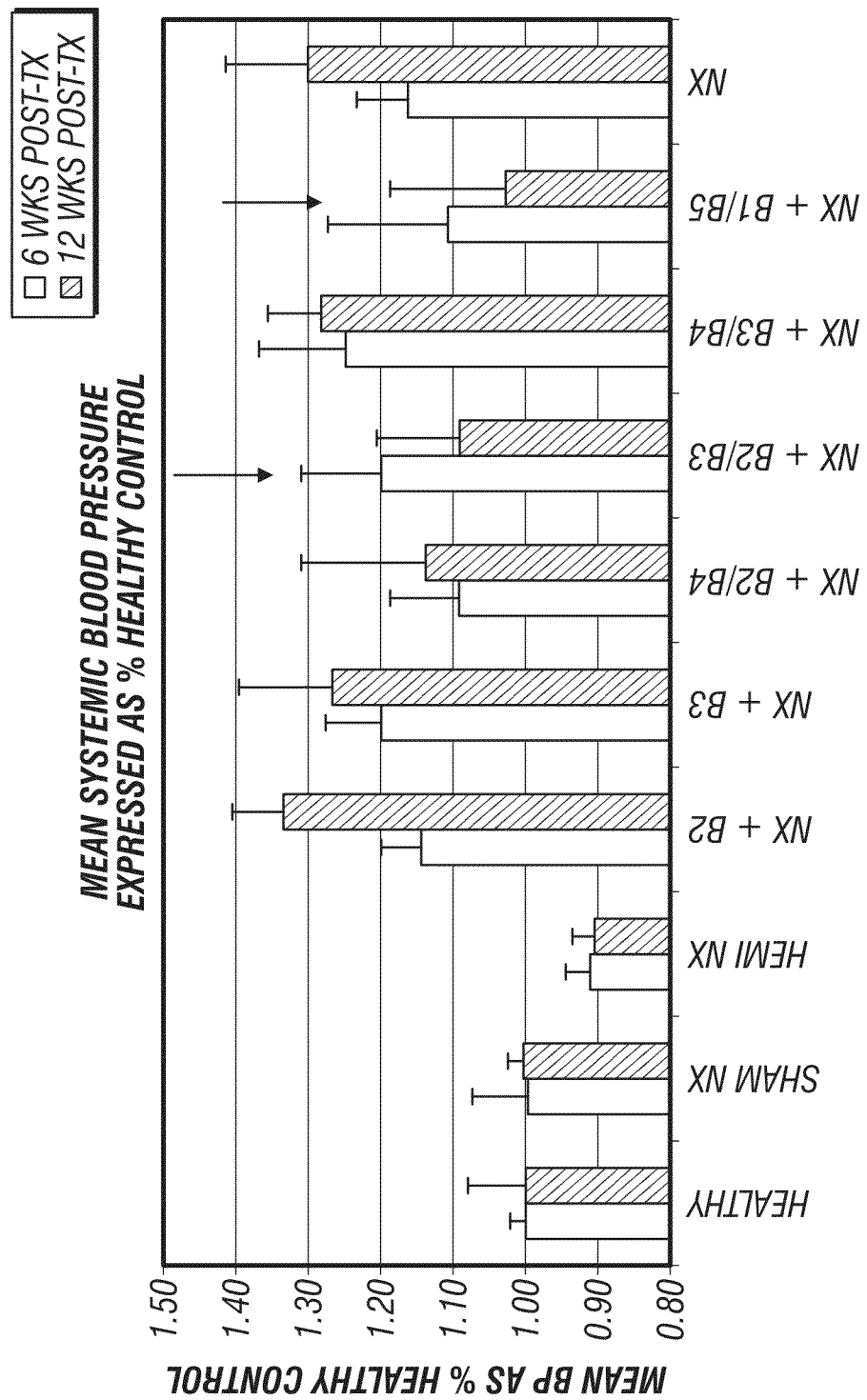
FIG. 102 depicts mean systemic blood pressure at 6 and 12 weeks post-treatment.

Hypertension is a measurable feature of the 5/6 nephrectomy model of renal failure, and is modulated partially by B2/B4, B2/B3, and B1/B5 prototypes (see FIG. 102). Based on the gross observations in Examples 9 and 13 that some treatments reduced cardiac hypertrophy in the 5/6 nephrectomized rats, blood pressure (BP) assessment was introduced at ~6-week intervals in this study. Systolic and diastolic BP was measured using a CODA non-invasive tail-cuff BP monitor (Kent Scientific). At least 10 software-validated measurements were taken per rat per timepoint. In order to compare BP trends among timepoints, data for each rat at each timepoint were calibrated to the average value at that timepoint for healthy controls. At the study midpoint (12 weeks), three prototypes (B2/B4, B2/B3, and B1/B5) exhibited trends (not statistically significant) of lowering mean BP compared to NX controls. Interestingly, two prototypes (B2/B3 and B1/B5) actually showed some evidence of reducing BP from the 6-week to the 12-week timepoints (see arrows on graph, FIG. 102).

Figure 103:
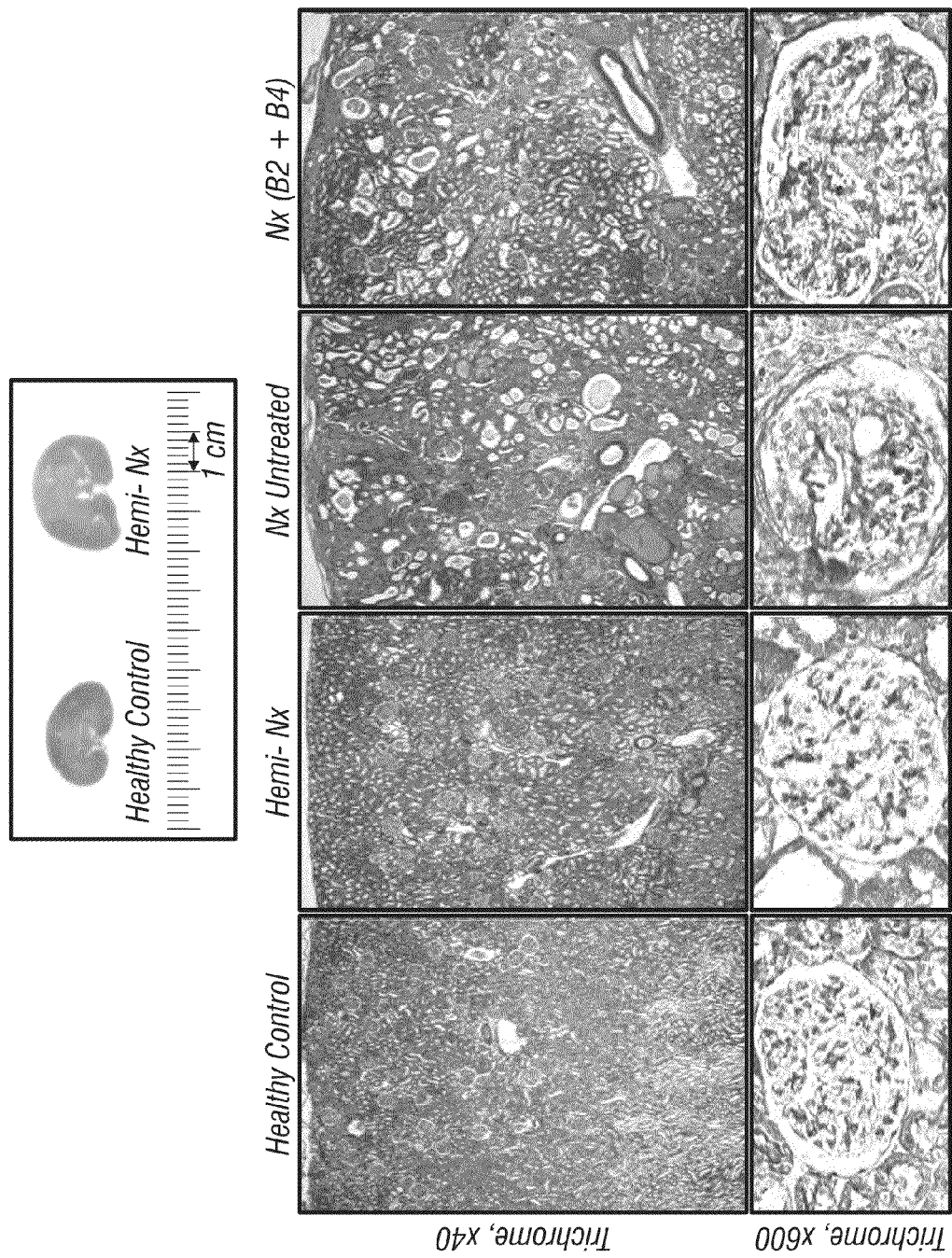
FIG. 103 depicts histological assessment at the 3-5 month time points.

As shown in FIG. 103, histological assessment at the 3-5M time points provides evidence of less fibrosis, more healthy tubules, less protein cast accumulation, and reduced glomerulosclerosis in B2/B4-treated rats, in sharp contrat to the Nx-Untreated animals. The renal hypertrophy associated with removal of one kidney is highlighted grossly in the top panel of FIG. 103 and histologically (Hemi-Nx) in the bottom panel of FIG. 103. In sharp contrast to the Nx-untreated animals (100% died of renal failure by 16 weeks), there is less fibrosis, and more healthy tubules, less protein cast accumulation, and reduced glomerulosclerosis. Stains shown in FIG. 103 are Masson's Trichrome, highlighting fibrosis in blue.

12-Weeks Post-Treatment Observations

At 12 weeks post-treatment, 100% of the NX+B2 rats survived, consistent with performance of this cellular prototype in Example 10 and 14. 100% survival at the 12-week timepoint was also achieved in the Healthy Controls, NX+B2/B4, NX+B3, and NX+B1/B5. At 12 weeks post-treatment, the poorest survival was in the NX+VEH (25%) and NX (untreated) (66%). All other prototypes were less than 100%, but greater than NX and NX+VEH.

As shown throughout the examples, weight gain over time has been associated with survival and is a good indicator of overall health. At the 12-week time point in the instant study, all groups (except NX+ VEH) gained some weight, but the NX+B2/B4 had the highest percent weight gain among all treated groups, gaining 11.3% (compared to 21% in healthy controls).

At 12 weeks post-treatment, erythropoiesis was closest to healthy (SHAM NX) in the NX+B2, B2/B4, and B1/B5 groups. Overall stabilization of renal filtration function (as determined by elimination of progressive decline in sCREAT) was achieved in NX+B2, B2/B4 and B1/B5.

The untreated NX or NX+VEH rats exhibited mean systemic blood pressures of 137 mm Hg (compared to 105 in healthy controls). A trend of reduction in mean systemic blood pressure (compared to NX controls) was noted in NX rats treated with prototypes B2/B4, B2/B3, and B1/B5.

Assessment of protein handling via urinalysis and serum chemistry revealed that: 1) there is a strong inverse correlation between the amount of protein excreted in the urine and the serum Albumin/Globulin (A/G) ratio; and 2) treatment with the B2/B4 prototype yields a significant reduction in urinary protein excretion with a concomitant elevation in the serum A/G ratio, suggesting that protein handling by the kidney is improved with this treatment.

When considering all parameters above, the combination of B2/B4 provided the strongest benefit, outperforming B2 and other prototypes across most parameters.

TABLE 15

| INTERIM SUMMARY | UNTX | CELLULAR PROTOTYPES | | | | | | CONTROLS | |
|---|---|---|---|---|---|---|---|---|---|
| CLINICAL PARAMETERS | NX | B2 | B3 | B2/B3 | B2/B4 | B3/B4 | B1/B5 | HEMI NX | HEALTHY |
| SURVIVAL (3 MONTH) | 3/7 | 5/5 | 5/5 | 4/5 | 5/5 | 4/5 | 3/3 | 5/5 | 3/3 |
| SURVIVAL (5 MONTH) | 0/7 | 4/5 | 4/5 | 4/5 | 5/5 | 3/5 | 3/3 | 5/5 | 3/3 |
| WEIGHT CHANGE | −3.48 | 6.15 | 10.56 | 10.36 | 11.33 | 1.78 | 3.24 | 20.67 | 20.76 |
| sCREAT | 1.95 | 1.85 | 2.25 | 1.1 | 0.97 | 0.8 | 1.5 | 0.4 | 0.4 |
| BUN (5 MO) | X | 64.5 | 97 | 43.7 | 39.7 | 66.3 | 61 | 19.7 | 16.5 |
| HCT (5 MO) | X | 40.5 | 38 | 41.2 | 40.2 | 40.7 | 39.1 | 43.3 | 43.6 |
| RBC (5 MO) | X | 8.11 | 7.8 | 8.51 | 7.86 | 8.35 | 8.09 | 8.73 | 8.75 |
| PROTEINURIA | 54 | 39.9 | 33.5 | 33.1 | 27.2 | 38.5 | 68.3 | 6.6 | 1.8 |
| SERUM A/G RATIO | 0.83 | 0.84 | 0.9 | 0.88 | 0.93 | 0.86 | 0.84 | 1.1 | 1.16 |
| MEAN SYSTEMIC BP | 137.2 | 140.6 | 133.7 | 115.1 | 120.1 | 135.4 | 108.4 | 95.5 | 105.5 |

Figure 104:
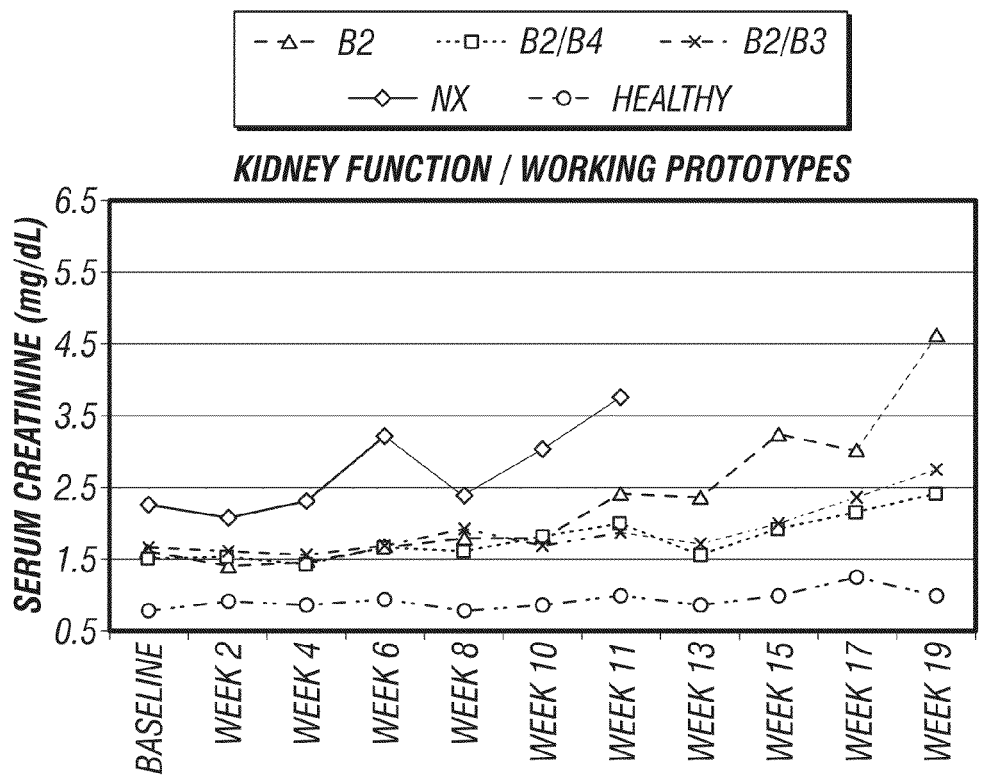
FIG. 104 shows the effects of the working prototypes on serum creatinine levels.
Figure 105:
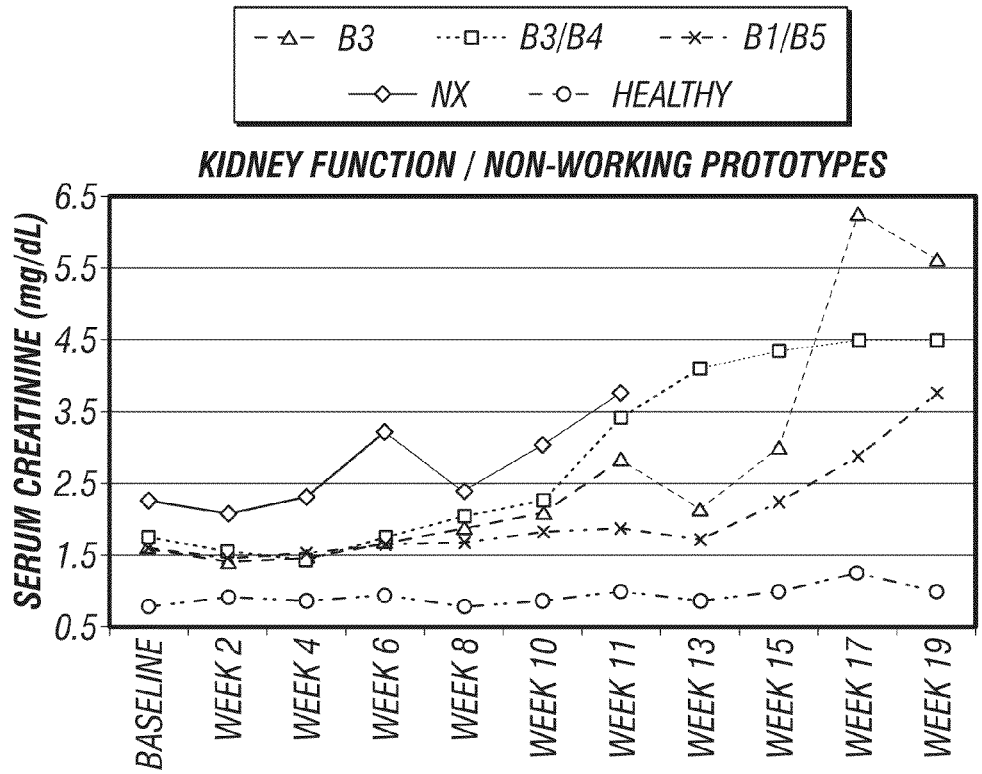
FIG. 105 depicts the effects of the non-working prototypes on serum creatinine levels.
Figure 106:
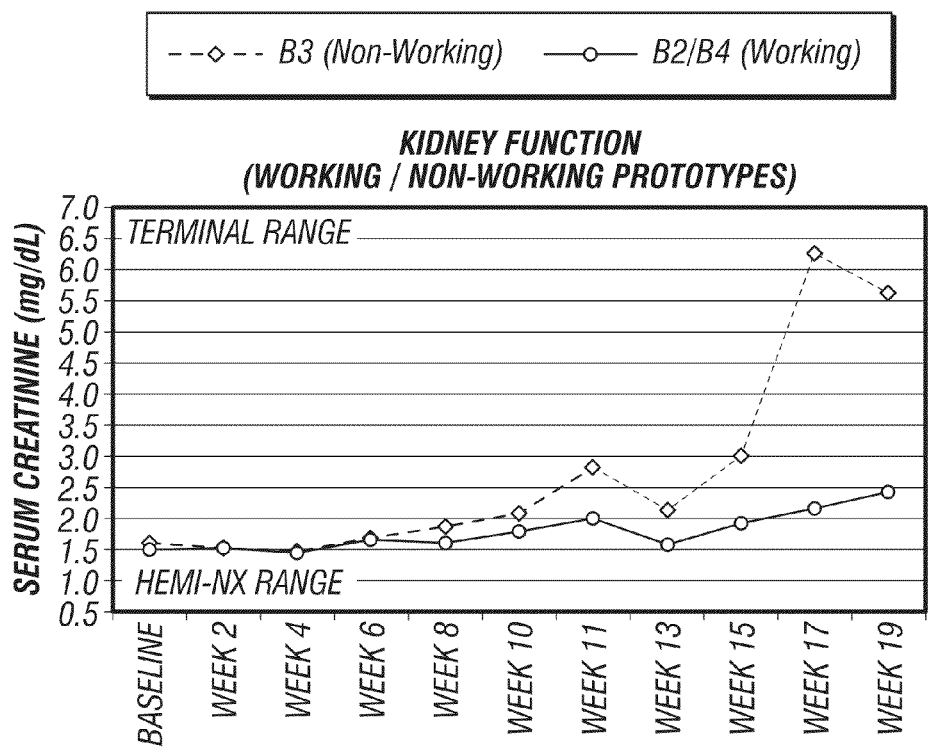
FIG. 106 depicts the effects of B3 and B2/B4 on serum creatinine levels.
Figure 107:
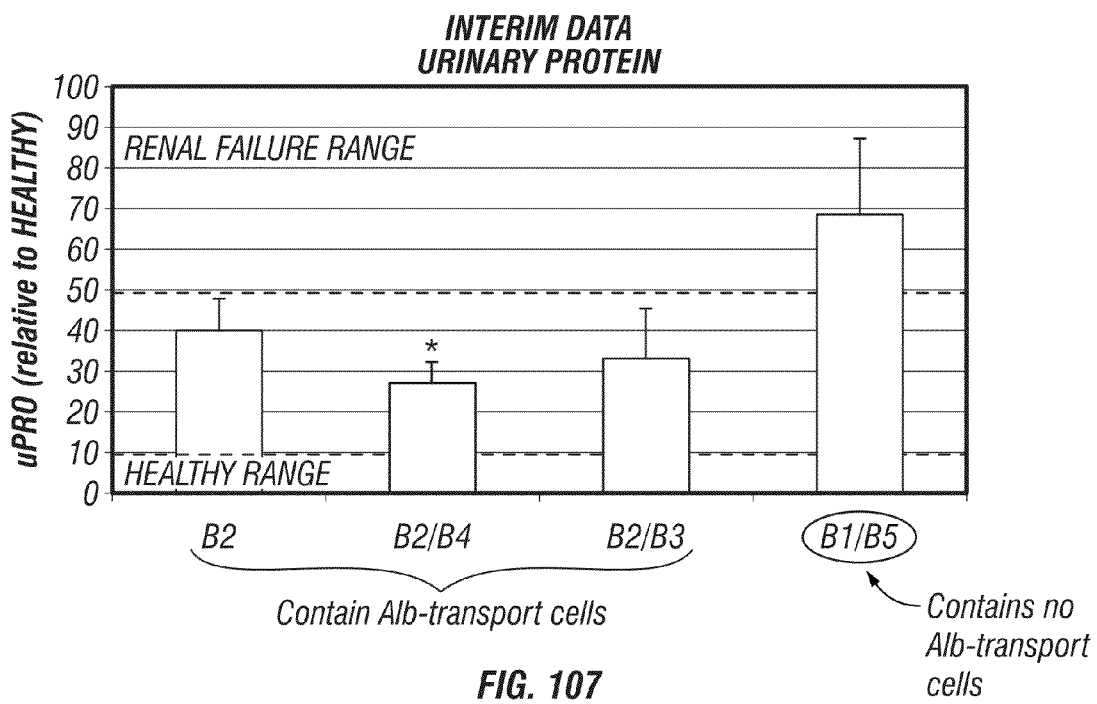
FIG. 107 shows the effects of B2, B2/B4 and B2/B3 on urinary protein levels.
Figure 108:
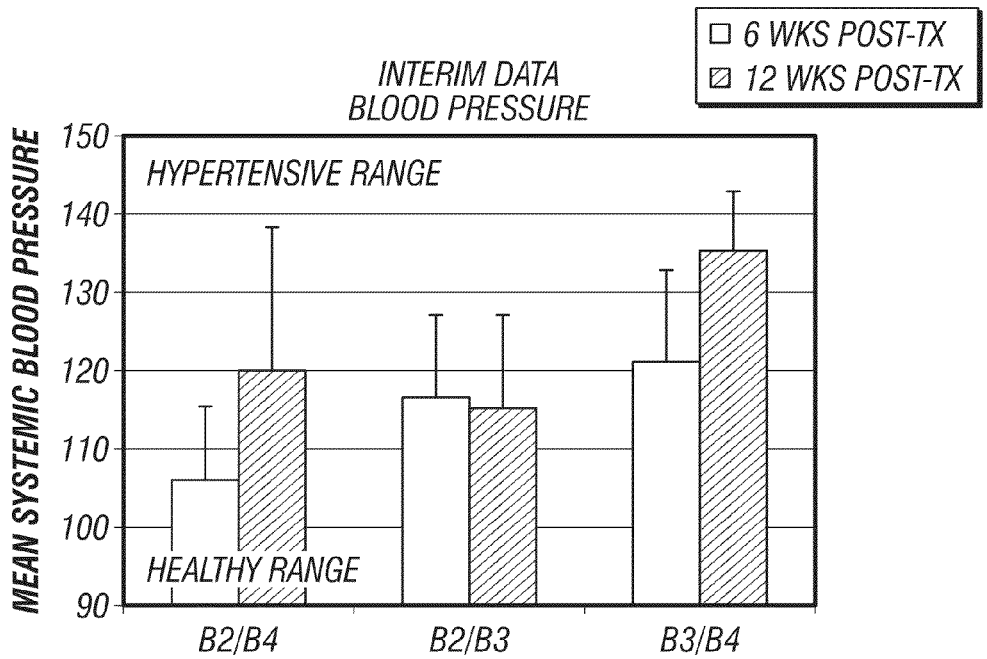
FIG. 108 depicts the effects of B2/B4, B2/B3 and B3/B4 on blood pressure.

The above data highlight important differences between the working prototypes versus the non-working prototypes. Overall, the working prototypes stabilize renal function better than the non-working prototypes. Specifically, the working prototypes provided 100% survival at 19 weeks, lower serum CREAT and BUN, 50% reduction in proteinuria, equivalent erythropoiesis and lower systemic blood pressure. For example, FIG. 104 shows improved serum creatinine levels in the working protopyes through Week 19. As comparison, FIG. 105 shows serum creatinine levels in the non-working prototypes through Week 19. (see PPT). FIG. 106 further shows the difference between the working protopyes versus the non-working prototypes. The working prototypes were also shown to reduce proteinuria better than the non-working prototypes. Reduced proteinuria correlates with the presence of albumin-transporting tubular cells and is optimal in combination with B4 components (glomerular, vascular) (see FIG. 107). The working prototypes were also shown to maintain blood pressure better than the non-working prototypes (see FIG. 108).

Without wishing to be bound by theory, it appears that the neo-kidney augmentation prototypes function in part via mediation of anti-fibrotic pathways, as evidenced by the reduced fibrosis (glomerular and interstitial). It also appears that the neo-kidney augmentation prototypes are capable of modulating extracellular matrix (ECM) environment (structural plasticity), as evidenced by the increased expression of HAS-2 (hyaluronic synthase 2)—which is responsible for synthesizing high-molecular-weight hyaluronic acid (HA), a form of HA associated with support of nephrogenesis. The disclosed neo-kidney augmentation prototypes also appear to be capable of modulating the immune system through macrophage activation, as leukocyte infiltration has been observed in injury models. As primitive structures were observed in some treated tissues, it also appears that the neo-kidney augmentation prototypes are capable of reinititating or stimulating the reinitiation of developmental programs, i.e., nephrogenesis. Furthermore, it appears that the neo-kidney augmentation prototypes may contain or reactivate tissue-specific progenitor cells capable of participating in, stimulating, or causing the regeneration of renal tissue.

Study-End Observations

Consistent with previous studies, specific bioactive subpopulations and/or specific cell/cell combinations of these subpopulations tested offered a distinct therapeutic benefit towards tubular, glomerular and/or endocrine function. The following data represent group averages of end of study clinical chemistries compared to baseline values.

Figure 109:
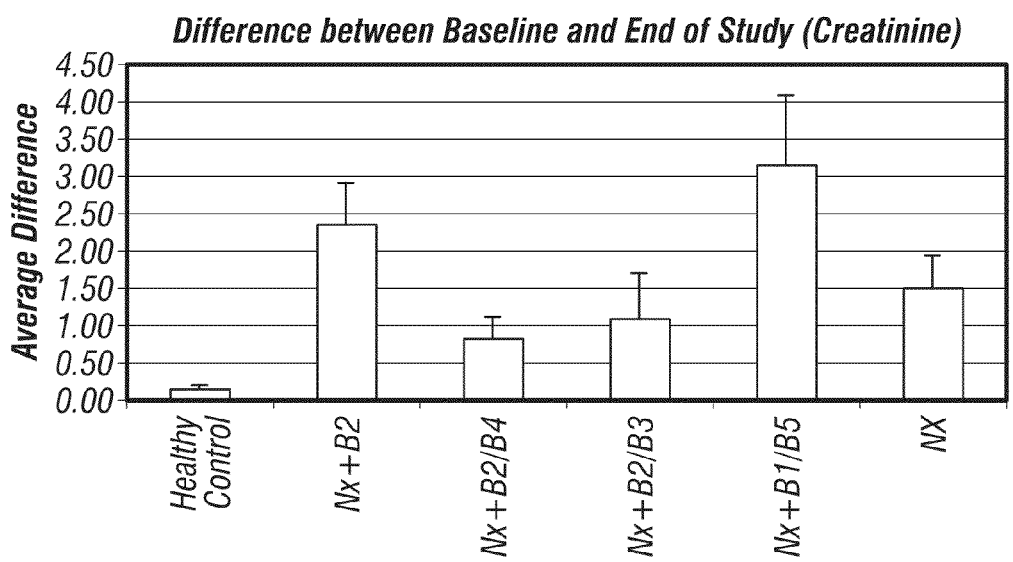
FIG. 109 shows the difference between baseline and end of study creatinine levels.

As shown in FIG. 109, end of study serum Creatinine was significantly improved or stabilized in the cell/cell combinations Nx+B2/B4 and Nx+B2/B3 compared to Nx controls. Baseline values were subtracted from end of study measurements for individual animals and then averaged across each treatment group. Mean and standard error are shown for the selected study groups.

Figure 110:
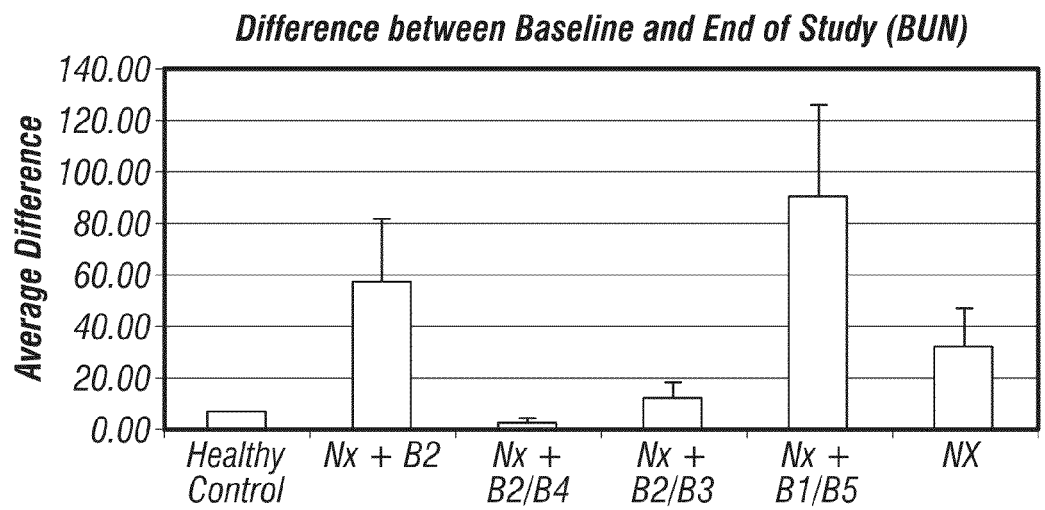
FIG. 110 depicts the difference between baseline and end of study BUN levels.

End of study BUN (Blood urea nitrogen) was significantly improved or stabilized in the cell/cell combinations Nx+B2/B4 and Nx+B2/B3 compared to Nx controls (see FIG. 110). Baseline values were subtracted from end of study measurements for individual animals and then averaged across each treatment group. Mean and standard error are shown for the selected study groups.

Figure 111:
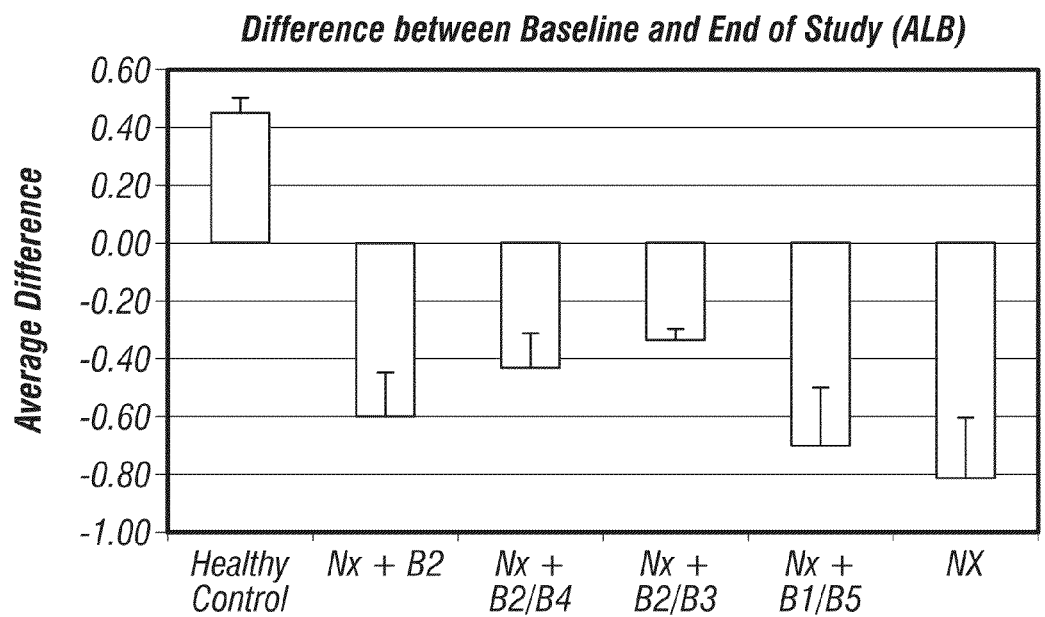
FIG. 111 depicts the difference between baseline and end of study ALB levels.

End of study serum Albumin (ALB) was significantly improved or stabilized in the cell/cell combinations Nx+B2/B4 and Nx+B2/B3 compared to Nx controls (see FIG. 111). Baseline values were subtracted from end of study measurements for individual animals and then averaged across each treatment group. Mean and standard error are shown for the selected study groups.

Figure 112:
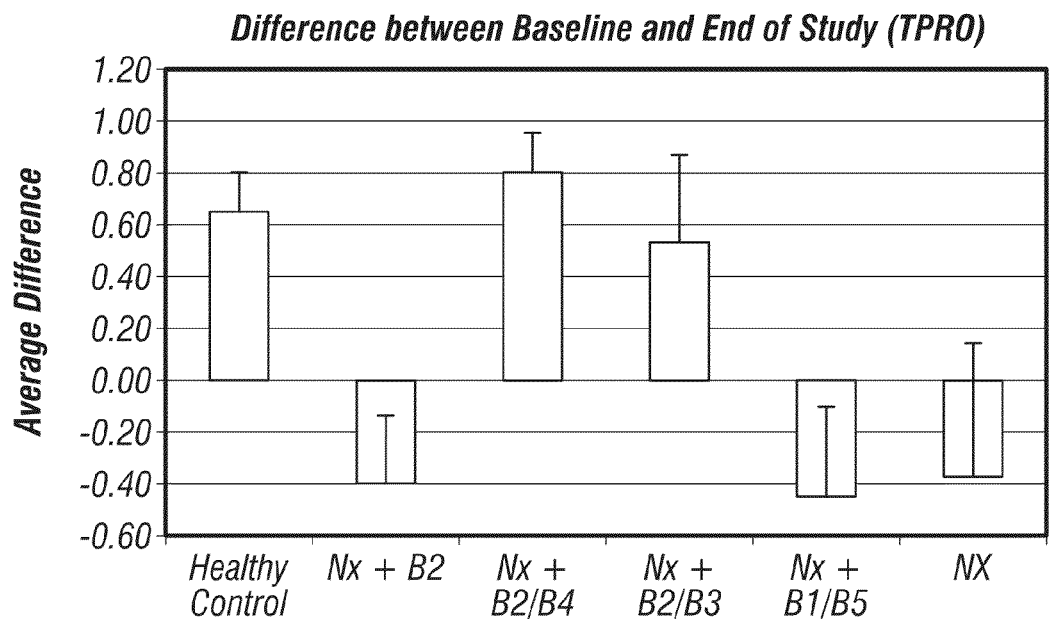
FIG. 112 shows the difference between baseline and end of study TPRO levels.

As shown in FIG. 112, end of study total serum protein (TPRO) was significantly improved or stabilized in the cell/cell combinations Nx+B2/B4 and Nx+B2/B3 compared to Nx controls. Baseline values were subtracted from end of study measurements for individual animals and then averaged across each treatment group. Mean and standard error are shown for the selected study groups.

Figure 113:
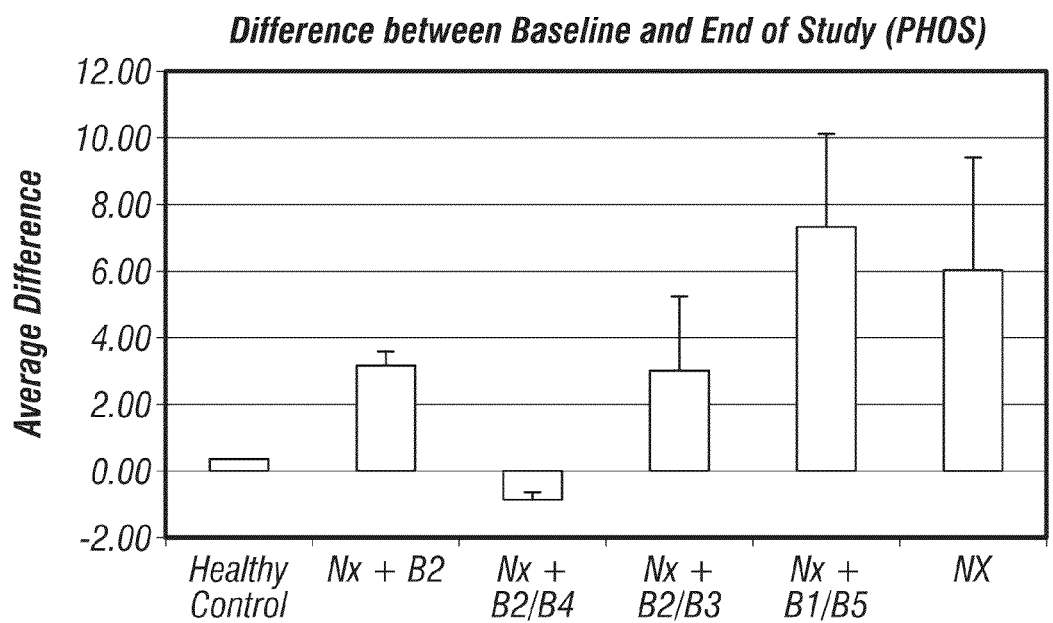
FIG. 113 depicts the difference between baseline and end of study PHOS levels.

End of study serum phosphorus (PHOS) was significantly improved or stabilized in the cell/cell combinations Nx+B2/B4 and Nx+B2/B3 compared to Nx controls (see FIG. 113). Baseline values were subtracted from end of study measurements for individual animals and then averaged across each treatment group. Mean and standard error are shown for the selected study groups.

Figure 114:
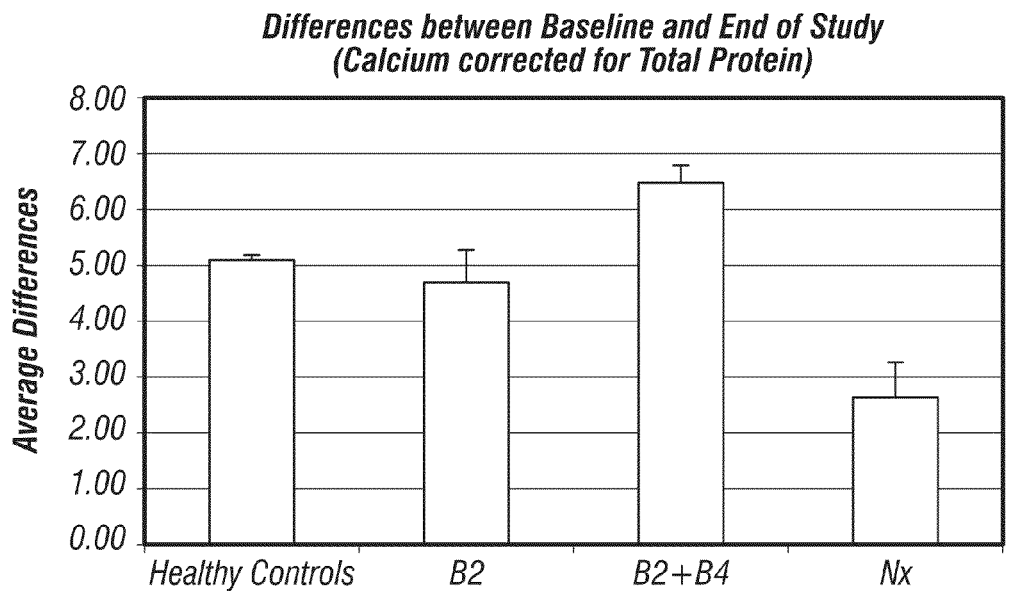
FIG. 114 depicts the difference between baseline and end of study calcium corrected for total protein.

As shown in FIG. 114, end of study serum calcium (corrected for total protein [Ca]−0.4[TP]+3.3=corrected for total protein) was significantly improved or stabilized in the cell/cell combination Nx+B2/B4 compared to Nx controls. Baseline values were subtracted from end of study measurements for individual animals and then averaged across each treatment group. Mean and standard error are shown for the selected study groups.

The functional outcomes of the prototypes tested across the studies described herein are shown below in Table 16 (below). As shown in Table 16, the cell/cell combination of B2/B4 and B2/B3 provided benefits above and beyond those offered by B2 alone.

In conclusion, the above data highlight significant improvements to the renal filtration (glomerular) and resorption (tubular) functions (sCREAT, BUN, protein retention, calcium balance) of the kidney. Importantly, the in vivo therapeutic activity of the cell/cell combination of B2/B4 and B2/B3 acted synergistically to enhance the regenerative outcome in vivo. These combination prototypes provided benefits above and beyond those offered by B2 alone.

Example 16

Isolation and Expansion of Renal Cells from Diseased Human Kidney Biopsy

The objective of this study was to determine the technical limits of cell yield, viability, and expansion from small biopsies of diseased human kidney.

Kidney Tissue Procurement: Kidney (Right) arrived from NDRI via courier, approximately 19 hours after surgical explant. Package was opened, cleansed thoroughly on the exterior with 70% ethanol and BacDown cleanser, and container housing kidney was located to the tissue culture hood.

Kidney Biopsy Collection: Fat and connective tissue were removed from the kidney, while leaving the kidney capsule intact. Sterile biopsy punches were utilized to collected biopsies (n=8) from the kidney (data not shown). Biopsies were trimmed of obvious calyx and capsule and weighed. Each biopsy was placed into a sterile 15 mL conical tube and subjected to a 10 minute rinse at 37° C. in either Calcium-free PBS (biopsies 1-4) or calcium-containing PBS (biopsies 5-8). Subsequently, the PBS rinse was discarded via aspiration and biopsies were subjected to digestion procedures.

Biopsy Digestion: Each biopsy was submerged in 3 mL of digestion buffer (4 Units of Dispase 1 (Stem Cell Technologies) in HBSS, 300 Units/mL of Collagenase type IV (Worthington) with 5 mM $CaCl_2$ (Sigma)) and incubated at 37° C. in a water bath with gentle agitation for 20 minutes. 2 mL of digest supernatant was removed to a fresh tube, combined with Media and centrifuged for 5 minutes/1,100 RPM in the swinging bucket centrifuge to pellet cells. Cells released during "Digest 1" were enumerated independently for each biopsy and the number recorded. The cells were then washed in media (1×) and resuspended in 1 mL of media and placed into a labeled T25 tissue-culture treated flask. 1 mL of fresh enzymatic digestion buffer was added to each biopsy remnant, the tissue remnants were additionally minced with sterile scissors, and the biopsy tissues were digested for an additional 40 minutes at 37° C. in a shaking water bath with gentle agitation ("Digest 2"). Digestion mixtures were filtered through 100 μm filters into clean, sterile, 15 mL conical tubes and combined with 5 mL of media.

After centrifugation and washing (2×) the cells were resuspended in media and enumerated. Viability was assessed at this step by the addition of 10% volume trypan blue. Cell number and % viability were recorded.

Plating: All cells released from each biopsy (Digest 1+Digest 2) were plated together in a single T25 flask. Cultures were subjected to a 100% media change and photomicrographs were taken 48 hours after plating.

Results

Patient Information/Confirmation of Disease State. HK0019 kidney was harvested from a female donor, 85 kg, 52 YO (Caucasian), with a history of Type II diabetes and renal failure. Cause of death was anoxia, secondary to cardiovascular failure. At the time of death, clear systemic evidence of renal failure with anemia was present (Table 17). Of note are the high BUN and Creatinine, high protein in urine combined with low serum protein, low serum calcium and high serum

TABLE 16

| Prototypes Tested | B1 | B2 | B3 | B4 | B5 | OPLA | HA FOAM | HA GEL | HA DIL | Survival (3M) | Survival (6M) | Weight Gain (3M) | Δs CREA DAILY (ΔsCREA/ (TO-TTERM) DAYS as % BASELINE VALUE | ΔsBUN DAILY (ΔsBUN/ (TO-TTERM) DAYS as % BASELINE | ΔHCT (Baseline to TERM) | ΔsALB DAILY (ΔsALB/ (TO-TTERM) DAYS as % BASELINE |
|---|---|---|---|---|---|---|---|---|---|---|---|---|---|---|---|---|
| 1 | | | | | | | | | | 3/3 | 2/3 | 3.24 | 2.33 | 1.47 | 1.57 | -0.140 |
| 2 | | | | | | | | | | 12/12 | 4/6 | 7.26 | 0.84 | 0.31 | -2.08 | -0.127 |
| 3 | | | | | | | | | | 5/5 | 2/3 | 10.56 | 2.60 | 1.73 | -1.38 | -0.108 |
| 4 | | | | | | | | | | 7/9 | 1/5 | 6.1 | 1.76 | 0.85 | -2.14 | -0.114 |
| 5 | | | | | | | | | | 2/5 | 1/2 | 10.36 | 0.90 | 0.29 | 7.32 | -0.063 |
| 6 | | | | | | | | | | 5/5 | 3/3 | 11.33 | 0.89 | 0.25 | 5.34 | -0.095 |
| 7 | | | | | | | | | | 4/5 | 1/2 | 0.74 | 1.77 | 0.96 | -2.40 | -0.161 |
| 8 | | | | | | | | | | 7/7 | 0/3 | 6.63 | 1.57 | 1.03 | 1.89 | -0.179 |
| 9 | | | | | | | | | | 0/6 | na | 3.85 | 2.97 | 1.64 | -3.80 | na |
| 10 | | | | | | | | | | 4/5 | na | -3.1 | 1.75 | 0.43 | -3.52 | -0.263 |
| 11 | | | | | | | | | | 3/5 | na | -2.75 | 1.28 | 0.15 | -3.76 | -0.253 |
| 12 | | | | | | | | | | 4/6 | na | -5.11 | 1.52 | 0.30 | -3.82 | -0.299 |
| 13 | | | | | | | | | | 3/3 | na | 4.07 | 0.82 | 0.28 | -0.67 | -0.151 |
| 14 | | | | | | | | | | 3/5 | na | -4.72 | 1.14 | -0.05 | -2.58 | -0.196 |
| 15 | | | | | | | | | | 5/5 | na | -3.93 | 1.46 | 0.24 | 0.18 | -0.163 |
| 16 | | | | | | | | | | 3/5 | na | 3.07 | 1.14 | 0.30 | -1.26 | -0.122 |
| 17 | | | | | | | | | | 0/1 | na | 7.8 | 4.03 | 3.80 | -6.40 | na |
| 18 | | | | | | | | | | 0/1 | na | 4.73 | 1.59 | -0.23 | 2.10 | -0.578 |
| NO TREATMENT | | | | | | | | | | 9/18 | 0/6 | 2.61 | 2.11 | 1.08 | 1.86 | -0.147 |
| NO DISEASE | | | | | | | | | | 18/18 | 8/8 | 28.26 | 0.09 | -0.07 | -0.42 | -0.026 | phosphorus, and significant anemia (low hematocrit, RBC, and hemoglobin). Parameters clearly outside of normal range are bolded in Table 17.

Kidney, Gross Observations. Upon gross observation, kidney was of normal size but appeared pale in color with clear areas of fibrosis. Upon bisection (see picture below), the tissue appeared poorly perfused and pale with poor demarcation between cortex and medulla. There was also a significant amount of perirenal fat invading the calyx of the kidney.

Biopsy Results (Yield & Viability). The initial weight, Digest 1 yield, Digest 2 yield, and final % viability was recorded for each biopsy (Table 18). Biopsies processed using the calcium-free rinse step tended to yield suspensions comprised predominantly of single cells, while biopsies processed using the calcium-containing rinse step yielded suspensions comprised predominantly of cell clusters 3-7 cells in size. Overall yield was slightly greater with calcium-containing rinse, but overall viability was greater with calcium-free rinse. The average cell yield from all biopsies was 7,604±807 cells/mg tissue. 8/8 (100%) of the biopsies resulted in cultures that established (data not shown) and expanded over a 6 day period.

Expansion Yield Results. The p0 cultures initiated from each of the (8) biopsies was harvested by trypsinization and enumerated using the Nexcellom cellometer. Viability was also calculated (See Table 19). Most (7/8) of the biopsy-initiated cultures underwent significant expansion (average 6.0-fold) over the period of 5 days, resulting in average viable cell yields of 1.18 million per biopsy, post-culture (data not shown).

In summary, the HK019 human donor kidney was procured from a patient with clear renal failure and anemia. As shown above, it is possible to establish cultures from biopsies of diseased human kidney that weigh as little as 0.02 g and comprise cortex/corticomedullary junction/medullary tissue but exclude calyx and capsule.

TABLE 17

| HK019 | | Final Serology/Hematology |
|---|---|---|
| Urinalysis | Protein | Positive (>300) |
| | Glucose | Positive (100A) |
| | Blood | Positive (large) |
| | RBC | Positive (2-5) |
| | WBC | Positive (2-5) |
| | Ketones | Positive (trace) |
| | Spec. Grav. | 1.014 |
| | pH | 7.5 |
| | appear. | cloudy |
| CBC | RBC | 2.79 |
| | WBC | 15.6 |
| | HGB | 8.4 |
| | Hct | 23.7 |
| | PLT | 104 |
| | Segs | 97 |
| | Lymphs | 9 |
| | Bands | — |
| | Mono | 2.2 |
| | Eos | 0 |
| Chemistry | Na+ | 140 |
| | K+ | 4.6 |
| | Cl− | 103 |
| | CO2 | 16.7 |
| | Creatinine | 6.1 |
| | Creatinine Clearance | 14.48 |
| | BUN | 157 |
| | Glucose | 125 |
| | Calcium | 6.1 |
| | Phosphorous | 12.4 |
| | Total Bili | 0.7 |
| | SGOT (AST) | 167 |
| | SGPT (ALT) | 30 |

TABLE 17-continued

| HK019 | Final Serology/Hematology |
|---|---|
| GGT | 103 |
| Albumin | 1 |
| Total Protein | 4 |
| Mg | 2.3 |
| Alk Phos | 229 |
| LDH | 1396 |
| PT | 13.9 |
| INR | 1.4 |
| PTT | 28.9 |
| Amylase | 56 |
| Lipase | 274 |

TABLE 18

Biopsy yield results.

| | Rinse | | Yield (Live Cells) | | |
|---|---|---|---|---|---|
| Biopsy # | Ca++ | Weight (g) | 1st Dig | 2nd Dig | # Dead |
| 1 | − | 0.03 | 70,000 | 165,000 | 10,000 |
| 2 | − | 0.03 | 55,000 | 150,000 | — |
| 3 | − | 0.02 | 35,000 | 60,000 | 10,000 |
| 4 | − | 0.03 | 115,000 | 105,000 | 20,000 |
| 5 | + | 0.03 | 35,000 | 230,000 | 60,000 |
| 6 | + | 0.02 | 20,000 | 85,000 | 70,000 |
| 7 | + | 0.02 | 40,000 | 145,000 | 40,000 |
| 8 | + | 0.02 | 80,000 | 135,000 | 60,000 |

| % Viable | total combined yield | # Cells/(g) biopsy | # Cells/(mg) |
|---|---|---|---|
| 94% | 235,000 | 7,833,333 | 7,833 |
| 100% | 205,000 | 6,833,333 | 6,833 |
| 86% | 95,000 | 4,750,000 | 4,750 |
| 84% | 220,000 | 7,333,333 | 7,333 |
| 79% | 265,000 | 8,833,333 | 8,833 |
| 55% | 105,000 | 5,250,000 | 5,250 |
| 78% | 185,000 | 9,250,000 | 9,250 |
| 69% | 215,000 | 10,750,000 | 10,750 |

TABLE 19

Post-expansion yield (p0).

| Biopsy # | Day 0 | Day 5 | Fold Expansion |
|---|---|---|---|
| BP1 | 235,000 | 1.75E+06 | 7.43 |
| BP2 | 205,000 | 1.22E+06 | 5.95 |
| BP3 | 95,000 | 2.51E+05 | 2.64 |
| BP4 | 220,000 | 1.30E+06 | 5.91 |
| BP5 | 265,000 | 1.35E+06 | 5.10 |
| BP6 | 105,000 | 1.41E+06 | 13.41 |
| BP7 | 185,000 | 1.15E+06 | 6.22 |
| BP8 | 215,000 | 1.04E+06 | 4.84 |
| AVG | 190,625 | 1,183,375 | 6 |

The average yield after enzymatic digestion of kidney biopsies from diseased human tissue was 7,604+/−807 cells/mg tissue. A calcium-free rinse step prior to enzymatic digestion improved viability and led to a suspension comprised predominantly of single cells. A calcium-containing rinse step prior to enzymatic digestion marginally improved yield, reduces overall viability, and led to a suspension comprised predominantly of cell clusters. All (8/8) biopsies initiated from HK0019 yielded viable cultures. The majority (7/8) of the biopsy-initiated cultures expanded significantly over time, with an average fold expansion of 6.0 during 5 days of culture.

Example 17

Isolation, Culture and Expansion of Renal Cells from Multiple Species

The objective of this analysis was to examine and compare key isolation, characterization, and expansion (ICE) performance characteristics of kidney cell isolates generated from rodent, canine, porcine, and human kidney specimens.

Kidney Tissue Procurement: All kidney tissues were collected/provided in compliance with FDA and institutional guidelines on the use of human or mammalian tissues for research. All human specimens were provided by National Disease Research Institute (NDRI). Porcine specimens (PK01 & PK02) and (2) canine specimens (DK01 and DK02) were provided by Dr. Timothy Nichols at the University of North Carolina at Chapel Hill. DK03 was sourced from a normal beagle (Jackson Laboratories).

Cell Isolation & Culture. Received tissues were weighed and dissociated. In some experiments, minimal tissue requirements were assessed through the use of various-sized biopsy needles. In other experiments, the maximum amount of tissue possible was dissociated in order to generate cryopreserved stocks of cells that could be used in future experiments. Tissues were subjected to enzymatic digestion methods or explant culture to establish p0 primary cultures. Established cultures were then passaged and/or cryopreserved.

Results

Figure 115:
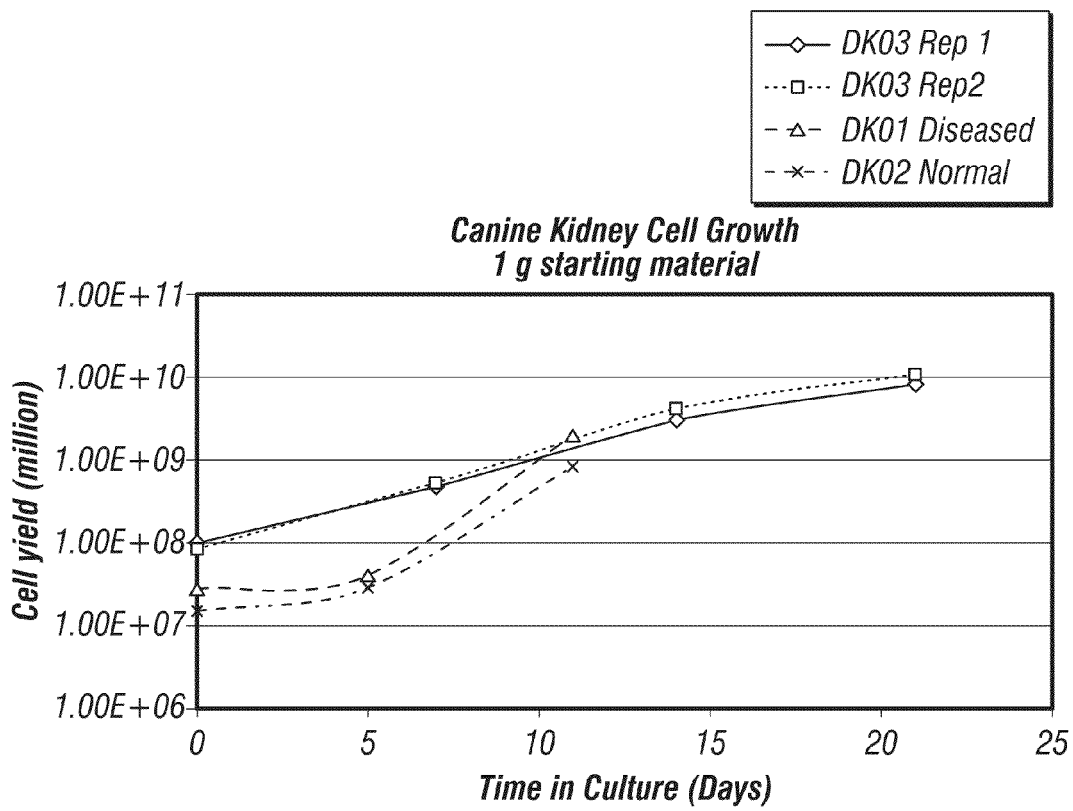
FIG. 115 shows canine kidney cell growth.
Figure 116:
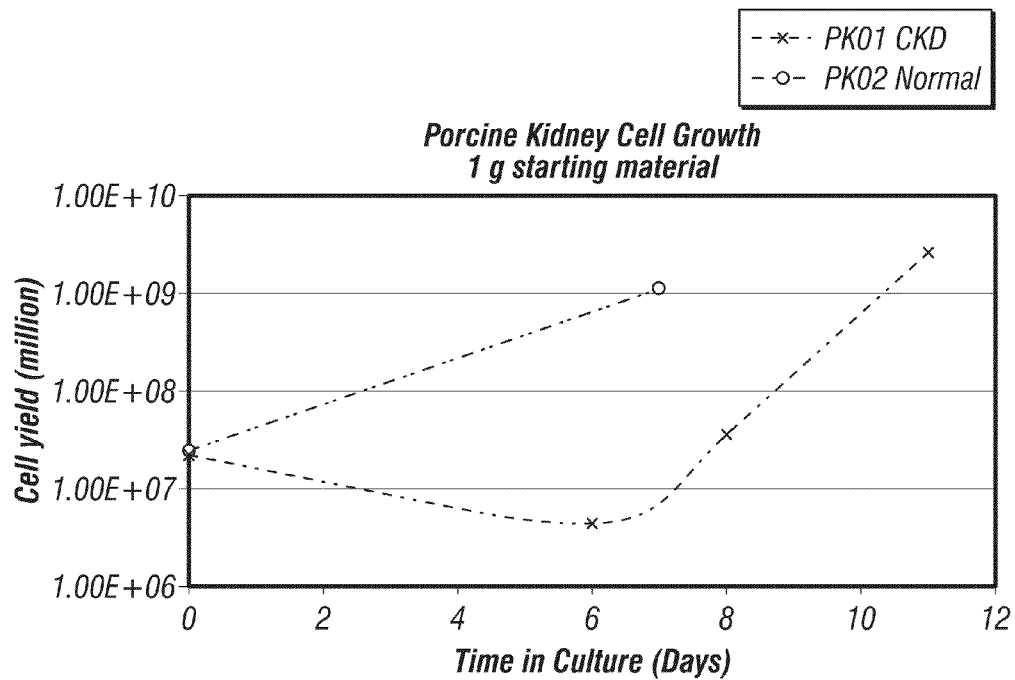
FIG. 116 shows porcine kidney cell growth.
Figure 117:
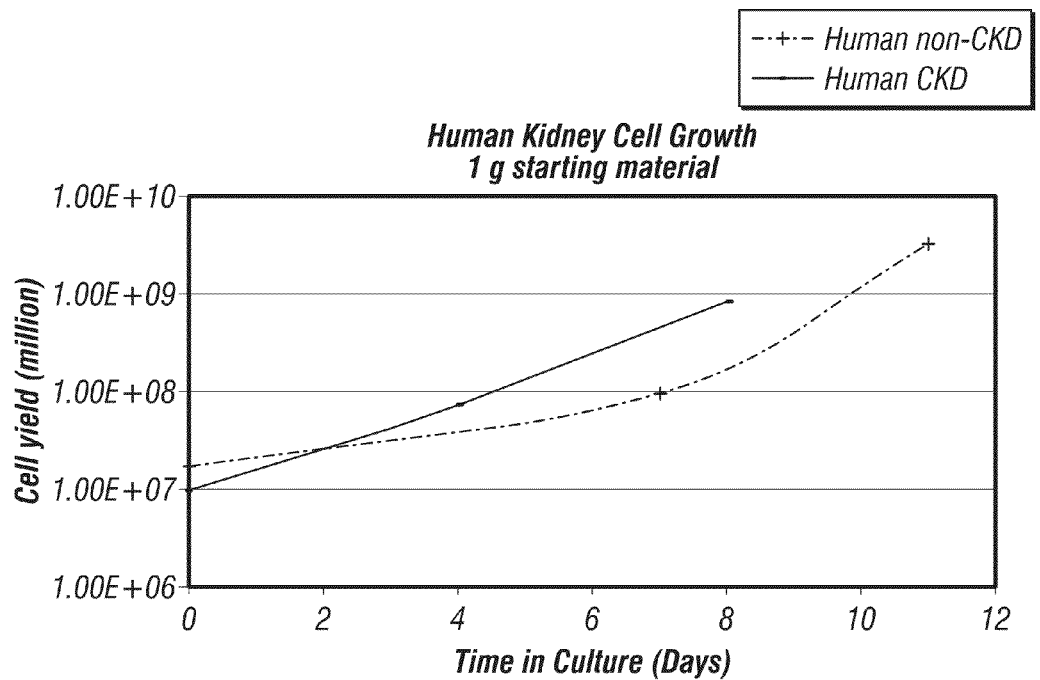
FIG. 117 shows human kidney cell growth.
Figure 118:
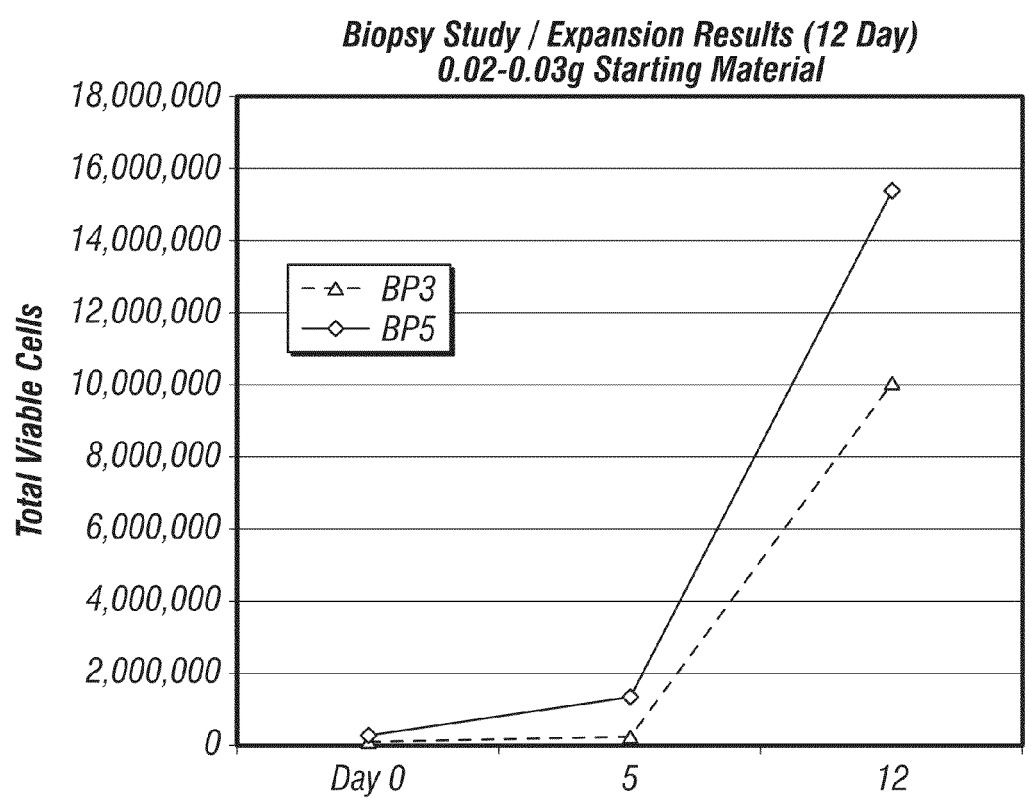
FIG. 118 depicts cell expansion results from human biopsy.
Figure 122A:
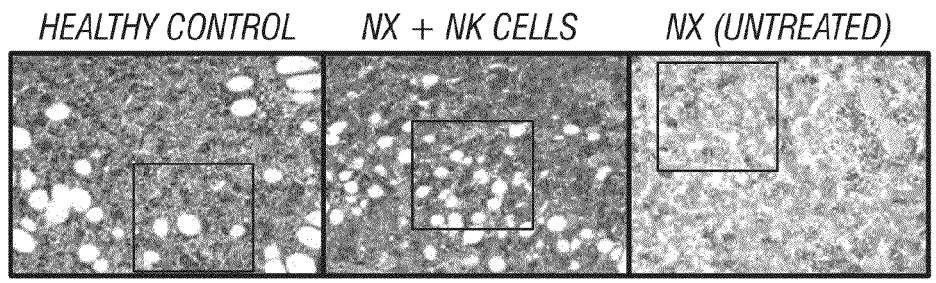
Figure 122B:
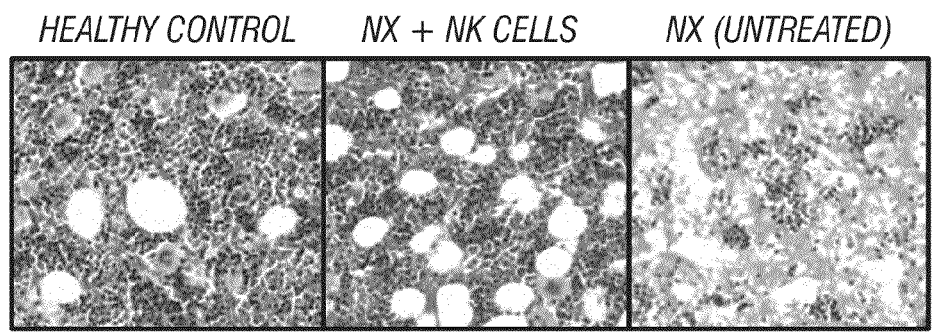
Figure 122C:
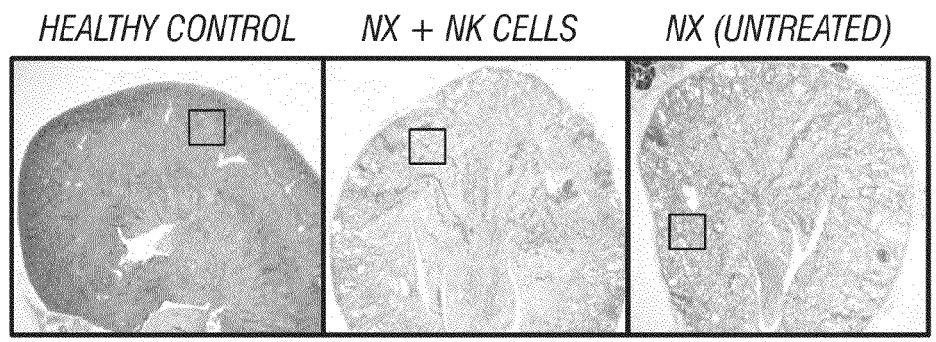
Figure 122D:
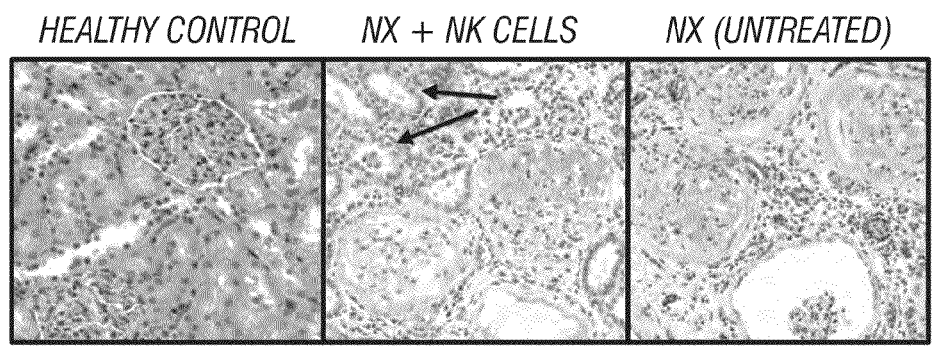

Yield/Feature Comparison. The average yield per gram tissue was calculated for each category (see Table 20 below). With the exception of juvenile rodent tissue and CKD human tissue, most yields fell within 17-25 million cells/gram. Expansion was achieved from all species as well (FIGS. 115-117), and with the exception of rodent-derived cultures, serial passaging and re-establishment of cultures from cryopreservation was achieved. Fractionation of the cultured cells into specific subpopulations was also achieved across all species. Detection of EPO gene expression was reliable in cultured cells from all species, even when cells were isolated from diseased kidney tissue. Hypoxia-stimulated induction of EPO expression was observed in all species, with the exception of normal adult rat (diseased adult rat cultures did exhibit hypoxic stimulation), and in a normal dog. Tubular cell presence/function was assayed by detection of specific tubular markers (Aquaporin, Vitamin D Hyroxylase, Cubilin, Megalin) and by functional albumin uptake assays. Examples of growth kinetics are shown for dog, pig, and human in (FIGS. 115-117). FIG. 118 is an example of human cell growth kinetics from HK019, CKD kidney cultures, generated from diseased tissue biopsies weighing between 0.02-0.03 g (see additional details above in Example 16). In FIG. 118, BP3 represents the lowest-yield biopsy (from a total of 8) while BP5 represents a high-yield biopsy.

TABLE 20

Kidney cell ICE, species comparison.

| Species | # Preps | # Successful Cell Isolations | Avg Cell Yield (cells/gm tissue) | EPO Expression | EPO Regulation | Tubular Cell Function | Tubular Cell Identified | Successful Expansion | Isolation of Prototypes | Successful Cryopreserve |
|---|---|---|---|---|---|---|---|---|---|---|
| Rat (Lewis) Juvenile | 49 | 49/49 | 177e6 | 49/49 | 49/49 | 6/7 | 49/49 | 49/49 | Y | Y |
| Rat (Lewis) Adult | 11 | 11/11 | 40e6 | 3/3 | 7/8 | ND | 8/8 | 4/4 | Y | Y |
| Rat (Lewis) Adult 5/6 NX | 1 | 1/1 | 16e6 | 1/1 | 1/1 | ND | 1/1 | 1/1 | ND | ND |
| Rat (ZSF1) Obese Adult | 5 | 5/5 | 42e6 | 5/5 | ND/1 | 1/1 | 5/5 | 5/5 | Y | Y |
| Rat (ZSF1) Lean Adult | 7 | 7/7 | 66e6 | 7/7 | ND/1 | 1/1 | 7/7 | 7/7 | Y | Y |
| Canine (Beagle) Normal | 2 | 2/2 | 67e6 | 1/1 | 1/1 | 1/1 | 1/1 | 2/2 | Y | Y |
| Canine (Mongrel) Normal | 5 | 5/5 | 34e6 | 5/5 | 4/5 | 5/5 | 5/5 | 5/5 | Y | Y |
| Canine (Mongrel) Diseased | 1 | 1/1 | 27e6 | 1/1 | 1/1 | 1/1 | 1/1 | 1/1 | Y | Y |
| Porcine Normal | 1 | 1/1 | 13e6 | 1/1 | 1/1 | 1/1 | 1/1 | 1/1 | Y | Y |
| Porcine Diseased | 1 | 1/1 | ND | 1/1 | 1/1 | 1/1 | 1/1 | 1/1 | Y | Y |
| Human Normal | 17 | 17/17 | 24e6 | 3/3 | 3/3 | 3/3 | 3/3 | 17/17 | Y | Y |
| Human Diseased | 4 | 3/4 | 7e6 | 3/3 | 3/3 | 2/3 | 3/3 | 3/3 | Y | Y |

In conclusion, renal cell isolation/expansion can be achieved from rodent, dog, pig, and human kidney tissues. Renal cell isolation/expansion can be achieved from confirmed cases of CKD. Small pieces of tissue, weighing as little as 0.02 g, can give rise to propagable cultures of renal cells. Functional tubular cells and hypoxia-responsive epo-expressing cells are components of isolated and expanded renal cell cultures.

Example 18

Cells with Therapeutic Potential can be Isolated and Propagated from Normal and Chronically-diseased Kidney Tissue The present study was designed to determine whether cultured populations of renal cells, including the recently-described EPO-producing cells (Aboushwareb, *World J. Urol.* 2008 August; 26(4):295-300. Epub 2008 Jul. 8), were capable of delivering systemic benefit(s) in a progressive and terminal model of renal failure, when delivered after the disease state was established. A pilot study conducted in rodents demonstrated clear multi-factorial therapeutic potential of cells contained within the population, and highlighted the heterogeneous nature of the cultured cells, which contained prominent populations of tubular cells and endocrine cells with clear functional attributes, as well as other cell types (glomerular, vascular, and collecting duct). As autologous regenerative medicine approaches are contemplated for the potential treatment of CKD, it is necessary to determine whether specific cellular component(s) with therapeutic potential are retained or lost as the disease progresses. Thus, whole kidney tissue was collected from human organ donors with established CKD to determine whether functional tubular and endocrine cells were present in the tissue and could be isolated and propagated successfully. The data presented herein provide evidence that: 1) isolated and propagated cell cultures that contain functional tubular and endocrine cells provide significant clinically-relevant benefits in a rodent model of progressive kidney disease; and 2) analogous cells are retained and can be isolated and propagated from severe cases of CKD. Taken together, these data support further investigation into autologous cell-based approaches for the treatment of CKD.

Materials & Methods
Cell Isolation and Culture

Initial tissue dissociation was performed as described previously to generate heterogeneous cell suspensions from mouse kidney tissue (Aboushwareb T, et al., World J Urol 2008, 26:295-300, Joraku A, et al., Methods 2009, 47:129-133). Briefly, the rat, swine, or human kidneys were washed with Hanks Balanced Salt Solution (HBSS) (Sigma, St. Louis Mo.) and macrodissected to select the corticomedullary junction tissue prior to employing the digestion techniques (Joraku A, et al., Methods 2009, 47:129-133). Macrodissected tissue was minced, weighed, and dissociated in buffer comprised of 4 Units of Dispase 1 (Stemcell Technologies, Vancouver BC) in Hanks Balanced Salt Solution (HBSS) (Sigma), 300 Units/ml of Collagenase type IV (Worthington Biochemical Corp., Lakewood N.J.) with 5 mM $CaCl2$ (Sigma). The resulting cell suspension was neutralized in Dulbecco's Modified Eagle Medium (D-MEM)+10% fetal bovine serum (FBS) (Invitrogen, Carlsbad Calif.), washed, and resuspended in serum-free, supplement-free, Keratinocyte Media (KSFM) (Invitrogen). Cell suspensions were then subjected to a 15% (w/v) iodixanol (OptiPrep™, Sigma) gradient to remove red blood cells and debris prior to initiation of culture onto tissue culture treated polystyrene flasks or dishes at a density of 25,000 cells per cm2 in a 1:1 mixture of high-glucose (4.5 g/L) DMEM:KSFM containing 5% (v/v) FBS, 2.5 μg human recombinant Epidermal Growth Factor 1-53 (rEGF 1-53), 25 mg Bovine Pituitary Extract (BPE), 1×ITS insulin/transferrin/selenium), and with 1× antibiotic/antimycotic (all from Invitrogen). In some cases, alternative cell isolation methods were employed and explant cultures were established from kidney tissue, which involved attachment of small (0.01-0.02 g) corticomedullary junction tissue cores to tissue culture-treated polystyrene dishes followed by humidified incubation at 37° C./5% CO2 in the same culture media described above. Within 7-14 days, explanted tissues gave rise to propagable cell cultures that were subcultured in the same manner as cultures established from enzymatically-digested tissue. Cells were detached for harvest or passage with 0.25% Trypsin with EDTA (Invitrogen). Viability was assessed via Trypan Blue exclusion and enumeration was performed manually using a hemacytometer or using the automated Cellometer® counting system (Nexcelom Bioscience, Lawrence Mass.).

Rodent Pilot Study

Donor rodent cultures were established from male Lewis rats (Hilltop) as described previously 25, 26. Monolayer cultures were maintained on tissue culture-treated polystyrene flasks in a 1:1 mixture of high-glucose DMEM and supplemented KSFM (Invitrogen). Prior to transplantation, cells were harvested with 0.25% Trypsin+EDTA (Invitrogen) and washed 3× in sterile Phosphate Buffered Saline (PBS), pH 7.4 (Invitrogen) to remove serum and media components. The harvested Neo-Kidney cells (NK-CELLS) were resuspended and aliquoted into sterile tubes at a concentration of 10 million cells/120 μL in sterile PBS, pH 7.4. Recipient rats were purchased from Charles Rivers Laboratories after having undergone a two-step 5/6 nephrectomy at the supplier. All handling, manipulation, and care of rats was conducted at RTI International (Research Triangle Park, N.C.) in compliance with IACUC and NIH policies on the use of laboratory animals. Age-matched unmanipulated female rats were carried as healthy controls (HEALTHY, n=5). Additional controls were generated by conducting a sham nephrectomy procedure, in which an incision was made but no kidney damage or tissue removal occurred (SHAM NX, n=5). In Series 1, (2) rats received cell transplants (10×106 NK-CELLS), and (4) nephrectomized rats were maintained as untreated controls (NX). In Series 2, (5) rats received cell transplants (5×106 NK-CELLS) and (4) rats were maintained as untreated controls (NX). Rats receiving NK-CELLS were sedated prior to surgical preparation with 0.3 mg/kg buprenorphine (Buprenex®, Reckitt Benckiser Pharmaceuticals, Inc., Richmond Va.) delivered via intraperitoneal injection. Anesthesia was initiated by placement in an isoflurane chamber and maintained via nose-cone throughout the procedure. The right dorsolateral area was shaved and cleansed with betadine and ethanol prior to making a small dorsolateral incision to expose the remnant kidney. NK-CELLS suspensions were delivered directly to the kidney parenchyma via a sterile 1.0 cc syringe fitted with a 23G needle (Becton Dickinson, Franklin Lakes N.J.). The muscle layer was closed with 4-0 Vicryl and the skin closed using wound clips (both from Ethicon, Somerville N.J.). Animals were administered oxygen and monitored post-operatively until awake and alert. All rats received an additional 0.3 mg/kg dose of Buprenex® after surgery. Blood was drawn weekly via tail vein or orbital bleed throughout the study to monitor serum BUN and CREAT, HCT and RBC#. All serology and hematology was conducted at Antech (Research Triangle Park, N.C.). When animals were sacrificed moribund or at the end of the study, body and organ weights were collected and tissue samples (kidney, femur, & sternum) were formalin-fixed and paraffin-embedded for histological analyses.

Swine and Human Tissue Procurement

Swine tissue was generously provided by Dr. Tim Nichols (Department of Pathology, University of North Carolina at Chapel Hill, School of Medicine). CKD and non-CKD swine kidney tissue was procured at the time of sacrifice from adult male swine (*Sus scrofa*), in compliance with all institutional policies in place at the University of North Carolina at Chapel Hill governing the use of laboratory animals. Sample PK001 was procured from an adult male breeder swine that developed idiopathic nephropathy persisting over the course of six months with increasing sCREAT and BUN values until sacrificed moribund with severe kidney failure. Sample PK002 was procured from an adult male swine without kidney disease. CKD and non-CKD human kidney tissue was provided by the National Disease Research Institute (NDRI) in compliance with all NIH guidelines governing the use of human tissues for research purposes. Age, gender, disease etiology and cause of death are presented below for each sample in Table 21. HK018 was procured from a donor with a 6 year history of vascular dialysis. HK019 was procured from a donor with a 23 year history of NIDDM and 8+years of renal failure without dialysis and non-compliant with medications. HK020 was procured from a donor with a>8-year history of peritoneal dialysis. Specimens were shipped on ice at 4° C. in either Viaspan™ organ preservation solution (DuPont, Wilmington Del.) (human) or Hypothermasol® (BioLife Solutions, Bothell Wash.) (swine tissue) and were received at Tengion Labs within 24 hours of harvest.

Histological Analyses

All tissues processed for histological analysis were placed in 10% buffered formalin for 24-48 hours and subsequently placed into 70% ethanol for transport to Premier Laboratory (Longmont, Colo.) for paraffin-embedding and staining Hematoxylin and eosin (H&E), Periodic Acid Schiff (PAS), and Masson's Trichrome staining were performed according to standard protocols. Images were captured at 100×, 400×, 1000× and 2000× on a Nikon Eclipse 50i microscope fitted with a Digital Sight (DS-U1) camera. Tissues were assessed by a veterinary pathologist and histopathologist to assess the degree of glomerulosclerosis, tubulointerstitial fibrosis, protein casts in tubular lumens, and basic compartmental organization.

Gene Expression Analysis

RNA was isolated from kidney tissue and cell culture samples as follows: tissue or cells were homogenized using the QIAshredder (Qiagen, Valencia Calif.) and RNA was isolated using an RNeasy Plus Mini isolation kit (Qiagen). RNA integrity was verified and samples were quantified via spectrophotometric analysis. cDNA was synthesized using the Superscript® Vilo cDNA synthesis kit (Invitrogen). Expression of Erythropoietin (EPO), E-Cadherin (E-CAD), N-Cadherin (N-CAD), Cubilin (CUB), 1 alpha, 25-Dihydroxyvitamin D3-24-Hyroxylase (CYP24), Aquaporin-1 (AQP-1), Aquaporin-2 (AQP-2), Nephrin (NEPH), Podocin (PODO), vascular Endothelial Growth Factor (vEGF), CD31, and vEGF receptor (KDR) were examined via quantitative real-time PCR using catalogued Taqman Probes and Primer sets from Applied Biosystems (Foster City, Calif.) and an ABI-Prism 7300 Real Time PCR System. Samples were normalized to cDNA amplified from endogenous 18s rRNA (for abundantly-expressed human or rodent genes), peptidylprolyl isomerase B (PPIB) (for intermediately-expressed rodent genes), or peptidylprolyl isomerase A (PPIA) (for intermediately-expressed human genes), and calibrated against the source kidney tissue or against kidney cDNA of the same species purchased from OriGene Technologies (Rockville, Md.).

Immunologic Analyses

Cell suspensions were generated from initial tissue dissociation or trypsinization of adherent cultures and analyzed by flow cytometry to identify and quantify cellular components. Antibodies employed included tubular markers E-CAD, N-CAD (both from Becton Dickinson), Cubilin (CUB) (Santa Cruz Biotechnology, Inc., Santa Cruz Calif.), AQP-1, and AQP-2 (Abeam, Inc., Cambridge Mass.). Glomerular cells were labeled with Nephrin (NEPH) (Zymed Laboratories, Inc., San Francisco Calif.). Vascular marker CD31 (Becton Dickinson) was used to identify endothelial cells. EPO-producing cells were identified using a monoclonal EPO antibody (US Biological, Swampscott Mass.) and standard indirect intracellular staining techniques. Collecting duct cells were identified via binding of Dolichos biflorus agglutinin (DBA) (Zymed Laboratories, Inc.). Lack of species-specific antibodies and poor cross-reactivity among antibody reagents prevented the application of all markers to cells derived from rat and swine. Isotype-specific primary antibody negative controls were used in all experiments. Labeled cells were analyzed with a FACSAria flow cytometer (Becton Dickinson) and FlowJo software (Treestar, Inc.). Appropriate isotype-matched controls were used to gate negative populations. Multi-parameter analysis was used to determine the relative percentages of tubular and EPO positive cells using intracellular indirect staining. After cells were labeled with surface tubular markers, the cells were then permeabilized using permeabilization/blocking buffer (PBS containing 0.2% Triton X-100 and 10% goat serum) for 60 minutes, pelleted, and resuspended in permeabilization/staining buffer (PBS containing 0.2% Triton X-100 and 2% goat serum) containing primary antibody to EPO (US Biological) at a concentration of 1 µg/mL/1×106 cells. After an overnight incubation at 4° C., the cells were pelleted, washed twice with Triton Buffer (0.2% Triton X-100 in PBS), resuspended in 1 mL of permeabilization/staining buffer containing secondary antibody goat anti-mouse IgG2A conjugated to the fluorochrome Alexa A647 (Invitrogen), and incubated for an additional 30 minutes. Cells were then washed and resuspended in 1 mL of PBS for analysis as per manufacturer instructions using FACSAria and FlowJo software. As a negative control, cells were incubated in parallel with isotype-matched monoclonal antibodies conjugated to the same fluorochrome. In some experiments, monolayer cultures were also stained with the antibodies listed above and visualized by fluorescence microscopy to further confirm presence and relative distribution of specific cells within the cultured population. Cells were cultured in a 96 well tissue culture treated plate (BD Falcon 353219) at a density of 10,000 cells per well to ~85% confluence and fixed for 1 hour at room temperature in 4% paraformaldehyde (PFA). Fixed cells were washed in PBS then blocked for 10 minutes in PBS with 0.5% BSA (Sigma). Blocked cells were labeled overnight at 4° C. with 3 µg/µl primary antibodies or matched isotype controls (Zymed Laboratories, Inc., San Francisco Calif.). Labeled cells were washed in PBS and labeled with isotype-matched secondary antibodies conjugated to Alexa 488 or Alexa 647 (Invitrogen) at a concentration of 1 µg/ml for 30 minutes at room temperature protected from light. Cells were washed in PBS and imaged using a BD Pathway 855 High-Content BioImager (Becton Dickinson).

Isoelectric Focusing & Western Blotting for Detection of EPO

Frozen whole kidney tissue embedded in Optimum Cutting Temperature (OCT) freezing media was utilized for protein sample collection. Non-serial 10-micron sections (7-8) of the kidney (encompassing capsule, cortex, medulla, and calyx) were pooled into a 1.5 mL polypropylene microfuge tube, allowed to thaw to 4° C., and centrifuged for 1 minute at 13,000 RPM. Residual OCT media was removed and tissue was lysed in a buffer consisting of 50 mM Tris (pH 8.0), 150 mM NaCl, 0.5% NP40, and protease inhibitor cocktail (Roche Applied Science, Indianapolis Ind.). Lysis proceeded for 10 minutes at room temperature with intermittent vortex every 2 minutes. Samples were centrifuged for 1 minute at 13,000 RPM and lysate supernatants were transferred to a fresh tube. Protein concentrations were determined via Bio-Rad Quick Start Bradford Assay using BSA as standard, and the samples were normalized to the least concentrated sample with lysis buffer. Lysates were also prepared from cultured HepG2 cells (a human liver celline known to express EPO) and NIH3T3 mouse fibroblasts (a negative control). Isoelectric focusing (IEF) was carried out by adding 40 μg of protein per sample to each well of pH 3-10 IEF Gels (Invitrogen). The gels were electrophoresed for 1 hour at 100V followed by 1 hour at 200V and finally 30 minutes at 500V in pH 3-10 cathode and anode buffer (Invitrogen). The proteins were then transferred to a nitrocellulose membrane using the I-Blot system (Invitrogen) following the manufacturer's instructions, and blocked with 30 mL of 4% w/v low-fat milk dissolved in Tris Buffered Saline with 0.1% Tween-20 (TBS-T) (Sigma, St. Louis, Mo.) for 2 hours at room temperature with rocking. The membrane was probed overnight at room temperature with anti-human EPO monoclonal IgG2a MAb 2871 (R&D Systems, Minneapolis Minn.) at a 1:600 dilution in 5 mL TBS-T (0.1% Tween 20) with 2% w/v low-fat milk. The membrane was washed 3 times/10 minutes each with TBS-T, then probed with an HRP-conjugated rabbit antimouse IgG (Zymed, San Francisco Calif.) at a 1:50,000 dilution in TBS-T with 2% w/v low-fat milk for 1.5 hours at room temperature with rocking. The membrane was washed three times/10 minutes each in TBS-T, followed by two 10-minute washes in diH2O. The blot was developed using ECL Advance chemiluminescent reagent (GE Healthcare Life Sciences, Piscataway N.J.) following the manufacturer's instructions.

Albumin Uptake Assay

Kidney proximal tubular cell function was assessed by the activation and inhibition of albumin endocytosis mediated by specific proximal tubule receptors, Megalin and Cubilin, as described by Zhai et al 27. Human and swine kidney cells were seeded at a density of 5,000 and 10,000 cells per well, respectively, or 25,000 and 40,000 cells per well (rat) in 96-well plates (Optiplate™, Becton Dickinson) in standard culture media (1:1 mixture of high glucose (4.5 g/L) DMEM: KSFM with all supplements as previously described). Cells were incubated at 37° C./5% CO2 and grown to ~85% confluency prior to conducting the assay. Growth media was replaced with phenol red-free, serum-free, low-glucose (1 g/L) DMEM containing 1× antibiotic/antimycotic and 2 mM glutamine 18-24 hours prior to assay initiation (all from Invitrogen). On the day of assay, cells were washed twice with assay buffer consisting of phenol red-free, low-glucose DMEM supplemented with 10 mM HEPES, 2 mM Glutamine, 1.8 mM CaCl2 and 1 mM MgCl2, and incubated with assay buffer for 30 minutes in a humidified chamber at 37° C./5% CO2 to ensure adequate exposure to cofactors. Cells were then exposed to a final concentration of 25 μg/mL fluorescein-conjugated or rhodamine-conjugated bovine albumin (Invitrogen) or human serum albumin (Abcam, Inc.) for 30 minutes at 37° C./5% CO2. Wells were washed three times with ice cold PBS to stop endocytosis and fixed immediately with 2% PFA containing 10 μg/mL Hoechst nuclear dye (Invitrogen). For inhibition studies, recombinant Receptor-associated Protein (RAP) (Ray Biotech, Inc., Norcross Ga.), a specific competitive inhibitor of Megalin:Cubilin-mediated albumin uptake 27, was utilized to demonstrate specificity of the reaction. Cultures were prepared as described above and incubated with 1 μM RAP and 12.5-25 μg/mL of fluorescently conjugated albumin. In further experiments, receptor-mediated albumin uptake was partially inhibited by lowering incubation temperature of the assay to 4° C. In all cases, cells were visualized and images captured via microscopy using a BD Pathway 855 High-Content Biolmager (Becton Dickinson).

Results

Functional Tubular and EPO-expressing Cells Provide Therapeutic Benefits in a Rodent Model of Renal Insufficiency Primary kidney cell cultures were isolated successfully from male Lewis rats according to the methods described by Aboushwareb et al. for mouse (Aboushwareb T, et al., World J Urol 2008, 26:295-30025), and characterized to confirm oxygen-regulated expression of the EPO gene by cells within the culture (included in FIG. 125C). Further immunocytochemical characterization of multiple established cultures showed that the predominant cell phenotype was tubular (proximal or distal), but that glomerular, collecting duct, and vascular cells were also present (FIG. 119). Flow cytometric analyses across multiple preparations established the relative frequency of both proximal and distal tubular cells to be 20-35% each, glomerular cells 10-15%, vascular cells<5%, collecting duct cells 10-15%, and EPO-producing endocrine cells<10%. The native EPO-producing cells in the kidney have been identified by Maxwell et al as highly specialized interstitial fibroblasts, enriched in the peritubular region of the corticomedullary junction 28. In vivo studies have shown that, under conditions of severe hypoxia, the number of interstitial fibroblasts expressing EPO increases (Eckardt K U, et al., Kidney Int 1993, 43:815-823), and EPO expression has been demonstrated in tubular cells as well upon exposure to cobalt chloride (Mujais S K, et al., Cell Biochem Biophys 1999, 30:153-166). Multi-parameter flow cytometry was utilized to demonstrate that the EPO-expressing cells contained within the rat cultures were distinct from both proximal and distal tubular cells (FIG. 120A, B). Functionality of cubilin-positive proximal tubular cells in the cultures was assessed via uptake of fluorescence-conjugated albumin, and specificity of the uptake was confirmed by the addition of a competitive inhibitor, RAP (FIG. 120C-F). Thus, the rodent cultures contained at least two cell types with potential therapeutically-relevant functions—the hypoxia-responsive EPO-expressing cells and the tubular cells capable of protein uptake.

Female Lewis rats, having been subjected to a two-step 5/6 nephrectomy at the vendor, were subjected to weekly blood draws to assess renal filtration function via sCREAT and BUN, and erythropoiesis via HCT and RBC. Within 4 weeks of the nephrectomy, sCREAT and BUN were nearly doubled, and the HCT was depressed compared to healthy matched controls that did not receive a nephrectomy, or had a sham nephrectomy procedure. 100% (15/15) of the rats that received the nephrectomy procedure progressed to a state of renal failure, with no spontaneous recovery observed. Between 7-8 weeks after nephrectomy, some rats received a bolus dose of cultured male NK-CELLS intrarenally. A second group of rats received no intervention. The rats were followed for up to 3 months post-treatment, with weekly monitoring of filtration function via sCREAT and BUN (sCREAT shown in FIG. 121A), and erythropoiesis via HCT and RBC number (HCT shown in FIG. 121B). In this study, all untreated rats died within 12-16 weeks of the nephrectomy procedure (4-8 weeks beyond the time of treatment). In contrast, all of the NK-CELL-treated rats survived until the study endpoint (3 months post-treatment). At termination, comparative clinical chemistry was conducted to identify additional potential therapeutic effects of the cell treatment (FIG. 121C), and histologic analyses were conducted to identify tissue-level effects in both the kidney and bone marrow (FIG. 122). Despite small sample numbers, statistically-significant improvements were associated with the NK-CELL treatment with regard to both renal function (sCREAT, BUN), and endocrine/erythropoiesis function (HCT). FIG. 121C highlights the key clinical features of the 5/6 Nx model, including significant reductions in HCT, RBC#, hemoglobin (HB), serum albumin (sALB), and serum total protein (TPRO), as well as significant increases in serum BUN, sCREAT, and serum phosphorous (sPHOS). Importantly, treatment with NK-CELLS led to serum BUN, sCREAT, and sPHOS levels that were significantly lower than those of untreated NX rats, and also provided significant enhancement of HCT, RBC#, sALB, and TPRO (FIG. 121C). Furthermore, comparative histological examination of the renal parenchyma showed a slight decrease in glomerulopathy in focal areas, as well as focal regeneration of tubules and a slight reduction in protein casts when compared to the nephrectomized untreated kidneys. The systemic positive effects noted on erythropoiesis throughout the study (HCT and RBC) were confirmed histologically upon examination of bone marrow of the proximal femur and sternum, which showed clearly that the bone marrow of NK-CELL-treated rats was more cellular with a greater presence of erythroid cells when compared to the untreated rats (FIG. 122). Presence of male donor cells in the female host kidney at the time of sacrifice was confirmed by detection of the y-chromosome-specific SRY gene in genomic DNA of the host kidney (data not shown). Taken together, these preliminary in vivo observations indicated that NK-CELLS are capable of providing therapeutic value in the 5/6 nephrectomy model of chronic progressive renal failure, resulting in enhanced overall survival, stabilization of renal filtration function, retention of serum protein, reduction of serum phosphorous, and restoration of erythroid homeostasis (FIG. 121C).

Successful Translation of Functional Renal Cell Isolation to Swine and Human with CKD Based on the work of Aboushwareb et al and on the results of the rodent pilot study, which showed that therapeutic benefits were derived from transplantation of the cultured renal cell population, we next sought to determine: 1) whether analogous cellular equivalents could be isolated and propagated from large mammal species; and 2) whether analogous cellular equivalents were present in cultures established from kidneys of subjects with CKD. A total of (2) swine and (5) human kidney specimens were utilized according to materials & methods. Renal failure was confirmed in human (HK018, HK019, and HK020) and swine (PK001) CKD specimen via serologic and histopathologic examination. Table 21 summarizes key systemic parameters associated with compromised kidney function as measured in CKD and non-CKD specimens at the time of death, and highlights the elevation in BUN and sCREAT in the swine and human CKD subjects. Furthermore, mild to moderate deficits in HCT and/or hemoglobin HB were noted in the CKD subjects, indicative of the anemia that typically accompanies the advanced stages of renal failure. Histopathologic features of the CKD specimens are presented in FIG. 123 and contrasted with histologic features of non-CKD kidney specimens from both swine and human. Note the hallmark fibrosis, glomerular sclerosis, and tubular dilatation with protein casts in the CKD tissues compared to non-CKD tissues. The three human CKD specimens represented a range of disease severity and etiology. Both HK018 and HK019 subjects had renal failure secondary to non-insulin-dependent diabetes mellitus (NIDDM) and hypertension; HK018 represented a compliant patient with a>6-yr history of vascular dialysis at the time of death, while HK019 represented a non-compliant patient who did not undergo dialysis or take medications reliably. HK020 had a history of renal failure secondary to autoimmune disease and was compliant with a>8-yr history of peritoneal dialysis. Interestingly, and unlike HK018 and HK019, the HK020 kidneys were severely undersized (<3 inches longitudinally) and appeared grossly as pale, fibrotic, and moderately cystic. FIG. 123 highlights the severity of the histologic disease in HK020, with few viable tubules or glomeruli present.

Isolation and Propagation of Functional Tubular Cells.

While multiple cell types were detected in the rodent cultures (see FIG. 119 and Table 22), the predominant phenotype was tubular in nature, and both systemic and histologic data from the rodent pilot study supported therapeutic benefit in the tubular compartment upon in vivo transplant of the rodent renal cell cultures. Therefore, we sought to determine the feasibility of functional tubular cell isolation and propagation from the swine and human tissues. Primary cell cultures were initiated from swine and human CKD tissues by methods established using non-CKD tissue as starting material. Regardless of disease state (non-CKD or CKD) or species (swine or human), cultures predominantly comprising tubular epithelial cells were established and propagated by either enzymatic-digestion methods or nonenzymatic explant methods using small (<0.02 g) pieces of tissue. In a direct comparison, no significant differences were noted in expansion capacity between CKD- and non-CKD-derived cultures (FIG. 124A). Tubular cell function was confirmed in the established cultures by observing receptor-mediated uptake of albumin in a portion of cubilin positive cells (FIGS. 124B-D, and Table 22). Cultured primary cells from swine and human CKD and non-CKD tissue retained tubular marker expression and albumin uptake function after serial passage (through p4). The presence and relative expression of tubular, glomerular, collecting duct, vascular, and endocrine markers in established cultures was evaluated by quantitative real-time PCR in swine and human cultures and compared to rodent (Table 22).

Isolation and Propagation of Oxygen-Responsive EPO-Expressing Cells.

Presence of EPO-expressing cells was confirmed in CKD and non-CKD tissues upon receipt via qRTPCR. Despite the presence of systemic anemia in the CKD subjects at the time of tissue procurement (see Table 1), EPO mRNA was expressed more abundantly in the CKD vs. non-CKD tissue specimens upon receipt (representative samples shown in FIG. 125A). Isoelectric focusing and western blot analysis of these samples confirmed that the gene expression patterns were recapitulated in general at the protein level (FIG. 125B). All CKD and non-CKD kidney tissues yielded propagable cultures that contained EPO expressing cells. Oxygen-responsiveness is a key feature required of EPO-expressing cells in vivo for the maintenance of erythroid homeostasis. We therefore examined the ability of cultured EPO-expressing cells to respond to a hypoxic stimulus with upregulation of EPO transcription. EPO-expressing cell cultures established from both CKD and non-CKD kidney specimens responded to a hypoxic stimulus with variable upregulation of EPO gene transcription within 24 hours of the stimulus (FIG. 125C). Specificity of the upregulation was confirmed by the observation that neither housekeeping nor tubular genes were induced by the hypoxic stimulus (not shown). Cultures that were established and propagated from both the CKD and non-CKD human and swine tissues retained EPO-expressing cells throughout multiple passages and after cryopreservation and culture re-initiation.

As shown in Table 21 below, Swine kidneys (PK001 and PK002), human kidneys (HK016-HK020), and rat kidneys were collected from CKD and non-CKD patients. *Rat data were collected and averaged from a group of female Lewis rats that underwent a two-step 5/6 nephrectomy procedure to induce progressive renal failure; healthy age-matched controls are shown for comparison. Numbers in BOLD represent values outside of normal range according to lab standard values.

As shown in Table 22 below, cultures were established from swine (PK001 and PK002), human (HK016-HK020), and rat (Lewis) kidneys according to materials & methods. The presence of cells within established cultures representing the major cellular compartments of the kidney (tubular, glomerular, ductular, vascular, and endocrine) was confirmed by qRTPCR. Availability of human-specific probes enabled a more quantitative and extensive analysis of human samples. Expression of each gene was normalized to an endogenous control and calibrated to species-matched fresh whole kidney tissue. Expression of EPO was examined at both 21% O2 and at 2% O2; values shown represent 21% O2 expression levels and (R) designates that upregulation was observed under 2% O2 conditions. Albumin uptake (ALB-U) was also assessed in each culture at multiple passages (p0-p4 for swine and human, p0-p1 for rat). The presence of a distinct low side scatter/low forward scatter (SSC/FSC) subpopulation, as determined by flow cytometric analysis, was confirmed in each culture.

TABLE 21

Renal function at time of death or sacrifice.

| Sample ID | Species | Age/Gender | Etiology of Renal Disease | Cause of Death | BUN | sCREAT | HCT | HB |
| --- | --- | --- | --- | --- | --- | --- | --- | --- |
| PK001 | swine | >1 yr/M | Idiopathic nephrpathy | Renal failure | 75 | 9.5 | 34.1 | 10.6 |
| PK002 | Swine | >1 yr/M | None | Sacrifice | NA | NA | NA | NA |
| HK016 | human | 2 mo/F | None | Head trauma | 13 | 0.4 | 26.6 | 9.6 |
| HK017 | human | 35 yr/F | Petechial hemorrhage secondary to DIC | CVA | 12 | 2.9 | NA | NA |
| HK018 | human | 48 yr/F | Secondary to hypertension, NIDDM, and heart disease | CV/Renal Failure | 40 | 8.6 | 24.6 | 8.1 |
| HK019 | human | 52 yr/F | Secondary to hypertension, NIDDM, and heart disease | CV/Renal Failure | 127 | 5.7 | 23.7 | 8.4 |
| HK020 | human | 54 yr/F | Auto-immune glomerulonephritis | CV/Stroke | 94 | 16.6 | 22.6 | 7.2 |
| CKD rats (5/6 NX) | Rat (Lewis) | 4-6 mo/F | Renal mass insufficiency | Renal Failure | 105.5* | 2.58* | 35.6* | 5.9* |
| Healthy rats (age-matched) | Rat (Lewis/F) | 4-6 mo/F | none | Sacrifice | 19.4* | 0.36 | 46.4 | 13.7 |

*Avg of all animals in group at time of death or sacrifice

TABLE 22

Compartmental analysis of cultured human, swine, and rat renal cells

| Sample ID | TUBULAR | | | | | | GLOMERULAR | |
| --- | --- | --- | --- | --- | --- | --- | --- | --- |
| | E-CAD | N-CAD | AQP-1 | CUB | CYP2H25 | ALB-U | NEPH | PODO |
| PK001 | + | nd | nd | nd | nd | ++ | nd | nd |
| PK002 | + | nd | nd | nd | nd | + | nd | nd |
| HK016 | 3.03 | 0.83 | 0.0001 | 0.0006 | 0.055 | + | 0.0004 | 0.0050 |
| HK017 | 0.66 | 0.83 | 0.0009 | 0.0002 | 0.046 | ++ | trace | 0.0001 |
| HK018 | 0.61 | 1.59 | 0.0001 | 0.0003 | 0.059 | + | 0.0002 | − |
| HK019 | 0.62 | 2.19 | 0.026 | 0.0008 | 0.068 | +/− | 0.0009 | 0.0003 |
| HK020 | 0.07 | 1.65 | 0.0003 | 0.0007 | 0.060 | +++ | − | − |
| Healthy rats (age-matched) | + | + | + | + | + | + | + | + |
| CKD rats (5/6 NX) | + | + | + | + | nd | nd | + | + |

Discussion

The intrarenal delivery of heterogeneous rodent NK-CELLS to a progressive and terminal model of renal failure enabled 100% of the treated rats to survive for the duration of the study (20 weeks after disease onset), while all untreated rats died within 16 weeks of disease onset. NK-CELLS were delivered 8 weeks after the 5/6 nephrectomy procedure, when rats had significant elevations in serum creatinine and BUN, and were at the midpoint of their post-nephrectomy lifespan. NK-CELL delivery clearly resulted in stabilization of renal filtration functions and improvements in erythropoiesis, either or both of which could have influenced overall survival in the model. Partial characterization of the transplanted cells demonstrated that component cells with specific therapeutically-relevant attributes (albumin-transporting tubular cells and oxygen-regulated EPO-producing cells) were present within the population and thus had the opportunity to contribute to the observed stabilization of disease progression in the rodent pilot study.

CKD in humans, and in rodent models such as the two-step 5/6 nephrectomy, is characterized by progressive deterioration of renal function, fibrosis, loss of glomerular and tubular mass, and loss of protein in the urine (de Zeeuw et al., Kidney Int 2004, 65:2309-2320). Protein loss is controlled in the kidney by two mechanisms: at the level of the glomerulus where the integrity of the podocytes and glomerular basement membrane determines how much protein is deposited into the urinary filtrate; and at the level of the renal tubules where the tubular cells uptake protein from the filtrate and return it to the circulation (Birn et al., Kidney Int 2006, 69:440-449). Receptor-mediated protein uptake function was confirmed in the tubular component of the cultured NK cells in vitro, and was also a feature that improved in the 5/6 Nx rats upon in vivo treatment with the NK-CELLS. Thus, without wishing to be bound to a particular theory, it is likely that the protein uptake-competent cells within the NK-CELL mixture were partially responsible for the observed in vivo improvement in protein retention. Since the NK-CELL cultures contained a proportion of glomerular cells as well, it is also plausible that some level of cellular repair and/or regeneration occurred at the level of the glomerulus. Histologic assessment of the NK-CELL-treated kidneys provided additional support for this hypothesis through the observations of reduced intralumenal protein casts in focal areas of the tubules and mildly reduced glomerulopathy.

Restoration of erythroid homeostasis was also observed in the NK-CELL-treated rats, with HCT and RBC levels reaching those of healthy controls and maintaining HB levels at near-normal levels for the duration of the study (3 months). Because of the long half-life of RBCs in the rat (~14 days) (Ganzoni et al., J Clin Invest 1971, 50:1373-1378), it was important to exclude the possibility that the positive systemic effects noted for HCT, RBC, and HB were due only to a short-term stimulus of the erythron at the time of NK-CELL delivery. A short-term bolus effect could have had a long-term impact on the peripheral measurements, but only a transient effect on the bone marrow. Importantly, the robust appearance of the bone marrow at the 3-month timepoint in the NK cell-treated rats provided evidence against a bolus effect related to delivery of EPO-producing NK-CELLS. Studies of single-dose recombinant EPO delivered to rodents have shown that effects in the bone marrow last for approximately 48 hours, while peripheral stimulation of RBCs peaks around 6 days, returning to pre-dosing levels by 21 days (Bugelski et al., Pharm Res 2008, 25:369-378); Woo et al., J Pharmacol Exp Ther 2006, 319:1297-1306).

Although paracrine effects have been described as a mechanism of action for cells transplanted into conditions of acute damage (Gnecchi et al., Circ Res 2008, 103:1204-1219), including kidney failure (Togel et al., Am J Physiol Renal Physiol 2005, 289:F31-42; Togel et al., Am J Physiol Renal Physiol 2007, 292:F1626-1635), it appears that the rodent NK-CELLS tested in these studies acted at least partially by direct enhancement of renal filtration function and stimulation of erythropoiesis. Molecular analyses of the explanted kidney remnants at 3 months revealed the persistent presence of male donor cells in the female recipient kidneys, but estimated the frequency to be low (<10%), suggesting that the systemic improvements observed were likely due to a combination of early direct effects of the transplanted cells and concurrent and subsequent indirect effects on the host cells and/or tissue microenvironment. Additional studies will be required to attribute observed in vivo outcomes to specific cellular component(s), and to discern precisely the cellular and molecular mechanism(s) involved in the slowing of progression upon delivery of NK-CELLS.

There are many inherent practical challenges in the development and delivery of autologous cell or regenerative medicine therapeutics. However, autologous approaches remain attractive clinically because they do not require immune suppression and may circumvent some concerns regarding pathogens. Autologous strategies may not be feasible when the cell(s) of therapeutic interest cannot be obtained from the patient due to their destruction as part of the disease mechanism, as in the loss of insulin-producing beta cells in Type 1 diabetes mellitus (Pirot et al., Arq Bras Endocrinol Metabol 2008, 52:156-165), or because the risk to the patient in obtaining the cells via biopsy is too great. These limitations have led many to pursue strategies whereby therapeutically-relevant cells are generated by isolation from an autologous ectopic site, which is relevant for derivation of common cell types such as endothelial cells or smooth muscle cells. Another approach has been directed differentiation of stem or progenitor cells isolated from sites other than the tissue of origin; these approaches have been slower to advance when the cell (s) of interest are highly-specialized tissue-specific cells, due to inefficiencies in the differentiation process, uncertainty of the role undifferentiated cells may play in the regeneration process, and safety concerns that have been raised around implantation of undifferentiated cells (Hentze et al., Stem Cell Res. 2009 Feb. 12). Thus, for any given target disease for which an autologous/homologous approach is desired, it is imperative to determine whether cells with therapeutic potential can be isolated from the tissue(s) of interest.

The presence and function of all major cell types (tubular, EPO-producing, glomerular, collecting duct, and vascular cells) was investigated in whole swine and human kidney tissue derived from CKD patients, as well as in cell cultures established and propagated from those tissues. Interestingly, cells positive for tubular markers and capable of receptor-mediated albumin uptake were present and propagated from all human and swine kidneys, regardless of etiology or severity of disease state. EPO-producing cells responsive to hypoxia were also isolated and propagated from all chronically-diseased kidneys, regardless of species or disease etiology. Interestingly, glomerular cells were not isolated and propagated from HK20, a very advanced case of autoimmune glomerulonephritis, although they were present in all other cultures, as were collecting duct cells and a small number of vascular cells.

Multiple hypotheses have been put forward with regard to the mechanisms of anemia secondary to chronic renal failure. In general it is accepted that the anemia of renal failure is due to an absolute or relative EPO deficiency, as serum EPO levels are decreased relative to the degree of anemia (Nangaku et al., Semin Nephrol 2006, 26:261-268). It has been hypothesized that the EPO-producing cells of the kidney may be lost as the disease progresses, or that they remain present in the kidney but fail to respond appropriately to production signals because the relationship between local oxygenation and the control mechanisms within the cells are perturbed (Maxwell et al., J Am Soc Nephrol 2003, 14:2712-2722). It is also plausible that the fibrosis and destruction of vasculature as part of the disease progression limits the ability of EPO protein produced in the kidney to be delivered effectively to the circulation. The uremic environment of CKD also contributes to anemia, with uremic solutes in plasma having been implicated in shortening RBC half-life (Nangaku et al., Semin Nephrol 2006, 26:261-268). The chronic inflammation of uremia and iron deficiency secondary to blood loss or dialysis may also contribute to the anemia of CKD. Our data provide evidence against the hypothesis that the EPO-expressing cells in the kidney are destroyed, as mRNA and protein were clearly present in the tissues, and cells expressing regulated EPO function were propagated from all CKD and non-CKD kidney specimens. It is of note that the human CKD specimen with autoimmune glomerulonephritis (HK20) had significantly lower EPO mRNA and protein expression at the tissue level and exhibited weak expression overall in culture as well. Taken together with the absence of glomerular cells in the culture, it may be suggested that CKD that develops secondary to autoimmune disease may not be a good target disease state for autologous cell-based therapeutics that require glomerular or endocrine cells as components.

In summary, these studies suggest that therapeutically-active cells can be isolated, expanded, and transplanted into a chronically-damaged renal parenchyma to stabilize renal functions and delay progression in a terminal model of CKD. The successful application of the NK-CELL isolation strategy to large animal and human CKD specimens highlights the translatable nature of this approach. Despite advanced fibrosis and complex underlying metabolic disease, pockets of tubular, endocrine, collecting duct, and glomerular cells persist within CKD-derived tissue, providing access to the 'building blocks' that may be necessary to establish an autologous regenerative medicine strategy for the treatment of CKD. The regenerative medicine therapy contemplated by these studies offers the potential to preserve renal function and extend lifespan in many patients with CKD who suffer from the complications of long-term dialysis and deal with the shortages and delays of organ donation.

Example 19

Isolation of Functional NKA Prototypes is not Age-dependent

This study was conducted to determine whether neo-kidney augmentation cell prototypes could be obtained from adult rodent kidney.

Adult rodent NKA cell preparations (RK102, RK105) were established from adult rat kidney (>3M of age) using standard procedures for rat cell isolation and culture initiation. All flasks were cultured for a total of 3 days. After the first 2 days in 21% (atmospheric) oxygen conditions, media was changed and the flasks were relocated to an oxygen-controlled incubator set to 2% oxygen for an additional 24 hours. Cells were then harvested using standard enzymatic harvesting procedures. Step gradients were prepared according to standard procedures and the cultures were harvested and applied to the step gradients. The resulting bands were similar in distribution and frequency (see FIG. 126, Table 23) to preparations generated from 2-week old (juvenile) kidney tissue. Gene expression patterns were comparable between adult-derived and juvenile-derived NKA prototypes, with expected enrichment of B2-specific and B4-specific cell types, determined by examining gene expression patterns of erythropoietin, nephrin, podocin, cubilin, and Cyp (see FIG. 127).

TABLE 23

Relative Frequency/band distribution

| Cell Fraction Band Distribution | Cell Fraction Band Frequency (Adult Rodent) |
| --- | --- |
| B1 | 8-9% |
| B2 | 15-25% |
| B3 | 4-7% |
| B4 | 1-3% |
| Pellet | 0-1.5% |

RK091 NKA cell preparation was generated from a terminal, chronically-diseased (5/6 nephrectomized) adult rodent kidney remnant, using standard procedures for rat cell isolation and culture initiation. After the first 2 days in 21% (atmospheric) oxygen conditions, the flasks were relocated to an oxygen-controlled incubator set to 2% oxygen for an additional 24 hours (FIG. 128). Cells were then harvested using standard enzymatic harvesting procedures. Although a density step gradient was not applied to this culture, gene expression of specific "B2 and "B4" genes (such as Cyp, EPO, HIF1a, Podocin, and VEGFA) demonstrates that the known B2- and B4-specific cell types were isolated and propagated in the culture (FIG. 129).

NKA cell preparations were prepared side-by-side from juvenile (2-week-old) or adult (3.5-month old) male Lewis rats. After standard culture regimens and step-gradient procedures, the 'B2' fraction, isolated from each preparation, was transplanted into anemic/uremic female Lewis rats (generated at CRL by a two-step 5/6 nephrectomy procedure). Baseline values for creatinine and BUN were measured the week prior to implant, and every two weeks thereafter for 16 weeks post-treatment (see FIGS. 130 and 131).

The above results show that it is feasible to separate tubular cells found in 'B2' from specific specialized cells (erythropoietin-producing cells, vascular cells, and glomerular cells) found in 'B4' cell populations in the adult rodent kidney using the same culture strategy and step gradient techniques employed for juvenile kidney-derived cultures. 'B4'—specific specialized cells (epo-producing, vascular, and glomerular) are present in adult rodent 'B4' band at the predicted density. As shown above, it is also feasible to obtain NKA cells (tubular and epo-producing) from a diseased adult rodent kidney obtained from a terminal animal. Both juvenile- and adult-derived NKA 'B2' cells delivered renal function stabilization when transplanted into an established model of uremia (2-step 5/6 Nx), after onset of disease.

Example 20

Genetic Profiling of Therapeutically Relevant Renal Bioactive Cell Populations

To determine the unbiased genotypic composition of specific subpopulations of renal cells isolated and expanded from kidney tissue, gene array and quantitative real time PCR (qrtpcr) analyses (Brunskill et al., 2008) were employed to identify differential cell-type-specific and pathway-specific gene expression patterns among the cell subfractions.

The isolation and primary culture of unfractionated heterogeneous mixtures of renal cells has been described previously (Aboushwareb et al., 2008). Subsequently, standard density-gradient methodology was utilized to generate cell subfractions, which were then characterized based on specific biological activity and phenotypic characteristics. Ultimately, two specific subfractions, termed "B2" and "B4" were demonstrated to be of particular therapeutic value, alone and in combination, when transplanted intrarenally into a progressive model of CKD generated by a two-step 5/6 Nx procedure in female Lewis rats.

Cells and Cell Culture Conditions:

An established heterogeneous culture of male Lewis rat kidney cells was fractionated according to Example 8. Prior to gradient fractionation, the renal cells were cultured in 50:50 mixture of high glucose DMEM containing 5% (v/v) FBS, 2.5 µg EGF, 25 mg BPE (bovine pituitary extract), 1×ITS (insulin/transferrin/sodium selenite medium supplement), antibiotic/antimycotic (MFR) and cultured at 37° C. under standardized conditions of humidity and oxygen tension. The resulting subfractions (B1, B2, B3, B4, and pellet) were sampled to obtain RNA for expression analysis and then implanted into uremic rats to assess biologic function in vivo.

Materials and Methods:

Microarray platform: Affymatrix GeneChip Rat Genome 230 2.0 Array; Contract facility: Wake Forest University Health Sciences, Microarray Core Facility; Validation method: ABI/Invitrogen 7300 quantitative real time PCR (qrtpcr) analysis; RNA isolation: Qiagen RNA Isolation kit; cDNA synthesis: Invitrogen Vilo superscript cDNA isolation kit; Primers & probes: ABI/Invitrogen Taqman assays ('Inventoried' primers and probe sets)

Procedure: Isolate and quantitate RNA from cell subfractions, immediately after subfractionation procedure (Table 24-25). Affymetrix Gene array analysis on normalize (2 µg) RNA samples (data not shown). Select differentially expressed genes based on p-value and fold change significance (data not shown). Use David annotation assignment (http://david.abcc.ncifcrf.gov/) to categorize differentially expressed genes (data not shown). Select genes to validate microarray by qrtpcr the specific subfractions, generated from a Lewis rat cell preparation, a normal human kidney cell preparation, and a human chronic kidney disease cell preparation. (Table 27)

TABLE 24

Culture conditions and gradient load.

| Cell Prep | Seeding Density | Culture time | Final Confluency | Gradient Load |
|---|---|---|---|---|
| RK086 | 17.5 e$^6$/flask | 3 d 21% O$_2$<br>1 d 2% O$_2$ | 100% | 72.8 e$^6$ |
| RK087 | 15 e$^6$/flask | 2 d 21% O$_2$<br>1 d 2% O$_2$ | 85% | 91 e$^6$ |
| RK097 | 19.3 e$^6$/flask | 2 d 21% O$_2$<br>1 d 2% O$_2$ | 85% | 92.5 e$^6$ |

Results:

Differential expression between fractions (B1-B4) and/or pre-gradient (PreG) was determined under the following stringent conditions: listed genes met both criteria of significance: p-value<0.05, and fold change<−0.5 or >0.5. Probe set IDs (ex.: 1395810_at|- - -|- - -) without a gene name/description correspond to gene array oligonucleotide (oligo) that has yet to be assigned. These oligos can be selected through the Affymetrix "Netaffx" web page https://www.affymetrix.com/analysis/netaffx and blasted against NCBI genomic databases to obtain a probability for gene assignment.

The summary of genes differentially expressed (Up/Down) between Pregradient and Post-gradient (B1-B4) cell populations is shown below in Table 26. The selection criteria for determining differences in gene expression: T-test pvalue≤0.05 with an absolute fold change≥0.5 between cell populations. For example, as shown in Table 26 below, the difference between Pre-gradient and B1: of the 165 differentially expressed genes, 32 were up in B1, and 133 were down in B1 from Pregradient. The genes that represent differences in expression between these cell populations were determined

TABLE 25

RNA concentration and normalization.
RNA Normalization

| | Fraction | Symbol | ng/ul | Vol, 2 µg | Norm 20 µl |
|---|---|---|---|---|---|
| 1 | RK086 | 3812 | PreG | 412.19 | 4.852 | 15.148 |
| 2 | | 3813 | B1 | 511.62 | 3.909 | 16.091 |
| 3 | | 3814 | B2 | 460.28 | 4.345 | 15.655 |
| 4 | | 3815 | B3 | 284.08 | 7.040 | 12.960 |
| 5 | | 3816 | B4 | 163.64 | 12.222 | 7.778 |
| 6 | | 3817 | Pellet | 354.38 | 5.644 | 14.356 |
| 7 | RK087 | 3821 | Macro | 213.05 | 9.387 | 10.613 |
| 8 | | 3825 | PreG | 301.08 | 6.643 | 13.357 |
| 9 | | 3826 | B1 | 363.74 | 5.498 | 14.502 |
| 10 | | 3827 | B2 | 351.53 | 5.689 | 14.311 |
| 11 | | 3828 | B3 | 370.35 | 5.400 | 14.600 |
| 12 | | 3829 | B4 | 387.13 | 5.166 | 14.834 |
| 13 | | 3830 | Pellet | 136.67 | 14.634 | 5.366 |
| 14 | RK097 | 4692 | Macro | 125.76 | 15.903 | 4.097 |
| 15 | | 4697 | PreG | 379.67 | 5.268 | 14.732 |
| 16 | | 4698 | B1 | 366.56 | 5.456 | 14.544 |
| 17 | | 4699 | B2 | 420.82 | 4.753 | 15.247 |
| 18 | | 4700 | B3 | 439.3 | 4.553 | 15.447 |
| 19 | | 4701 | B4 | 350.43 | 5.707 | 14.293 |
| 20 | | 4702 | Pellet | 167.94 | 11.909 | 8.091 |

TABLE 26

Summary of genes Expressed up/down between pregradient and post-gradient (B1-B4) cell populations.

| | B1 | B2 | B3 | B4 |
|---|---|---|---|---|
| PreG | 165 (32/133) T4/T5 | 21 (11/10) T6/T7 | 100 (58/42) T8/T9 | 227 (201/25) T10/T11 |
| B1 | | 74 (45/28) T12/T13 | 488 (258/230) T14/T15 | 534 (359/175) T16/T17 |
| B2 | | | 149 (107/42) T18/T19 | 242 (226/16) T20/T21 |
| B3 | | | | 30 (27/2) T22/23 |

Discussion. The present report describes the genetic profiling of specific bioactive renal cell subpopulations, generated in this case by density gradient separation. Microarray analysis represents an unbiased approach for determining the expression levels of normalized signal intensities in one sample relative to another (data not shown). Cluster analysis and Treeview applications further allow visualization of the intensities and patterns of gene expression across multiple samples (data not shown). The cell fractions examined in the present report have been extensively studied in vivo (Lewis male donors into Lewis female CKD recipients (Kelley et al., 2009)).

TABLE 27

Validation of the Lewis rat microarray results by qrtpcr in the rat and translation of enrichment to gradients of normal human kidney and human CKD kidney Blood Vessel Development

| | Sample | Target Gene | Rat RQ | HK19 CKD RQ | HK21 Non-CKD RQ |
|---|---|---|---|---|---|
| CDH5 | B2 | CDH5 | 0.742 | 1.052 | 1.387 |
| | B4 | CDH5 | 8.065 | 6.205 | 2.340 |
| KDR | B2 | KDR | 0.708 | 0.607 | 0.233 |
| | B4 | KDR | 10.348 | 20.637 | 6.344 |
| PLAT | B2 | PLAT | 1.008 | 1.224 | 0.430 |
| | B4 | PLAT | 3.088 | 4.266 | 0.430 |
| ANGPT2 | B2 | ANGPT2 | 0.737 | 0.872 | 0.812 |
| | B4 | ANGPT2 | 6.697 | 14.115 | 13.446 |

Whole organism improvements (i.e., survival, weight gain), serological profiling and histological evidence overwhelmingly support B2 as the cell fraction with the greatest therapeutic relevance when transplanted alone into diseased kidneys, although fraction B4 did provide limited therapeutic benefits in vivo.

A follow-up partial factorial in vivo study indicated that combinations of B2 and B4 exceeded the benefits of B2 alone. The present microarray study discovered differences between all cell fractions, with an emphasis on the differences between B2 and B4 that include gene classification through David Annotation freeware (data not shown). Interestingly, genes differentially expressed between B2 and B4 represent 33 different Functional Groups and 163 annotations among these groups with significant p-values (pv≤0.05). The array was validated by qrtpcr using a selected panel of genes that represent 7 different David (Go) gene annotation categories (data not shown). Remarkably, the genes selected to validate the rodent array, translated to both a normal human and human CKD patient (see Table 27). As is typical with gene array analyses, caution must be taken in interpretation until all purported markers of the subfractions can be verified at the protein level. Furthermore, rare components of either subfraction are not likely to be detected using gene expression analysis, and must be pursued independently using methods that discriminate on a per-cell basis.

In conclusion, the microarray analysis validated density gradient separation as an effective means of separating renal cells into subfractions with specific functions and characteristics. Hierarchical Cluster Analysis demonstrated that each subfraction is distinct from all others and from the pre-gradient starting cell population. As shown above, the expression pattern of unfractionated cells is most like that found in the B2 subfraction, likely due to the high frequency (~80%) of tubular and collecting duct cells comprising the heterogeneous culture as well as the B2 subfraction. Also, and as expected, the greatest difference in gene expression occurs between the first and last fractions of the density gradient (B1 vs B4).

A cluster analysis (based on multiple group comparisons, Kruskal Wallace significance), and a T-test comparison between all groups suggest that fractions B1-B2 separate from B3-B4 in the gradient. The B2 fraction is comprised predominantly of the most plentiful cell(s) in the heterogeneous culture (tubular & collecting duct); only trace quantities of other cell types are present in this fraction, while the B4 fraction is heavily enriched with factors that regulate growth and development, especially blood vessel development. Notably, the B1 and B3 fractions contain immune/inflammatory elements that might offset the therapeutic value of the B2 fraction. The difference in microarray gene expression observed between B2 and B4 was validated by 13/13 rodent markers. Rodent cell fractionation and gene expression strongly translates to both normal and CKD human specimens with >90% of the markers tested. The above data support the proposition that human CKD kidneys are architecturally deficient, but that most cell types are viably present and are propagable ex vivo.

Example 21

Hyaluronic Acid Synthesis by B2

Surprisingly, HAS-2 (a species of hyaluronic acid synthase responsible for synthesizing high-molecular-weight hyaluronic acid (HA)) was produced by the B2 cell preparation, and to a lesser extent, by the B4 cell preparation in vitro prior to implantation., FIG. 132 shows in vitro expression of HAS-2 by B2 and B4. As shown in FIG. 132, the predominant expression of hyaluronic acid synthase (HAS) in vitro was in the B2 cell preparation, although there was detectable expression in the B4 cell preparation.

The in vivo expression of HAS mRNA and protein is shown in FIG. 133. As shown in FIG. 133, the implantation of B2 cells into the 5/6 Nx chronic renal failure rodents yielded an upregulation of HAS-2 at the gene level (qRTPCR, bottom graph) and at the protein level (top figure, western blot) in the treated tissue compared to the Nx untreated tissue.

Example 22

Study Plan for Assessment of Neo-Kidney Augment in a Metabolic Disease Model

The objective of the study is to assess a Neo-Kidney (NK) prototype (i.e., a cell preparation or cell population) in the ZSF1 rodent model of metabolic disease with chronic progressive renal failure. The obese ZSF1 rat strain represents a widely-used model of metabolic syndrome and is characterized by multiple related disorders, including: hyperphagia, obesity, hypertension, severe dyslipidemia, non-insulin-dependent diabetes mellitus (NIDDM), left ventricular dysfunction, and secondary progressive nephropathy. Obese ZSF1 rats have a ~50% 1-year mortality rate and typically die of end-stage renal disease and congestive heart failure. The obese ZSF1 strain was derived from a hybrid crossing of lean female Zucker Diabetic Fatty (ZDF+/fa) rats crossed with lean male Spontaneously HTN (hypertension) Heart Failure (SHHF/Mcc-fa$^{cP}$, +/fa) rats to yield obese ZDFxSHHF-fa/fa$^{cP}$ F1 offspring (ZSF1); Charles River Laboratories nomenclature: ZSF1—Lepr$^{fa}$ Lepr$^{cP}$. Each parent strain has a distinct leptin receptor mutation (fa and fa$^{cP}$, cp, 'corpulent' gene mutation). The ZSF1 hybrid offspring have the same MHC II haplotype, making the hybrid offspring a good transplantation model, one similar to matched living related donor scenario in human cell and tissue transplantation.

The Zucker-derived animals strains, including ZSF1, have been studied extensively and are well-described in the literature (Duarte et al., 1999 *Eur J. Pharmacol.* 365:225-32; Griffin et al., 2007 *Am J Physiol Renal Physiol.* 293:F1605-13; Harmon et al., 1999 *Diabetes.* 48:1995-2000; Jackson et al., 2001 *J Pharmacol Exp Ther.* 299:978-87; Joshi et al., 2009 *J Cardiovasc Pharmacol.* July; 54(1):72-81; Khan et al., 2005 *Am J Physiol Renal Physiol.* 289:F442-50; Mizuno et al., 2006 *Cardiovasc Pharmacol.* 48:135-42; Rafikova et al., 2008 *Metabolism.* 57:1434-44; Renaud et al., 2004 *Fundam Clin Pharmacol.* 18:437-47; Tofovic and Jackson, 2003 *Methods Mol. Med.* 86:29-46; Tofovic et al., 2001b *Ren Fail.* 23:159-73; Uhlenius et al., 2002, *Kidney Blood Press Res.* 25:71-9.). The ZDF1 strain has been used in preclinical studies to evaluate risk factors for kidney disease, including obesity and NIDDM.

The proposed strategy for the delivery of the NK prototype to the ZSF1 rats is based on the following cell isolation and delivery strategy. Briefly, rats will be rendered uremic and anemic via a 2-step 5/6 nephrectomy procedure to provide the test model. NKA cell prototypes derived from either lean or obese ZSF1 donor rats will be suspended in a delivery medium and delivered intra-renally. Perioperative assessment of the animals will be performed during the period of time when they recover from the procedure. Health and renal functions will be monitored semi-monthly via serum chemistry, urinalysis, blood pressure, survival, and weight gain, from the time of delivery (~3 months of age) up to 1 year of age. Parameters measured will include serum creatinine, blood urea nitrogen, serum albumin, total protein, and A/G ratio, cholesterol and triglycerides, serum sodium, phosphorous and calcium, urine protein, and hematocrit. At the time of sacrifice (6-9 months post-transplantation), full histopathologic analyses will be conducted of the kidneys, bone marrow, liver, lungs, spleen, and heart. As it has been shown that both a low-protein diet and a standard-of-care pharmacologic regimen (blood pressure control, glucose control) can slow progression of renal failure secondary to metabolic diseases in humans and laboratory animals (including Zucker-derived rat strains), other studies may be conducted to examine the performance of NKA prototypes+/−during these palliative treatments. Additional study protocols may evaluate a follow-on treatment intervention (re-intervention) with or without dietary and/or pharmacological intervention in order to extend animal quality of life and survival.

Of the metabolic rat strains (including Zucker, ZDF and SHHF), the ZSF1 model exhibits the characteristics common to human obesity and NIDDM, with a disease state severe enough (Tofovic et al., 2000 *Ren Fail.* 22:387-406; Vora et al., 1996 *J Am Soc Nephrol.* 7:113-7) to enable evaluation of NKA therapy in a timely manner (~6 mo after NKA prototype delivery). ZSF1 rats develop the hallmark symptoms of NIDDM, including insulin resistance and consequent hyperglycemia, obesity, severe dyslipidemia, significantly-elevated blood pressure, end-stage renal failure, cardiac hypertrophy, and shortened lifespan (Tofovic and Jackson, 2003 *Methods Mol. Med.* 86:29-46). The disease characteristics of the ZSF1 precursor rat strains are listed in Table 28 (Charles River).

TABLE 28

Commercially available metabolic rat strains.

| Characteristic | SHR | SHROB | Zucker | ZDF | ZSF1 |
| --- | --- | --- | --- | --- | --- |
| Insulin Resistance | + | + | + | + | + |
| Hyperinsulinemia | + | + | + | + | + |
| Type 2 Diabetes (NIDDM) | − | − | − | + | + |
| Fasting Hyperglycemia | − | − | − | + | + |
| Hypertension | + | + | − | − | + |
| Obesity | − | + | + | + | + |
| Cardiovascular Disease | − | − | − | − | − |
| Hypertriglyceridemia | + | + | + | + | + |
| Hypercholesterolemia | + | + | + | + | + |
| Nephropathy | + | + | +, 1 | +, 1 | +, 2 |
| Leptin Receptor Defect | − | + | + | + | + |
| Special Diet Requirements | − | − | − | + | + |
| Genetics | I | I | O | I | H |

+ = exhibits characteristic;
− = does not exhibit characteristic
I = Inbred;
O = Outbred;
H = Hybrid
1 = Hydronephrosis;
2 = Hydronephrosis is found infrequently The ZSF1 rat strain is available commercially through Charles Rivers Laboratories (CRL). A survey was performed across published ZSF1 studies (Griffin et al., 2007 supra; Joshi et al., 2009 supra; Rafikova et al., 2008 supra; Tofovic et al., 2001a *J Pharmacol Exp Ther.* 299:973-7; Tofovic and Jackson, 2003 supra; Tofovic et al., 2001b supra; Tofovic et al., 2000 *Ren Fail.* 22:387-406) to evaluate disease progression over time (ZSF1 ages 2-47 weeks). A recent blood analysis of 5 ZSF1 rats at 12 weeks was also performed to confirm the age-dependent progression of several key disease parameters. Although the progression to end-stage disease and death is relatively slow (~1 yr), kidney function declines significantly by week 20 (serum creatinine more than doubles from 0.77 mg/dl at 8 weeks of age to 1.47 mg/dl at 20 weeks) (Tofovic and Jackson, 2003 supra).

Although some limitations exist, other metabolic models may be considered. The Obese Zucker model exhibits many of the symptoms of diabetes; however these rats are normotensive, and more importantly are an outbred strain potentially unsuitable as a transplant model without the concomitant use of immunosuppressive therapy. The Zucker-derived ZDF model is an inbred model that better represents diabetic disease (compared to the Obese Zucker) including symptoms such as nephropathy and mild hypertension, often associated with insulin resistance and hyperglycemia of NIDDM. However, this model is potentially unsuitable for intra-renal transplantation strategies due to a high incidence of spontaneous severe hydronephrosis (Vora et al., 1996 supra). The spontaneously hypertensive heart failure (SHHF): rats of this strain have a similar metabolic status as ZSF1. However, the SHHF is characterized by a relatively mild nephropathy, resulting in a slow progression to end-stage renal failure in comparison to the ZSF1 hybrids.

The ZSF1 metabolic model of kidney disease is suited for in vivo studies of renal failure due to the following: literature precedent for the model; commercial availability and reproducibility of the model; and suitability of the model for syngeneic donor approaches. In addition, this model is advantageous over the SHHF and ZDF parent strains because SHHF do not develop Diabetes, and the ZDF model exhibit a proclivity to severe hydronephrosis. The severity of renal disease is also greater in the obese ZSF1 compared to parent strains. There are no current therapies that can cure chronic kidney disease (CKD), other than kidney transplantation. All existing therapies (diet control and pharmacological intervention) are palliative over a finite period, defined by overt and irreversible renal damage. The present protocol will allow for the assessment of NKA cell prototypes in an experimental model of human CKD secondary to metabolic syndrome. The primary objective is to test delivery of NKA during the progression of renal disease (mild, moderate and severe CKD).

Additional studies may consider an additional follow-on renal cell transplantation procedure (re-intervention) that might extend the durability of the initial treatment effects. Re-intervening with renal cell transplantation may be accompanied by dietary control and pharmacological intervention. An autologous sourcing strategy might be considered in future studies with the ZSF1 model. In theory, both the inbred parent strains of ZSF1, or back a generation to the outbred strain used to derive ZDFs, the Zucker rat might be used as an allogeneic donor source of kidney tissue to ZSF1s with advanced CKD or end stage renal disease (ESRD).

A standard-of-care drug regimen and/or a low calorie (fat, protein, sugar), low salt diet may accompany the evaluation of NKA in the ZSF1 model as the organism enters late stage renal disease (i.e. ESRD) in the present study and/or during follow-up study protocols.

Renin-Angiotensin System (RAS) therapy including Angiotensin Receptor Blockers (ARB) and Angiotensin-converting enzyme (ACE) inhibitors (such as captopril or perindopril) represent a class of anti-hypertensive medications that are routinely used in humans and have been shown to be effective in Zucker rats (Duarte et al., 1999 supra; Tofovic and Jackson, 2003 supra; Uhlenius et al., 2002 supra). An insulin sensitizer drug, such as Rosiglitazone or Troglitazone, routinely used to improve insulin-mediated cellular glucose uptake in humans, has also been shown to be effective in Zucker rats (Harmon et al., 1999 supra; Khan et al., 2005 supra). Statins, inhibitors of the HMG CoA Reductase Enzyme that regulate cholesterol synthesis, are a widely used class of drugs used to treat dyslipidemia (Yoshimura et al., 1999 supra). Table 29 describes a representative matrixed approach proposed for testing both lean-derived and obese-derived NKA cells in rats that are managed across a spectrum of dietary and pharmacologic regimens that emulate patient compliance.

TABLE 29

Study groups for treating male Obese ZSF1 rats.

| High Calorie Diet (Purina 5008) | ZSF1 Obese Cells | ZSF1 Lean Cells | Sham controls No Cells (vehicle) | Unmanipulated controls No Cells |
|---|---|---|---|---|

Example 23

Immunosuppressive Research Plan

The in vivo performance NKA prototypes from non-autologous source may be assessed using an immunosuppressive research plan. Various immunosuppressive regimens are possible including cyclosporine A (CsA) (10 mg/kg) daily by gavage; tacrolimus (Tac) (0.2 mg/kg) daily by gavage ($2^{nd}$ choice); rapamycin (Rapa) (1 mg/kg) daily by gavage ($1^{st}$ choice); and mycophenolate mofetil (MMF) (10 mg/kg) daily by gavage (Yang, H. C., Nephrol Dial Transplant. 2003 May; 18 Suppl 1:i16-20). A tolerance-based immunosuppressive regimen may also be implemented where donor specific blood transfusion are performed 12 days prior to transplant to trend towards tolerance (Koshiba T, Li Y, Takemura M, Wu Y, Sakaguchi S, Minato N, Wood K J, Haga H, Ueda M, Uemoto S. Transpl Immunol 2007 February; 17(2):94-7; Jovanovic V, Lair D, Soulillou J P, Brouard S. Transpl Int. 2008 March; 21(3):199-206. Epub 2007 Dec. 5. Review. Several rat models for the administration of NKA prototypes are possible. One model is the allotransplant model wherein using the inbred rat strain DA (d=d blood group, A=agouti) donors to rat strain Wistar-Furth (WF) (strong histocompatibility).

1. MHC compatible pairs: Fisher rat strain (F344) to Lewis rat strain (LEW)
2. ZSF rat:
    a. Generated from the first-generation (F1) offspring of the spontaneously hypertensive shhf (severe hypertension & heart failure) rat×Zucker Diabetic Fatty (ZDF) rat.
        i. Obese, diabetic, hypertensive; proteinuria
        ii. Offspring of the ZDF×SHHF are syngeneic in litter
            1. Half the offspring are obese+disease; other half are lean
        iii. F1 offspring can accept transplants from parent SHHF and ZDF strains
3. Allogeneic donor options
    a. Original lean Zucker Fatty rat (ZF)—an outbred strain
    b. Parent strain of the ZF—the Wistar
4. ZSF1 and SHHF testing with RT1.B and RT1.D (Major Histo Compatibility Class II assays)
    a. ZSF1—L/K haplotypes
    b. SHHF—K haplotype
Experimental Design
Methodology—Injectable Cells
1. Control and autologous arms
    a. ZSF no transplant; no immunosuppression (n=3)—Pure control
    b. ZSF no transplant; with immunosuppression (n=3)—Med effect
    c. ZSF with empty vehicle; with immunosuppression (n=3)—Med effect and vehicle impact
    d. ZSF to ZSF; no immunosuppression (n=5)—Cell effect; no med component
    e. ZSF to ZSF; with immunosuppression (n=5)—Med effect with procedure
2. Allotransplant Experiments
    a. Wistar to ZSF (or lean Zucker to ZSF); with immunosuppression (n=5)—Med effect on allotransplantation model
    b. One or more of the following immunosuppressive regimes would be implemented in conjunction with delivery of the allogeneic cells:
        i. Cyclosporin A (CsA) (10 mg/kg) daily by gavage
        ii. Tacrolimus (0.2 mg/kg) daily by gavage ($2^{nd}$ choice)
        iii. Rapamycin (1 mg/kg) daily by gavage ($1^{st}$ choice)
        iv. Mycophenolate Mofetil (10 mg/kg) daily by gavage

What is claimed is:

1. An implantable construct for providing improved kidney function to a subject in need comprising:
   a) a biomaterial comprising one or more biocompatible synthetic polymers; and
   b) an isolated human renal cell population coated with, deposited on or in, entrapped in, suspended in, embedded in and/or otherwise combined with the biomaterial, wherein the human renal cell population is depleted of a B1 cell population comprising large granular cells of the collecting duct and tubular system, wherein the B1 cell population has a density of about <1.045 g/ml.

2. The construct of claim 1 wherein the biomaterial is configured as a three-dimensional (3-D) porous biomaterial suitable for entrapment and/or attachment of the cell population.

3. The construct of claim 1 wherein the biomaterial is configured as a liquid or semi-liquid gel suitable for embedding, attaching, suspending, or coating the cell population.

4. The construct of claim 1, wherein the biomaterial is comprised of a predominantly high-molecular weight species of hyaluronic acid (HA) in hydrogel form.

5. The construct of claim 1, wherein the biomaterial is comprised of a predominantly high-molecular weight species of hyaluronic acid in porous foam form.

6. The construct of claim 1, wherein the biomaterial is comprised of a poly-lactic acid-based foam having pores of between about 50 microns to about 300 microns.

7. The construct of claim 1, wherein the human renal cell population is further depleted of a B5 cell population comprising debris and small cells of low granularity and viability, wherein the B5 cell population has a density of about >1.091 g/ml.

8. The construct of claim 1 or 7, wherein the human renal cell population is enriched for renal tubular cells.

9. The construct of claim 1 or 7, wherein the human renal cell population is enriched for one or more bioactive cell populations.

10. The construct of claim 9, wherein the one or more bioactive cell populations is obtainable by centrifugation on a density gradient after ex vivo culture.

11. The construct of claim 10, wherein the one or more bioactive cell population comprises a B2 cell population comprising an enriched population of tubular cells and having a density between about 1.045 g/mL and about 1.052 g/mL.

12. The construct of claim 10, wherein the one or more bioactive cell population comprises a B3 cell population comprising erythropoietin (EPO)-producing cells, glomerular cells and vascular cells and having a density between about 1.052 g/ml and about 1.063 g/ml.

13. The construct of claim 10, wherein the one or more bioactive cell population comprises a B4 cell population comprising erythropoietin (EPO)-producing cells, glomerular cells and vascular cells and having a density between about 1.063 g/ml and about 1.091 g/ml.

14. The construct of claim 10, wherein the one or more bioactive cell population comprises
   (a) a B2 cell population comprising an enriched population of tubular cells and having a density between about 1.045 g/mL and about 1.052 g/mL;

(b) a B3 cell population comprising erythropoietin (EPO)-producing cells, glomerular cells and vascular cells and having a density between about 1.052 g/ml and about 1.063 g/ml; and (c) a B4 cell population comprising erythropoietin (EPO)-producing cells, glomerular cells and vascular cells and having a density between about 1.063 g/ml and about 1.091 g/ml.

15. The construct of claim 10, wherein the one or more bioactive cell population comprises
   (a) a B2 cell population comprising an enriched population of tubular cells and having a density between about 1.045 g/mL and about 1.052 g/mL; and
   (b) a B3 cell population comprising erythropoietin (EPO)-producing cells, glomerular cells and vascular cells and having a density between about 1.052 g/ml and about 1.063 g/ml.

16. The construct of claim 10, wherein the one or more bioactive cell population comprises
   (a) a B2 cell population comprising an enriched population of tubular cells and having a density between about 1.045 g/mL and about 1.052 g/mL; and
   (b) a B4 cell population comprising erythropoietin (EPO)-producing cells, glomerular cells and vascular cells and having a density between about 1.063 g/ml and about 1.091 g/ml.

* * * * *